US011499195B2

(12) United States Patent
Hopkins et al.

(10) Patent No.: US 11,499,195 B2

(45) Date of Patent: Nov. 15, 2022

(54) MITOCHONDRIAL DNA PROSTATE CANCER MARKER AND RELATED SYSTEMS AND METHODS

(71) Applicants: ONTARIO INSTITUTE FOR CANCER RESEARCH (OICR), Toronto (CA); UNIVERSITY HEALTH NETWORK, Toronto (CA)

(72) Inventors: Julia A. Hopkins, Toronto (CA); Paul Boutros, Toronto (CA); Robert G. Bristow, Toronto (CA)

(73) Assignees: Ontario Institute for Cancer Research, Ontario (CA); University Health Network, Ontario (CA)

( * ) Notice: Subject to any disclaimer, the term of this patent is extended or adjusted under 35 U.S.C. 154(b) by 0 days.

(21) Appl. No.: 16/306,724

(22) PCT Filed: Jun. 2, 2017

(86) PCT No.: PCT/CA2017/000139

§ 371 (c)(1),
(2) Date: Dec. 3, 2018

(87) PCT Pub. No.: WO2017/205963

PCT Pub. Date: Dec. 7, 2017

(65) Prior Publication Data

US 2019/0112672 A1 Apr. 18, 2019

Related U.S. Application Data

(60) Provisional application No. 62/344,723, filed on Jun. 2, 2016.

(51) Int. Cl.

| | |
|---|---|
| ***C12Q 1/6886*** | (2018.01) |
| ***G01N 33/574*** | (2006.01) |
| ***G16H 50/30*** | (2018.01) |
| ***G16H 50/20*** | (2018.01) |
| ***C12Q 1/6881*** | (2018.01) |

(52) U.S. Cl.

CPC ......... *C12Q 1/6886* (2013.01); *C12Q 1/6881* (2013.01); *G01N 33/57434* (2013.01); *G16H 50/20* (2018.01); *G16H 50/30* (2018.01); *C12Q 2600/118* (2013.01); *C12Q 2600/156* (2013.01)

(58) Field of Classification Search

None

See application file for complete search history.

(56) References Cited

U.S. PATENT DOCUMENTS

2007/0190534 A1 8/2007 Birch-Machin et al.

OTHER PUBLICATIONS

Jonckheere (J Med Genet 2008 vol. 45 pp. 129-133).*

Giorgi (Cancer Epidemiol Biomarkers Prev 25(6) pp. 1001-1003 pub online Mar. 28, 2016).*

Borque (BJU International 2012 vol. 111 pp. 549-558).*

Kloss-Brandstatter (The American Journal of Human Genetics 87 802-812, Dec. 10, 2010).*

Dorff (Journal of Clinical Oncology vol. 29 No May 15, 2020, 2011 pp. 2040-2045).*

Behar (The American Journal of Human Genetics 90 675-684 Apr. 6, 2012).*

Adzhubei, et al., "Predicting Functional Effect of Human Missense Mutations Using PolyPhen-2," *Current Protocols in Human Genetic*, 7; Unit 7.20, 2013.

Alioto, et al., "A Comprehensive Assessment of Somatic Mutation Detection in Cancer Using Whole-Genome Sequencing," *Nature Communications*, 6; 10001, 2015.

Baca, et al., "Punctuated Evolution of Prostate Cancer Genomes," *Cell*, 153' 666-677, 2013.

Barbieri, et al., "Exome Sequencing Identifies Recurrent SPOP, FOXA1, and MED12 Mutations in Prostate Cancer," *Nature Genetics*, 44; 685-689, 2012.

Barbieri, et al., "The Mutational Landscape of Prostate Cancer," *European Urology*, 64; 567-576, 2013.

Behar, et al., "A 'Copernican' Reassessment of the Human Mitochondrial DNA Tree From Its Root," *American Journal of Human Genetics*, 90; 675-684, 2012.

Berger, et al., "The Genomic Complexity of Primary Human Prostate Cancer," *Nature*, 470; 214-220, 2011.

Boutros, et al., "Spatial Genomic Heterogeneity Within Localized, Multifocal Prostate Cancer," *Nature Genetics*, 47; 736-745, 2015.

Calabrese, et al., "MToolBox: A Highly Automated Pipeline for Heteroplasmy Annotation and Prioritization Analysis of Human Mitochondrial Variants in High-Throughput Sequencing," *Bioinformatics*, 30; 3115-3117, 2014.

Cancer Genome Atlas Research Network, "The Molecular Taxonomy of Primary Prostate Cancer," *Cell*, 163; 1011-1025, 2015.

Chen, et al., "Extensive Somatic Mitochondrial Mutations in Primary Prostate Cancer Using Laser Capture Microdissection," *Cancer Research*, 62; 6470-6474, 2002.

Cooper, et al., Analysis of the Genetic Phylogeny of Multifocal Prostate Cancer Identifies Multiple Independent Clonal Expansions in Neoplastic and Morphologically Normal Prostate Tissue, *Nature Genetics* 47; 367-372, 2015.

Corral-Debrinski, et al., "Association of Mitochondrial DNA Damage with Aging and Coronary Atherosclerotic Heart Disease," *Mutation Research*, 275(3-6); 169-180, 1992.

(Continued)

*Primary Examiner* — Amanda Haney

(74) *Attorney, Agent, or Firm* — Norton Rose Fulbright US LLP; Gina Shishima

(57) ABSTRACT

There is described herein a method of prognosing and/or predicting disease progression and/or in subject with prostate cancer, the method comprising: a) providing a sample containing mitochondrial genetic material from prostate cancer cells; b) sequencing the mitochondrial genetic material with respect to at least 1 patient biomarker selected from CSB1, OHR, ATP8 and HV1 (hypervariable region 1); c) comparing the sequence of the patient biomarkers to control or reference biomarkers to determine mitochondrial single nucleotide variations (mtSNVs); and d) determining the a prostate cancer prognosis; wherein a relatively worse outcome is associated with the presence of mtSNVs in CSB1, OHR, ATP8 and a relatively better outcome is associated with the presence of mtSNVs in HV1.

13 Claims, 15 Drawing Sheets

Specification includes a Sequence Listing.

(56) References Cited

OTHER PUBLICATIONS

Cortopassi & Arnheim, "Detection of a Specific Mitchondriai DNA Deletion in Tissues of Older Humans," *Nucleic Acids Research*, 18; 6927-6933, 1990.
Ding, et al., "Assessing Mitochondrial DNA Variation and Copy Number in Lymphocytes of ~2,000 Sardinians Using Tailored Sequencing Analysis Tools," *PLoS Genetics*, 11; e1005306, 2015.
Edgar, "MUSCLE: Multiple Sequence Alignment with High Accuracy and High Throughout," *Nucleic Acids Research*, 32; 1792-1797, 2004.
Erho, et al., "Discovery and Validation of a Prostate Cancer Genomic Classifier that Predicts Early Metastasis Following Radical Prostatectomy," *PloS One* 8; c66855, 2013.
Fraser, et al., "Genomic Hallmarks of Localized, Non-Indolent Prostate Cancer," *Nature*, 541; 359-364, 2017.
Gomez-Zaera, et al., "Identification of Somatic and Germline Mitochondrial DNA Sequence Variants in Prostate Cancer Patients, " *Mutation Research*, 595; 42-51, 2006.
Govind, et al., "ShatterProof: Operational Detection and Quantification of Chromothripsis," *BMC Bionformatics*, 15; 78, 2014.
Guo, et al., "The Use of Next Generation Sequencing Technology to Study the Effect of Radiation Therapy on Mitochondrial DNA Mutation," *Mutation Research*, 744; 154-160, 2012.
He, et al., "Heteroplasmic Mitchondrial DNA Mutations in Normal and Tumour Cells," *Nature*, 464; 610-614, 2010.
International Search Report and Written Opinion Issued in PCT Application No. PCT/CA2017/000139, dated Aug. 8, 2017.
Ju, et al., "Origins and Functional Consequences of Somatic Mitochondrial DNA Mutations in Human Cancer," *eLife*, 3; 2014.
Kervinen, et al., "The MELAS Mutations 3946 and 3949 Perturb the Critical Structure in a Conserved Loop of the ND1 Subunit of Mitochondrial Complex I;" *Human Molecular Genetics*, 15; 2543-2552, 2006.
Kloss-Brandstatter, et al., "Somatic Mutations Throughout the Entire Mitochondrial Genome Are Associated with Elevated PSA Levels in Prostate Cancer Patients," *American Journal Human Genetics*, 87; 802-812, 2010.
Krjutskov , et al., "Tissue-Specific Mitochondrial Heteroplasmy at Position 16,093 Within the Same Individual," *Curr Genet* 60; 11-16, 2014.
Krzywinski, et al., "Circos: An Information Aesthetic for Comparative Genomics," *Genome Research*, 2009.
Kumimoto, et al., "Frequent Somatic Mutations of Mitochondrial DNA in Esophageal Squamous Cell Carcinoma," *International Journal Cancer*; 108; 228-231, 2004.
Lalonde, et al, "Tumour Genomic and Microenvironmental Heterogeneity for Integrated Prediction of 5-Year Biochemical Recurrence of Prostate Cancer: A Retrospective Cohort Study," *Lancet Oncology*, 15; 1521-1532, 2014.
Larman, et al., "Spectrum of Somatic Mitochondrial Mutations in Five Cancers," *PNAS*, 109;14087-14091, 2012.
Larson, et al., "SomaticSniper: Identification of Somatic Point Mutations in Whole Genome Sequencing Data," *Bioinformatics*, 28; 311-317, 2012.
Li, et al., "Automated Inference of Molecular Mechanisms of Disease from Ammo Acid Substitutions," *Bioinformatics* , 25; 2744-2750, 2009.
Li, et al., "Myc Stimulates Nuclearly Encoded Mitochondrial Genes and Mitochondrial Biogensis," *Molecular Cellular Biology*, 25; 5225-6234, 2005.
Li, et al., "The Sequence Alignment/Map Format SAMtools," *Bioinformatics*, 25; 2078-2079, 2009.
Lott, et al., mtDNA Variation and Analysis Using Mitomap and Mitomaster, *Current Protocols in Bioinformatics*, 44; 1.23; 1-26, 2013.
Lozano, et al., "Global and Regional Mortality from 235 Causes of Death for 20 Age Groups in 1990 and 2010: A Systematic Analysis for the Global Burden of Disease Study 2010," *Lancet*, 380; 2095-2128, 2012.
Masella, et al., "BAMQL: A Query Language for Extracting Reads from BAM Files," *BMC Bioinformatics*, 17; 305, 2016.
McCrow, et al., "Spectrum of Mitochondrial Genomic Variation and Associated Clinical Presentation of Prostate Cancer in South African Men," *Prostate*, 76; 349-358, 2016.
McMahon & LaFramboise, "Mutational Patterns in the Breast Cancer Mitochondrial Genome with Clinical Correlates," *Carcinogenesis*, 35; 1046-4054, 2014.
Michikawa, et al., "Aging-Dependent Large Accumulation of Point Mutations in the Human mtDNA Control Region for Replication," *Science*, 286; 774-779, 1999.
Nicholls & Minczuk, "In D-Loop: 40 Years of Mitochondrial 7S DNA," *Experimental Gerontology*, 56; 175-181, 2014.
Petros, et al., "mtDNA Mutations Increase Tumorgenicity in Prostate Cancer," *PNAS*, 102; 719-724, 2005.
Putz, et al., "Mamit-tRNA, A Database of Mammalian Mitochondrial rRNA Primary and Secondary Structures," *RNA*, 13; 1184-1190, 2007.
Quinlan, et al., "BEDTools: A Flexible Suite of Utilities for Comparing Genomic Features," *Bioinformatics*, 26; 841-842, 2010.
Rausch, et al., "DELLY: Structural Variant Discovery by Integrated Paired-End and Split-Read Analysis," *Bioinformatics*, 28; i333-i339, 2012.
Robinson, et al., "Accurate Prediction of Repeat Prostate Biopsy Outcomes by a Mitochondrial DNA Deletion Assay," *Prostate Cancer Prostatic Dis*, 13; 126-131, 2010.
Rubino, et al., "HmtDB, A Genomic Resource for Mitochondrian-Based Human Variability Studies," *Nucleic Acids*, 40; D1150-1159, 2012.
Samuels, et al., "Recurrent-Tissue-Specific mtDNA Mutations are Common in Humans," *PLoS Genet*, 9; e1003929, 2013.
Sancho, et al., "MYC/PGC-lα Balance Determines the Metabolic Phenotype and Plasticity of Pancreatic Cancer Stem Cells," *Cell Metabolism*, 22; 590-605, 2015.
Song, et al., "qpure: A Tool to Estimate Tumor Cellularity from Genome-Wide Single-Nucleotide Polymorphism Profiles," *PLoS One*, 7; e45835, 2012.
Wallace, et al., "Mitochondria and Cancer," *Nature Reviews Cancer*, 12;685-698, 2012.
Wang, et al., "ANNOVAR: Functional Annotation of Genetic Variants From High-Throughput Sequencing Data," *Nucleic Acids Res*, 38; e164, 2010.
Weischenfeldt, et al., "Integrative Genomic Analyses Reveal and Androgen-Driven Somatic Alteration Landscape in Early-Onset Prostate Cancer," *Cancer Cell*, 23; 159-170, 2013.
Wu, et al., "Development and Validation of a 32-Gene Prognostic Index for Prostate Cancer Progression," *PNAS*, 110; 6121-6126, 2013.
Wu, et al., "GMAP: A Genomic Mapping and Alignment Program for mRNA and EST Sequences," *Bioinformatics*, 21; 1859-1875, 2005.
Zhang, et al., "Differential Occurrence of Mutations in Mitochondrial DNA of Human Skeletal Muscle During Aging," *Hum Mutat*, 11; 360-371, 1998.

* cited by examiner a b

SEQUENCE LISTING

<160> NUMBER OF SEQ ID NOS: 42

<210> SEQ ID NO 1
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 1
tctatcaccc tattaaccac actcacg 27

<210> SEQ ID NO 2
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 2
aggctggtgt tagggttctt tg 22

<210> SEQ ID NO 3
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 3
aaaaatttcc accaaacccc c 21

<210> SEQ ID NO 4
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 4
actggaacgg ggatgcttg 19

<210> SEQ ID NO 5
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 5
acgggaaaca gcagtgatta ac 22

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
agggctaagc atagtggggt 20

<210> SEQ ID NO 7
<211> LENGTH: 20
<212> TYPE: DNA
<213> ORGANISM: Artificial Sequence -continued
<220> FEATURE:
<223> OTHER INFORMATION: Synthetic Polynucleotide

<400> SEQUENCE: 7
cagcaaaccc tgatgaaggc 20

<210> SEQ ID NO 8
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 8
tggtagtaag gtggagtggg t 21

<210> SEQ ID NO 9
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 9
taccctaggg ataacagcgc a 21

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
gggaaggcgc tttgtgaagt 20

<210> SEQ ID NO 11
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 11
tactcctgcc atcatgaccc t 21

<210> SEQ ID NO 12
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 12
gttcagggga gagtgcgtc 19

<210> SEQ ID NO 13
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 13
ataccccgaa aatgttggtt atac 24

<210> SEQ ID NO 14
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 14
ggcttacgtt tagtgaggga gag 23

<210> SEQ ID NO 15
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 15
ctgacatccg gcctgctt 18

<210> SEQ ID NO 16
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 16
caggtgcgag atagtagtag ggtc 24

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
catcgccctt accacgctac 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
cggcgggaga agtagattga 20

<210> SEQ ID NO 19
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 19
cataaacaac ataagcttct gactcttacc t 31

<210> SEQ ID NO 20
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 20
ggtctcctcc tccggcg 17

<210> SEQ ID NO 21
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 21
tatcctacca ggcttcggaa t 21

<210> SEQ ID NO 22
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 22
acctacggtg aaaagaaaga tga 23

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
accacagttt catgcccatc 20

<210> SEQ ID NO 24
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 24
ggtgagggag gtaggtggta g 21

<210> SEQ ID NO 25
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 25
caaaaaggcc ttcgatacgg g 21

<210> SEQ ID NO 26
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 26
tagttggcgg atgaagcaga t 21

<210> SEQ ID NO 27

<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 27
tgggcctagc cctactagtc tc 22

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
gggtcggagg aaaaggttgg 20

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
tacgaacgca ctcacagtcg 20

<210> SEQ ID NO 30
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 30
tgtagaggga gtatagggct gt 22

<210> SEQ ID NO 31
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 31
atctcgaact gacactgagc c 21

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
aaggcgagga tgaaaccgat 20

<210> SEQ ID NO 33
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 33
ctaacaacat ttcccccgca tc 22

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
ggtggagatt tggtgctgtg 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35
cccaccccat ccaacatctc 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
caagcaggag gataatgccg 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 37
ggcgtccttg ccctattact 20

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
acccaaatct gctttcccat 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
atggggaagc agatttgggt 20

<210> SEQ ID NO 40
<211> LENGTH: 20
<212> TYPE: DNA

-continued

```
<213> ORGANISM: Artificial Sequence
<220> FEATURE:
<223> OTHER INFORMATION: Synthetic Polynucleotide

<400> SEQUENCE: 40

gggtgggtag gtttgttggt                                            20


<210> SEQ ID NO 41
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 41

gaacatactt actaaagtgt gt                                         22


<210> SEQ ID NO 42
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 42

gaacatacyt actaaagtgt gt                                         22
```

MITOCHONDRIAL DNA PROSTATE CANCER MARKER AND RELATED SYSTEMS AND METHODS

CROSS REFERENCE TO RELATED APPLICATIONS

This application is a national phase application under 35 U.S.C. § 371 of International Application No. PCT/CA2017/000139 filed Jun. 2, 2017, which claims the benefit of priority of U.S. Provisional Patent Application No. 62/344,723 filed Jun. 2, 2016, the entire contents of which are incorporated herein by reference.

SEQUENCE LISTING

The instant application contains a Sequence Listing which has been submitted in ASCII format and is hereby incorporated by reference in its entirety. Said ASCII copy, created on Mar. 28, 2022, is named UCLA_P0101US_Sequence_Listing.txt and is 8,301 bytes in size.

FIELD OF INVENTION

The present disclosure relates generally to a prostate cancer biomarker signature. More particularly, the present disclosure relates to a mitochondrial DNA for the prognosis of prostate cancer outcomes, which can inform treatment decisions and guide therapy.

BACKGROUND

Prostate cancer remains the most prevalent non-skin cancer in men[1] and exhibits a remarkably quiet mutational profile[2]. Exome sequencing studies of localized tumours have revealed few recurrent somatic single nucleotide variants (SNVs)[3,4], while whole-genome sequencing studies have not identified highly recurrent driver non-coding SNVs or genomic rearrangements (GRs)[5-8]. Although strong mutagenic field effects have been observed[9,10], their underlying mechanisms and to what extent they drive tumour initiation or progression are unknown. Nevertheless, promising molecular diagnostics predictive of aggressive disease have been created using supervised machine-learning techniques, both from RNA abundance data[11,12] and from DNA copy number data[13], showing strong linkage between molecular features of prostate tumour cells and patient outcome.

Most studies of the prostate cancer genome have focused on mutations occurring in the nuclear genome, and have ignored the other genome of the cell: the mitochondrial genome. Mitochondria are maternally inherited and play critical roles in pathways dysregulated in cancer cells, including energy production, metabolism and apoptosis[14]. While mitochondrial mutations have been observed in several tumour types[15-17], including prostate cancer[18-22], their global frequency and clinical impact have not yet been comprehensively characterized. Previous studies have found that mitochondrial mutations are associated with increased serum prostate-specific antigen (PSA) levels[21], have suggested that mtDNA mutations increase cancer cell tumourigenicity[20], and indicate that overall mitochondrial mutation burden is correlated with higher Gleason Scores[22].

SUMMARY OF INVENTION

In an aspect, there is provided a method of prognosing and/or predicting disease progression and/or in subject with prostate cancer, the method comprising: a) providing a sample containing mitochondrial genetic material from prostate cancer cells; b) sequencing the mitochondrial genetic material with respect to at least 1 patient biomarker selected from CSB1, OHR, ATP8 and HV1 (hypervariable region 1); c) comparing the sequence of said patient biomarkers to control or reference biomarkers to determine mitochondrial single nucleotide variations (mtSNVs); and d) determining the a prostate cancer prognosis; wherein a relatively worse outcome is associated with the presence of mtSNVs in CSB1, OHR, ATP8 and a relatively better outcome is associated with the presence of mtSNVs in HV1.

In an aspect, there is provided a computer-implemented method of prognosing or predicting disease progression in a patient with prostate cancer, the method comprising: a) receiving, at at least one processor, sequencing data of mitochondrial genetic material from prostate cancer cells of the patient, the sequencing data reflecting at least 1 patient biomarker selected from CSB1, OHR, ATP8 and HV1 (hypervariable region 1); b) comparing, at the at least one processor, said sequencing data to corresponding control or reference sequences to determine mitochondrial single nucleotide variations (mtSNVs); d) determining, at the at least one processor, a prostate cancer prognosis; wherein a relatively worse outcome is associated with the presence of mtSNVs in CSB1, OHR, ATP8 and a relatively better outcome is associated with the presence of mtSNVs in HV1.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer readable medium having stored thereon a data structure for storing the computer program product described herein.

In an aspect, there is provided a device for prognosing or predicting disease progression in a patient with prostate cancer, the device comprising: at least one processor; and electronic memory in communication with the at one processor, the electronic memory storing processor-executable code that, when executed at the at least one processor, causes the at least one processor to: a) receive sequencing data of mitochondrial genetic material from prostate cancer cells of the patient, the sequencing data reflecting at least 1 patient biomarker selected from CSB1, OHR, ATP8 and HV1 (hypervariable region 1); b) compare said sequencing data to corresponding control or reference sequences to determine mitochondrial single nucleotide variations (mtSNVs); and c) determining, at the at least one processor, a prostate cancer prognosis; wherein a relatively worse outcome is associated with the presence of mtSNVs in CSB1, OHR, ATP8 and a relatively better outcome is associated with the presence of mtSNVs in HV1. In some embodiments, the processor further displays the prostate cancer prognosis on a user display.

In an aspect, there is provided a kit for prognosing or predicting disease progression in a patient with prostate cancer, the kit comprising primer sequences that permit the sequencing of a mitochondrial genome to determine mtSNVs in ATP8, OHR, ND4L and CSB1.

Other aspects and features of the present disclosure will become apparent to those ordinarily skilled in the art upon review of the following description of specific embodiments in conjunction with the accompanying figures.

BRIEF DESCRIPTION OF FIGURES

Embodiments of the present disclosure will now be described, by way of example only, with reference to the attached Figures and Tables.

SNVs and ND5 mtSNVs, and MYC CNAs and RNR2 mtSNVs. (c) The total number of mtSNVs for 384 patients at each ΔHF threshold (unadjusted).

Figure 12:
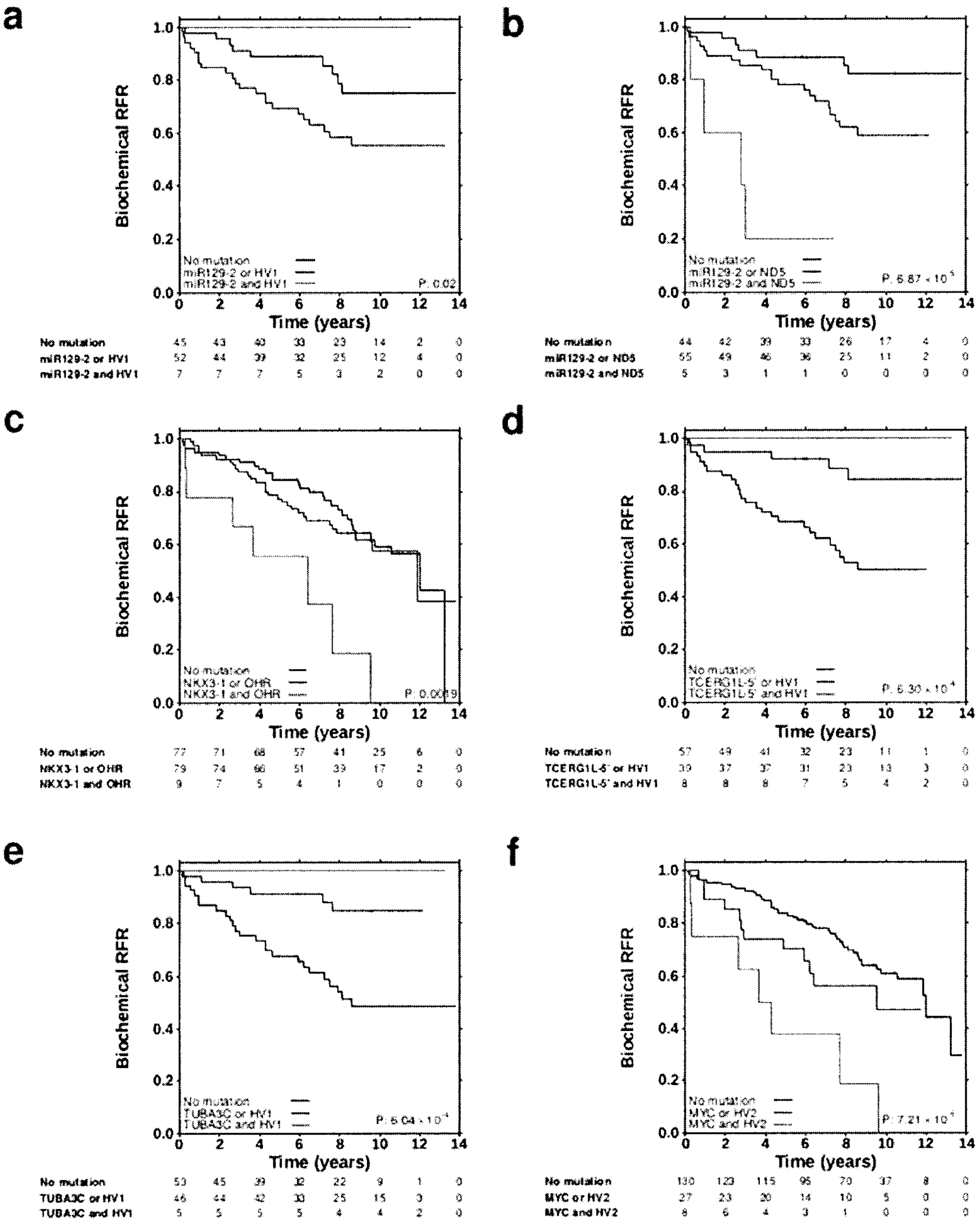

FIG. 12 shows prognostic synergy between mitochondrial and nuclear mutations. Kaplan-Meier plots of patients with (a) methylation events in miR129-2 and mtSNVs in HV1 or (b) ND5; (c) NKX3-1 CNAs and OHR mtSNVs; (d) mtSNVs in HV1 and methylation events in TCERG1L-5' or (e) TUBA3C; and (f) MYC CNAs and HV2 mtSNVs. Patients were grouped according to whether they had no mutations (black line), either a mtSNV or nuclear genomic mutation (blue) or had both (red line).

Figure 13:
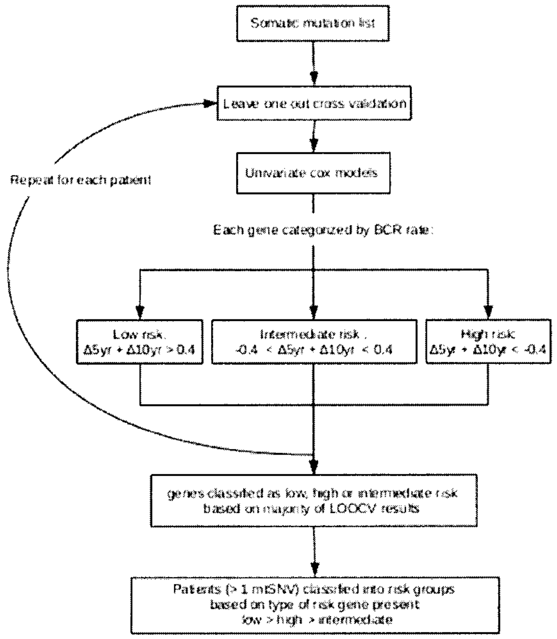
Figure 13:
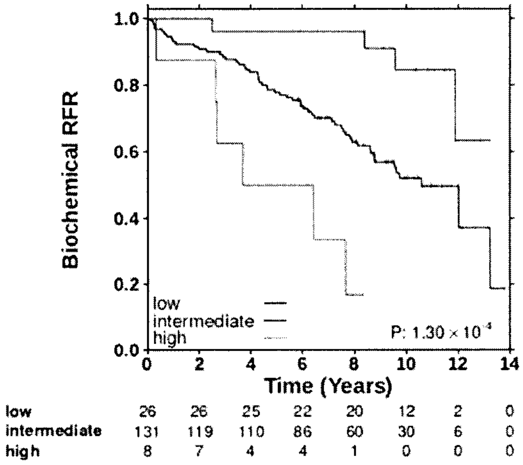

FIG. 13 shows signature flow chart and subset signature. (a) Flowchart showing details of the leave-one-out cross validation method. (b) Mitochondrial signature using three genes (HV1, OHR, CO3).

Figure 14:
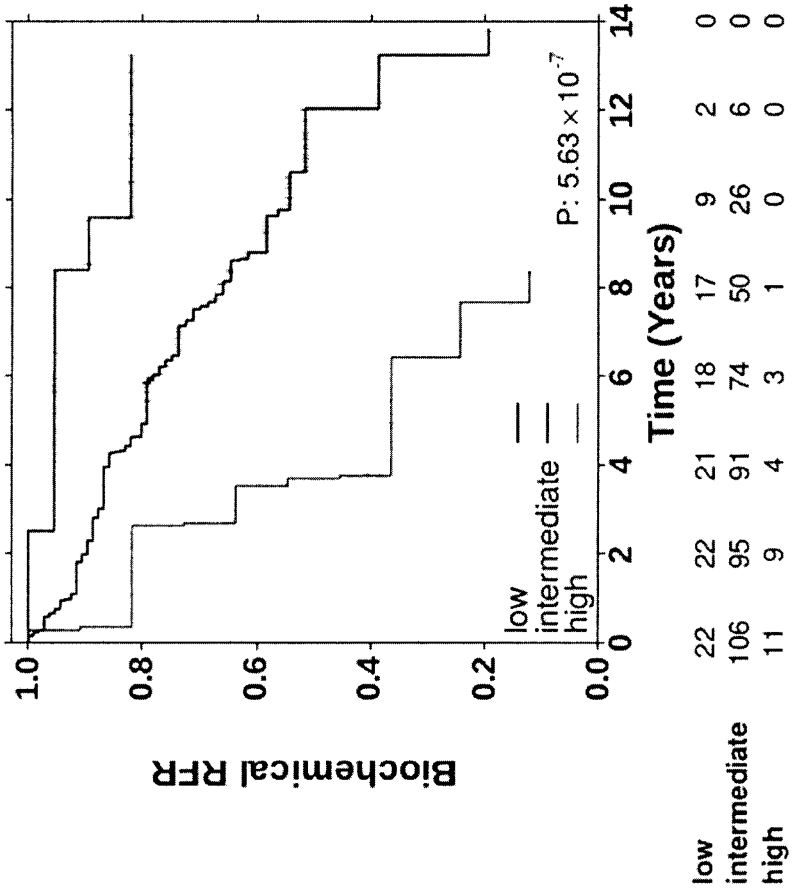

FIG. 14 shows mitochondrial signature in intermediate risk patients. Only patients classified as NCCN-intermediate risk were used with the mtSNV signature and were separated into three risk-prediction groups, 'high' (red line), 'intermediate' (black line), and 'low' (blue line).

Figure 15:
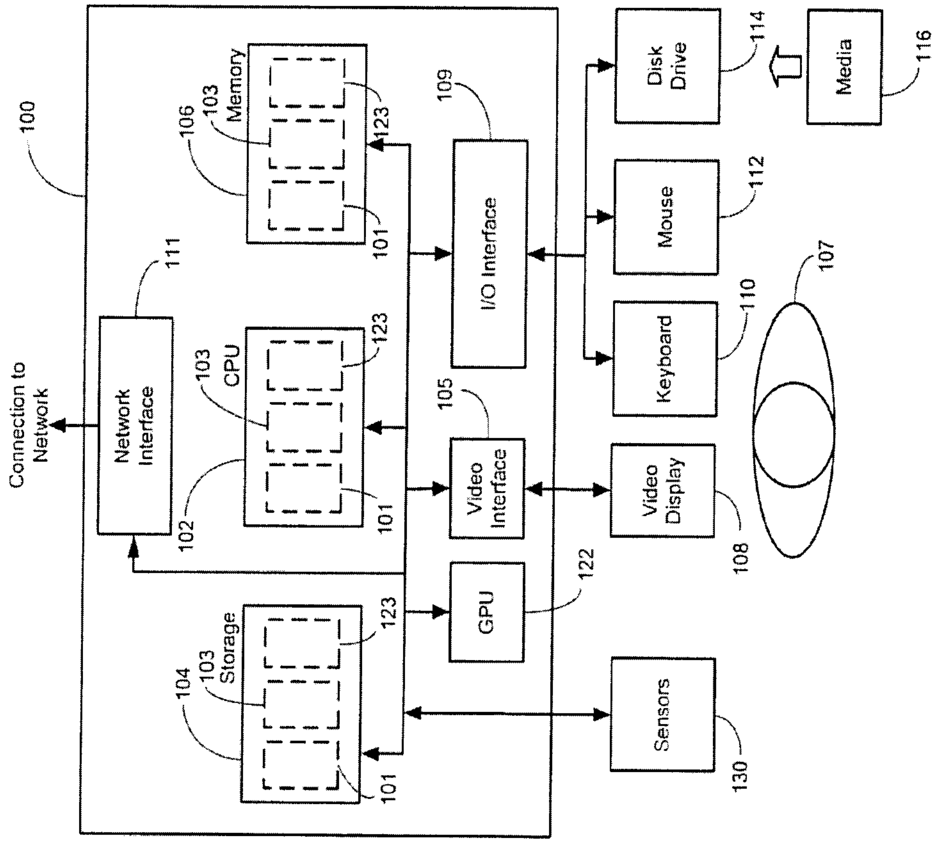

FIG. 15 shows suitable configured computer device, and associated communications networks, devices, software and firmware to provide a platform for enabling one or more embodiments as described herein.

Table 1 shows results of PCR validation of 25 mtSNVs. The table includes the mtSNV position, which PCR primers were used to validate, the heteroplasmy fraction (adjusted by cellularity) of the major allele for both tumour and normal and the results of the PCR amplification and Sanger sequencing.

Table 2 shows results from univariate Cox proportional modeling. Hazard ratios were calculated for the different mitochondrial loci individually, the table includes the HR and 95% CI, p-values, the change in 10 year survival and the number of patients with a mtSNV in that loci.

Table 3 shows the sequence and mtDNA targeted region of 20 forward and reverse PCR primers.

Table 4 shows clinical and sequencing data per patient. The data includes patient age at treatment, Gleason Score, T-category, PSA (ng/mL) level, tumour cellularity, number of mtSNVs and the mean coverage depth, mitochondrial copy number for both normal and tumour sample and the aligner used for each wgs. The presence or absence of mutations in each of 20 mitochondrial regions and MYC and NKX3-1 copy number aberrations is indicated for each sample and the amount of DNA that was sent for sequencing for the CPC-GENE samples are included.

Table 5 shows 293 somatic mtSNVs. List of mtSNVs, including heteroplasmic fractions (HF), reference allele nucleotide, identity of tumour and normal major alleles and major allele heteroplasmy fractions (both adjusted and unadjusted by tumour cellularity), tumour and normal coverage at each position, the mtDNA gene or region and pathogenicity scores from MutPred and Polyphen2 obtained from MToolBox.

Table 6 shows mitochondrial mutation recurrence for 41 nuclear genomic features. The table includes the number of patients that had a specific nuclear genome CNA, GR, methylation event or SNV and of those patients the number that also harbours an mtSNV in any of 22 mtDNA features.

Table 7 shows mtSNVs with ΔHF values between 0.1 and 0.2. List of 265 mtSNVs, that had ΔHF values greater than 0.1, but less than 0.2. The table includes heteroplasmic frequencies, reference allele nucleotide, identity of tumour and normal major alleles and major allele heteroplasmy fractions, tumour and normal coverage at each position and the mtDNA gene or region.

DETAILED DESCRIPTION

Nuclear mutations are well-known to drive tumour incidence, aggression and response to therapy. By contrast, the frequency and roles of mutations in the maternally-inherited mitochondrial genome are poorly understood. To characterize the mitochondrial mutation landscape of prostate cancer, we analyzed the mitochondrial genomes of 384 adenocarcinomas of the prostate across all National Comprehensive Cancer Network (NCCN) defined risk categories, including 164 early-onset prostate cancers (EOPCs, age at diagnosis less than 50). We identified a median of one mitochondrial single nucleotide variant (mtSNV) per patient.

We identify recurrent mutational hotspots in the mitochondrial genome, which included recurrently mutated bases or recurrently mutated genes or regions. We also confirm increasing mutation burden with patient age[23-26], identify interactions between nuclear and mitochondrial mutation profiles and reveal specific mitochondrial mutations enriched in aggressive prostate tumours. For example certain control region mtSNVs co-occur with gain of the MYC oncogene, and these mutations are jointly associated with patient survival.

These data demonstrate frequent mitochondrial mutation in prostate cancer, and suggest interplay between nuclear and mitochondrial mutational profiles in prostate cancer.

The methods described herein are useful for prognosing the outcome of a subject that has, or has had, a cancer associated with the prostate. The cancer may be prostate cancer or a cancer that has metastasized from a cancer of the prostate.

In an aspect, there is provided a method of prognosing and/or predicting disease progression and/or in subject with prostate cancer, the method comprising: a) providing a sample containing mitochondrial genetic material from prostate cancer cells; b) sequencing the mitochondrial genetic material with respect to at least 1 patient biomarker selected from CSB1, OHR, ATP8 and HV1 (hypervariable region 1); c) comparing the sequence of said patient biomarkers to control or reference biomarkers to determine mitochondrial single nucleotide variations (mtSNVs); and d) determining the a prostate cancer prognosis; wherein a relatively worse outcome is associated with the presence of mtSNVs in CSB1, OHR, ATP8 and a relatively better outcome is associated with the presence of mtSNVs in HV1.

The term "subject" as used herein refers to any member of the animal kingdom, preferably a human being and most preferably a human being that has, has had, or is suspected of having prostate cancer.

The term "sample" as used herein refers to any fluid (e.g. blood, urine, semen), cell, tumor or tissue sample from a subject which can be assayed for the biomarkers described herein.

The term "genetic material" used herein refers to materials found/originate in the nucleus, mitochondria and cytoplasm, which play a fundamental role in determining the structure and nature of cell substances, and capable of self-propagating and variation. In the context of the present methods, the genetic material is any material from which one can measure the biomakers described herein. The genetic material is preferably DNA.

The term "prognosis" as used herein refers to the prediction of a clinical outcome associated with a disease subtype which is reflected by a reference profile such as a biomarker reference profile. The prognosis provides an indication of disease progression and includes an indication of likelihood of death due to cancer. The prognosis may be a prediction of metastasis, or alternatively disease recurrence. In one embodiment the clinical outcome class includes a better survival group and a worse survival group. The term "prognosing or classifying" as used herein means predicting or identifying the clinical outcome of a subject according to the subject's similarity to a reference profile or biomarker associated with the prognosis. For example, prognosing or classifying comprises a method or process of determining whether an individual has a better or worse survival outcome, or grouping individuals into a better survival group or a worse survival group, or predicting whether or not an individual will respond to therapy.

The term "biomarker profile" as used herein refers to a dataset representing the state or expression level(s) of one or more biomarkers. A biomarker profile may represent one subject, or alternatively a consolidated dataset of a cohort of subjects, for example to establish a reference biomarker profile as a control.

As used herein, the term "control" refers to a specific value or dataset that can be used to prognose or classify the value e.g the measured biomarker or reference biomarker profile obtained from the test sample associated with an outcome. In one embodiment, a dataset may be obtained from samples from a group of subjects known to have cancer having different tumor states and/or healthy individuals. The state or expression data of the biomarkers in the dataset can be used to create a control value that is used in testing samples from new patients. In some embodiments, a cohort of subjects is used to obtain a control dataset. A control cohort patients may be a group of individuals with or without cancer. In a particularly embodiment, the control is a patient's own matched normal profile (e.g. from blood or normal tissue).

As used herein, "overall survival" refers to the percentage of or length of time that people in a study or treatment group are still alive following from either the date of diagnosis or the start of treatment for a disease, such as cancer. In a clinical trial, measuring the overall survival is one way to see how well a new treatment works.

As used herein, "relapse-free survival" refers to, in the case of caner, the percentage of or length of time that people in a study or treatment group survive without any signs or symptoms of that cancer after primary treatment for that cancer. In a clinical trial, measuring the relapse-free survival is one way to see how well a new treatment works. It is defined as any disease recurrence or relapse (local, regional, or distant).

The term "good survival" or "better survival" as used herein refers to an increased chance of survival as compared to patients in the "poor survival" group. For example, the biomarkers of the application can prognose or classify patients into a "good survival group". These patients are at a lower risk of death after surgery and can also be categorized into a "low-risk group".

The term "poor survival" or "worse survival" as used herein refers to an increased risk of disease progression or death as compared to patients in the "good survival" group. For example, biomarkers or genes of the application can prognose or classify patients into a "poor survival group". These patients are at greater risk of death or adverse reaction from disease or surgery, treatment for the disease or other causes, and can also be categorized into a "high-risk group".

A person skilled in the art would understand how to implement differing cut-offs for good survival vs. worse survival, depending on the clinical outcome one is predicting and the biomarkers being assayed.

In some embodiments, the at least 1 patient biomarker, is at least 2, 3 or 4 patient biomarkers.

In some embodiments, the prostate cancer is localized prostate cancer, preferably non-indolent localized prostate cancer.

In some embodiments, the method further comprises building a patient biomarker profile from the determined or measured patient biomarkers.

In some embodiments, the prostate cancer prognosis is the likelihood of disease recurrence, preferably measured by biochemical relapse.

In some embodiments, the method further comprises classifying the patient into a high risk group if the likelihood of disease recurrence is relatively high or a low risk group if the likelihood of disease recurrence is relatively low.

In some embodiments, the method further comprises treating the patient with more aggressive therapy if the patient is in the high risk group. Preferably, the more aggressive therapy comprises adjuvant therapy, preferably hormone therapy, chemotherapy or radiotherapy.

In some embodiments, the patient biomarkers further comprise 002, CO3 and ND4L. Preferably, the at least 1 biomarker is at least 5, 6 or all 7 biomarkers. Further preferably, the at least 1 biomarker is all 7 biomarkers.

In some embodiments, the subject is classified as low risk if there exists mtSNVs in CO2, CO3, and HV1 and high risk if there exists mtSNVs in ATPS, OHR, ND4L and CSB1.

In some embodiments, the mtSNVs are the mtSNVs identified in Table 5. [NTD: Please confirm]

The present system and method may be practiced in various embodiments. A suitably configured computer device, and associated communications networks, devices, software and firmware may provide a platform for enabling one or more embodiments as described above. By way of example, FIG. 15 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 115, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown). One or more different types of sensors 135 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

In an aspect, there is provided a computer-implemented method of prognosing or predicting disease progression in a patient with prostate cancer, the method comprising: a) receiving, at at least one processor, sequencing data of mitochondrial genetic material from prostate cancer cells of the patient, the sequencing data reflecting at least 1 patient biomarker selected from CSB1, OHR, ATP8 and HV1 (hypervariable region 1); b) comparing, at the at least one processor, said sequencing data to corresponding control or reference sequences to determine mitochondrial single nucleotide variations (mtSNVs); d) determining, at the at least one processor, a prostate cancer prognosis; wherein a relatively worse outcome is associated with the presence of mtSNVs in CSB1, OHR, ATP8 and a relatively better outcome is associated with the presence of mtSNVs in HV1.

In some embodiments, the method further comprises displaying the prostate cancer prognosis on a user display.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer readable medium having stored thereon a data structure for storing the computer program product described herein.

In an aspect, there is provided a device for prognosing or predicting disease progression in a patient with prostate cancer, the device comprising: at least one processor; and electronic memory in communication with the at one processor, the electronic memory storing processor-executable code that, when executed at the at least one processor, causes the at least one processor to: a) receive sequencing data of mitochondrial genetic material from prostate cancer cells of the patient, the sequencing data reflecting at least 1 patient biomarker selected from CSB1, OHR, ATP8 and HV1 (hypervariable region 1); b) compare said sequencing data to corresponding control or reference sequences to determine mitochondrial single nucleotide variations (mtSNVs); and c) determining, at the at least one processor, a prostate cancer prognosis; wherein a relatively worse outcome is associated with the presence of mtSNVs in CSB1, OHR, ATP8 and a relatively better outcome is associated with the presence of mtSNVs in HV1. In some embodiments, the processor further displays the prostate cancer prognosis on a user display.

As used herein, "processor" may be any type of processor, such as, for example, any type of general-purpose microprocessor or microcontroller (e.g., an Intel™ x86, PowerPC™, ARM™ processor, or the like), a digital signal processing (DSP) processor, an integrated circuit, a field programmable gate array (FPGA), or any combination thereof.

As used herein "memory" may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. Portions of memory 102 may be organized using a conventional file-system, controlled and administered by an operating system governing overall operation of a device.

As used herein, "computer readable storage medium" (also referred to as a machine-readable medium, a processor-readable medium, or a computer usable medium having a computer-readable program code embodied therein) is a medium capable of storing data in a format readable by a computer or machine. The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The computer readable storage medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the computer readable storage medium. The instructions stored on the computer readable storage medium can be executed by a processor or other suitable processing device, and can interface with circuitry to perform the described tasks.

As used herein, "data structure" a particular way of organizing data in a computer so that it can be used efficiently. Data structures can implement one or more particular abstract data types (ADT), which specify the operations that can be performed on a data structure and the computational complexity of those operations. In comparison, a data structure is a concrete implementation of the specification provided by an ADT.

In an aspect, there is provided a kit for prognosing or predicting disease progression in a patient with prostate cancer, the kit comprising primer sequences that permit the sequencing of a mitochondrial genome to determine mtSNVs in ATPS, OHR, ND4L and CSB1.

In some embodiments, the primers further permit sequencing of CO2, CO3 and ND4L.

The above listed aspects and/or embodiments may be combined in various combinations as appreciated by a person of skill in the art. The advantages of the present disclosure are further illustrated by the following examples. The examples and their particular details set forth herein are presented for illustration only and should not be construed as a limitation on the claims of the present invention.

EXAMPLES

Methods/Materials

Patient Cohort

We collected 384 prostate cancer tumour samples with matched normal samples (381 blood, 3 tissue-derived). The samples had Gleason Scores ranging from 3+3 to 5+4. The 165 patients from the Canadian Prostate Cancer Genome Network (CPC-GENE) underwent either radical prostatectomy or image-guided radiotherapy as detailed in Fraser et al. (2017)[7]. In addition, 51 samples from publicly available datasets were included in the somatic mutation analysis and correlations with clinical variables, age, Gleason Score and T-category[4-6,8], three of TOGA samples had tissue-derived normal samples as opposed to blood-normals. All samples were manually macro-dissected and were assessed by an expert urological pathologist to have tumour cellularity >70%. All tumour specimens were taken from the index lesion. Publicly available tumour tissues were obtained and used following University Health Network Research Ethics Board (REB) approved study protocols (UHN 06-0822-CE, UHN 11-0024-CE, CHUQ 2012-913:H12-03-192). Local REB and ICGC guidelines were used to collect whole blood and informed consent from CPC-GENE patients at the time of clinical follow-up.

EOPC Patient Cohort and Sample Processing

We collected 168 tumour samples from EOPC patients. Informed consent and an ethical vote (institutional reviewing board) were obtained according to the current ICGC guidelines. The patients did not receive any neo-adjuvant radiotherapy, androgen deprivation therapy, or chemotherapy prior to the surgical removal of tumor tissue. Tumor samples and a normal blood control were frozen at −20° C. and subsequently stored at −80° C.

EOPC DNA Library Preparation, Sequencing and Alignment

DNA library preparation and whole-genome sequencing was performed on Illumina sequencers with the raw length of the reads displaying a median of 101 bp. Reads were aligned to the hg19 reference genome using BWA-MEM version 0.7.8-r455 [arXiv:1303.3997v2] and duplicates were removed using Picard (available on the World Wide Web at broadinstitute.github.io/picard). Mitochondrial reads were extracted using SAMtools[39].

Nuclear Mutation Calling

Recurrent nuclear genomic features were obtained from Fraser et al. (2017)[7], which included five recurrent coding SNVs from commonly mutated genes in prostate cancer; the six most recurrent noncoding SNVs; CNAs from eight commonly mutated prostate cancer genes; the 10 GRs included the five most recurrent translocations and the four most recurrent inversions plus a recurrent inversion containing the PTEN gene; the TMPRSS-ERG fusion; presence or absence of kataegis events; chromothripsis; 3 metrics of mutation density (median dichotomized PGA estimates, number of SNVs and number of GRs); six methylation events were identified through univariate CoxPH modelling as associated with disease progression. Nuclear somatic single nucleotide variants were predicted by SomaticSniper (v1.0.2)[38], (n=172 samples) setting the mapping quality threshold to 1, otherwise with default parameters. Nuclear SNVs were filtered using SAMtools (v0.1.6)[39] and SomaticSniper (v1.0.2) provided filters, as well as a mapping quality filter and false positive filter from bam-readcount (downloaded Jan. 10, 2014). Nuclear SNVs were then annotated by ANNOVAR (v2015-06-17)[40]. The nuclear mutation rate was obtained by dividing the number of SNVs after filtering by the number of callable loci. Copy number aberrations were analyzed by Affymetrix OncoScan microarrays (n=194) and methylation data was generated by Illumina Infinium Human Methylation 450k BeadChip kits (n=104). Genomic rearrangements were called using Delly (v0.5.5)[41] (n=172). Chromothripsis scores (n=159) were calculated by ShatterProof (v0.14)[42] and subsequently dichotomized with a 0.517 threshold. Sample processing, whole genome sequencing and whole genome sequencing data analysis are as described in detail by Fraser et al. (2017)[7].

Mitochondrial SNV Calling

Reads mapped to the mitochondria during whole genome alignment were extracted using BAMQL (v1.1)[43] using the command:

bamql -I -o out_mito_reads.bam -f input_wgs.bam '(chr(M) & mate_chr(M)) |(chr(Y) & after(59000000) & mate_chr(M))';

The second part of the query statement collects reads where one of the pair mapped to chrM and the other unmapped which in our data was also assigned to an unresolved region in chrY.

The output files from BAMQL were used as input bam files for the mitochondrial genome analysis program MToolBox (v0.2.2)[44]. The versions of the various system requirements were: Python v2.7.2; gmap v.2013-07-20[45]; samtools v0.1.18[39]; java v1.7.0_72; picard v1.92 (available on the World Wide Web at broadinstitute.github.io/picard); muscle v3.8.31[46]. We used default parameters for MToolBox and used the default RSRS[47] as the reference genome. The default parameters include a minimum base quality score of 25, samples that failed the MToolBox program using default parameters, but successfully completed at a lower base quality parameter setting of 20, were nonetheless removed from the analysis.

MToolBox_v0.2.2/MToolBox.sh bam -r RSRS -M -I -m'-D genome_index/-H hg19RSRS -M chrRSRS'-a'-r genome_fasta/-F -P -C'

The predicted mitochondrial genome for each tumour sample and the number of reads supporting each base were compared to the corresponding normal sample if available, from each patient. Positions where the absolute difference in heteroplasmy fraction (ΔHF) was greater than 0.2 were considered to be mitochondrial SNVs (mtSNVs). While this does not preclude the possibility of tissue-specific heteroplasmy being mislabeled as somatic mutations, this allowed us to identify somatic variants as well as ignore those positions that could be called population variants, reducing the number of potentially false positive variant calls. Heteroplasmy fraction estimates were adjusted to account for tumour cellularity using cellularity values calculated by qpure[48]. Tumour HF values were adjusted with the following equation:

$$\text{Tumour HF}_{cellularity}=(\text{Tumour HF}_{MToolBox}-(1-\text{cellularity})*\text{Normal HF}_{MToolBox})/\text{cellularity}$$

If there were no cellularity values available we assumed cellularity=1.0. Those values of Tumour $\text{HF}_{cellularity}$ that were less than zero or greater than one were rounded to zero and one respectively.

In the mitochondrial reference genome there are three positions encoded as 'N' to preserve historical numbering, (523, 524 and 3107), in addition position 310 is located within a homopolymer region and is a common variant[28]. These four positions can result in misalignments[49], therefore they were filtered out of our analyses, as in previous studies[50]. We also filtered out those positions with relatively low coverage of less than 100 read depth. Positions of mitochondrial genes and subregions of the noncoding control region were obtained from the World Wide Web at mitomap.org. Pathogenicity scores from MutPred[51], PolyPhen-2[52] and SiteVar[53] were obtained from the MToolBox output. Mutations in tRNA genes were compared to the Mamit-tRNA database[54].

Figure 11:
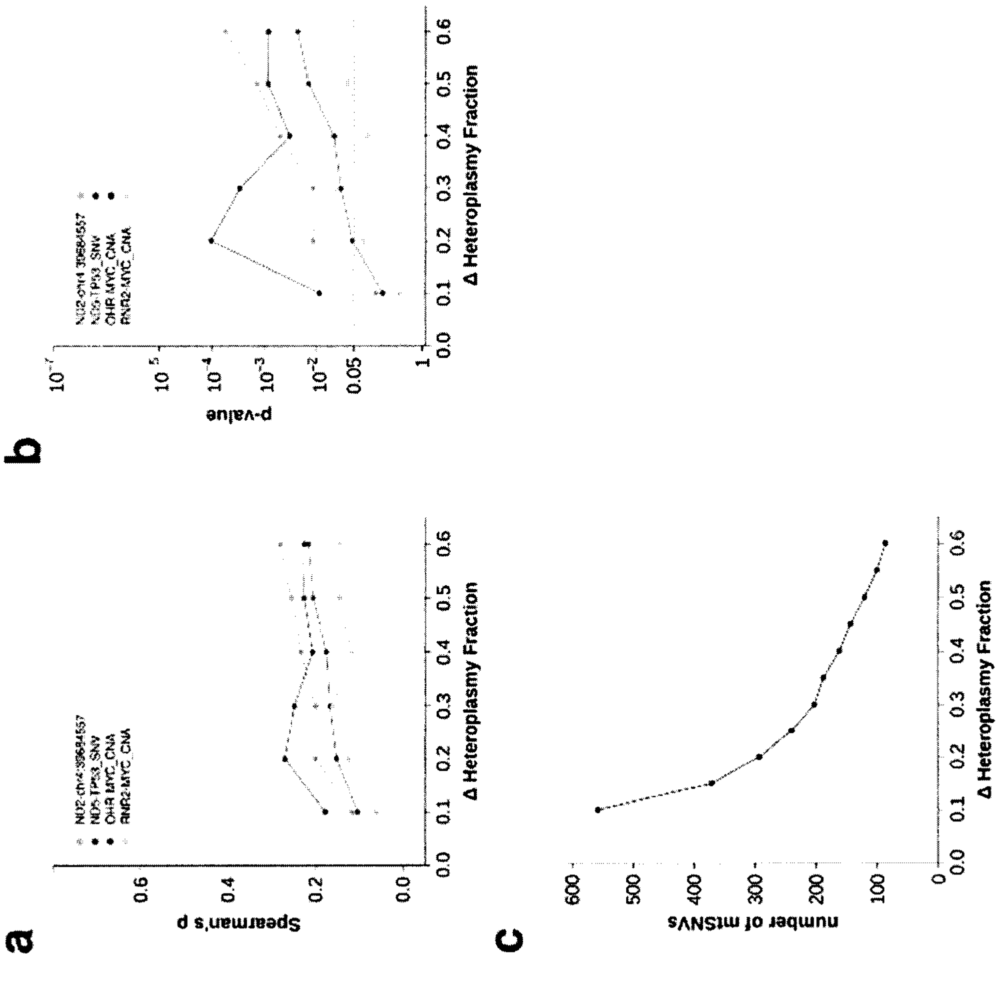
FIG. 11 shows correlations between nuclear and mitochondrial features as a function of heteroplasmy fraction. Spearman's ρ (a) and p-values (b) were calculated using increasing ΔHF cutoffs for mtSNVs for several nuclear and mitochondrial features: MYC CNAs and OHR mtSNVs, the non-coding SNV chr4:39684557 and ND2 mtSNVs, TP53

We chose to a threshold of 0.2 ΔHF in order to balance removing false positives without excluding a large number of mtSNVs unnecessarily (FIG. 11*c*). As part of this assessment, we looked at four correlations between different nuclear and mitochondrial features using mtSNVs assessed at increasing ΔHF cutoffs from 0.1-0.6 (FIG. 11, Table 7). In each of these four cases, raising ΔHF from 0.1 to 0.2 led to increasing correlation coefficients between the two features. Three of the correlations that were not significant at 0.1 ΔHF, became significant at higher ΔHF, suggesting that some mtSNVs with lower HF values may be either false positives or low-level tissue specific heteroplasmies. Any further increases in ΔHF had differing effects on the four correlations.

mtDNA Copy Number

Mitochondrial copy number per cell (MCN) was calculated using the equation: (mitochondrial coverage/nuclear coverage) ×2, using nuclear coverage data from the whole genome alignment[7] and mitochondrial coverage data calculated by bedtools genomecov (v2.24.0)[55]. The mitochondrial mutation rate per megabase DNA was calculated by dividing the number of mtSNVs by the tumour MCN multiplied by the number of callable bases, 16565, accounting for the 4 positions that were removed.

Survival and Statistical Analyses

The mtSNV data were compared to patient clinical features in the R statistical environment (v3.2.3). Binomial regression (age, PSA) and Chi-square tests (T-category, Gleason Score) were used to identify associations between the clinical variables and mtSNVs for all 384 patients. Survival analyses were performed on 165 patients due to survival data availability. Cox proportional hazards models were used to calculate HRs for mtSNVs in the different mitochondrial features such as genes or MCN, with verification of the proportional hazards assumption. The mitochondrial feature MT-ND4L was removed from this analysis as only one patient in the 165 cohort had a mtSNV in this gene. Change in 10 year percent survival was calculated using survival rates. Kaplan-Meier plots were created comparing biochemical recurrence with the presence or absence of mutations in certain mitochondrial loci, (genes or noncoding regions) or median-dichotomized tumour MCN. Nuclear genomic features were chosen based on recurrence in a previous prostate cancer study[7]. Data was visualized using the R-environment and lattice (v0.20-31), latticeExtra (v0.6-26) and circos (v0.67-4)[56]. Associations between nuclear and mitochondrial genome features were calculated using Spearman's correlation.

PCR Validation

Single nucleotide variants in mitochondrial DNA were validated by Sanger re-sequencing, as previously reported[7]. Briefly, 10 ng of total genomic DNA (including mitochondrial DNA) was subjected to PCR amplification using primer pairs flanking SNVs identified from whole-genome sequencing (Table 3). Sequence data surrounding the region of interest was obtained from the World Wide Web at mitomap.org/bin/view.pl/MITOMAP/HumanMitoSeq. The amplicon sequence generated by the in silico PCR was then entered into the NCBI genome BLAST search engine to identify non-mitochondrial sequences that were similar. This was done to ensure that there were some differences between the designed primers and nuclear sequences, as well as to identify any sequence regions that could confound downstream analyses. The genome used for the BLAST search was GRCh38.p2 reference assembly top-level. These web pages were used on Aug. 20 and 21, 2015 and verified on Sep. 13, 2016. PCR reactions were purified using the QIAquick PCR purification kit (Qiagen, Toronto, Canada). Sanger re-sequencing was performed using amplicon-specific primers on an ABI 3730XL capillary electrophoresis instrument (Thermo Fisher Scientific, Burlington, Canada) at The Centre for Applied Genomics, Hospital for Sick Children, Toronto, Canada.

Data Availability Statement

Sequencing data is available at the European Genotype-Phenotype Archive (EGA) repository under accession EGAS00001001782.

Results

Mitochondrial Genome Sequence Analysis

Figure 5:
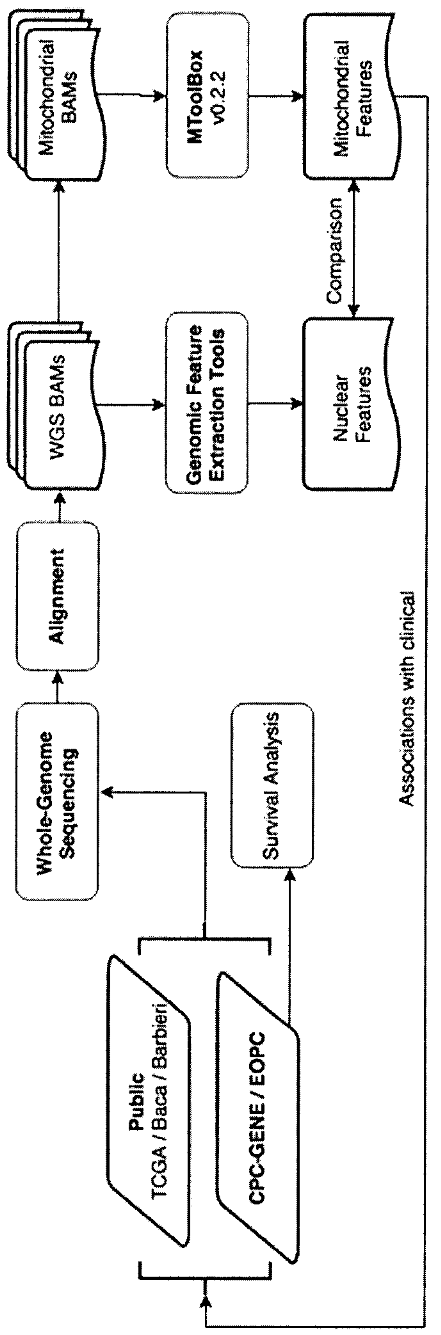
FIG. 5 shows the experimental design/experimental workflow for the project. Whole genome sequencing was performed on 333 CPC-GENE and EOPC samples. In addition, 51 publicly available samples with whole genome sequences were included in the dataset and realigned. Mitochondrial reads were extracted and the mitochondrial analysis tool MToolBox was run on the resulting BAM files. Heteroplasmic fractions (HF) were calculated for each nucleotide and only those positions that differed by ≥0.2 HF between the tumour and matched normal were included in the list of mtSNVs.
Figure 6:
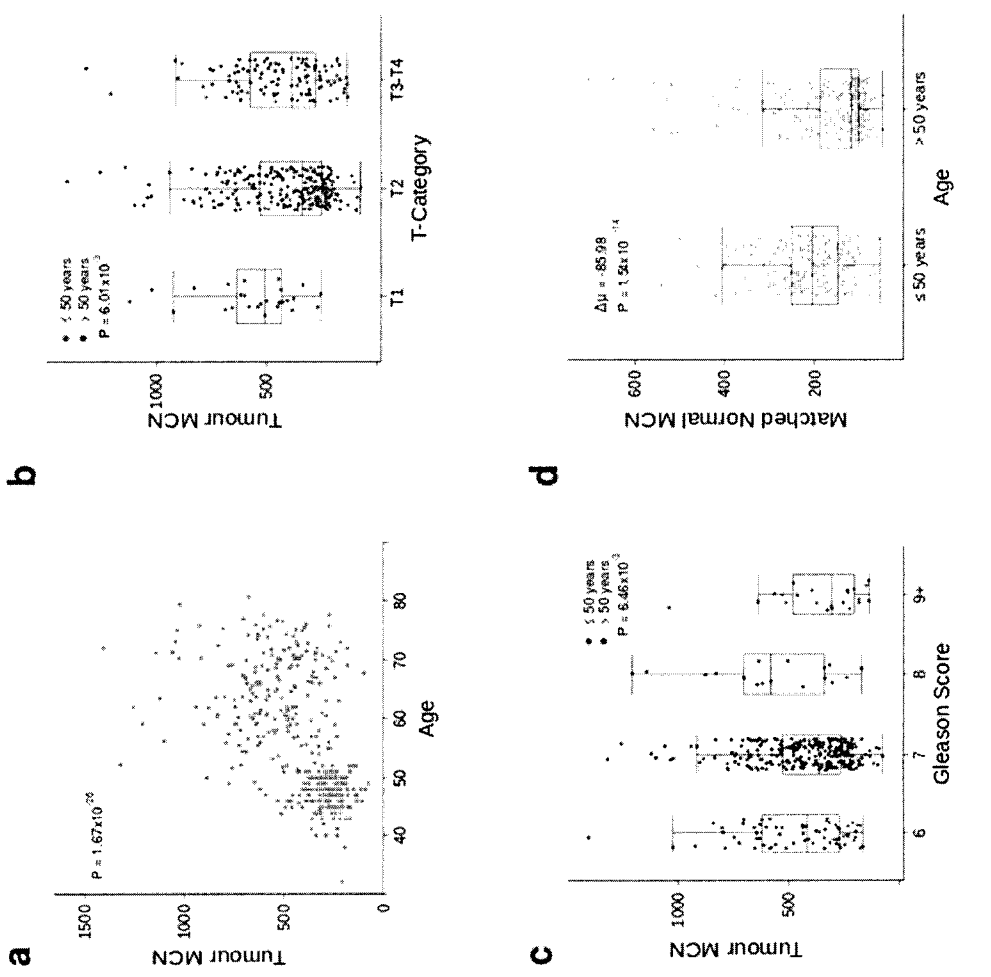
FIG. 6 shows MCN association with clinical variables. Tumour MCN categorized by age (a), T-category (b), and Gleason score (c). EOPC patients are indicated by red dots, LOPC by blue dots. (d) MCN of the matched normal samples show a significant difference between the two age groups.

We collected 384 tumours from patients with localized prostate cancer, comprising 164 EOPCs and 220 late-onset prostate cancers (LOPC; Table 4; FIG. 5). The LOPC patients represented the three NCCN risk groups: 19 low-risk, 151 intermediate-risk and 36 high-risk. The average sequencing depth of the mitochondrial genome was 13,577x, allowing extremely sensitive mutation detection. This cohort does not include any nuclear whole genome duplication events, as demonstrated by SNP microarray analysis[7]. We first evaluated the mitochondrial copy number (MCN) for each sample from the sequencing coverage of the mitochondrial and nuclear genomes. MCN ranged from 75 to 1405 (mean: 431) across the cohort, and was strongly associated with age (linear model, $p=1.67\times10^{-26}$), as well with clinical indices such as T-category (ANOVA, $p=6.01\times10^{-3}$) and Gleason Score (GS; ANOVA, $p=6.46\times10^{-3}$; FIG. 6).

Figure 1:
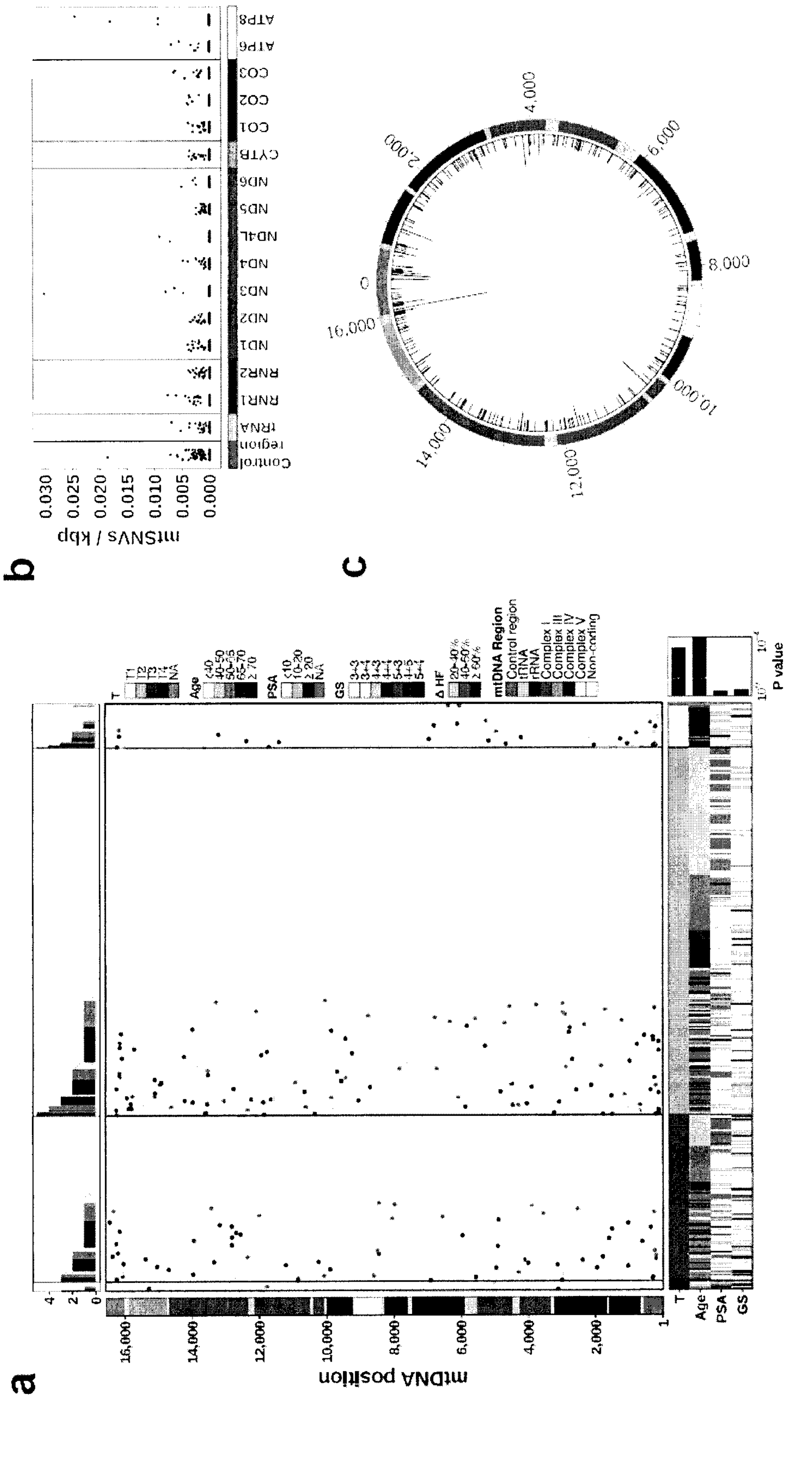
FIG. 1 shows panorama of mitochondrial mutations in prostate cancer. (a) The top panel displays the number of mtSNVs per patient sorted first by T-Category and then by the number of mtSNVs; histogram bars are coloured by the average difference in the heteroplasmy fraction (ΔHF) between tumour and normal samples, light-blue 20-40%, medium-blue 40-60%, dark-blue ≥60%. A heatmap showing the location of each mtSNV on the mitochondrial genome (middle), where the colour of each dot represents ΔHF. The mitochondrial genome is represented on the left. The bottom panel shows the clinical covariates for all 384 patients: Age, Gleason Score, PSA and T-Category. Bottom right: Associations between the covariates and number of mtSNVs. (b) Frequency and distribution of single nucleotide variants (SNVs) within the mitochondrial genome. Mutation frequency normalized by dividing the number of mutations per locus of each patient by (length of the locus (kbp)×MCN). (c) Distribution of mtSNVs across the mitochondrial genome. mtSNVs were fairly evenly distributed across the genome (black bars) and recurrent mutation positions are indicated by the histogram.
Figure 7:
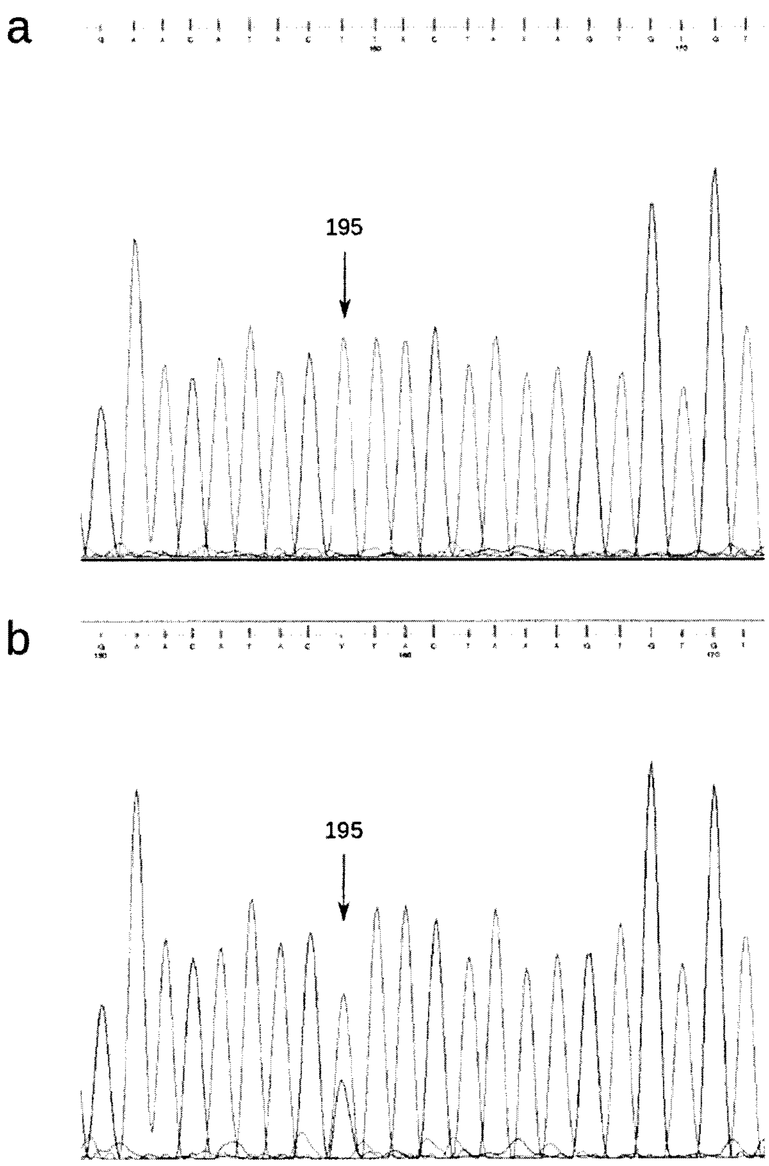
FIG. 7 shows PCR validation confirms predicted mtSNVs. A comparison of chromatograms after PCR amplification and Sanger sequencing from (a) normal and (b) tumour samples from patient CPCG0196 for the mtDNA region: 187-208 (SEQ ID NOs: 41 and 42 respectively). Arrow indicates position 195 which has significant heteroplasmy in tumour.
Figure 8:
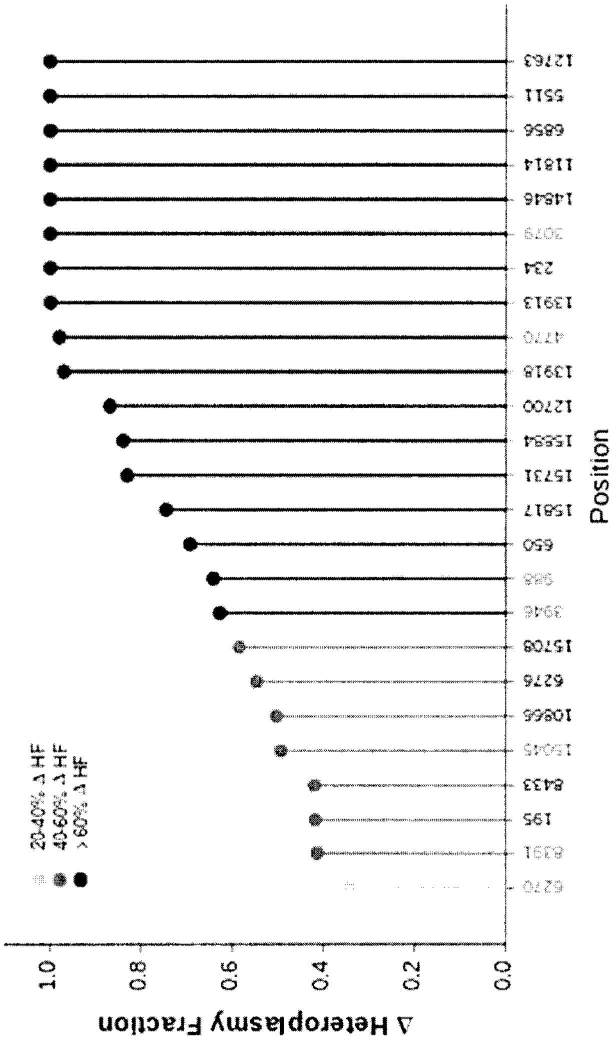
FIG. 8 shows mtSNVs chosen for PCR validation. The 25 mtSNVs validated by PCR amplification and Sanger sequencing had varying levels in the difference in heteroplasmy (ΔHF) between tumour and normal samples. Light blue 20-40%, medium blue 40-60% and dark blue 60% ΔHF. mtDNA position on x-axis. Labels in red indicate those mtSNVs that failed PCR validation.

We next conservatively identified mitochondrial SNVs (mtSNVs) as those positions that had an absolute difference in their heteroplasmy fraction (ΔHF) between purity-adjusted tumour and paired-normal samples of at least 0.20 (FIG. 5). Because the number of identified mtSNVs is dependent on the heteroplasmy fraction threshold, we chose to balance false positives and false negatives with an intermediate value. There were 293 mtSNVs across all patients, with 47.4% of tumours (182/384) harbouring at least one and 6.8% (26/384) harbouring three or more FIG. 1*a*; Table 5). Proportions of patients with 0, 1, 2, ≥3 mtSNVs are 202/384 (52.6%), 110/384 (28.6%), 46/384 (12.0%) and 26/384 (6.8%), respectively. The number of patients with no mtSNVs was greater than expected by chance, suggesting significant variability in mtSNV burden (permutation test; $p=3.4\times10^{-5}$). Tumours with a larger number of mitochondria were more likely to have an mtSNV (generalized linear model (GLM) family binomial; $p=8.38\times10^{-7}$). mtSNVs were associated with tumour size (T-category; $x^2$ test; $p=2.47\times10^{-4}$), but not other clinical prognostic indices like pre-treatment PSA and GS (FIG. 1*a*). PCR followed by Sanger sequencing validated 18/25 predicted mtSNVs (FIG. 7; FIG. 8; Table 1), suggesting precision of ~75%, comparable to somatic indel detection accuracy[27].

Frequently Mutated Mitochondrial Loci

Figure 9:
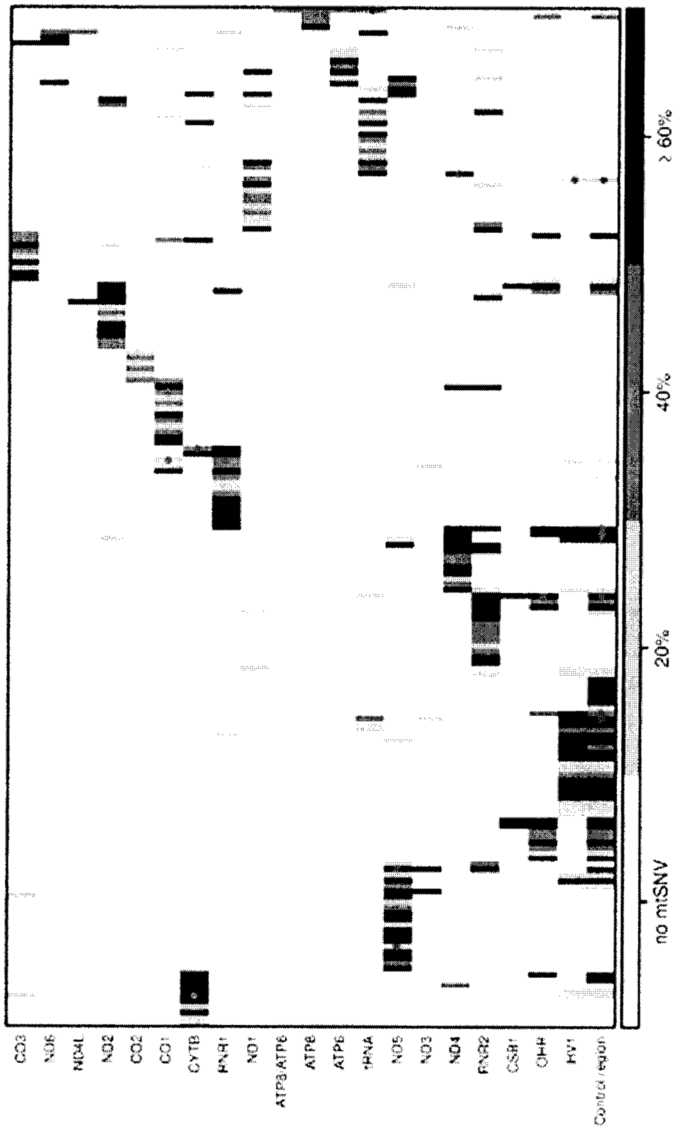
FIG. 9 shows frequency of mutations by patient and mitochondrial loci. Heatmap showing the distribution of mutations in the different mitochondrial regions (y-axis) by patients (x-axis). The difference in heteroplasmy fraction between tumour and normal sample (ΔHF) is indicated by colour, white: no mutation; light-blue: 20-40%; blue: 40-60% and dark blue ≥60%. Patients with more than one mtSNV in a particular mtDNA region are indicated by gray dots. Note: CSB1 and OHR are overlapping regions with the mtDNA Control region, mtSNVs in CSB1 are necessarily mtSNVs in OHR and both are mtSNVs within the Control region.

The noncoding control region of the mitochondria (mtDNA positions: 1-576 and 16024-16569), was the most frequently mutated region with 15.4% (59/384) of tumours harbouring mutations in that region (Table 5; FIG. 9). The control region comprises several elements, including the heavy- and light-strand promoters, as well as the origins of replication for the heavy strand (OHR), two hypervariable regions (HV1, HV2) and three conserved sequence blocks (CSB1, CSB2, CSB3). All functional locations were defined from mitmap.org[28]. Of these regions, HV1 was the most frequently mutated (mtDNA positions: 16024-16383). Overall, mutation rates were generally consistent across regions of the mitochondrial genome (FIG. 1*b*).

There were 157 mtSNVs in the 13 protein coding genes, 82% (129/157) of which were nonsynonymous, including 6 premature stop codons and two mutated stop codons. The most frequently mutated protein coding gene was ND5 (30/157). We identified 21 specific positions mutated in at least two patients (FIG. 1*c*): ten within the control region, eight in protein-coding regions and three in rRNA subunits. Of the coding mutations, seven were non-synonymous and one introduced a premature stop codon. In the control region, position 16093—a common site of tissue specific heteroplasmy[29,30]—was the most frequently mutated position (nine patients; FIG. 1*c*). Of protein-coding genes, ND1 was frequently mutated, with two patients having G3946A mutations (ΔHF: 0.63, 0.24), leading to a structure-disrupting E214K amino acid change, resulting in a reduction of complex assembly[31]. A second mutation, G4142A was found in two patients (ΔHF: 1.0, 0.21; R279Q) and a third mutation, G3842A, in three patients (ΔHF: 0.45, 0.21, 0.95; premature stop codon).

There were 22 mutations within mitochondrial tRNA genes, and eight of these were located within anticodon stems. In CO1 there were non-synonymous mutations at G5910A (A2T in one patient; ΔHF: 0.84) and T6664C (1254T in one patient; ΔHF: 0.46), two amino acids previously observed to be mutated in prostate cancer cells[20]. Two patients with mutations at position 6419 were detected within the CO1 gene (ΔHF: 0.2, 0.23), although these two showed heteroplasmy within the normal samples and homoplasmy in the tumour suggesting that these mtSNVs represent either tissue-specific heteroplasmy[32] or mutations that have gone to fixation in the tumour. Overall CO1 was mutated in 4.7% (18/384) of patients, markedly lower than the 11% rate previously reported[20].

Age Effect on the Distribution of mtSNVs in Prostate Cancer

Figure 2:
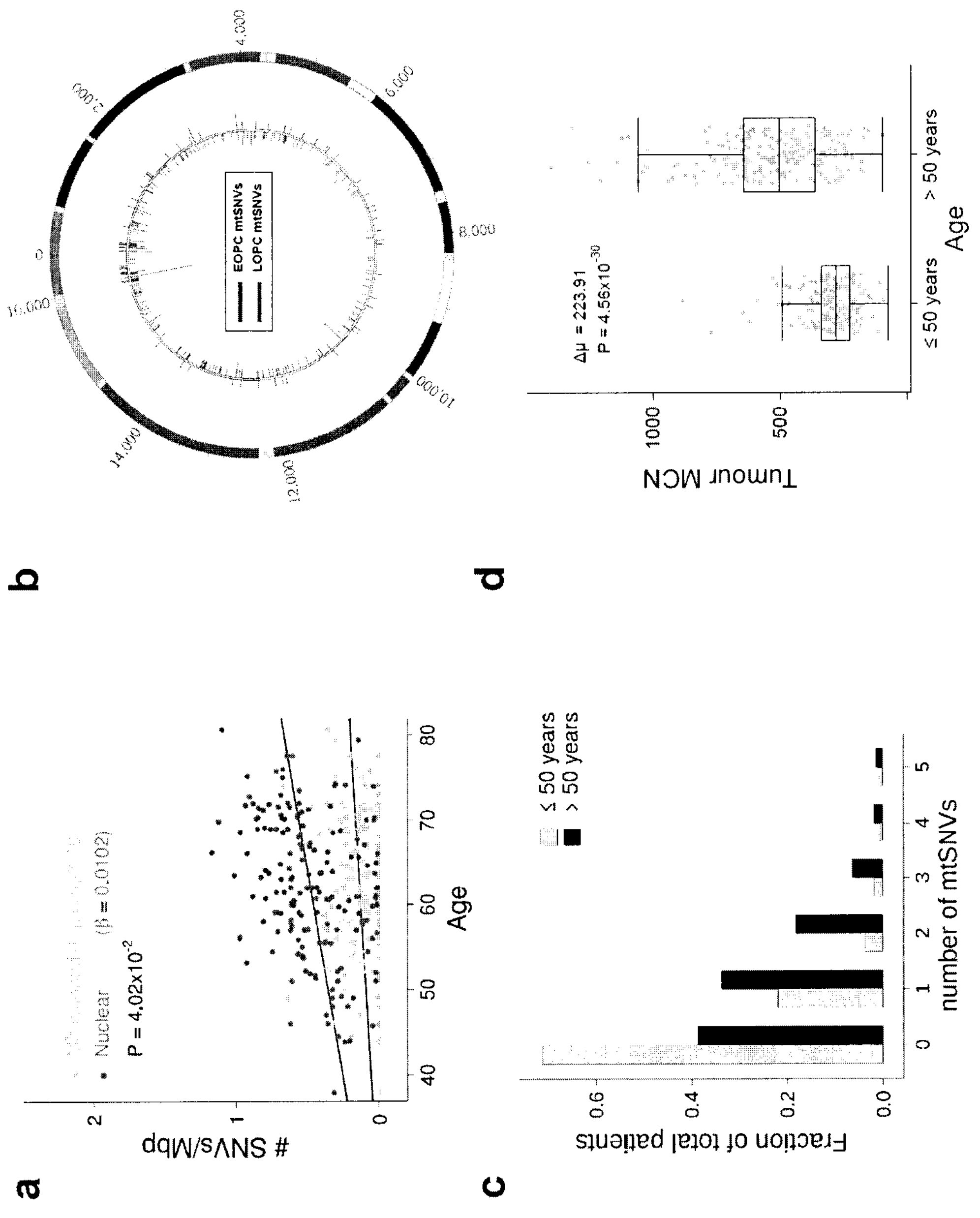
FIG. 2 shows the difference in mitochondrial mutational frequency and copy number with age. (a) Association of nuclear (green) and mitochondrial (yellow) mutation SNV/Mbp rates with patient age. Mitochondrial mutation rate normalized by MCN. (b) Distribution of mtSNVs in EOPC (red) and LOPC (blue) patients. The histogram indicates presence and frequency of a mtSNV. The most recurrent mtSNV was at position 16093. (c) The fraction of patients by number of mtSNVs, EOPC (gray bars), LOPC (black bars). (d) Tumour mitochondrial copy number (MCN) for both patient age groups. EOPC: n=164; LOPC: n=220.
Figure 10:
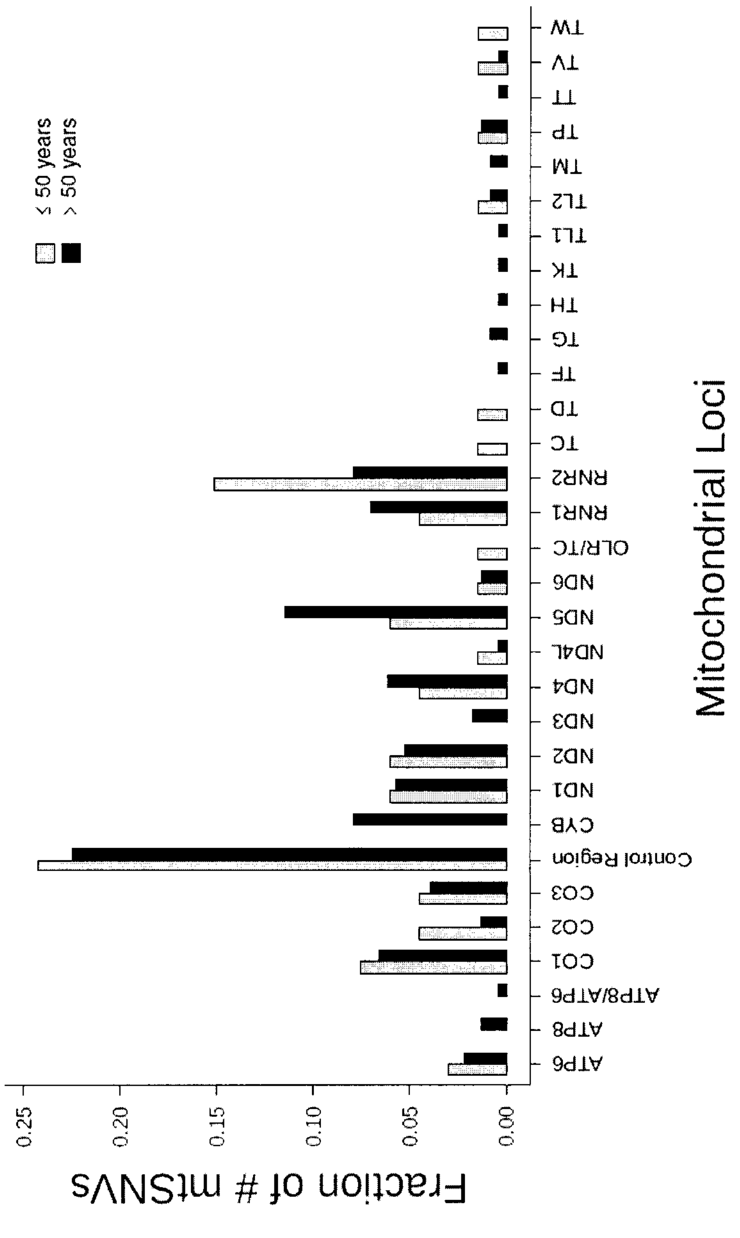
FIG. 10 shows distributions of mtSNV fractions by mitochondrial genome loci for EOPC and LOPC patients. The fraction of total mtSNVs per loci for EOPC and LOPC cohorts, those 50 years old (164 patients) and those >50 year old (220 patients) respectively.

As expected, the occurrence of mitochondrial mutations was strongly associated with patient age (GLM family binomial; $p=5.88\times10^{-9}$; FIG. 1*a*)[23-26]. The mitochondrial mutation rate was significantly lower than that of the nuclear genome mutation rate (FIG. 2*a*; p=0.040, F-test), which may in part be explained by differential mutation detection accuracy in the two genomes. To further understand the association of mtSNVs with age, we separated patients into those 50 and under years of age (EOPC; n=164) and those over 50 (LOPC; n=220). The median ages of the EOPC and LOPC cohorts were 47 and 63.5 years old, respectively. Patients with EOPC were significantly more likely to have no mitochondrial mutations, 117/164 (71.3%), than those with LOPC (85/220, 38.6%; $p=4.22\times10^{-10}$, proportion test; FIG. 2*b, c*). Despite this difference in mutational load, the two groups have similar distributions of mtSNVs across the mitochondrial genome, with the highest fraction of mtSNVs within the control region (FIG. 10). EOPC patients had about 224 fewer copies of the mitochondria than LOPC patients (Mann-Whitney test; $p=4.56\times10^{-30}$; FIG. 2*d*). This effect was inverted in the normal samples with EOPC patients having 86 more copies (Mann-Whitney; $p=1.54\times10^{-14}$; FIG. 6*d*), consistent with the decline in lymphocyte MCN with age[33].

Associations Between mtSNVs and Nuclear Genomic Mutations

Figure 3:
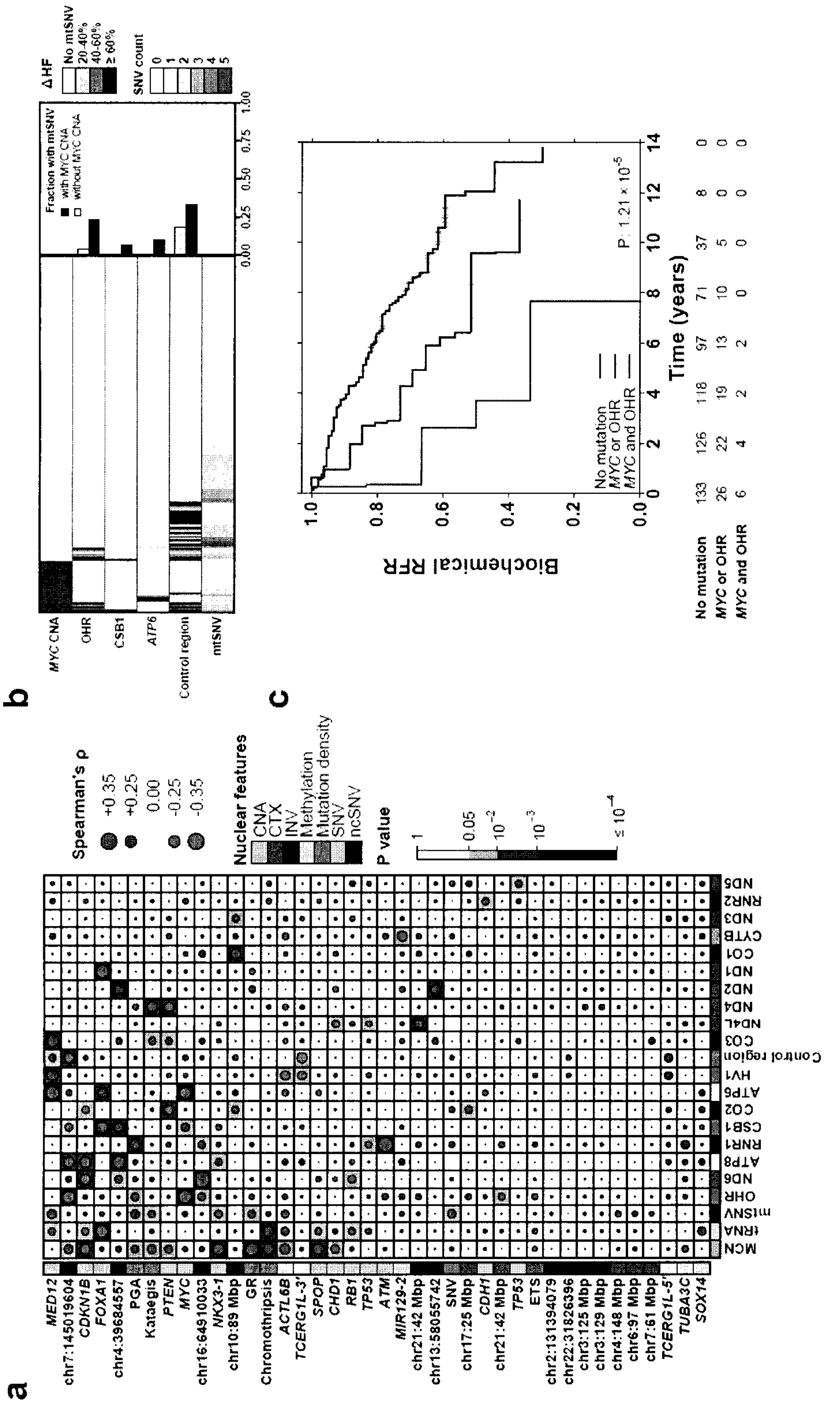
FIG. 3 shows associations between mitochondrial and nuclear genome mutations. (a) Correlations of mitochondrial features with nuclear genome features. The size and colour of the dot represents the Spearman correlation and the background shading represents the p-value. Nuclear features: SNVs, CTXs, INVs, kataegis data available for 172 patients; Chromothripsis: n=159; CNAs: MYC, NKX3-1 (n=203); CDH1, CDKN1B, CHD1, PTEN, RB1, TP53 (n=194); Methylation: n=104. Mitochondrial features: 216 patients. (b) Mutations in OHR are associated with CNAs in MYC. Heatmap showing those patients with CNA gains (red) in MYC and those with mtSNVs in OHR, CSB1, the control region and ATP6, mtSNV colour represents the ΔHF. Since CSB1 is a subregion within OHR, mutations in CSB1 are also considered as OHR mtSNVs, similarly, mtSNVs in OHR are also within the control region (n=203). The barplot on the right shows the fraction of patients with or without a MYC CNA that have a specific mtSNV. (c) Kaplan-Meier plot of 165 patients with OHR and MYC mutations. Patients were grouped according to whether they had neither MYC CNAs nor OHR SNVs (black line), a MYC CNA or an OHR mtSNV (blue) or had both (red line). The group that had a CNA gain in MYC and an mtSNV in the OHR region had significantly worse outcomes than those without the mutations. Biochemical RFR (Biochemical relapse-free rate).

Intriguingly, mutations in the large rRNA subunit (RNR2) were significantly correlated with mutations in the mitochondrial gene ND4 (Spearman's ρ=0.19; p=0.00015), suggesting to us an inter-play between different mutational types. To rigorously assess this phenomenon, we studied mutational associations between the nuclear and mitochondrial genomes. We exploited a set of 40 candidate nuclear somatic driver events recently identified through recurrence analyses, including five measures of mutation density, six methylation events, six non-coding SNVs, five coding SNVs, five measures of mutational density, ten genomic rearrangements and eight copy number aberrations (CNAs)[7]. The SNVs included recurrent coding SNVs in genes that are commonly mutated in prostate cancer, as well as the six most recurrent non-coding SNVs. To characterize per-region mtSNVs, we defined 22 mutational features representing the broad functional aspects of the mitochondria, 13 protein coding genes, 2 rRNAs, tRNAs (treated as one group), the control region and 3 subregions within the control region, along with mtSNV number and MCN. For each of the nuclear features, we evaluated their correlation to 22 mitochondrial mutational features in 194 LOPCs with nuclear mutational data (Table 6). We detected multiple nuclear-mitochondrial mutational associations (FIG. 3*a*). For example, SNVs in FOXA1 were significantly positively correlated with multiple mitochondrial features, as were SNVs in MED12. Nuclear-mitochondrial correlations were weakly dependent on the ΔHF threshold used to call mtSNVs (FIG. 11, Table 7).

One prominent nuclear-mitochondrial mutational interactions was co-occurrence of MYC copy number gain and mtSNVs within the OHR (FIG. 3*b*). Mutations within the OHR may dysregulate mtDNA replication, while MYC induces mitochondrial biogenesis by activating genes required for mitochondrial function[34] and influences metabolic plasticity in cancer stem cells[35]. Risk of biochemical failure (BCR) after primary definitive treatment by radiotherapy or surgery was significantly higher for patients whose tumours harboured both MYC CNAs and OHR mtSNVs relative to those with neither or one of these two mutations, suggesting a synergistic mitochondrial-nuclear effect on disease aggression (FIG. 3*c*). Several other similar instances of apparent synergistic mitochondrial-nuclear effects on disease aggression were observed (FIG. 12*a-e*), suggesting that this is a common phenomenon in prostate cancer. While we have used the region defined as OHR (mtDNA positions: 110-441) as the mitochondrial feature, this subregion of the Control Region significantly overlaps with a region defined as HV2 (mtDNA positions: 57-372). We confirmed that HV2 mtSNVs show the same synergistic effect with MYC CNAs as mtSNVs defined as OHR (FIG. 12*f*). Interestingly, MYC CNAs were more common in LOPCs (14.5%; 29/200) than in EOPCs (8.4%; 10/119) making it impossible to assess if the same nuclear-mitochondrial interactions occur in both disease states. Further evaluation of changes in nuclear-mitochondrial associations across disease progression will be revealing.

Clinical Impact of mtSNVs in Prostate Cancer

The recurrence of mitochondrial mutations in specific regulatory regions and their association with prognostic nuclear mutations strongly suggested their ability to drive disease aggression. We therefore systematically evaluated the association of individual mitochondrial somatic mutational features with disease aggression in 165 patients with clinical follow-up using Cox proportional hazards modeling.

Figure 4:
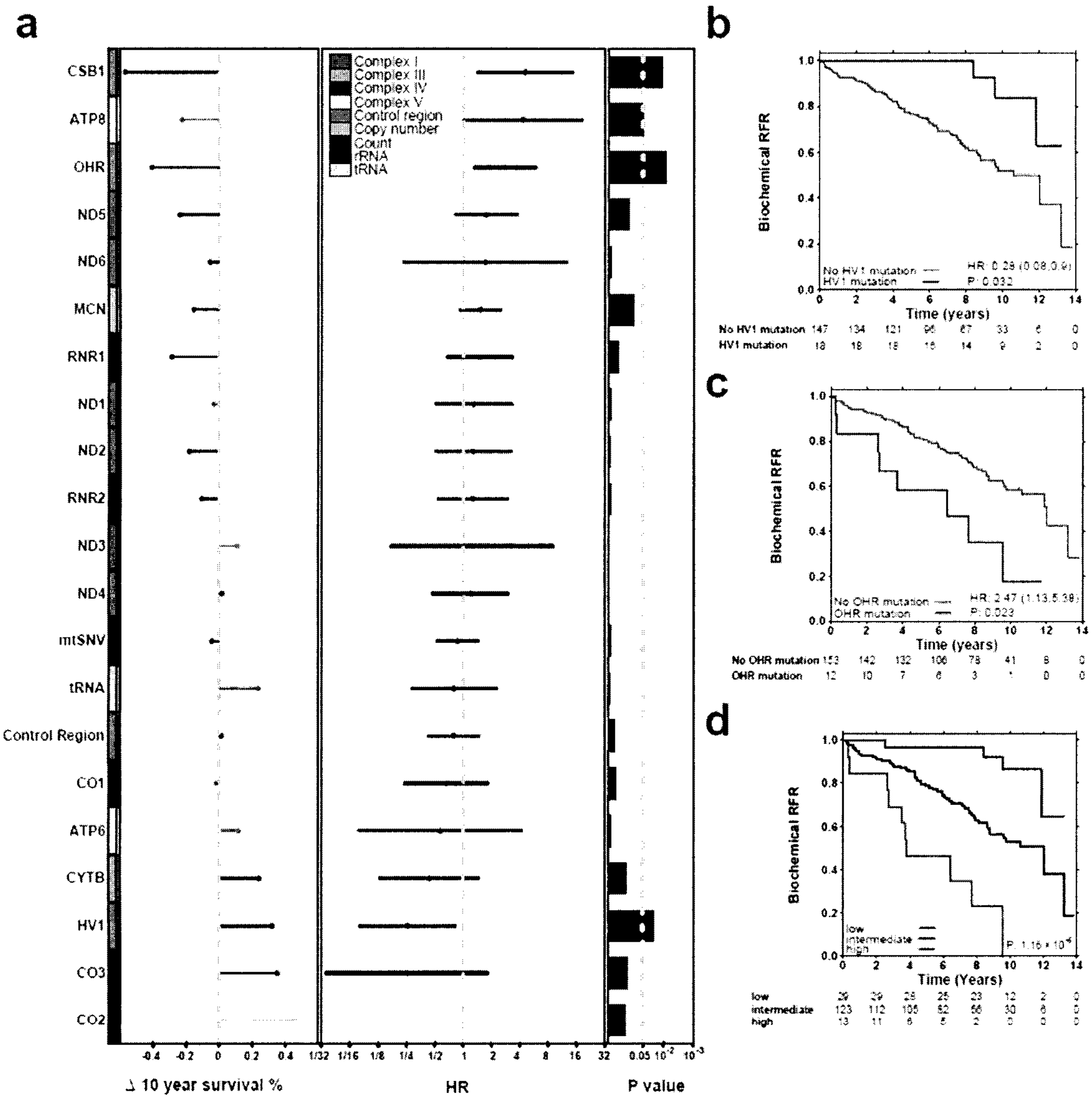
FIG. 4 shows clinical impact of mitochondrial mutations in prostate cancer. (a) The associations of biochemical recurrence (BCR) and 21 mitochondrial features: 19 mitochondrial genes or regions, MCN (median-dichotomized), and mtSNV count (0 vs. 1+) were calculated using Cox models in 165 LOPC patients. Hazard ratios (HRs) are shown in the middle panel and p-values from the log-rank test in the right panel. The change in the 10 year survival for patients with mutations in each mitochondrial region is indicated (left panel). The colour of the bars indicate the average ΔHF for mtSNVs in that region; light-blue 20-40%, medium-blue 40-60%, dark-blue ≥60%. (b) Kaplan-Meier plots of mtSNVs occurring within HV1 and (c) OHR. (d) Kaplan-Meier plot of results of leave-one-out cross-validation predictions (p-value from log-rank test).

Of our 22 mitochondrial mutational features (FIG. 3*a*), four were significantly associated with biochemical relapse rates (FIG. 4*a*; Table 2): mutations in CSB1, OHR, ATP8 and HV1. We should note that MT-ND4L was not included in this analysis as only one patient of the 165 had a mtSNV in this gene. To evaluate if these mutations were independent prognostic variables, we employed multivariable modeling to adjust for age, pre-treatment PSA, T-category and GS. After adjustment, mtSNVs in HV1 were associated with better patient outcome (FIG. 4*b*; Hazard Ratio, HR=0.28, 95% CI=0.08-0.9, p=0.032, Wald test), while mtSNVs in OHR were associated with significantly worse patient outcome (FIG. 4*c*; HR=2.47, 95% CI=1.13-5.38, p=0.023, Wald test).

These data suggested that mtSNVs might comprise a novel way to predict patient outcome. We therefore assessed the ability of a multi-mtSNV signature to identify patients at elevated risk for biochemical failure (who therefore might benefit from treatment intensification) and those at low risk (who might therefore be appropriate for surveillance protocols). Using leave-one-out cross-validation and univariate feature-selection, we created a three-class signature that separated patients into three distinct risk groups for biochemical failure (FIG. 13*a*). The signature identified both patients at elevated risk (FIG. 4*d*; HR=3.41, 95% CI=1.71-6.80, p=0.0005, Wald test) and patients at low-risk (HR=0.23, 95% CI=0.08-0.65, p=0.005, Wald test). These effects are independent of clinical features: when we considered only the clinically-homogeneous NCCN intermediate risk group, the same mtSNV signature again separated three groups with distinct risk profiles (FIG. 14). The cross-validation method identified seven genes (CO2, CO3, ATP8, HV1, OHR, CSB1, ND4L) as informative for classification. Patients with mtSNVs in (CO2, CO3, HV1) were classified as low-risk and patients with mtSNVs in (ATP8, OHR, ND4L, CSB1) were classified as high-risk. To show that this does not lead to over-fitting, we chose the three most frequently mutated regions of the seven (CO3, HV1, OHR) which also clearly separated patients into three groups (FIG. 13*b*).

Discussion

The mitochondrial mutational landscape of cancer has been relatively unexplored. Previous work has shown a large-scale mtDNA deletion has predictive value in the prostate biopsy outcomes[36], suggesting the feasibility of mtDNA-based molecular tests. We identify a large number of mtSNVs in localized prostate cancer. These mutations show complex interplay with nuclear mutational characteristics, and appear to work together to drive tumour aggressiveness.

Mitochondrial mutations also show associations with risk of biochemical relapse. Interestingly, mtSNVs within the control region can have conflicting outcomes, however when separated into the different noncoding subregions (HV1, OHR) we found that certain loci were associated with better outcomes and others with worse outcomes. The overlap of the OHR and HV2 within the control region and their association with MYC CNAs highlight the need for better understanding of the functions of the control region[37]. In future, treating the control region as distinct regulatory regions may provide further insight into the roles of these regions, as well as any contribution they may make towards tumour aggression. We note that the number of pairs of nuclear-mitochondrial mutational features tested may elevate false-positive rates, and it will be key to perform validation studies in larger cohorts to verify their effect-sizes and biological significance.

The differences observed in the mitochondrial mutational profiles of EOPC and LOPC patients show a need to better understand the association between mtSNVs and aging and how this may relate to the development of prostate cancer. While the mitochondrial copy number of matched-normal samples decreases with patient age, a previously observed trend[33], tumour MCN estimates were significantly higher in older patients which could account for the higher frequency of mtSNVs in these patients. However, since the majority of the samples of each age group come from different research centres, this striking difference in tumour MCN will require further investigation to exclude any confounding effects.

Further studies will be needed to assess when different mtSNVs occur during tumour evolution, their timing relative to common nuclear mutations and the effects of these mutations on mitochondrial function. This will more clearly identify the mitochondrial mutations that are important for mitochondrial-nuclear communication and how they may interact to drive tumour formation. Localized prostate cancer remains the most diagnosed non-skin cancer in men, and identification of aggressive disease remains an urgent clinical dilemma. Addition of mtSNVs to prognostic biomarkers may be an effective way of improving prediction of patient outcome, supporting triage of patients with low-risk disease to surveillance protocols and with high-risk disease to adjuvant therapy regimens.

All documents disclosed herein, including those in the following reference list, are incorporated by reference. Although preferred embodiments of the invention have been described herein, it will be understood by those skilled in the art that that the detailed description and the specific examples while indicating preferred embodiments of the invention are given by way of illustration only, since various changes and modifications within the spirit and scope of the invention will become apparent to those skilled in the art from this detailed description.

REFERENCES

1. Lozano, R. et al. Global and regional mortality from 235 causes of death for 20 age groups in 1990 and 2010: a systematic analysis for the Global Burden of Disease Study 2010. *Lancet* 380, 2095-2128 (2012).
2. Barbieri, C. E. et al. The mutational landscape of prostate cancer. Eur. Urol. 64, 567-576 (2013).
3. Barbieri, C. E. et al. Exome sequencing identifies recurrent SPOP, FOXA1 and MED12 mutations in prostate cancer. Nat. Genet. 44, 685-689 (2012).
4. Cancer Genome Atlas Research Network. The Molecular Taxonomy of Primary Prostate Cancer. *Cell* 163, 1011-1025 (2015).
5. Baca, S. C. et al. Punctuated evolution of prostate cancer genomes. *Cell* 153, 666-677 (2013).
6. Berger, M. F. et al. The genomic complexity of primary human prostate cancer. *Nature* 470, 214-220 (2011).
7. Fraser, M. et al. Genomic hallmarks of localized, non-indolent prostate cancer. *Nature* 541, 359-364 (2017).
8. Weischenfeldt, J. et al. Integrative genomic analyses reveal an androgen-driven somatic alteration landscape in early-onset prostate cancer. *Cancer Cell* 23, 159-170 (2013).
9. Boutros, P. C. et al. Spatial genomic heterogeneity within localized, multifocal prostate cancer. Nat. Genet. 47, 736-745 (2015).

10. Cooper, C. S. et al. Analysis of the genetic phylogeny of multifocal prostate cancer identifies multiple independent clonal expansions in neoplastic and morphologically normal prostate tissue. Nat. Genet. 47, 367-372 (2015).

11. Erho, N. et al. Discovery and validation of a prostate cancer genomic classifier that predicts early metastasis following radical prostatectomy. *PloS One* 8, e66855 (2013).

12. Wu, C.-L. et al. Development and validation of a 32-gene prognostic index for prostate cancer progression. *Proc. Natl. Acad. Sci. U.S.A* 110,6121-6126 (2013).

13. Lalonde, E. et al. Tumour genomic and microenvironmental heterogeneity for integrated prediction of 5-year biochemical recurrence of prostate cancer: a retrospective cohort study. *Lancet Oncol.* 15,1521-1532 (2014).

14. Wallace, D. C. Mitochondria and cancer. *Nat. Rev. Cancer* 12,685-698 (2012).

15. Kumimoto, H. et al. Frequent somatic mutations of mitochondrial DNA in esophageal squamous cell carcinoma. *Int. J. Cancer* 108,228-231 (2004).

16. Larman, T. C. et al. Spectrum of somatic mitochondrial mutations in five cancers. *Proc. Natl. Acad. Sci. U.S.A* 109,14087-14091 (2012).

17. McMahon, S. & LaFramboise, T. Mutational patterns in the breast cancer mitochondrial genome, with clinical correlates. *Carcinogenesis* 35,1046-1054 (2014).

18. Chen, J. Z., Gokden, N., Greene, G. F., Mukunyadzi, P. & Kadlubar, F. F. Extensive somatic mitochondrial mutations in primary prostate cancer using laser capture microdissection. *Cancer Res.* 62,6470-6474 (2002).

19. Gómez-Zaera, M. et al. Identification of somatic and germline mitochondrial DNA sequence variants in prostate cancer patients. *Mutat. Res.* 595,42-51 (2006).

20. Petros, J. A. et al. mtDNA mutations increase tumorigenicity in prostate cancer. *Proc. Natl. Acad. Sci. U.S.A* 102,719-724 (2005).

21. Kloss-Brandstätter, A. et al. Somatic mutations throughout the entire mitochondrial genome are associated with elevated PSA levels in prostate cancer patients. *Am. J. Hum. Genet.* 87,802-812 (2010).

22. McCrow, J. P. et al. Spectrum of mitochondrial genomic variation and associated clinical presentation of prostate cancer in South African men. *Prostate* 76,349-358 (2016).

23. Cortopassi, G. A. & Arnheim, N. Detection of a specific mitochondrial DNA deletion in tissues of older humans. *Nucleic Acids Res.* 18,6927-6933 (1990).

24. Corral-Debrinski, M., Shoffner, J. M., Lott, M. T. & Wallace, D. C. Association of mitochondrial DNA damage with aging and coronary atherosclerotic heart disease. *Mutat. Res.* 275, 169-180 (1992).

25. Zhang, C. et al. Differential occurrence of mutations in mitochondrial DNA of human skeletal muscle during aging. *Hum. Mutat.* 11, 360-371 (1998).

26. Michikawa, Y., Mazzucchelli, F., Bresolin, N., Scarlato, G. & Attardi, G. Aging-dependent large accumulation of point mutations in the human mtDNA control region for replication. *Science* 286, 774-779 (1999).

27. Alioto, T. S. et al. A comprehensive assessment of somatic mutation detection in cancer using whole-genome sequencing. *Nat. Commun.* 6, 10001 (2015).

28. Lott, M. T. et al. mtDNA Variation and Analysis Using Mitomap and Mitomaster. *Curr. Protoc. Bioinforma.* 44, 1.23.1-26 (2013).

29. Krjutškov, K. et al. Tissue-specific mitochondrial heteroplasmy at position 16,093 within the same individual. *Curr. Genet.* 60, 11-16 (2014).

30. Samuels, D. C. et al. Recurrent tissue-specific mtDNA mutations are common in humans. *PLoS Genet.* 9, e1003929 (2013).

31. Kervinen, M. et al. The MELAS mutations 3946 and 3949 perturb the critical structure in a conserved loop of the ND1 subunit of mitochondrial complex I. *Hum. Mol. Genet.* 15, 2543-2552 (2006).

32. He, Y. et al. *Heteroplasmic mitochondrial DNA mutations in normal and tumour cells. Nature* 464, 610-614 (2010).

33. Ding, J. et al. Assessing Mitochondrial DNA Variation and Copy Number in Lymphocytes of ~2,000 Sardinians Using Tailored Sequencing Analysis Tools. *PLoS Genet.* 11, e1005306 (2015).

34. Li, F. et al. Myc stimulates nuclearly encoded mitochondrial genes and mitochondrial biogenesis. *Mol. Cell. Biol.* 25, 6225-6234 (2005).

35. Sancho, P. et al. MYC/PGC-1a Balance Determines the Metabolic Phenotype and Plasticity of Pancreatic Cancer Stem Cells. *Cell Metab.* 22, 590-605 (2015).

36. Robinson, K. et al. Accurate prediction of repeat prostate biopsy outcomes by a mitochondrial DNA deletion assay. *Prostate Cancer Prostatic Dis.* 13, 126-131 (2010).

37. Nicholls, T. J. & Minczuk, M. In D-loop: 40 years of mitochondrial 7S DNA. *Exp. Gerontol.* 56, 175-181 (2014).

38. Larson, D. E. et al. SomaticSniper: identification of somatic point mutations in whole genome sequencing data. *Bioinformatics* 28, 311-317 (2012).

39. Li, H. et al. The Sequence Alignment/Map format and SAMtools. *Bioinformatics* 25, 2078-2079 (2009).

40. Wang, K., Li, M. & Hakonarson, H. ANNOVAR: functional annotation of genetic variants from high-throughput sequencing data. *Nucleic Acids Res.* 38, e164 (2010).

41. Rausch, T. et al. DELLY: structural variant discovery by integrated paired-end and split-read analysis. *Bioinformatics* 28, i333-i339 (2012).

42. Govind, S. K. et al. ShatterProof: operational detection and quantification of chromothripsis. *BMC Bioinformatics* 15, 78 (2014).

43. Masella, A. P. et al. BAMQL: a query language for extracting reads from BAM files. *BMC Bioinformatics* 17, 305 (2016).

44. Calabrese, C. et al. MToolBox: a highly automated pipeline for heteroplasmy annotation and prioritization analysis of human mitochondrial variants in high-throughput sequencing. *Bioinformatics* 30, 3115-3117 (2014).

45. Wu, T. D. & Watanabe, C. K. GMAP: a genomic mapping and alignment program for mRNA and EST sequences. *Bioinformatics* 21, 1859-1875 (2005).

46. Edgar, R. C. MUSCLE: multiple sequence alignment with high accuracy and high throughput. *Nucleic Acids Res.* 32, 1792-1797 (2004).

47. Behar, D. M. et al. A 'Copernican' reassessment of the human mitochondrial DNA tree from its root. *Am. J. Hum. Genet.* 90, 675-684 (2012).

48. Song, S. et al. qpure: A Tool to Estimate Tumor Cellularity from Genome-Wide Single-Nucleotide Polymorphism Profiles. *PLOS ONE* 7, e45835 (2012).

49. Guo, Y. et al. The use of Next Generation Sequencing Technology to Study the Effect of Radiation Therapy on Mitochondrial DNA Mutation. *Mutat. Res.* 744, 154-160 (2012).

50. Ju, Y. S. et al. Origins and functional consequences of somatic mitochondrial DNA mutations in human cancer. *eLife* 3, (2014).

51. Li, B. et al. Automated inference of molecular mechanisms of disease from amino acid substitutions. *Bioinformatics* 25, 2744-2750 (2009).

52. Adzhubei, I., Jordan, D. M. & Sunyaev, S. R. Predicting functional effect of human missense mutations using PolyPhen-2. *Curr. Protoc. Hum. Genet.* 7, Unit7.20 (2013).

53. Rubino, F. et al. HmtDB, a genomic resource for mitochondrion-based human variability studies. *Nucleic Acids Res.* 40, D1150-1159 (2012).

54. Pütz, J., Dupuis, B., Sissler, M. & Florentz, C. Mamit-tRNA, a database of mammalian mitochondrial tRNA primary and secondary structures. RNA 13, 1184-1190 (2007).

55. Quinlan, A. R. & Hall, I. M. BEDTools: a flexible suite of utilities for comparing genomic features. *Bioinformatics* 26, 841-842 (2010).

56. Krzywinski, M. I. et al. Circos: An information aesthetic for comparative genomics. *Genome Res.* (2009).

TABLE 1

Results of PCR validation of 25 mtSNVs

| Sample | Position | Amplicon | Validated? | HF - Tumour | HF - Normal |
|---|---|---|---|---|---|
| CPCG0196 | 195 | 1 | Y | 0.58T | 1.0T |
| CPCG0242 | 234 | 1 | Y | 1.0G | 1.0A |
| CPCG0189 | 650 | 2 | Y | 0.69C | 1.0T |
| CPCG0248 | 988 | 3 | N | 0.64A | 1.0G |
| CPCG0324 | 3079 | 5 | N | 1.0A | 1.0G |
| CPCG0233 | 3946 | 6 | N | 0.63A | 1.0G |
| CPCG0407 | 4770 | 7 | N | 0.98A | 1.0G |
| CPCG0242 | 5511 | 9 | Y | 1.0C | 1.0T |
| CPCG0189 | 6270 | 10 | N | 0.66G | 1.0G |
| CPCG0251 | 6276 | 10 | Y | 1.0A | 0.55G |
| CPCG0331 | 6856 | 11 | Y | 1.0C | 1.0T |
| CPCG0345 | 8391 | 12 | N | 0.59G | 1.0G |
| CPCG0196 | 8433 | 12 | Y | 0.58T | 1.0T |
| CPCG0340 | 10866 | 14 | Y | 1.0T | 0.5C |
| CPCG0410 | 11814 | 15 | Y | 1.0C | 1.0T |
| CPCG0352 | 12700 | 16 | Y | 0.87A | 1.0C |
| CPCG0236 | 12763 | 16 | Y | 1.0A | 1.0G |
| CPCG0217 | 13913 | 17 | Y | 1.0C | 1.0T |
| CPCG0410 | 13918 | 17 | Y | 1.0C | 0.97T |
| CPCG0340 | 14846 | 18 | Y | 1.0A | 1.0G |
| CPCG0412 | 15045 | 18 | N | 0.51G | 1.0G |
| CPCG0412 | 15708 | 19 | Y | 0.58A | 1.0G |
| CPCG0269 | 15731 | 19 | Y | 0.83A | 1.0G |
| CPCG0269 | 15817 | 19 | Y | 0.91G | 0.83A |
| CPCG0356 | 15884 | 19 | Y | 1.0A | 0.84G |

TABLE 2

Results from univariate Cox proportional modeling

| | Loci | HR | lower 95% CI | upper 95% CI | p-value (wald test) | p-value (logrank test) | 10 year survival difference | number of patients with mitoSNV |
|---|---|---|---|---|---|---|---|---|
| 1 | Control Region | 0.79 | 0.429 | 1.45 | 0.447 | 0.446 | 0.01 | 35 |
| 2 | RNR1 | 1.48 | 0.671 | 3.28 | 0.329 | 0.326 | −0.29 | 12 |
| 3 | RNR2 | 1.25 | 0.538 | 2.91 | 0.603 | 0.602 | −0.11 | 15 |
| 4 | tRNAs | 0.80 | 0.285 | 2.22 | 0.663 | 0.662 | 0.24 | 9 |
| 5 | ND1 | 1.28 | 0.508 | 3.24 | 0.597 | 0.596 | −0.03 | 10 |
| 6 | ND2 | 1.27 | 0.507 | 3.16 | 0.613 | 0.613 | −0.18 | 12 |
| 7 | ND3 | 1.24 | 0.171 | 9.02 | 0.832 | 0.831 | 0.11 | 3 |
| 8 | ND4 | 1.19 | 0.476 | 2.98 | 0.709 | 0.709 | 0.02 | 12 |
| 9 | ND5 | 1.74 | 0.825 | 3.67 | 0.145 | 0.140 | −0.24 | 16 |
| 10 | ND6 | 1.69 | 0.234 | 12.25 | 0.601 | 0.597 | −0.06 | 2 |
| 11 | CO1 | 0.66 | 0.239 | 1.82 | 0.422 | 0.419 | −0.02 | 12 |
| 12 | CO2 | 0.00 | 0.000 | Inf | 0.997 | 0.196 | 0.45 | 3 |
| 13 | CO3 | 0.25 | 0.035 | 1.80 | 0.168 | 0.136 | 0.35 | 9 |
| 14 | ATP6 | 0.57 | 0.079 | 4.11 | 0.577 | 0.572 | 0.11 | 4 |
| 15 | ATP8 | 4.25 | 1.014 | 17.84 | 0.048 | 0.031 | −0.23 | 3 |
| 16 | CYB | 0.44 | 0.132 | 1.47 | 0.181 | 0.172 | 0.24 | 11 |
| 17 | HV1 | 0.26 | 0.080 | 0.82 | 0.022 | 0.013 | 0.32 | 18 |
| 18 | CSB1 | 4.52 | 1.410 | 14.46 | 0.011 | 0.005 | −0.57 | 3 |
| 19 | OHR | 2.73 | 1.294 | 5.74 | 0.008 | 0.006 | −0.41 | 12 |
| 20 | MCN | 1.50 | 0.918 | 2.46 | 0.105 | 0.103 | −0.15 | 165 |
| 21 | mtSNV | 0.87 | 0.525 | 1.43 | 0.574 | 0.574 | −0.047 | 105 |

TABLE 3

| PCR primers | | | |
|---|---|---|---|
| Primer | | Targets Region: | Seq ID NO. |
| 1F | tctatcaccctattaaccacactcacg | 10-385 | 1 |
| 1R | aggctggtgttagggttctttg | | 2 |
| 2F | aaaaatttccaccaaaccccc | 287-718 | 3 |
| 2R | actggaacggggatgcttg | | 4 |
| 3F | acgggaaacagcagtgattaac | 809-1103 | 5 |
| 3R | agggctaagcatagtggggt | | 6 |
| 4F | cagcaaaccctgatgaaggc | 1273-1710 | 7 |
| 4R | tggtagtaaggtggagtgggt | | 8 |
| 5F | taccctagggataacagcgca | 2927-3171 | 9 |
| 5R | gggaaggcgctttgtgaagt | | 10 |
| 6F | tactcctgccatcatgaccct | 3828-4067 | 11 |
| 6R | gttcaggggagagtgcgtc | | 12 |
| 7F | ataccccgaaaatgttggttatac | 4434-4927 | 13 |
| 7R | ggcttacgtttagtgagggagag | | 14 |
| 8F | ctgacatccggcctgctt | 4840-5171 | 15 |
| 8R | caggtgcgagatagtagtagggtc | | 16 |
| 9F | catcgcccttaccacgctac | 5457-5742 | 17 |
| 9R | cggcgggagaagtagattga | | 18 |
| 10F | cataaacaacataagcttctgactcttacct | 6192-6586 | 19 |
| 10R | ggtctcctcctccggcg | | 20 |
| 11F | tatcctaccaggcttcggaat | 6642-6957 | 21 |
| 11R | acctacggtgaaaagaaagatga | | 22 |
| 12F | accacagtttcatgcccatc | 8194-8482 | 23 |
| 12R | ggtgagggaggtaggtggtag | | 24 |
| 13F | caaaaaggccttcgatacggg | 9433-9876 | 25 |
| 13R | tagttggcggatgaagcagat | | 26 |
| 14F | tgggcctagccctactagtctc | 10688-10939 | 27 |
| 14R | gggtcggaggaaaaggttgg | | 28 |
| 15F | tacgaacgcactcacagtcg | 11760-11988 | 29 |
| 15R | tgtagagggagtatagggctgt | | 30 |
| 16F | atctcgaactgacactgagcc | 12524-12894 | 31 |
| 16R | aaggcgaggatgaaaccgat | | 32 |
| 17F | ctaacaacatttcccccgcatc | 13743-14056 | 33 |
| 17R | ggtggagatttggtgctgtg | | 34 |
| 18F | cccaccccatccaacatctc | 14811-15111 | 35 |
| 18R | caagcaggaggataatgccg | | 36 |
| 19F | ggcgtccttgccctattact | 15615-16051 | 37 |
| 19R | acccaaatctgctttcccat | | 38 |
| 20F | atggggaagcagatttgggt | 16032-16298 | 39 |
| 20R | gggtgggtaggtttgttggt | | 40 |

TABLE 4

| Clinical and sequencing data per patient | | | | | | | | | | | |
|---|---|---|---|---|---|---|---|---|---|---|---|
| Patient | Age At Treat-ment | Gleason Score | T cate-gory | PSA (ng/mL) | mitoSNVs | Normal mito-chondrial mean coverage d | Normal mito-chondrial copy num | Tumour mito-chondrial mean coverage | Tumour mito-chondrial copy nu | mtSNVs/Mb | MT-DLOOP |
| Baca-P03-1426 | 69 | 4 + 3 | T2c | 13.9 | 1 | 9973.43 | 528.32 | 9639.89 | 430.02 | 0.14 | 0 |
| Baca-P05-1657 | 47 | 3 + 4 | T2b | 9.3 | 1 | 5301.26 | 541.65 | 13952.8 | 455.87 | 0.132 | 0 |
| Baca-PR-05-3595 | 64 | 3 + 4 | T2c | 7.2 | 2 | 7848.46 | 366.84 | 13517.9 | 378.68 | 0.319 | 1 |
| Baca-P05-3852 | 62 | 4 + 3 | T3a | 12.5 | 2 | 9535.11 | 517.82 | 14571 | 483.77 | 0.25 | 0 |
| Baca-PR-06-1749 | 60 | 4 + 3 | T2c | 6.7 | 1 | 3687.29 | 518.5 | 22823.8 | 543.38 | 0.111 | 0 |
| Baca-PR-06-3199 | 54 | 4 + 3 | T3a | 25 | 1 | 7265.49 | 374.58 | 13011.3 | 320.31 | 0.188 | 1 |
| Baca-PR-07-4610 | 69 | 3 + 4 | T3a | 5.6 | 1 | 5986.71 | 206.44 | 6899.3 | 181.05 | 0.333 | 1 |
| Baca-P07-4941 | 57 | 3 + 3 | T2c | 4.1 | 1 | 9583.63 | 505.45 | 11448.7 | 231.43 | 0.261 | 0 |
| Baca-P07-5037 | 68 | 4 + 3 | T3a | 11 | 0 | 12286.3 | 703.49 | 12188.3 | 349.15 | 0 | 0 |
| Baca-PR-08-4154 | 58 | 3 + 4 | T4 | 36 | 1 | 7155.13 | 381.71 | 13066.7 | 322.03 | 0.187 | 0 |
| Baca-P08-716 | 59 | 3 + 4 | T3a | 4.1 | 0 | 13055.6 | 648.03 | 13959 | 466.2 | 0 | 0 |
| Baca-P09-37 | 76 | 3 + 4 | T3b | 9 | 1 | 5974.65 | 316.06 | 9801.68 | 388.03 | 0.156 | 0 |
| Baca-PR-0410 | 60 | 3 + 3 | T2c | 4.5 | 0 | 808.985 | 48.58 | 17039.6 | 653.48 | 0 | 0 |
| Baca-PR-STID0000002872 | 62 | 3 + 4 | T3a | 6 | 1 | 2953.47 | 150.82 | 17440.3 | 452.67 | 0.133 | 0 |
| Berger-PR-0508 | 57 | 3 + 4 | T2c | 7.8 | 3 | 2664.78 | 143.98 | 11557.9 | 601.49 | 0.301 | 0 |
| Berger-PR-0581 | 69 | 4 + 5 | T3b | 9.2 | 0 | 794.518 | 59.07 | 7999.43 | 460.05 | 0 | 0 |
| Berger-PR-1701 | 62 | 3 + 4 | T3a | 2.1 | 0 | 2023.96 | 94.9 | 9496.81 | 447.2 | 0 | 0 |
| Berger-PR-1783 | 66 | 4 + 4 | T2c | 9.8 | 0 | 1856 | 104.29 | 11199 | 634.19 | 0 | 0 |
| Berger-PR-2832 | 66 | 3 + 4 | T2c | 6.6 | 0 | 1630.41 | 84.31 | 13476.4 | 682.17 | 0 | 0 |
| Berger-PR-3027 | 66 | 4 + 4 | T3b | 10.2 | 1 | 1624.68 | 97.23 | 5624.32 | 314.53 | 0.192 | 0 |
| Berger-PR-3043 | 69 | 3 + 4 | T2c | 7.2 | 3 | 1969.11 | 106.24 | 14276.4 | 776.69 | 0.233 | 0 |
| CPCG0001 | 69.4 | 3 + 4 | T2b | 7.7 | 1 | 2010.51 | 91.23 | 15343.8 | 536.19 | 0.113 | 1 |
| CPCG0003 | 71.8 | 3 + 4 | T2a | 10 | 1 | 1592 | 98.23 | 16387.8 | 563.25 | 0.107 | 0 |
| CPCG0004 | 76.5 | 4 + 4 | T2b | 14.1 | 0 | 2360.43 | 76.6 | 21736 | 504.1 | 0 | 0 |
| CPCG0005 | 72.5 | 3 + 3 | T2a | 5.4 | 1 | 1954.36 | 105.73 | 14676.7 | 428.18 | 0.141 | 0 |
| CPCG0006 | 73.5 | 4 + 3 | T2b | 8.4 | 0 | 11969.9 | 368.42 | 19269.2 | 631.66 | 0 | 0 |
| CPCG0007 | 65.9 | 4 + 4 | T1c | 8.4 | 0 | 2622.67 | 107.85 | 19394.9 | 618.46 | 0 | 0 |
| CPCG0008 | 74.3 | 3 + 4 | T2a | 4.7 | 0 | 8033.1 | 216.69 | 8220.56 | 487.07 | 0 | 0 |
| CPCG0015 | 70 | 4 + 4 | T2a | 5.6 | 0 | 2445.52 | 123.29 | 11664.1 | 338.77 | 0 | 0 |
| CPCG0019 | 71.4 | 4 + 5 | T2a | 7.3 | 1 | 1855.12 | 103.89 | 7508.09 | 235.48 | 0.256 | 0 |
| CPCG0020 | 70.8 | 3 + 4 | T1c | 16 | 1 | 2152.74 | 102.61 | 15986.9 | 451.44 | 0.134 | 0 |
| CPCG0022 | 70.3 | 3 + 3 | T1c | 12.6 | 0 | 6126.42 | 191.2 | 27763.9 | 427.62 | 0 | 0 |
| CPCG0027 | 64.6 | 3 + 3 | T1c | 5 | 2 | 2309.34 | 124.47 | 18997.1 | 540.68 | 0.223 | 0 |
| CPCG0030 | 73.1 | 4 + 4 | T1c | 8 | 2 | 1860.72 | 88.54 | 24737.1 | 435.4 | 0.277 | 0 |
| CPCG0036 | 75.9 | 3 + 4 | T2a | 5.3 | 0 | 1546.25 | 83.47 | 21118.1 | 641.24 | 0 | 0 |
| CPCG0040 | 71.5 | 3 + 4 | T1c | 9 | 3 | 2234.77 | 109.46 | 12738.2 | 385.35 | 0.47 | 1 |
| CPCG0042 | 75.5 | 4 + 3 | T2b | 5.6 | 0 | 2661.75 | 127.13 | 12385.6 | 394.09 | 0 | 0 |
| CPCG0046 | 79.4 | 4 + 3 | T1c | 5.1 | 5 | 1944.65 | 106.17 | 23558.9 | 1020.68 | 0.296 | 1 |
| CPCG0047 | 71.9 | 4 + 3 | T2c | 13.2 | 0 | 1773.42 | 87.23 | 6868.3 | 181.08 | 0 | 0 |
| CPCG0048 | 74.3 | 3 + 3 | T2b | 5.1 | 0 | 1965.81 | 100.43 | 18063.2 | 630.52 | 0 | 0 |

TABLE 4-continued

Clinical and sequencing data per patient

| Patient | Age At Treat-ment | Gleason Score | T cate-gory | PSA (ng/mL) | mitoSNVs | Normal mito-chondrial mean coverage d | Normal mito-chondrial copy num | Tumour mito-chondrial mean coverage | Tumour mito-chondrial copy nu | mtSNVs/Mb | MT-DLOOP |
|---|---|---|---|---|---|---|---|---|---|---|---|
| CPCG0050 | 75.8 | 3 + 3 | T1c | 7.7 | 1 | 2326.01 | 107.27 | 35390.2 | 922.94 | 0.065 | 0 |
| CPCG0057 | 70.4 | 3 + 3 | T2a | 10 | 1 | 2814.45 | 142.84 | 7928.7 | 270.69 | 0.223 | 0 |
| CPCG0063 | 68.6 | 4 + 3 | T2a | 3.8 | 2 | 2644.85 | 126.2 | 16387.6 | 538.02 | 0.224 | 0 |
| CPCG0067 | 62 | 3 + 4 | T2b | 10 | 4 | 2540.37 | 113.15 | 26440.2 | 1255.88 | 0.192 | 0 |
| CPCG0070 | 67.3 | 3 + 3 | T2a | 5.9 | 2 | 3288.57 | 130.51 | 23488.5 | 703.48 | 0.172 | 1 |
| CPCG0071 | 74.9 | 4 + 3 | T1c | 14.7 | 2 | 2038.28 | 100.32 | 13083.5 | 407.14 | 0.297 | 0 |
| CPCG0072 | 75.7 | 4 + 5 | T2a | 9.3 | 1 | 2087.05 | 114.92 | 18531.3 | 566.05 | 0.107 | 0 |
| CPCG0073 | 71.6 | 4 + 3 | T1c | 10.3 | 2 | 2207.67 | 104.47 | 17129.6 | 500.64 | 0.241 | 1 |
| CPCG0075 | 70.8 | 4 + 4 | T2a | 4.1 | 0 | 2219.17 | 110.59 | 11392.5 | 303.91 | 0 | 0 |
| CPCG0076 | 76.6 | 3 + 3 | T2a | 12.7 | 1 | 1742.35 | 84.34 | 19549.5 | 531.43 | 0.114 | 0 |
| CPCG0078 | 61 | 4 + 3 | T2b | 3.3 | 2 | 1105.04 | 49.32 | 14594.2 | 581.48 | 0.208 | 1 |
| CPCG0081 | 75 | 4 + 3 | T2a | 17.8 | 2 | 2160.59 | 98.52 | 37008.6 | 1033.84 | 0.117 | 1 |
| CPCG0082 | 70.3 | 4 + 3 | T2a | 7.8 | 1 | 1857.84 | 88.02 | 17730.5 | 440.85 | 0.137 | 0 |
| CPCG0083 | 61.5 | 3 + 4 | T2b | 12.7 | 1 | 2672.43 | 109.97 | 13413.7 | 477.54 | 0.126 | 0 |
| CPCG0084 | 70.8 | 3 + 3 | T2b | 7 | 1 | 2455.36 | 211.71 | 19898.8 | 557.13 | 0.108 | 1 |
| CPCG0087 | 72.8 | 3 + 4 | T1c | 9.4 | 0 | 2124.21 | 90.43 | 10965.7 | 378.22 | 0 | 0 |
| CPCG0089 | 73.9 | 4 + 4 | T1c | 4.8 | 1 | 6316.55 | 109.74 | 9884.38 | 579.96 | 0.104 | 0 |
| CPCG0090 | 77.6 | 3 + 3 | T1c | 11.2 | 2 | 3146.06 | 107.25 | 26497.8 | 601.53 | 0.201 | 0 |
| CPCG0094 | 77.6 | 4 + 3 | T2b | 16.41 | 0 | 1772.67 | 85.84 | 9333.85 | 270.47 | 0 | 0 |
| CPCG0095 | 68.5 | 4 + 3 | T2a | 4 | 1 | 3226.28 | 116.97 | 9627.27 | 284.66 | 0.212 | 0 |
| CPCG0096 | 71.2 | 3 + 3 | T1c | 6.1 | 1 | 2354.53 | 112.19 | 10526 | 336.77 | 0.179 | 0 |
| CPCG0097 | 75.1 | 3 + 3 | T1c | 13.7 | 2 | 3186.24 | 114.53 | 15025 | 437.56 | 0.276 | 1 |
| CPCG0098 | 80.7 | 4 + 3 | T1c | 7.5 | 4 | 3141.66 | 92.39 | 19866.5 | 675.49 | 0.357 | 1 |
| CPCG0099 | 66.2 | 3 + 4 | T2c | 6.96 | 0 | 3088.28 | 123.68 | 20339.1 | 619.84 | 0 | 0 |
| CPCG0100 | 55.3 | 4 + 5 | T2c | 5.56 | 2 | 1592.37 | 65.62 | 11999.8 | 325.79 | 0.371 | 1 |
| CPCG0102 | 58.1 | 4 + 3 | T3b | 8.65 | 1 | 3756.32 | 117.24 | 19274.1 | 553.3 | 0.109 | 0 |
| CPCG0103 | 65 | 3 + 4 | T3b | 5.2 | 2 | 3051.27 | 95.84 | 27103.1 | 669.18 | 0.18 | 0 |
| CPCG0114 | 67.7 | 4 + 3 | T2b | 4.4 | 4 | 13818.6 | 425.97 | 3370.65 | 95.95 | 2.517 | 1 |
| CPCG0117 | 71.3 | 3 + 4 | T2a | 10.1 | 1 | 2116.03 | 93.89 | 17318.3 | 1057.43 | 0.057 | 0 |
| CPCG0120 | 73.1 | 4 + 5 | T2a | 14.79 | 1 | 4556 | 79.41 | 17038.8 | 1040.35 | 0.058 | 0 |
| CPCG0121 | 63.5 | 3 + 4 | T1c | 7.2 | 0 | 1819.09 | 81.46 | 16843.6 | 507.7 | 0 | 0 |
| CPCG0122 | 65.6 | 3 + 3 | T1c | 6.4 | 0 | 1587.25 | 73.44 | 26709.7 | 655.79 | 0 | 0 |
| CPCG0123 | 70.7 | 3 + 4 | T2a | 8.8 | 1 | 2153.44 | 93.95 | 14680.6 | 408.31 | 0.148 | 0 |
| CPCG0124 | 72 | 4 + 3 | T2a | 72 | 2 | 1693.03 | 103.91 | 16616.7 | 471.18 | 0.256 | 0 |
| CPCG0126 | 70 | 3 + 3 | T2a | 6.1 | 0 | 2146.19 | 112.82 | 16857.3 | 511.86 | 0 | 0 |
| CPCG0127 | 54.4 | 3 + 4 | T2a | 29.9 | 1 | 1410.98 | 82.03 | 22778.4 | 687.22 | 0.088 | 0 |
| CPCG0128 | 70.2 | 3 + 4 | T1c | 30.3 | 2 | 1895.38 | 94.61 | 19629.6 | 527.03 | 0.229 | 1 |
| CPCG0154 | 55.4 | 3 + 3 | T2a | 13.8 | 0 | 1661.73 | 94.48 | 12384.6 | 411.8 | 0 | 0 |
| CPCG0158 | 70.3 | 3 + 4 | T1c | 10 | 1 | 1543.38 | 107.49 | 9261.13 | 444.37 | 0.136 | 1 |
| CPCG0166 | 74 | 3 + 4 | T2a | 6.8 | 5 | 2756.4 | 101.74 | 15269.5 | 449.28 | 0.672 | 1 |
| CPCG0182 | 57 | 4 + 3 | T2c | 7.64 | 0 | 2366.95 | 101.87 | 14861.1 | 429.06 | 0 | 0 |
| CPCG0183 | 64.3 | 4 + 3 | T3a | 5.67 | 2 | 2002.32 | 89.43 | 24135.9 | 654.71 | 0.184 | 1 |
| CPCG0184 | 51.8 | 4 + 3 | T3a | 5.53 | 0 | 2836.72 | 106.41 | 20155.2 | 504.67 | 0 | 0 |
| CPCG0185 | 60 | 3 + 4 | T3a | 4.49 | 1 | 1921.47 | 79.18 | 15534.6 | 452.91 | 0.133 | 0 |
| CPCG0187 | 72.4 | 4 + 4 | T1c | 13 | 1 | 2078.85 | 119.32 | 22991.9 | 828.01 | 0.073 | 1 |
| CPCG0188 | 59 | 4 + 5 | T2c | 7.23 | 0 | 2202.35 | 89.99 | 25035.8 | 638.01 | 0 | 0 |
| CPCG0189 | 57.4 | 3 + 4 | T2b | 6.52 | 5 | 2523.89 | 102.02 | 26654.4 | 775.6 | 0.389 | 1 |
| CPCG0190 | 74.1 | 3 + 4 | T3a | 4.3 | 1 | 3002.16 | 117.98 | 23557.5 | 623.93 | 0.097 | 0 |
| CPCG0191 | 60.7 | 4 + 3 | T3a | 11.1 | 0 | 1834.4 | 94.75 | 21490.7 | 646.17 | 0 | 0 |
| CPCG0194 | 69.8 | 3 + 4 | T1c | 8.7 | 0 | 1901.55 | 196.32 | 7805.15 | 255.37 | 0 | 0 |
| CPCG0196 | 52.5 | 4 + 3 | T3b | 4.88 | 2 | 3327.15 | 151.6 | 12536 | 343.95 | 0.351 | 1 |
| CPCG0198 | 60.7 | 3 + 4 | T2a | 5.2 | 1 | 3099.65 | 146.67 | 29684.5 | 829.49 | 0.073 | 1 |
| CPCG0199 | 74.2 | 4 + 3 | T2a | 6.3 | 0 | 2826.11 | 107.59 | 21647.3 | 676.99 | 0 | 0 |
| CPCG0201 | 63.4 | 4 + 3 | T1c | 1.6 | 2 | 3002.98 | 97.47 | 39114.2 | 1120.3 | 0.108 | 0 |
| CPCG0204 | 75.7 | 3 + 4 | T1b | 9.7 | 3 | 3464.6 | 105.94 | 10867.3 | 270.65 | 0.669 | 1 |
| CPCG0205 | 65 | 3 + 4 | T2a | 20.4 | 1 | 1544.7 | 101.98 | 17086.3 | 532.21 | 0.113 | 1 |
| CPCG0206 | 66.9 | 4 + 3 | T1c | 8 | 1 | 2110.22 | 103.11 | 19211.1 | 687.44 | 0.088 | 1 |
| CPCG0208 | 60.4 | 3 + 4 | T2c | 5.7 | 0 | 2030.64 | 102.22 | 27846.3 | 833.35 | 0 | 0 |
| CPCG0210 | 51.4 | 4 + 3 | T2c | 3.51 | 0 | 2301.46 | 125.14 | 13751.7 | 428.21 | 0 | 0 |
| CPCG0211 | 75.2 | 3 + 4 | T2a | 4.5 | 3 | 1966.24 | 89.91 | 20019.9 | 601.45 | 0.301 | 0 |
| CPCG0212 | 71.2 | 3 + 4 | T1c | 7 | 1 | 1851.09 | 99.03 | 9954.72 | 600.39 | 0.101 | 0 |
| CPCG0213 | 67.2 | 3 + 4 | T2a | 9.3 | 3 | 2302.15 | 113.57 | 11806.2 | 356.88 | 0.507 | 0 |
| CPCG0217 | 61.5 | 3 + 3 | T3b | 6.5 | 3 | 2862.32 | 126.84 | 22997.4 | 613.9 | 0.295 | 0 |
| CPCG0232 | 71.6 | 3 + 4 | T3a | 8.15 | 1 | 1888.72 | 96.56 | 16843.7 | 497.16 | 0.121 | 0 |
| CPCG0233 | 70.3 | 4 + 3 | T3a | 4.63 | 2 | 2754.55 | 124.79 | 31553 | 914.29 | 0.132 | 0 |
| CPCG0234 | 70.1 | 3 + 4 | T1c | 5.7 | 2 | 2178.87 | 107.66 | 12593.3 | 446.63 | 0.27 | 0 |
| CPCG0235 | 59.2 | 4 + 4 | T3a | 8.04 | 0 | 3220.53 | 123.34 | 37607.4 | 1206.8 | 0 | 0 |
| CPCG0236 | 59.1 | 4 + 3 | T3a | 10.92 | 1 | 2509.78 | 114.9 | 30744.4 | 900.49 | 0.067 | 0 |
| CPCG0237 | 60.4 | 3 + 3 | T2a | 10.7 | 1 | 1916.74 | 100.66 | 21603.4 | 479.47 | 0.126 | 0 |
| CPCG0238 | 55.6 | 3 + 4 | T3a | 7.92 | 0 | 2171.64 | 86.06 | 14799.9 | 386.3 | 0 | 0 |
| CPCG0241 | 66.6 | 3 + 4 | T3a | 5.64 | 0 | 1392.4 | 81.71 | 19837 | 522.61 | 0 | 0 |

TABLE 4-continued

Clinical and sequencing data per patient

| Patient | Age At Treatment | Gleason Score | T category | PSA (ng/mL) | mitoSNVs | Normal mitochondrial mean coverage d | Normal mitochondrial copy num | Tumour mitochondrial mean coverage | Tumour mitochondrial copy nu | mtSNVs/Mb | MT-DLOOP |
|---|---|---|---|---|---|---|---|---|---|---|---|
| CPCG0242 | 56 | 4 + 3 | T3a | 4 | 3 | 2229.79 | 104.54 | 21398 | 618.51 | 0.293 | 1 |
| CPCG0243 | 63.7 | 3 + 3 | T2b | 13.6 | 0 | 2108.3 | 101.41 | 27303.7 | 705.69 | 0 | 0 |
| CPCG0246 | 60.6 | 3 + 3 | T2c | 5.64 | 0 | 3078.8 | 106.59 | 21908.6 | 586.08 | 0 | 0 |
| CPCG0248 | 54.2 | 3 + 4 | T3a | 5.1 | 1 | 2177.55 | 87.09 | 13487.4 | 357.01 | 0.169 | 0 |
| CPCG0249 | 66.1 | 3 + 4 | T3b | 7.1 | 2 | 1341.68 | 70.87 | 23315.6 | 637.4 | 0.189 | 0 |
| CPCG0250 | 62 | 3 + 3 | T2c | 4.23 | 1 | 2919.61 | 104.25 | 14478.6 | 435.33 | 0.139 | 1 |
| CPCG0251 | 52.1 | 3 + 4 | T2c | 13.41 | 1 | 2438.75 | 116.04 | 26111.1 | 713.14 | 0.085 | 0 |
| CPCG0255 | 72 | 3 + 3 | T2c | 6.9 | 0 | 1692.11 | 105.24 | 47617 | 1404.64 | 0 | 0 |
| CPCG0256 | 63.9 | 3 + 4 | T3a | 7.32 | 3 | 2237.41 | 94.99 | 18998.2 | 574.56 | 0.315 | 1 |
| CPCG0257 | 75.3 | 3 + 3 | T2a | 8 | 0 | 1875.56 | 96.61 | 30453.9 | 801.83 | 0 | 0 |
| CPCG0258 | 49.2 | 3 + 3 | T2c | 5.13 | 0 | 2816.13 | 137.62 | 27975 | 645.84 | 0 | 0 |
| CPCG0259 | 55.9 | 3 + 3 | T3a | 11.65 | 1 | 2343.37 | 112.81 | 25185.2 | 787.31 | 0.077 | 1 |
| CPCG0260 | 65.3 | 4 + 3 | T2b | 6.59 | 0 | 2215.3 | 114.94 | 16393.6 | 439.11 | 0 | 0 |
| CPCG0262 | 63 | 3 + 4 | T2c | 5.7 | 2 | 1748.24 | 96.8 | 22867 | 665.8 | 0.181 | 0 |
| CPCG0263 | 66.4 | 3 + 3 | T2a | 13.9 | 1 | 2153.77 | 90.92 | 14025.9 | 376.94 | 0.16 | 1 |
| CPCG0265 | 63.2 | 3 + 3 | T3a | 9.34 | 1 | 2865.36 | 125.95 | 24767.3 | 746.34 | 0.081 | 0 |
| CPCG0266 | 66.1 | 3 + 4 | T2c | 1.74 | 1 | 1989.51 | 109.53 | 12392.6 | 357.7 | 0.169 | 0 |
| CPCG0267 | 44.5 | 3 + 4 | T2c | 17.1 | 1 | 2632.29 | 102.84 | 12520.1 | 321.02 | 0.188 | 0 |
| CPCG0268 | 59.3 | 3 + 3 | T3a | 12.35 | 1 | 1783.77 | 89.65 | 20844.9 | 632.34 | 0.095 | 0 |
| CPCG0269 | 68.3 | 3 + 3 | T2c | 13.21 | 4 | 1862.44 | 75.85 | 20396.5 | 578.59 | 0.417 | 1 |
| CPCG0324 | 64.7 | 3 + 4 | T3a | 12.1 | 2 | 1627.2 | 96.53 | 15641.5 | 461.67 | 0.262 | 0 |
| CPCG0331 | 69.9 | 3 + 4 | T3a | 11.08 | 3 | 2214.28 | 118.64 | 22194.1 | 685.07 | 0.264 | 0 |
| CPCG0334 | 53.7 | 3 + 4 | T3a | 7.41 | 0 | 2205.65 | 120.17 | 17649.3 | 526.22 | 0 | 0 |
| CPCG0336 | 60.9 | 3 + 3 | T3a | 9.08 | 1 | 2531.23 | 122.84 | 22760.1 | 619.98 | 0.097 | 0 |
| CPCG0339 | 57.7 | 3 + 4 | T3a | 14.29 | 2 | 2439.27 | 109.25 | 21027.2 | 575.8 | 0.21 | 0 |
| CPCG0340 | 62 | 3 + 4 | T2c | 4.41 | 2 | 3925.02 | 145.3 | 28167.6 | 940.05 | 0.128 | 0 |
| CPCG0341 | 56.8 | 4 + 3 | T2c | 11.3 | 0 | 1780 | 96.57 | 13179.1 | 450.01 | 0 | 0 |
| CPCG0342 | 52.2 | 4 + 3 | T3a | 6.3 | 1 | 2051.9 | 102.5 | 42684.1 | 1317.94 | 0.046 | 1 |
| CPCG0344 | 60.9 | 3 + 3 | T2c | 5.5 | 1 | 2169.22 | 107.1 | 21245.2 | 644.68 | 0.094 | 1 |
| CPCG0345 | 60.4 | 3 + 4 | T3b | 6.6 | 1 | 2076.81 | 85.49 | 23445.5 | 669.58 | 0.09 | 0 |
| CPCG0346 | 59.7 | 3 + 4 | T3a | 6.5 | 2 | 3160.71 | 122.58 | 17265.9 | 361.98 | 0.334 | 0 |
| CPCG0348 | 57 | 3 + 4 | T3a | 4.22 | 0 | 2469.37 | 105.23 | 19175.6 | 627.9 | 0 | 0 |
| CPCG0349 | 61.8 | 4 + 4 | T2c | 7.1 | 1 | 3936.14 | 141.05 | 29956.4 | 876.02 | 0.069 | 0 |
| CPCG0350 | 53.2 | 4 + 3 | T3b | 39.47 | 1 | 3186.42 | 175.12 | 16436.5 | 553.25 | 0.109 | 0 |
| CPCG0352 | 55.5 | 4 + 3 | T2c | 9.1 | 2 | 4267.8 | 210.29 | 21746 | 629.93 | 0.192 | 1 |
| CPCG0353 | 65.6 | 3 + 4 | T3b | 9 | 0 | 5165.99 | 171.98 | 15483 | 445.09 | 0 | 0 |
| CPCG0354 | 61.4 | 3 + 4 | T2c | 6.7 | 0 | 10612.5 | 369.9 | 15967.2 | 479.46 | 0 | 0 |
| CPCG0355 | 55.5 | 3 + 3 | T2c | 6.7 | 2 | 10942.8 | 413.22 | 24203.7 | 722.52 | 0.167 | 1 |
| CPCG0356 | 51.6 | 4 + 3 | T2c | 8.49 | 3 | 5522.17 | 183.24 | 24184.8 | 758.82 | 0.239 | 0 |
| CPCG0357 | 59.1 | 3 + 4 | T2c | 3.11 | 0 | 2936.46 | 144.62 | 13756 | 432.86 | 0 | 0 |
| CPCG0358 | 68.8 | 3 + 4 | T2a | 5.88 | 1 | 11783.1 | 558.8 | 19095.4 | 640.92 | 0.094 | 0 |
| CPCG0360 | 66.2 | 3 + 4 | T3b | 14 | 0 | 2459.98 | 102.12 | 20880.2 | 626.95 | 0 | 0 |
| CPCG0361 | 70.1 | 3 + 4 | T3a | 4.6 | 1 | 4085.15 | 171.45 | 23547.5 | 424.85 | 0.142 | 0 |
| CPCG0362 | 57.6 | 3 + 4 | T3b | 8.77 | 0 | 5073.01 | 232.26 | 16830.4 | 543.17 | 0 | 0 |
| CPCG0363 | 56.6 | 3 + 4 | T2c | 4.27 | 0 | 3803.3 | 134.64 | 22238.6 | 676.72 | 0 | 0 |
| CPCG0364 | 63.2 | 3 + 3 | T3a | 8.11 | 0 | 2119.11 | 90.51 | 32021.9 | 585.73 | 0 | 0 |
| CPCG0365 | 71.7 | 3 + 3 | T2c | 4.23 | 0 | 2595.34 | 108 | 20792.3 | 560.3 | 0 | 0 |
| CPCG0366 | 60.5 | 3 + 4 | T3a | 15 | 0 | 2832.85 | 118.99 | 10542.6 | 284.93 | 0 | 0 |
| CPCG0368 | 63.7 | 3 + 3 | T2c | 4.39 | 1 | 3212.27 | 136.26 | 26323.3 | 795.63 | 0.076 | 1 |
| CPCG0369 | 63.7 | 3 + 4 | T3a | 7.18 | 0 | 4818.33 | 216.57 | 21784.1 | 636.84 | 0 | 0 |
| CPCG0371 | 60.7 | 3 + 4 | T3a | 7.52 | 0 | 6744.86 | 304.1 | 15628.5 | 492.43 | 0 | 0 |
| CPCG0372 | 60.2 | 3 + 4 | T2c | 4 | 1 | 3635.5 | 178.11 | 22791.2 | 726.25 | 0.083 | 0 |
| CPCG0373 | 59.8 | 3 + 4 | T2c | 4.9 | 0 | 6165.27 | 290.47 | 15628.5 | 478.66 | 0 | 0 |
| CPCG0374 | 63.6 | 3 + 3 | T2c | 4.7 | 1 | 5552.69 | 251.7 | 30129 | 839.05 | 0.072 | 0 |
| CPCG0375 | 70.2 | 3 + 3 | T2c | 7.01 | 0 | 5556.59 | 228.69 | 30332 | 1023.21 | 0 | 0 |
| CPCG0377 | 76.9 | 4 + 4 | T2c | 6.9 | 1 | 5674.91 | 238.24 | 24080.1 | 701.87 | 0.086 | 0 |
| CPCG0378 | 69.1 | 3 + 4 | T3b | 8.7 | 1 | 6663.66 | 277.53 | 25862.6 | 756.27 | 0.08 | 0 |
| CPCG0379 | 68.6 | 3 + 4 | T3a | 14.6 | 1 | 3991.82 | 194.66 | 16985.8 | 471.18 | 0.128 | 0 |
| CPCG0380 | 58.1 | 3 + 4 | T2c | 6.29 | 1 | 3479.34 | 177.05 | 23339.2 | 716.88 | 0.084 | 0 |
| CPCG0381 | 64.9 | 3 + 4 | T2c | 5.76 | 0 | 4173.25 | 180.55 | 18670.6 | 576.26 | 0 | 0 |
| CPCG0382 | 71.1 | 4 + 4 | T2c | 6.8 | 0 | 3774.09 | 157.43 | 35627.8 | 1141.52 | 0 | 0 |
| CPCG0387 | 67.1 | 4 + 3 | T2c | 4.52 | 2 | 6376.56 | 286.84 | 18213.4 | 529.95 | 0.228 | 0 |
| CPCG0388 | 54.5 | 3 + 4 | T3a | 2.5 | 1 | 2485.18 | 106.06 | 22595.6 | 707.36 | 0.085 | 0 |
| CPCG0391 | 60.8 | 3 + 3 | T2c | 5.3 | 0 | 6416.64 | 265.25 | 17324.3 | 438.19 | 0 | 0 |
| CPCG0392 | 61.4 | 3 + 4 | T3b | 19.5 | 0 | 1868.71 | 87.57 | 18631.4 | 511.01 | 0 | 0 |
| CPCG0401 | 58.1 | 3 + 4 | T2c | 36 | 0 | 4357.69 | 191.91 | 17145.6 | 532.82 | 0 | 0 |
| CPCG0404 | 56.2 | 3 + 4 | T2c | 36 | 1 | 5948.57 | 243.78 | 40464.9 | 1098.8 | 0.055 | 1 |
| CPCG0407 | 57.9 | 3 + 4 | T2a | 11.5 | 2 | 3378.68 | 206.76 | 17177.2 | 477.4 | 0.253 | 0 |
| CPCG0408 | 67.9 | 4 + 4 | T2c | 3.47 | 0 | 6495.59 | 276.71 | 22309.9 | 641.83 | 0 | 0 |
| CPCG0409 | 59.1 | 3 + 4 | T3a | 6.3 | 1 | 2922.04 | 173.92 | 28278 | 742.69 | 0.081 | 0 |
| CPCG0410 | 62 | 3 + 4 | T2c | 5 | 3 | 5203.82 | 217.73 | 26133.8 | 741.72 | 0.244 | 0 |

TABLE 4-continued

Clinical and sequencing data per patient

| Patient | Age At Treat-ment | Gleason Score | T cate-gory | PSA (ng/mL) | mitoSNVs | Normal mito-chondrial mean coverage d | Normal mito-chondrial copy num | Tumour mito-chondrial mean coverage | Tumour mito-chondrial copy nu | mtSNVs/Mb | MT-DLOOP |
|---|---|---|---|---|---|---|---|---|---|---|---|
| CPCG0411 | 45.7 | 4 + 3 | T2c | 10.55 | 0 | 4019.65 | 163.77 | 14003 | 424.03 | 0 | 0 |
| CPCG0412 | 58.7 | 4 + 3 | T2a | 3.36 | 3 | 2780.6 | 164.49 | 15645.1 | 479.17 | 0.378 | 0 |
| CPCG0413 | 59.1 | 3 + 4 | T2c | 6.89 | 0 | 3915.74 | 186.91 | 21079.7 | 737.96 | 0 | 0 |
| CPCG0414 | 43.8 | 4 + 3 | T2c | 5.4 | 0 | 3877.37 | 172.59 | 15891.4 | 508.01 | 0 | 0 |
| Weischenfeldt-EOPC-010 | 46 | 3 + 4 | T2c | 6 | 2 | 3077.42 | 136 | 8577.51 | 368.3 | 0.328 | 0 |
| Weischenfeldt-EOPC-011 | 48 | 3 + 4 | T2c | 4.8 | 0 | 1839.24 | 123 | 4632.61 | 299.45 | 0 | 0 |
| Weischenfeldt-EOPC-02 | 51 | 3 + 4 | T2c | 23.8 | 0 | 3352.84 | 200.42 | 5115.26 | 370.21 | 0 | 0 |
| Weischenfeldt-EOPC-03 | 46 | 5 + 4 | T3a | 12 | 1 | 3258.08 | 237.37 | 17967.1 | 528.61 | 0.114 | 0 |
| Weischenfeldt-EOPC-04 | 51 | 4 + 3 | T3b | 72 | 2 | 5386.42 | 163.11 | 6291.77 | 427.88 | 0.282 | 1 |
| Weischenfeldt-EOPC-05 | 50 | 3 + 4 | T3a | 5 | 1 | 1840.62 | 119.72 | 4111.36 | 258.28 | 0.234 | 1 |
| Weischenfeldt-EOPC-06 | 38 | 3 + 4 | T3b | 18.2 | 0 | 2104.12 | 103.53 | 4020.19 | 193.78 | 0 | 0 |
| Weischenfeldt-EOPC-07 | 49 | 3 + 4 | T2c | 5.4 | 4 | 1995.09 | 130.76 | 5886.36 | 375.09 | 0.644 | 0 |
| Weischenfeldt-EOPC-08 | 44 | 3 + 4 | T2c | 7.8 | 0 | 3107.47 | 196.85 | 7331.15 | 347.3 | 0 | 0 |
| Weischenfeldt-EOPC-09 | 48 | 3 + 4 | T2c | 5.1 | 0 | 4594.3 | 228.69 | 6755.4 | 408.36 | 0 | 0 |
| ICGC_PCA001 | 45 | 3 + 4 | T3a | 30 | 0 | 2827.22 | 128.51 | 9654.26 | 459.73 | 0 | 0 |
| ICGC_PCA012 | 48 | 3 + 4 | T2c | 4.8 | 0 | 1901.03 | 126.74 | 4799.33 | 309.63 | 0 | 0 |
| ICGC_PCA013 | 45 | 3 + 4 | T2c | NA | 1 | 4499.82 | 243.23 | 17577.1 | 491.46 | 0.123 | 0 |
| ICGC_PCA014 | 45 | 3 + 4 | T2a | NA | 0 | 3804.42 | 234.55 | 11582.8 | 254.76 | 0 | 0 |
| ICGC_PCA015 | 48 | 3 + 4 | T3b | NA | 1 | 4139.76 | 232.51 | 7798.35 | 183.08 | 0.33 | 1 |
| ICGC_PCA016 | 44 | 3 + 4 | T2a | NA | 0 | 3967.64 | 227.96 | 7782.91 | 217.1 | 0 | 0 |
| ICGC_PCA017 | 48 | 3 + 4 | T2c | 13.2 | 0 | 4965.55 | 264.69 | 4464.28 | 233.37 | 0 | 0 |
| ICGC_PCA018 | 49 | 3 + 3 | T2c | 4.6 | 0 | 7169.97 | 300.19 | 3978.88 | 198.99 | 0 | 0 |
| ICGC_PCA019 | 46 | 3 + 4 | T2c | 6.74 | 0 | 4594.35 | 256.45 | 4238.89 | 224.99 | 0 | 0 |
| ICGC_PCA020 | 49 | 3 + 3 | T3a | NA | 0 | 2643.11 | 166.23 | 11609.6 | 317.25 | 0 | 0 |
| ICGC_PCA021 | 45 | 3 + 4 | T2c | 5.35 | 0 | 4498.3 | 208.64 | 4629.81 | 208.88 | 0 | 0 |
| ICGC_PCA022 | 49 | 3 + 4 | T2c | 5.88 | 0 | 5958.51 | 222.46 | 4028.03 | 195.82 | 0 | 0 |
| ICGC_PCA023 | 50 | 3 + 4 | T2c | 2.56 | 1 | 7928.37 | 330.28 | 10306.4 | 373.49 | 0.162 | 0 |
| ICGC_PCA024 | 43 | 3 + 4 | T2c | 11.7 | 0 | 2382.34 | 115.03 | 4937.3 | 219.63 | 0 | 0 |
| ICGC_PCA025 | 47 | 3 + 4 | T2c | 9.79 | 0 | 1837.06 | 111.03 | 4018.61 | 211.56 | 0 | 0 |
| ICGC_PCA026 | 48 | 3 + 3 | T2c | 3.8 | 1 | 2183.34 | 127.53 | 5286.37 | 267.53 | 0.226 | 0 |
| ICGC_PCA027 | 49 | 3 + 4 | T2c | NA | 0 | 3878.45 | 187.36 | 4240.61 | 224.61 | 0 | 0 |
| ICGC_PCA028 | 40 | 3 + 4 | T2c | NA | 0 | 4063.62 | 213.65 | 4881.5 | 229.56 | 0 | 0 |
| ICGC_PCA029 | 48 | 4 + 3 | T3b | 15.5 | 3 | 4670.4 | 178.6 | 5589.59 | 213.38 | 0.849 | 0 |
| ICGC_PCA030 | 48 | 4 + 3 | T3b | 62.4 | 0 | 4655.41 | 178.99 | 9524.12 | 361.17 | 0 | 0 |
| ICGC_PCA031 | 48 | 3 + 4 | T2c | 22.5 | 1 | 5953.36 | 222.93 | 6554.49 | 230.1 | 0.262 | 1 |
| ICGC_PCA032 | 44 | 3 + 4 | T2a | 4.23 | 5 | 3258.41 | 177.67 | 3955.93 | NA | NA | 1 |
| ICGC_PCA033 | 43 | 3 + 4 | T2c | 5 | 0 | 2815.95 | 163.29 | 4980.66 | NA | NA | 0 |
| ICGC_PCA034 | 46 | 3 + 4 | T2c | 5.27 | 0 | 2350.99 | 119.31 | 6313.81 | 278.94 | 0 | 0 |
| ICGC_PCA035 | 49 | 4 + 3 | T3b | 70.43 | 0 | 4548.29 | 245.85 | 13510.3 | 773.12 | 0 | 0 |
| ICGC_PCA036 | 57 | 3 + 4 | T3a | 6.52 | 2 | 4422.45 | 175.49 | 9231.92 | 362.04 | 0.333 | 0 |
| ICGC_PCA037 | 50 | 3 + 4 | T3a | 6.98 | 0 | 3709.63 | NA | 15562.3 | 884.22 | 0 | 0 |
| ICGC_PCA038 | 49 | 3 + 4 | T2c | 3.99 | 0 | 6205.3 | 250.06 | 5214.15 | 244.34 | 0 | 0 |
| ICGC_PCA040 | 50 | 3 + 3 | T2c | 6.13 | 0 | 6296.73 | 263.24 | 5967.76 | 246.35 | 0 | 0 |
| ICGC_PCA041 | 48 | 5 + 4 | T4 | 58 | 1 | 4421.8 | 231.63 | 3387.42 | 149.19 | 0.405 | 0 |
| ICGC_PCA043 | 47 | 4 + 5 | NA | NA | 0 | 2911.35 | 169.46 | 8698.75 | 373.5 | 0 | 0 |
| ICGC_PCA044 | 48 | 4 + 3 | T2c | 12 | 0 | 4142.43 | 244.97 | 9927.41 | 377.83 | 0 | 0 |
| ICGC_PCA045 | 47 | 3 + 4 | T2c | 7.65 | 0 | 4123.21 | 245.79 | 8784.67 | 374.29 | 0 | 0 |
| ICGC_PCA046 | 49 | 3 + 4 | T2c | 9.36 | 0 | 3982.15 | 229.12 | 6158.4 | 185.33 | 0 | 0 |
| ICGC_PCA048 | 50 | 3 + 3 | T2a | 8.2 | 1 | 5147.5 | 253.07 | 5545.16 | 212.13 | 0.285 | 0 |
| ICGC_PCA049 | 48 | 3 + 3 | T2c | 6.09 | 0 | 5441.71 | 196.27 | 7249.09 | 272.27 | 0 | 0 |
| ICGC_PCA050 | 48 | 3 + 4 | T2c | NA | 0 | 3497.67 | 145.98 | 6475.02 | 261.19 | 0 | 0 |
| ICGC_PCA051 | 41 | 3 + 4 | T2c | NA | 1 | 2606.4 | 108.46 | 5413.56 | 230.22 | 0.262 | 0 |
| ICGC_PCA052 | 40 | 3 + 4 | T2c | NA | 0 | 6947.3 | 264.31 | 5799.31 | 233.8 | 0 | 0 |
| ICGC_PCA053 | 48 | 4 + 3 | T2c | 9.9 | 0 | 6203.75 | 230.88 | 6614 | 259.63 | 0 | 0 |
| ICGC_PCA054 | 50 | 3 + 4 | T2c | 6.4 | 0 | 4053.86 | 213.7 | 5865.11 | 232.88 | 0 | 0 |
| ICGC_PCA055 | 48 | 3 + 4 | T2c | 6.15 | 0 | 4154.49 | 242.1 | 6373.99 | 292.45 | 0 | 0 |
| ICGC_PCA056 | 47 | 3 + 4 | T2c | NA | 0 | 4748.29 | 193.29 | 6807.71 | 319.99 | 0 | 0 |
| ICGC_PCA057 | 50 | 3 + 4 | T2c | 5.07 | 1 | 4296.18 | 220.09 | 6351.99 | 288.2 | 0.209 | 0 |
| ICGC_PCA058 | 47 | 3 + 4 | T2c | 5.4 | 0 | 4131.73 | 204.29 | 7484.18 | 298.12 | 0 | 0 |
| ICGC_PCA059 | 47 | 3 + 4 | T2c | 14.1 | 0 | 2733.23 | 113.62 | 5098.51 | 228.84 | 0 | 0 |
| ICGC_PCA060 | 41 | 3 + 3 | T2c | 5.74 | 1 | 7267.63 | 285.01 | 9625.05 | 360.89 | 0.167 | 0 |

TABLE 4-continued

Clinical and sequencing data per patient

| Patient | Age At Treat-ment | Gleason Score | T cate-gory | PSA (ng/mL) | mitoSNVs | Normal mito-chondrial mean coverage d | Normal mito-chondrial copy num | Tumour mito-chondrial mean coverage | Tumour mito-chondrial copy nu | mtSNVs/Mb | MT-DLOOP |
|---|---|---|---|---|---|---|---|---|---|---|---|
| ICGC_PCA061 | 47 | 3 + 4 | T2a | 6.47 | 0 | 6088.55 | 256.58 | 5563.43 | 213.36 | 0 | 0 |
| ICGC_PCA062 | 45 | 3 + 4 | T2c | 8.21 | 0 | 5973.57 | 232.62 | 10047.6 | 405.8 | 0 | 0 |
| ICGC_PCA063 | 46 | 3 + 4 | T2c | 13 | 0 | 3077.46 | 177.38 | 8342.93 | 352.02 | 0 | 0 |
| ICGC_PCA064 | 47 | 3 + 3 | T2a | 5.3 | 0 | 6441.14 | 398.83 | 10255.3 | 420.64 | 0 | 0 |
| ICGC_PCA065 | 48 | 3 + 4 | T2c | 8.9 | 2 | 1325.05 | 75.46 | 11750 | 619.56 | 0.195 | 1 |
| ICGC_PCA068 | 50 | 3 + 4 | T2c | 12.9 | 1 | 5040.31 | 276.33 | 5742.06 | 236.93 | 0.255 | 0 |
| ICGC_PCA069 | 50 | 4 + 3 | T3a | 6.45 | 0 | 2451.17 | 143.26 | 5556.66 | 262.17 | 0 | 0 |
| ICGC_PCA070 | 47 | 3 + 4 | T2c | 5.2 | 1 | 3953.56 | 231.81 | 5395.4 | 260.33 | 0.232 | 0 |
| ICGC_PCA071 | 49 | 4 + 3 | T2c | 24.5 | 1 | 3776.54 | 223.33 | 6539.71 | 301.58 | 0.2 | 1 |
| ICGC_PCA072 | 49 | 3 + 4 | T2c | 11 | 0 | 4492.12 | 269.55 | 6647.67 | 314.24 | 0 | 0 |
| ICGC_PCA074 | 42 | 3 + 4 | T2c | 5.7 | 0 | 3321.15 | 251.03 | 5395.89 | 300.36 | 0 | 0 |
| ICGC_PCA075 | 40 | 3 + 3 | T2a | 5.4 | 2 | 5151.89 | 266.66 | 5965.86 | 338.87 | 0.356 | 0 |
| ICGC_PCA076 | 49 | 3 + 4 | T2c | NA | 0 | 3491.55 | 192.11 | 3316.82 | 213.37 | 0 | 0 |
| ICGC_PCA077 | 44 | 4 + 3 | T2a | 5.48 | 0 | 7752.06 | 405.76 | 8308.19 | 337.25 | 0 | 0 |
| ICGC_PCA078 | 47 | 3 + 4 | T2c | 16 | 0 | 4355.82 | 237.7 | 3346.03 | 133.55 | 0 | 0 |
| ICGC_PCA079 | 46 | 3 + 4 | T2c | 6.3 | 0 | 6685.66 | 343.82 | 2601.73 | 105.83 | 0 | 0 |
| ICGC_PCA081 | 50 | 4 + 5 | T3b | 13 | 1 | 2714.44 | 116.32 | 4814.68 | 183.35 | 0.329 | 0 |
| ICGC_PCA082 | 41 | 5 + 4 | T3b | 7.5 | 0 | 6940.57 | 290.7 | 5926.09 | 232.03 | 0 | 0 |
| ICGC_PCA083 | 45 | 3 + 4 | T2c | 16 | 1 | 11499.2 | 500.95 | 3934.47 | 165.31 | 0.365 | 0 |
| ICGC_PCA084 | 45 | 5 + 4 | T3b | NA | 0 | 5001.32 | 177.57 | 5497.65 | 205.17 | 0 | 0 |
| ICGC_PCA085 | 47 | 3 + 4 | T2c | NA | 0 | 3163.24 | 117.88 | 5796.65 | 222.73 | 0 | 0 |
| ICGC_PCA086 | 50 | 4 + 3 | T3b | NA | 1 | 2093.52 | 79.68 | 7527.37 | 284.86 | 0.212 | 0 |
| ICGC_PCA087 | 45 | 3 + 3 | T2c | NA | 0 | 4426.2 | 173.41 | 6051.99 | 237.24 | 0 | 0 |
| ICGC_PCA088 | 43 | 3 + 3 | T2c | NA | 0 | 4838.29 | 172.92 | 4928.1 | 189.51 | 0 | 0 |
| ICGC_PCA089 | 48 | 3 + 4 | T2c | NA | 0 | 3071.35 | 125.49 | 5624.6 | 219.75 | 0 | 0 |
| ICGC_PCA090 | 40 | 3 + 4 | T2c | NA | 0 | 3773.1 | 133.25 | 7026.47 | 285.17 | 0 | 0 |
| ICGC_PCA091 | 50 | 3 + 4 | T2c | NA | 1 | 7940.39 | 357.03 | 6353.35 | 326.23 | 0.185 | 0 |
| ICGC_PCA094 | 45 | 3 + 4 | T2c | NA | 0 | 1580.49 | 110.87 | 4981.62 | 249.77 | 0 | 0 |
| ICGC_PCA095 | 50 | 3 + 3 | T2c | NA | 1 | 2460.92 | 179.24 | 5146.51 | 196.13 | 0.308 | 0 |
| ICGC_PCA096 | 49 | 3 + 3 | T2a | NA | 0 | 2575.05 | 190.82 | 6107.44 | 232.27 | 0 | 0 |
| ICGC_PCA097 | 48 | 3 + 3 | T2a | 8.5 | 1 | 3853.91 | 280.28 | 8780.53 | 391.46 | 0.154 | 1 |
| ICGC_PCA098 | 45 | 4 + 5 | T3a | NA | 3 | 4548.38 | 376.83 | 6023.84 | 308.36 | 0.587 | 1 |
| ICGC_PCA102 | 48 | 3 + 3 | T2c | NA | 0 | 3897.72 | 304.27 | 6101.24 | 299.3 | 0 | 0 |
| ICGC_PCA103 | 48 | 3 + 3 | T2c | NA | 1 | 3976.32 | 300.1 | 7233.16 | 338.95 | 0.178 | 0 |
| ICGC_PCA104 | 44 | 3 + 4 | T2a | NA | 0 | 3427.5 | 247.03 | 5674.02 | 243.73 | 0 | 0 |
| ICGC_PCA105 | 49 | 3 + 4 | T2c | NA | 0 | 4097.07 | 175.58 | 7762.64 | 289.33 | 0 | 0 |
| ICGC_PCA106 | 43 | 3 + 4 | T2c | NA | 0 | 8923.14 | 375 | 5921.86 | 250.34 | 0 | 0 |
| ICGC_PCA107 | 47 | 3 + 3 | T2c | NA | 0 | 4825.85 | 196.81 | 6644.75 | 252.32 | 0 | 0 |
| ICGC_PCA108 | 50 | 3 + 4 | T3a | NA | 0 | 6116.57 | 213.75 | 8639.65 | 317.23 | 0 | 0 |
| ICGC_PCA110 | 48 | 3 + 3 | T2c | NA | 0 | 5878.11 | 243.55 | 4948.4 | 329.78 | 0 | 0 |
| ICGC_PCA111 | 43 | 3 + 4 | T2c | NA | 0 | 7863.32 | 459.98 | 7416.78 | 309.48 | 0 | 0 |
| ICGC_PCA112 | 47 | 4 + 3 | T3b | NA | 0 | 2980.66 | 168.21 | 5585.02 | 262.95 | 0 | 0 |
| ICGC_PCA113 | 48 | 4 + 5 | T3b | NA | 0 | 2915.6 | 229.57 | 4126.11 | 223.7 | 0 | 0 |
| ICGC_PCA116 | 46 | 3 + 4 | T3a | NA | 0 | 4955.88 | 254.74 | 7505.96 | 283.24 | 0 | 0 |
| ICGC_PCA118 | 50 | 3 + 3 | T2c | NA | 1 | 3994.34 | 192.73 | 8046.52 | 337.81 | 0.179 | 1 |
| ICGC_PCA121 | 44 | 3 + 4 | T2c | NA | 0 | 5487.62 | 190.05 | 7985.31 | 261.26 | 0 | 0 |
| ICGC_PCA122 | 50 | 4 + 3 | T3b | NA | 1 | 4089.29 | 139.16 | 16881.6 | 274.74 | 0.22 | 0 |
| ICGC_PCA123 | 46 | 3 + 4 | T3a | NA | 1 | 6229.33 | 201.83 | 23838.9 | 390.26 | 0.155 | 0 |
| ICGC_PCA124 | 46 | 3 + 4 | T3a | NA | 0 | 3088.17 | 103.27 | 18666.6 | 289.76 | 0 | 0 |
| ICGC_PCA125 | 44 | 5 + 4 | T4 | NA | 3 | 6218.51 | 206.29 | 37206.4 | 513.19 | 0.353 | 1 |
| ICGC_PCA126 | 47 | 4 + 3 | T3b | NA | 0 | 4562.1 | 264.16 | 18594.5 | 589.83 | 0 | 0 |
| ICGC_PCA127 | 49 | 3 + 4 | T2c | NA | 0 | 3722.96 | 213.53 | 9790.9 | 314.37 | 0 | 0 |
| ICGC_PCA129 | 49 | 4 + 5 | T2c | NA | 0 | 4966.04 | 279.15 | 13371.3 | 395.19 | 0 | 0 |
| ICGC_PCA130 | 46 | 3 + 4 | T3a | NA | 0 | 1157.65 | 64.66 | 10770.6 | 318.28 | 0 | 0 |
| ICGC_PCA131 | 50 | 3 + 4 | T2c | NA | 0 | 3322.29 | 180.76 | 9669.45 | 304.17 | 0 | 0 |
| ICGC_PCA132 | 48 | 3 + 4 | T3b | NA | 0 | 2513.39 | 153.77 | 8557.46 | 261.06 | 0 | 0 |
| ICGC_PCA133 | 49 | 3 + 3 | T2c | NA | 0 | 4382.32 | 287.84 | 11193.9 | 325.5 | 0 | 0 |
| ICGC_PCA134 | 48 | 3 + 4 | T2c | NA | 0 | 3757.47 | 228.28 | 6793.07 | 225.09 | 0 | 0 |
| ICGC_PCA135 | 47 | 3 + 4 | T2c | NA | 0 | 3768.45 | 222.46 | 13255.5 | 269.37 | 0 | 0 |
| ICGC_PCA136 | 47 | 3 + 4 | T2c | NA | 0 | 2273.13 | 136.73 | 7783.32 | 234.65 | 0 | 0 |
| ICGC_PCA137 | 49 | 3 + 4 | T2c | NA | 0 | 2698.04 | 168.42 | 9615.6 | 308.54 | 0 | 0 |
| ICGC_PCA138 | 48 | 3 + 4 | T2c | NA | 0 | 2118.75 | 133.68 | 4218.26 | 91.54 | 0 | 0 |
| ICGC_PCA140 | 45 | 3 + 3 | T2c | NA | 1 | 5669.67 | 169.93 | 8477.17 | 179.01 | 0.337 | 0 |
| ICGC_PCA141 | 49 | 3 + 4 | T2c | NA | 0 | 3703.42 | 235.29 | 3519.06 | 75.73 | 0 | 0 |
| ICGC_PCA142 | 46 | 5 + 4 | T4 | NA | 1 | 6249.11 | 397.65 | 14694.7 | 479.36 | 0.126 | 0 |
| ICGC_PCA143 | 48 | 3 + 4 | T3a | NA | 0 | 4739.26 | 144.27 | 10439.3 | 324.05 | 0 | 0 |
| ICGC_PCA144 | 46 | 3 + 4 | T2c | NA | 0 | 9066.31 | 138.77 | 6515.96 | 203.56 | 0 | 0 |
| ICGC_PCA145 | 32 | 3 + 3 | T2a | NA | 0 | 2457.97 | 155.08 | 6448.05 | 207.27 | 0 | 0 |
| ICGC_PCA148 | 46 | 3 + 4 | T3a | NA | 0 | 2547.86 | 139.34 | 7361.85 | 134.36 | 0 | 0 |
| ICGC_PCA149 | 45 | 4 + 3 | T2c | NA | 0 | 2529.97 | 148.52 | 7028.07 | 222.41 | 0 | 0 |
| ICGC_PCA150 | 40 | 3 + 3 | T2c | NA | 0 | 3151.92 | 193.85 | 8846 | 287.53 | 0 | 0 |

TABLE 4-continued

Clinical and sequencing data per patient

| Patient | Age At Treatment | Gleason Score | T category | PSA (ng/mL) | mitoSNVs | Normal mitochondrial mean coverage d | Normal mitochondrial copy num | Tumour mitochondrial mean coverage | Tumour mitochondrial copy nu | mtSNVs/Mb | MT-DLOOP |
|---|---|---|---|---|---|---|---|---|---|---|---|
| ICGC_PCA151 | 49 | 3 + 4 | T3a | NA | 0 | 2056.8 | 131.17 | 6984.15 | 214.76 | 0 | 0 |
| ICGC_PCA152 | 45 | 3 + 4 | T2c | NA | 0 | 4032.42 | 251.71 | 9519.33 | 318 | 0 | 0 |
| ICGC_PCA153 | 50 | 3 + 4 | T2c | NA | 0 | 2467.2 | 149.3 | 9858.98 | 310.71 | 0 | 0 |
| ICGC_PCA154 | 48 | 3 + 4 | T2c | NA | 0 | 2957.33 | 171.59 | 9626.51 | 308.59 | 0 | 0 |
| ICGC_PCA155 | 45 | 3 + 4 | T2a | NA | 1 | 917.007 | 53.64 | 9799.51 | 306.62 | 0.197 | 0 |
| ICGC_PCA156 | 45 | 3 + 4 | T2c | NA | 1 | 4236.17 | 251.78 | 10226.1 | 408.15 | 0.148 | 0 |
| ICGC_PCA157 | 44 | 3 + 3 | T3a | NA | 0 | 3006.29 | 197.59 | 9086.25 | 313.43 | 0 | 0 |
| ICGC_PCA158 | 45 | 4 + 3 | T3a | NA | 0 | 4184.84 | 226.94 | 9004.93 | 281.4 | 0 | 0 |
| ICGC_PCA159 | 44 | 4 + 3 | T2c | NA | 0 | 4889.47 | 341.56 | 10928.6 | 327.3 | 0 | 0 |
| ICGC_PCA160 | 50 | 4 + 3 | T2c | NA | 0 | 2034.2 | 133.7 | 12007.2 | 363.41 | 0 | 0 |
| ICGC_PCA161 | 48 | 4 + 5 | T3b | NA | 2 | 1916.61 | 124.46 | 5272.41 | 182.18 | 0.663 | 0 |
| ICGC_PCA162 | 50 | 3 + 4 | T2c | NA | 0 | 3516.02 | 220.23 | 7845.21 | 239.88 | 0 | 0 |
| ICGC_PCA163 | 45 | 3 + 4 | T2c | NA | 1 | 3013.52 | 175.46 | 8769.99 | 268.11 | 0.225 | 0 |
| ICGC_PCA164 | 50 | 3 + 4 | T3a | NA | 0 | 4510.1 | 265.14 | 5838.26 | 354.37 | 0 | 0 |
| ICGC_PCA165 | 48 | 3 + 4 | T2c | NA | 0 | 2058.3 | 125.77 | 12277.9 | 379.59 | 0 | 0 |
| ICGC_PCA166 | 47 | 4 + 3 | T2a | NA | 2 | 2459.89 | 154.71 | 6601.8 | 206.31 | 0.585 | 1 |
| ICGC_PCA167 | 43 | 3 + 4 | T2c | NA | 0 | 3481.01 | 216.01 | 11925.1 | 357.9 | 0 | 0 |
| ICGC_PCA168 | 50 | 3 + 4 | T2a | NA | 1 | 4869.54 | 314.27 | 12045.6 | 279.19 | 0.216 | 0 |
| ICGC_PCA169 | 46 | 3 + 4 | T3a | NA | 2 | 5858.35 | 390.84 | 17049.7 | 470.86 | 0.256 | 1 |
| ICGC_PCA170 | 51 | 4 + 3 | T2c | NA | 2 | 3144.62 | 246.06 | 17963.1 | 324.48 | 0.372 | 1 |
| ICGC_PCA171 | 50 | 3 + 4 | T2c | NA | 1 | 5702.95 | 322.93 | 12983.8 | 353.49 | 0.171 | 0 |
| ICGC_PCA172 | 43 | 3 + 3 | T2c | NA | 0 | 6141.82 | 341.59 | 6015.86 | 166 | 0 | 0 |
| ICGC_PCA173 | 46 | 3 + 4 | T2c | NA | 0 | 6063 | 355.91 | 17240.8 | 463.59 | 0 | 0 |
| ICGC_PCA174 | 51 | 3 + 4 | T3b | NA | 1 | 4700.36 | 278.37 | 9175.36 | 260.85 | 0.231 | 0 |
| ICGC_PCA175 | 48 | 4 + 3 | T3a | NA | 0 | 3023.26 | 179.85 | 8788.83 | 257.43 | 0 | 0 |
| ICGC_PCA176 | 47 | 5 + 5 | T4 | NA | 0 | 5185.27 | 302.08 | 4916.06 | 139.5 | 0 | 0 |
| ICGC_PCA177 | 46 | 3 + 4 | T3a | NA | 0 | 1713.44 | 98.87 | 6854.12 | 210.6 | 0 | 0 |
| ICGC_PCA178 | 51 | 3 + 3 | T2a | NA | 0 | 1792.49 | 105.66 | 8523.97 | 279.43 | 0 | 0 |
| ICGC_PCA179 | 45 | 3 + 4 | T2c | NA | 0 | 4142.21 | 236.83 | 9055.59 | 271.86 | 0 | 0 |
| ICGC_PCA180 | 51 | 3 + 4 | T2c | NA | 2 | 2446.26 | 139.43 | 12616 | 389.92 | 0.31 | 0 |
| ICGC_PCA181 | 51 | 3 + 4 | T2c | NA | 0 | 9884.16 | 557.48 | 7422.03 | 250.36 | 0 | 0 |
| ICGC_PCA182 | 51 | 3 + 4 | T2c | NA | 1 | 3777.99 | 213.81 | 13779.1 | 421.64 | 0.143 | 0 |
| ICGC_PCA183 | 52 | 3 + 4 | T3a | NA | 1 | 2994.8 | 167.45 | 5766.19 | 151.34 | 0.399 | 1 |
| ICGC_PCA184 | 51 | 3 + 4 | T2c | NA | 2 | 4889.25 | 277.56 | 8793.69 | 249.22 | 0.484 | 1 |
| ICGC_PCA185 | 51 | 3 + 3 | T2c | NA | 1 | 6046.69 | 350.23 | 10357 | 285.87 | 0.211 | 0 |
| ICGC_PCA186 | 51 | 3 + 4 | T2c | NA | 0 | 8935.55 | 150.08 | 16333.1 | 498.49 | 0 | 0 |
| ICGC_PCA187 | 46 | 3 + 3 | T2c | NA | 1 | 24761.9 | 420.19 | 8581.43 | 266.01 | 0.227 | 0 |
| ICGC_PCA188 | 48 | 3 + 4 | T2c | NA | 0 | 6424.8 | 115.1 | 3947.88 | 116.18 | 0 | 0 |
| ICGC_PCA189 | 51 | 3 + 4 | T2c | NA | 0 | 11625.9 | 211 | 9484.56 | 293.64 | 0 | 0 |
| ICGC_PCA190 | 51 | 4 + 3 | T2c | NA | 0 | 10871.4 | 206.33 | 5180.94 | 169.2 | 0 | 0 |
| ICGC_PCA191 | 51 | 3 + 4 | T2c | NA | 0 | 2626.94 | 150.24 | 7651.09 | 232.7 | 0 | 0 |
| ICGC_PCA192 | 52 | 4 + 4 | T3b | NA | 1 | 3697.6 | 215.29 | 5591.91 | 171.06 | 0.353 | 0 |
| ICGC_PCA193 | 52 | 5 + 4 | T3b | NA | 3 | 4695.07 | 262 | 8394.14 | 253.71 | 0.714 | 0 |
| ICGC_PCA194 | 52 | 3 + 4 | T2c | NA | 0 | 5640.21 | 314.13 | 16449.8 | 482.61 | 0 | 0 |
| ICGC_PCA195 | 47 | 3 + 3 | T2c | NA | 0 | 1946.43 | 109.94 | 6144.92 | 178.42 | 0 | 0 |
| ICGC_PCA196 | 52 | 4 + 5 | T3b | NA | 1 | 2681.47 | 146.21 | 4994.05 | 137.48 | 0.439 | 0 |
| ICGC_PCA197 | 50 | 3 + 4 | T3a | NA | 1 | 3413.79 | 183.69 | 10603.2 | 309.85 | 0.195 | 1 |
| ICGC_PCA198 | 52 | 4 + 5 | T3b | NA | 2 | 3070.23 | 172.58 | 10961.7 | 304.15 | 0.397 | 1 |
| ICGC_PCA199 | 51 | 3 + 4 | T2c | NA | 0 | 2438.98 | 141.68 | 13931.1 | 265.61 | 0 | 0 |
| ICGC_PCA200 | 47 | 3 + 4 | T2c | NA | 0 | 2912.99 | 178.33 | 25583.2 | 277.99 | 0 | 0 |
| TCGA-CH-5750 | 72 | 3 + 4 | T2c | 13.2 | 2 | 4645.1 | 256.1 | 8771.03 | 332.78 | 0.363 | 0 |
| TCGA-CH-5763 | 66 | 3 + 4 | T3a | 14.8 | 0 | 4837.75 | 275.63 | 9349.95 | 321.39 | 0 | 0 |
| TCGA-CH-5771 | 63 | 4 + 3 | T2c | 8.1 | 0 | 4387.57 | 267.28 | 6988.53 | 222.02 | 0 | 0 |
| TCGA-CH-5788 | 69 | 4 + 3 | T3b | 19.4 | 1 | 5554.92 | 288.62 | 21678.6 | 606.25 | 0.1 | 1 |
| TCGA-CH-5789 | 61 | 3 + 4 | T3a | 5.7 | 0 | 7282.33 | 418.19 | 8021.94 | 306.89 | 0 | 0 |
| TCGA-EJ-5503 | 50 | 5 + 3 | T3a | 18.4 | 0 | 5531.64 | 289.41 | 7616.2 | 237.24 | 0 | 0 |
| TCGA-EJ-5506 | 67 | 5 + 3 | T3b | 7.2 | 2 | 4952.82 | 291.73 | 8754.14 | 336.74 | 0.359 | 1 |
| TCGA-EJ-7791 | 67 | 3 + 4 | T2c | 4.5 | 0 | 2665.12 | 159.65 | 7271.3 | 244.69 | 0 | 0 |
| TCGA-G9-6336 | 57 | 3 + 4 | NA | 10.6 | 2 | 2003.55 | 105.24 | 9463.51 | 334.99 | 0.36 | 0 |
| TCGA-G9-6365 | 71 | 3 + 4 | T4 | 11.6 | 0 | 2230.56 | 107.99 | 9664.85 | 342.25 | 0 | 0 |
| TCGA-G9-6370 | 52 | 3 + 4 | T3b | 6.4 | 0 | 2373.22 | 120.83 | 8885.26 | 304.54 | 0 | 0 |
| TCGA-G9-7522 | 49 | 3 + 4 | T2c | 6.8 | 0 | 1974.77 | 115.85 | 5812.83 | 211.12 | 0 | 0 |
| TCGA-HC-7075 | 63 | 3 + 3 | T2a | 5.1 | 1 | 2362.13 | 136.21 | 8765.79 | 285.05 | 0.212 | 1 |
| TCGA-HC-7079 | 51 | 3 + 4 | T3a | 5.5 | 0 | 2660.98 | 143.62 | 4529.49 | 170.1 | 0 | 0 |
| TCGA-HC-7233 | 73 | 4 + 3 | T2a | 7.7 | 0 | 2402.06 | 119.2 | 6346.51 | 214.41 | 0 | 0 |
| TCGA-HC-7737 | 55 | 3 + 4 | T2c | 18.1 | 0 | 3231.25 | 180.11 | 7132.52 | 264.64 | 0 | 0 |
| TCGA-HC-7740 | 59 | 3 + 4 | T2c | 5.9 | 0 | 2747.27 | 170.09 | 6201.89 | 241.73 | 0 | 0 |
| TCGA-HC-7744 | 46 | 4 + 3 | T3b | 4.4 | 0 | 3770.56 | 211 | 9518.19 | 327.16 | 0 | 0 |
| TCGA-HC-8258 | 56 | 3 + 3 | T2c | 4.3 | 0 | 2585.8 | 143.5 | 9352.13 | 272.82 | 0 | 0 |
| TCGA-HI-7169 | 55 | 3 + 4 | T3a | 2.2 | 0 | 1802.28 | 99.46 | 8035.46 | 278.59 | 0 | 0 |

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 1 | 0 | 0 | 0 | 0 | 0 | 0 | 0 | 0 | 1 | 0 | bwa/0.5.7 | NA | 0 | 0 | NA |
| 0 | 0 | 1 | 1 | 0 | 0 | 0 | 0 | 0 | 0 | 0 | 0 | 0 | 0 | 0 | 0 | 0 | 0 | 0 | bwa/0.5.7 | NA | 0 | −1 | NA |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | NA | 1 | −1 | NA |
| 0 | 0 | 0 | 0 | 0 | 0 | 0 | 0 | 0 | 0 | 0 | 0 | 0 | 0 | 0 | 1 | 0 | 0 | 1 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 1 | 0 | 0 | 1 | bwa/0.5.7 | NA | 1 | 0 | NA |
| 1 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 1 | 0 | 0 | 0 | 0 | 0 | 0 | 0 | 0 | 0 | 0 | 0 | 0 | 0 | 0 | 0 | 0 | 0 | 0 | bwa/0.5.7 | NA | 1 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 1 | 0 | 0 | 0 | 0 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | NA | NA |
| 1 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 1 | 1 | 0 | 0 | 0 | 1 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 1 | 0 | bwa/0.5.7 | 356.5 | 0 | −1 | 0.85 |
| 0 | 0 | 0 | 1 | 0 | 0 | 0 | 0 | 0 | 0 | 0 | 0 | 0 | 0 | 0 | 0 | 0 | 0 | 0 | bwa/0.5.7 | 226.2 | 1 | −1 | 0.76 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 198 | 0 | −1 | 0.84 |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.12 | 222.32 | 0 | 0 | 0.78 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 121.16 | 1 | −1 | 0.92 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 267.3 | 0 | −1 | 0.7 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 129 | 1 | 0 | 0.89 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 239.9 | 0 | −1 | 0.24 |
| 0 | 1 | 0 | 0 | 0 | 0 | 0 | 0 | 0 | 0 | 0 | 0 | 0 | 0 | 0 | 0 | 0 | 0 | 0 | bwa-mem/0.7.12 | 399.82 | 0 | 0 | 0.26 |
| 0 | 0 | 0 | 0 | 1 | 0 | 0 | 0 | 0 | 0 | 0 | 0 | 0 | 0 | 0 | 0 | 0 | 0 | 0 | bwa/0.5.7 | 232.5 | 0 | 0 | 0.89 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 295.2 | 0 | 0 | 0.92 |
| 0 | 0 | 1 | 1 | 0 | 0 | 0 | 0 | 0 | 0 | 0 | 0 | 0 | 0 | 0 | 0 | 0 | 0 | 0 | bwa-mem/0.7.12 | 259 | 0 | 0 | 0.18 |
| 0 | 0 | 0 | 0 | 0 | 0 | 0 | 0 | 1 | 0 | 0 | 0 | 0 | 0 | 0 | 0 | 0 | 0 | 0 | bwa-mem/0.7.12 | 232.2 | 0 | −1 | 0.88 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 227.34 | 0 | 0 | NA |
| 0 | 0 | 1 | 0 | 0 | 0 | 1 | 0 | 0 | 0 | 0 | 0 | 0 | 0 | 0 | 0 | 0 | 1 | 0 | bwa/0.5.7 | 392.06 | 1 | 0 | 0.83 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 391.89 | 0 | −1 | 0.88 |
| 0 | 0 | 0 | 0 | 1 | 0 | 1 | 0 | 1 | 0 | 0 | 0 | 0 | 0 | 0 | 0 | 0 | 1 | 0 | bwa/0.5.7 | 228.64 | 0 | 0 | 0.89 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 424.02 | 0 | 0 | 0.85 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 512.4 | 0 | 0 | 0.71 |
| 0 | 0 | 0 | 0 | 0 | 0 | 0 | 0 | 0 | 0 | 1 | 0 | 0 | 0 | 0 | 0 | 0 | 0 | 0 | bwa-mem/0.7.12 | 159.8 | 0 | 0 | 0.92 |
| 1 | 0 | 0 | 0 | 0 | 0 | 0 | 0 | 0 | 0 | 0 | 0 | 0 | 0 | 0 | 0 | 0 | 0 | 0 | bwa/0.5.7 | 310.77 | 0 | −1 | 0.63 |
| 0 | 0 | 0 | 1 | 0 | 0 | 0 | 0 | 0 | 0 | 0 | 0 | 0 | 0 | 1 | 0 | 0 | 0 | 0 | bwa/0.5.7 | 513.84 | 1 | −1 | 0.24 |
| 1 | 0 | 0 | 1 | 0 | 0 | 0 | 0 | 0 | 0 | 0 | 0 | 0 | 0 | 0 | 0 | 0 | 0 | 0 | bwa-mem/0.7.15 | 500 | 0 | 0 | NA |
| 0 | 0 | 0 | 0 | 0 | 0 | 0 | 0 | 0 | 0 | 0 | 0 | 1 | 0 | 0 | 1 | 0 | 0 | 1 | bwa-mem/0.7.12 | 270.96 | 0 | 0 | 0.85 |
| 0 | 0 | 0 | 1 | 1 | 0 | 0 | 0 | 0 | 0 | 0 | 0 | 0 | 0 | 0 | 0 | 0 | 0 | 0 | bwa-mem/0.7.12 | 308.14 | 0 | 0 | 0.85 |
| 0 | 0 | 0 | 0 | 0 | 0 | 0 | 0 | 0 | 0 | 0 | 0 | 1 | 0 | 0 | 0 | 0 | 0 | 0 | bwa/0.5.7 | 663.36 | 1 | −1 | 0.78 |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 1 | 0 | 0 | 0 | 0 | 0 | 0 | 0 | 0 | 0 | 0 | 0 | 0 | 0 | 1 | 0 | 0 | 1 | bwa/0.5.7 | 500 | 1 | −1 | 0.75 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 242.19 | 0 | 0 | 0.77 |
| 0 | 0 | 0 | 0 | 0 | 0 | 1 | 0 | 0 | 0 | 0 | 0 | 0 | 0 | 0 | 0 | 0 | 0 | 0 | bwa-mem/0.7.12 | 408.2 | 0 | 0 | 0.85 |
| 1 | 0 | 0 | 0 | 0 | 0 | 0 | 0 | 0 | 0 | 0 | 0 | 0 | 0 | 0 | 0 | 0 | 0 | 1 | bwa/0.5.7 | 252.59 | 1 | −1 | 0.59 |
| 0 | 0 | 1 | 0 | 0 | 0 | 0 | 0 | 0 | 0 | 0 | 0 | 0 | 0 | 0 | 1 | 0 | 0 | 1 | bwa/0.5.7 | 675.13 | 1 | −1 | 0.41 |
| 0 | 0 | 0 | 0 | 0 | 0 | 0 | 0 | 0 | 0 | 0 | 0 | 0 | 1 | 0 | 0 | 0 | 0 | 0 | bwa-mem/0.7.12 | 253.71 | 1 | −1 | 0.86 |
| 0 | 1 | 0 | 0 | 0 | 0 | 0 | 0 | 0 | 0 | 0 | 0 | 0 | 0 | 0 | 0 | 0 | 0 | 0 | bwa/0.5.7 | 299.1 | 1 | −1 | 0.6 |
| 0 | 0 | 0 | 0 | 0 | 0 | 0 | 0 | 0 | 0 | 0 | 0 | 0 | 0 | 0 | 0 | 0 | 1 | 0 | bwa-mem/0.7.12 | 664.9 | 0 | 0 | 0.87 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 275.1 | 0 | −1 | 0.98 |
| 0 | 0 | 0 | 0 | 0 | 0 | 0 | 0 | 0 | 0 | 0 | 0 | 1 | 0 | 0 | 0 | 0 | 0 | 0 | bwa-mem/0.7.12 | 250 | 0 | 0 | 0.83 |
| 0 | 1 | 0 | 0 | 0 | 0 | 0 | 0 | 0 | 0 | 1 | 0 | 0 | 0 | 0 | 0 | 0 | 0 | 0 | bwa-mem/0.7.12 | 300 | 0 | 0 | 0.8 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 417.15 | 0 | 0 | 0.48 |
| 0 | 0 | 0 | 0 | 0 | 0 | 1 | 0 | 0 | 0 | 0 | 0 | 0 | 0 | 0 | 0 | 0 | 0 | 0 | bwa/0.5.7 | 359.22 | 0 | 0 | 0.9 |
| 0 | 0 | 0 | 0 | 0 | 0 | 0 | 0 | 0 | 0 | 1 | 0 | 0 | 0 | 0 | 0 | 0 | 0 | 0 | bwa-mem/0.7.12 | 100 | 0 | 0 | 0.86 |
| 0 | 0 | 0 | 0 | 0 | 0 | 0 | 0 | 0 | 0 | 0 | 0 | 0 | 0 | 0 | 0 | 0 | 1 | 0 | bwa/0.5.7 | 186.62 | 0 | 0 | 0.78 |
| 0 | 0 | 1 | 0 | 0 | 0 | 0 | 0 | 0 | 0 | 0 | 0 | 0 | 0 | 0 | 1 | 1 | 0 | 1 | bwa/0.5.7 | 250.29 | 1 | −1 | 0.78 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1093.12 | 0 | −1 | 0.84 |
| 0 | 0 | 1 | 0 | 0 | 0 | 0 | 0 | 0 | 0 | 0 | 0 | 0 | 0 | 0 | 1 | 0 | 0 | 1 | bwa/0.5.7 | 318.32 | 1 | −1 | 0.68 |
| 0 | 0 | 0 | 0 | 0 | 0 | 0 | 0 | 0 | 0 | 1 | 0 | 0 | 0 | 0 | 0 | 0 | 0 | 0 | bwa/0.5.7 | 642.75 | 0 | 0 | NA |
| 0 | 0 | 0 | 0 | 0 | 0 | 1 | 0 | 0 | 0 | 0 | 0 | 0 | 0 | 1 | 0 | 0 | 0 | 0 | bwa-mem/0.7.10 | 552.6 | 0 | 0 | NA |
| 0 | 0 | 0 | 0 | 0 | 1 | 0 | 0 | 0 | 0 | 0 | 0 | 0 | 0 | 0 | 0 | 0 | 1 | 1 | bwa/0.5.7 | 339.15 | 0 | 0 | 0.23 |
| 0 | 0 | 0 | 0 | 1 | 0 | 0 | 0 | 0 | 0 | 0 | 0 | 0 | 0 | 0 | 0 | 0 | 0 | 0 | bwa/0.5.7 | 677.5 | 0 | 0 | 0.62 |
| 0 | 0 | 0 | 1 | 0 | 0 | 0 | 0 | 0 | 0 | 0 | 0 | 0 | 0 | 0 | 0 | 0 | 0 | 0 | bwa-mem/0.7.12 | 205.47 | 1 | −1 | 0.79 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 952.8 | 0 | −1 | 0.25 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 937.68 | 0 | 0 | 0.8 |
| 0 | 0 | 0 | 0 | 0 | 0 | 0 | 0 | 0 | 0 | 1 | 0 | 0 | 0 | 0 | 0 | 0 | 0 | 0 | bwa/0.5.7 | 242.5 | 0 | 0 | 0.83 |
| 0 | 0 | 0 | 0 | 0 | 0 | 0 | 0 | 0 | 0 | 1 | 1 | 0 | 0 | 0 | 0 | 0 | 0 | 0 | bwa/0.5.7 | 980.4 | 0 | 0 | 0.8 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 177.25 | 0 | −1 | 0.92 |
| 0 | 0 | 0 | 1 | 0 | 0 | 0 | 0 | 0 | 0 | 0 | 0 | 0 | 0 | 0 | 0 | 0 | 0 | 0 | bwa/0.5.7 | 503.84 | 0 | 0 | 0.92 |
| 0 | 0 | 0 | 0 | 0 | 0 | 0 | 0 | 0 | 0 | 0 | 0 | 0 | 0 | 0 | 0 | 0 | 1 | 0 | bwa/0.5.7 | 1098.8 | 0 | −1 | 0.92 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 950.96 | 0 | 0 | 0.84 |
| 0 | 0 | 0 | 0 | 0 | 0 | 0 | 0 | 0 | 0 | 0 | 0 | 0 | 0 | 0 | 1 | 0 | 0 | 1 | bwa/0.5.7 | 848.68 | 0 | 0 | 0.62 |
| 0 | 0 | 1 | 0 | 0 | 1 | 0 | 0 | 1 | 0 | 0 | 0 | 0 | 0 | 0 | 0 | 0 | 0 | 1 | bwa/0.5.7 | 150 | 0 | 0 | 0.23 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 501.12 | 0 | 0 | NA |
| 0 | 0 | 1 | 0 | 0 | 0 | 0 | 0 | 0 | 0 | 0 | 0 | 0 | 0 | 0 | 0 | 0 | 1 | 0 | bwa/0.5.7 | 586.8 | 0 | −1 | 0.7 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 774.52 | 1 | −1 | 0.66 |
| 0 | 1 | 0 | 0 | 0 | 0 | 0 | 0 | 0 | 0 | 0 | 0 | 0 | 0 | 0 | 0 | 0 | 0 | 0 | bwa/0.5.7 | 2064 | 0 | −1 | 0.59 |
| 0 | 0 | 0 | 0 | 0 | 0 | 0 | 0 | 0 | 0 | 0 | 0 | 0 | 0 | 0 | 0 | 0 | 0 | 1 | bwa/0.5.7 | 2901.44 | 1 | −1 | 0.89 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1510.32 | 0 | −1 | 0.76 |
| 0 | 1 | 0 | 0 | 0 | 0 | 0 | 0 | 0 | 0 | 1 | 0 | 0 | 0 | 0 | 0 | 0 | 1 | 0 | bwa/0.5.7 | 2036.8 | 0 | −1 | 0.72 |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | 2020.36 | 0 | 0 | 0.36 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1722.16 | 0 | −1 | 0.62 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 522.09 | 0 | −1 | 0.85 |
| 0 | 0 | 0 | 0 | 0 | 0 | 0 | 0 | 0 | 0 | 0 | 0 | 0 | 0 | 1 | 1 | 0 | 0 | 1 | bwa/0.5.7 | 1513.8 | 0 | 0 | 0.89 |
| 0 | 0 | 0 | 0 | 0 | 0 | 0 | 0 | 0 | 0 | 0 | 0 | 0 | 0 | 0 | 0 | 0 | 1 | 0 | bwa-mem/0.7.12 | 262.8 | 0 | 0 | 0.88 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 259.5 | 0 | 0 | 0.35 |
| 0 | 0 | 0 | 0 | 1 | 0 | 0 | 0 | 0 | 0 | 0 | 0 | 0 | 0 | 0 | 0 | 0 | 0 | 0 | bwa/0.5.7 | 271.2 | 0 | −1 | 0.82 |
| 0 | 1 | 0 | 0 | 1 | 0 | 0 | 0 | 0 | 0 | 0 | 0 | 0 | 0 | 0 | 1 | 0 | 0 | 1 | bwa-mem/0.7.12 | 991.44 | 0 | −1 | 0.88 |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 1 | 1 | 0 | 1 | bwa/0.5.7 | 203.44 | 0 | −1 | 0.27 |
| 0 | 0 | 0 | 0 | 0 | 0 | 0 | 0 | 0 | 0 | 0 | 0 | 0 | 0 | 0 | 1 | 0 | 0 | 1 | bwa/0.5.7 | 335.52 | 1 | −1 | 0.16 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 2304.48 | 0 | −1 | 0.83 |
| 0 | 1 | 0 | 0 | 0 | 1 | 0 | 0 | 0 | 0 | 0 | 0 | 0 | 0 | 0 | 0 | 0 | 0 | 0 | bwa/0.5.7 | 1001.2 | 0 | −1 | 0.3 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1000 | 0 | −1 | 0.53 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1001.64 | 0 | −1 | 0.85 |
| 1 | 0 | 0 | 1 | 0 | 0 | 0 | 0 | 1 | 0 | 0 | 0 | 0 | 0 | 0 | 0 | 0 | 0 | 0 | bwa/0.5.7 | 1515.8 | 0 | −1 | 0.23 |
| 0 | 0 | 1 | 0 | 0 | 0 | 0 | 0 | 1 | 0 | 0 | 0 | 0 | 1 | 0 | 0 | 0 | 0 | 0 | bwa/0.5.7 | 1002.56 | 0 | 0 | 0.2 |
| 0 | 0 | 0 | 0 | 0 | 0 | 0 | | 1 | 0 | 0 | 0 | 0 | 0 | 0 | 0 | 0 | 0 | 0 | bwa/0.5.7 | 2006 | 0 | −1 | 0.79 |
| 0 | 0 | 0 | 1 | 0 | 0 | 0 | 0 | 0 | 0 | 0 | 0 | 0 | 0 | 0 | 0 | 0 | 0 | 0 | bwa/0.5.7 | 2015.2 | 0 | −1 | 0.63 |
| 0 | 0 | 0 | 0 | 0 | 0 | 0 | 0 | 1 | 0 | 0 | 0 | 1 | 0 | 0 | 0 | 0 | 0 | 0 | bwa/0.5.7 | 500 | 0 | 0 | 0.93 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 2000 | 1 | −1 | 0.81 |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | 388.8 | 1 | −1 | 0.51 |
| 0 | 0 | 0 | 0 | 0 | 0 | 0 | 0 | 1 | 0 | 0 | 0 | 0 | 0 | 0 | 0 | 0 | 0 | 0 | bwa-mem/0.7.12 | 635.75 | 0 | 0 | 0.88 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 2000 | 0 | 0 | 0.6 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 2000 | 0 | −1 | 1 |
| 0 | 0 | 0 | 0 | 1 | 0 | 0 | 0 | 1 | 0 | 0 | 0 | 0 | 0 | 0 | 1 | 1 | 0 | 1 | bwa/0.5.7 | 618 | 1 | −1 | 0.69 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 1498 | 0 | 0 | 0.87 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 339 | 0 | 0 | 0.15 |
| 0 | 1 | 0 | 0 | 0 | 0 | 0 | 0 | 0 | 0 | 0 | 0 | 0 | 0 | 0 | 0 | 0 | 0 | 0 | bwa/0.5.7 | 394.8 | 0 | −1 | 0.65 |
| 0 | 0 | 0 | 0 | 0 | 0 | 0 | 0 | 0 | 1 | 0 | 0 | 1 | 0 | 0 | 0 | 0 | 0 | 0 | bwa/0.5.7 | 563.4 | 0 | −1 | 0.64 |
| 0 | 0 | 0 | 0 | 0 | 0 | 0 | 0 | 0 | 0 | 0 | 0 | 0 | 0 | 0 | 0 | 0 | 1 | 0 | bwa/0.5.7 | 1500 | 0 | 0 | 0.37 |
| 0 | 0 | 0 | 0 | 0 | 0 | 0 | 0 | 0 | 0 | 1 | 0 | 0 | 0 | 0 | 0 | 0 | 0 | 0 | bwa/0.5.7 | 1000 | 0 | 0 | 0.23 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 259.2 | 0 | 0 | 0.64 |
| 0 | 0 | 0 | 0 | 0 | 0 | 1 | 0 | 0 | 0 | 0 | 0 | 0 | 0 | 0 | 1 | 0 | 1 | 1 | bwa/0.5.7 | 429 | 0 | −1 | 0.2 |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.12 | 1006.4 | 0 | −1 | 0.86 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1500 | 0 | −1 | 0.27 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 279 | 0 | 0 | 0.16 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1500 | 0 | 0 | 0.55 |
| 0 | 0 | 0 | 0 | 1 | 0 | 0 | 0 | 0 | 0 | 0 | 0 | 1 | 0 | 0 | 0 | 0 | 0 | 0 | bwa/0.5.7 | 253.2 | 0 | −1 | 0.81 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 85.2 | 0 | −1 | 0.31 |
| 0 | 0 | 0 | 1 | 0 | 0 | 0 | 0 | 0 | 0 | 0 | 0 | 0 | 0 | 0 | 0 | 0 | 0 | 0 | bwa/0.5.7 | 287.4 | 0 | −1 | 0.76 |
| 0 | 0 | 0 | 0 | 0 | 0 | 0 | 0 | 0 | 0 | 0 | 1 | 0 | 0 | 0 | 0 | 0 | 0 | 0 | bwa/0.5.7 | 306.6 | 0 | −1 | 0.19 |
| 0 | 0 | 0 | 0 | 1 | 0 | 0 | 0 | 0 | 0 | 0 | 0 | 0 | 0 | 0 | 0 | 0 | 0 | 0 | bwa/0.5.7 | 271.2 | 0 | 0 | 0.3 |
| 0 | 1 | 0 | 0 | 0 | 0 | 0 | 0 | 0 | 0 | 0 | 0 | 0 | 0 | 0 | 0 | 0 | 0 | 0 | bwa/0.5.7 | 268.4 | 0 | 0 | 0.22 |
| 1 | 0 | 0 | 0 | 0 | 0 | 0 | 0 | 0 | 0 | 0 | 0 | 1 | 0 | 0 | 0 | 0 | 1 | 0 | bwa/0.5.7 | 110.4 | 0 | −1 | 0.75 |
| 0 | 0 | 1 | 0 | 0 | 0 | 1 | 0 | 0 | 0 | 0 | 0 | 0 | 0 | 0 | 0 | 0 | 0 | 0 | bwa/0.5.7 | 416.5 | 0 | −1 | 0.31 |
| 0 | 0 | 1 | 0 | 0 | 0 | 1 | 0 | 0 | 0 | 1 | 0 | 0 | 0 | 0 | 0 | 0 | 0 | 0 | bwa/0.5.7 | 312.2 | 0 | −1 | 0.22 |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | 318.5 | 0 | −1 | 0.66 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 445.9 | 0 | 0 | 0.23 |
| 0 | 0 | 1 | 0 | 1 | 0 | 0 | 0 | 0 | 0 | 0 | 0 | 0 | 0 | 0 | 0 | 0 | 0 | 0 | bwa/0.5.7 | 342 | 1 | 0 | 0.23 |
| 1 | 0 | 0 | 0 | 0 | 0 | 1 | 0 | 0 | 0 | 0 | 0 | 0 | 0 | 0 | 0 | 0 | 0 | 0 | bwa/0.5.7 | 588 | 0 | −1 | 0.62 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 543.9 | 0 | −1 | 0.53 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 310.1 | 0 | 0 | 0.27 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 363.6 | 0 | 0 | 0.28 |
| 0 | 0 | 0 | 0 | 0 | 0 | 0 | 0 | 0 | 0 | 0 | 0 | 0 | 0 | 1 | 0 | 0 | 0 | 0 | bwa/0.5.7 | 489 | 1 | 1 | 0.78 |
| 1 | 1 | 0 | 0 | 0 | 0 | 0 | 0 | 0 | 0 | 0 | 0 | 0 | 0 | 0 | 0 | 0 | 0 | 0 | bwa/0.5.7 | 484.2 | 0 | 0 | 0.26 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 246 | 0 | −1 | 0.67 |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 1 | 0 | 0 | 0 | 0 | 0 | 0 | bwa/0.5.7 | 253 | 0 | −1 | 0.61 |
| 0 | 0 | 0 | 0 | 0 | 0 | 0 | 0 | 0 | 0 | 1 | 0 | 0 | 0 | 0 | 0 | 0 | 0 | 0 | bwa/0.5.7 | 297.6 | 0 | −1 | 0.79 |
| 0 | 0 | 0 | 0 | 0 | 0 | 0 | 0 | 1 | 0 | 0 | 0 | 0 | 0 | 0 | 0 | 0 | 1 | 0 | bwa/0.5.7 | 271.2 | 0 | −1 | 0.63 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 250.8 | 0 | 0 | 0.51 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 298 | 0 | −1 | 0.25 |
| 1 | 0 | 0 | 0 | 0 | 0 | 0 | 0 | 0 | 0 | 0 | 0 | 0 | 0 | 0 | 0 | 0 | 1 | 0 | bwa/0.5.7 | 256 | 0 | 0 | 0.15 |
| 1 | 0 | 0 | 0 | 0 | 0 | 0 | 0 | 0 | 0 | 1 | 0 | 1 | 0 | 0 | 0 | 0 | 0 | 0 | bwa/0.5.7 | 277.6 | 0 | 1 | 0.61 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 346.2 | 0 | 0 | 0.69 |
| 0 | 0 | 1 | 0 | 0 | 0 | 0 | 0 | 0 | 0 | 0 | 0 | 0 | 0 | 0 | 0 | 0 | 0 | 0 | bwa/0.5.7 | 265.5 | 0 | 0 | 0.27 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 252.8 | 0 | −1 | 0.23 |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | 347.4 | 0 | −1 | 0.31 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 330.4 | 0 | 0 | 0.38 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 277.2 | 0 | 0 | 0.32 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 237.2 | 0 | 0 | 0.7 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 2361.68 | 0 | 0 | 0.13 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1542 | 0 | −1 | 0.6 |
| 0 | 0 | 0 | 0 | 0 | 0 | 0 | 0 | 0 | 0 | 0 | 0 | 0 | 0 | 0 | 0 | 0 | 1 | 0 | bwa/0.5.7 | 309.4 | 0 | 0 | 0.2 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 294.6 | 1 | −1 | 0.72 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 355.68 | 0 | −1 | 0.61 |
| 0 | 0 | 0 | 0 | 0 | 0 | 0 | 0 | 0 | 1 | 0 | 0 | 0 | 0 | 0 | 0 | 0 | 0 | 0 | bwa/0.5.7 | 304 | 0 | 0 | 0.28 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 350.4 | 0 | 0 | 0.33 |
| 0 | 0 | 0 | 0 | 0 | 0 | 1 | 0 | 0 | 0 | 0 | 0 | 0 | 0 | 0 | 0 | 0 | 0 | 0 | bwa/0.5.7 | 309.6 | 0 | 0 | 0.19 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 428 | 0 | 0 | 0.47 |
| 0 | 0 | 0 | 0 | 0 | 0 | 1 | 0 | 0 | 0 | 0 | 0 | 0 | 0 | 0 | 0 | 0 | 0 | 0 | bwa/0.5.7 | 315 | 0 | −1 | 0.28 |
| 0 | 0 | 0 | 0 | 0 | 0 | 0 | 0 | 0 | 0 | 0 | 1 | 0 | 0 | 0 | 0 | 0 | 0 | 0 | bwa/0.5.7 | 288 | 0 | −1 | 0.63 |
| 0 | 0 | 0 | 0 | 0 | 0 | 0 | 0 | 1 | 0 | 0 | 0 | 0 | 0 | 0 | 0 | 0 | 0 | 0 | bwa/0.5.7 | 536.2 | 1 | −1 | 0.77 |
| 0 | 0 | 0 | 0 | 0 | 0 | 0 | 0 | 0 | 0 | 0 | 0 | 0 | 1 | 0 | 0 | 0 | 0 | 0 | bwa/0.5.7 | 282.6 | 1 | −1 | 0.55 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 280.8 | 0 | 0 | 0.26 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 598 | 1 | 1 | 0.69 |
| 1 | 0 | 0 | 0 | 0 | 0 | 0 | 0 | 0 | 0 | 0 | 0 | 0 | 0 | 0 | 0 | 0 | 0 | 0 | bwa/0.5.7 | 348 | 0 | 0 | 0.49 |
| 0 | 0 | 1 | 0 | 0 | 0 | 0 | 0 | 0 | 0 | 0 | 0 | 0 | 0 | 0 | 0 | 0 | 0 | 0 | bwa/0.5.7 | 673 | 0 | −1 | 0.74 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 374.4 | 0 | 0 | 0.21 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 1180 | 0 | 0 | 0.7 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 603 | 0 | 0 | 0.15 |
| 0 | 0 | 0 | 0 | 0 | 0 | 0 | 0 | 0 | 0 | 0 | 0 | 0 | 0 | 0 | 0 | 0 | 1 | 0 | bwa/0.5.7 | 754 | 0 | 0 | 0.71 |
| 0 | 0 | 0 | 0 | 1 | 0 | 0 | 1 | 0 | 0 | 0 | 0 | 0 | 0 | 0 | 0 | 0 | 0 | 0 | bwa/0.5.7 | 588 | 0 | −1 | 0.77 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 326 | 0 | −1 | 0.13 |
| 0 | 0 | 0 | 0 | 1 | 0 | 0 | 0 | 0 | 0 | 0 | 0 | 0 | 0 | 0 | 0 | 0 | 0 | 0 | bwa/0.5.7 | 399 | 0 | −1 | 0.31 |
| 0 | 0 | 1 | 0 | 0 | 0 | 1 | 0 | 1 | 0 | 0 | 0 | 0 | 0 | 0 | 0 | 0 | 0 | 0 | bwa/0.5.7 | 392 | 0 | −1 | 0.27 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 445.2 | 0 | 0 | 0.12 |
| 1 | 1 | 0 | 0 | 0 | 0 | 0 | 0 | 0 | 0 | 0 | 0 | 0 | 0 | 0 | 0 | 0 | 0 | 0 | bwa/0.5.7 | 422 | 0 | −1 | 0.63 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 442.4 | 0 | 0 | 0.51 |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | 336 | 0 | 0 | 0.17 |
| 0 | 0 | 0 | 0 | 0 | 0 | 0 | 0 | 0 | 0 | 1 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | −1 | NA |
| 0 | 0 | 0 | 0 | 1 | 0 | 0 | 0 | 0 | 0 | 0 | 0 | 0 | 0 | 0 | 0 | 0 | 0 | 0 | bwa/0.5.7 | NA | 1 | −1 | NA |
| 0 | 1 | 0 | 0 | 0 | 0 | 0 | 0 | 0 | 0 | 0 | 0 | 0 | 0 | 0 | 0 | 0 | 1 | 0 | bwa/0.5.7 | NA | 0 | 0 | NA |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 1 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 1 | 0 | 0 | 0 | 0 | 0 | 1 | 0 | 1 | 0 | 0 | 0 | 0 | 0 | 0 | 0 | 0 | 0 | bwa/0.5.7 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 1 | 0 | 0 | 1 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 1 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 1 | 0 | 0 | 0 | 0 | 0 | 0 | 0 | 1 | 0 | 0 | 1 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 1 | −1 | NA |
| 0 | 0 | 0 | 0 | 0 | 0 | 0 | 0 | 0 | 0 | 0 | 0 | 0 | 0 | 0 | 1 | 1 | 0 | 1 | bwa-mem/0.7.8-r455 | NA | 0 | −1 | NA |
| 0 | 1 | 0 | 0 | 0 | 1 | 0 | 0 | 0 | 0 | 0 | 0 | 0 | 0 | 1 | 0 | 1 | 1 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 1 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 1 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 1 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 1 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 1 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 1 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 1 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 1 | 0 | 0 | 0 | 0 | 0 | 0 | 0 | 0 | 1 | 0 | bwa-mem/0.7.8-r455 | NA | 1 | 0 | NA |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 1 | 0 | 0 | 0 | 0 | 0 | 1 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 1 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 1 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 1 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 1 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 1 | 0 | bwa-mem/0.7.8-r455 | NA | NA | NA | NA |
| 0 | 0 | 0 | 1 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 1 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 1 | 0 | 0 | 1 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 1 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 1 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 1 | 1 | 0 | 0 | 0 | 0 | 0 | 0 | 0 | 0 | 0 | 0 | 0 | 0 | 0 | 0 | 0 | bwa-mem/0.7.8-r455 | NA | 1 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 1 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 1 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 1 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 1 | 0 | 0 | 1 | 0 | 0 | 1 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 1 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 1 | 0 | 1 | 1 | bwa-mem/0.7.8-r455 | NA | 0 | 0 | NA |
| 0 | 0 | 0 | 0 | 0 | 0 | 0 | 0 | 1 | 0 | 0 | 0 | 0 | 0 | 0 | 0 | 0 | 1 | 0 | bwa-mem/0.7.8-r455 | NA | NA | NA | NA |
| 0 | 0 | 0 | 0 | 1 | 0 | 0 | 0 | 0 | 0 | 0 | 0 | 0 | 0 | 0 | 0 | 0 | 0 | 0 | bwa-mem/0.7.8-r455 | NA | 0 | 0 | NA |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 1 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 1 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 1 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 1 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 1 | 1 | 0 | 0 | 0 | 0 | bwa-mem/0.7.8-r455 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 1 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 1 | 0 | bwa-mem/0.7.8-r455 | NA | 0 | 0 | NA |
| 1 | 0 | 0 | 0 | 0 | 0 | 0 | 0 | 0 | 0 | 0 | 0 | 0 | 0 | 0 | 1 | 0 | 0 | 1 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa-mem/0.7.8-r455 | NA | NA | NA | NA |
| 0 | 0 | 1 | 1 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | NA | NA |
| 0 | 0 | 0 | 0 | 0 | 0 | 0 | 0 | 0 | 0 | 0 | 0 | 0 | 0 | 0 | 0 | 0 | 0 | 1 | bwa/0.5.7 | NA | 0 | −1 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | 0 | NA |
| 0 | 0 | 0 | 0 | 0 | 0 | 0 | 0 | 0 | 0 | 0 | 0 | 0 | 0 | 0 | 0 | 0 | 0 | 1 | bwa/0.5.7 | NA | NA | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 1 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | NA | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |

-continued

| MT-CYB | MT-RNR1 | MT-RNR2 | MT-ND1 | MTND2 | MT-ND3 | MT-ND4 | MT-ND4L | MT-ND5 | MT-ND6 | MT-CO1 | MT-CO2 | MT-CO3 | MT-ATP6 | MT-ATP8 | OHR | CSB1 | HV1 | HV2 | bwa version | sample_size (Amt_DNA. sent.for. sequencing | MYC CNA | NKX3-1 CNA | cellularity |
|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |
| 0 | 0 | 0 | 0 | 0 | 0 | 0 | 0 | 0 | 0 | 0 | 0 | 0 | 0 | 0 | 0 | 0 | 0 | 0 | bwa/0.5.7 | NA | 0 | 0 | NA |

TABLE 5

Table of 293 somatic mtSNVs

| Patient | Position Re-ference | Tu-mour | Tu-mour.H.F | Tu-mour.HF | Tu-mour.HF | Tumour.H. Normal | Nor-mal.HF.A | Nor-mal.HF.C | Nor-mal.HF.G | Nor-mal.HF.G | Tumour Covering Normal | Cover-agemt DNA | Locus Difference in H | nucleo-tide.vari-ability.sco |
|---|---|---|---|---|---|---|---|---|---|---|---|---|---|---|
| CPCG0187 | 60 T | T | 0 | 0.22 | 0 | 0.78 T | 0 | 0 | 0 | 1 | 7399 | 1019 CR | 0.22 | 0.00186 |
| CPCG0078 | 72 T | C | 0 | 0.72 | 0 | 0.27 T | 0 | 0 | 0 | 1 | 6109 | 427 CR | 0.73 | 0.0925 |
| CPCG0114 | 72 T | T | 0 | 0 | 0 | 1 C | 0 | 1 | 0 | 0 | 1191 | 4684 CR | 1 | 0.0925 |
| CPCG0263 | 72 T | T | 0 | 0.5 | 0 | 0.5 T | 0 | 0 | 0 | 1 | 5744 | 867 CR | 0.5 | 0.0925 |
| ICGC_PCA071 | 72 T | C | 0 | 0.89 | 0 | 0.11 T | 0 | 0 | 0 | 1 | 3206 | 1797 CR | 0.89 | 0.0925 |
| CPCG0166 | 73 G | A | 0.75 | 0 | 0.25 | 0 A | 0.99 | 0 | 0.01 | 0 | 157 | 1517 CR | 0.24 | 0.941 |
| CPCG0098 | 146 C | C | 0 | 0.7 | 0 | 0.3 T | 0 | 0 | 0 | 1 | 7027 | 1946 CR | 0.7 | 0.661 |
| CPCG0100 | 146 C | T | 0 | 0.42 | 0 | 0.58 T | 0 | 0.01 | 0 | 0.99 | 6441 | 961 CR | 0.41 | 0.661 |
| ICGC_PCA169 | 146 C | C | 0 | 0.69 | 0 | 0.31 T | 0 | 0.2 | 0 | 0.8 | 7149 | 3256 CR | 0.49 | 0.661 |
| ICGC_PCA198 | 146 C | T | 0 | 0.18 | 0 | 0.82 C | 0 | 0.83 | 0 | 0.17 | 6081 | 1906 CR | 0.66 | 0.661 |
| CPCG0206 | 152 C | C | 0 | 0.84 | 0 | 0.16 C | 0 | 0.18 | 0 | 0.82 | 6953 | 1192 CR | 0.66 | 0.841 |
| Baca07-4610 | 152 C | T | 0 | 0.27 | 0 | 0.73 T | 0 | 0 | 0 | 1 | 1429 | 3202 CR | 0.27 | 0.841 |
| ICGC_PCA032 | 152 C | C | 0 | 0.99 | 0 | 0.01 T | 0 | 0 | 0 | 1 | 2545 | 1947 CR | 0.99 | 0.841 |
| CPCG-0204 | 183 A | G | 0.49 | 0 | 0.51 | 0 A | 1 | 0 | 0 | 0 | 4619 | 2424 CR | 0.51 | 0.0184 |
| CPCG0073 | 195 C | T | 0 | 0.26 | 0 | 0.74 T | 0 | 0 | 0 | 1 | 7698 | 1420 CR | 0.26 | 0.721 |
| CPCG0196 | 195 C | T | 0 | 0.37 | 0 | 0.63 T | 0 | 0 | 0 | 1 | 7693 | 1938 CR | 0.37 | 0.721 |
| ICGC_PCA118 | 195 C | C | 0 | 0.56 | 0 | 0.43 T | 0 | 0.11 | 0 | 0.89 | 3858 | 1854 CR | 0.46 | 0.721 |
| ICGC_PCA166 | 199 T | C | 0 | 0.86 | 0 | 0.14 T | 0 | 0.15 | 0 | 0.85 | 3353 | 1316 CR | 0.71 | 0.161 |
| ICGC_PCA015 | 207 G | G | 0.2 | 0 | 0.8 | 0 A | 0.71 | 0 | 0.29 | 0 | 3875 | 2173 CR | 0.51 | 0.15 |
| CPCG0098 | 215 A | G | 0.24 | 0 | 0.76 | 0 A | 1 | 0 | 0 | 0 | 6941 | 1904 CR | 0.76 | 0.0275 |
| CPCG0205 | 227 A | A | 0.82 | 0 | 0.18 | 0 G | 0.16 | 0 | 0.84 | 0 | 7020 | 1057 CR | 0.67 | 0.017 |
| CPCG0242 | 234 A | G | 0.19 | 0 | 0.81 | 0 A | 1 | 0 | 0 | 0 | 5708 | 1313 CR | 0.81 | 0.0218 |
| ICGC_PCA031 | 234 A | G | 0.16 | 0 | 0.84 | 0 A | 0.93 | 0 | 0.07 | 0 | 3788 | 3533 CR | 0.77 | 0.0218 |
| CPCG0070 | 248 A | A | 0.99 | 0 | 0.01 | 0 A | 0.74 | 0 | 0.26 | 0 | 7301 | 1864 CR | 0.24 | 0.00171 |
| CPCG0256 | 255 G | G | 0.44 | 0.01 | 0.55 | 0 G | 0 | 0 | 1 | 0 | 5127 | 836 CR | 0.45 | 0.00081 |
| CPCG0158 | 307 C | C | 0 | 0.64 | 0 | 0.36 C | 0 | 1 | 0 | 0 | 3733 | 418 CR | 0.36 | 0.00028 |
| CPCG0081 | 309 C | C | 0 | 0.62 | 0 | 0.38 C | 0 | 1 | 0 | 0 | 4648 | 833 CR | 0.38 | 0.00196 |
| Baca06-3199 | 309 C | T | 0 | 0.22 | 0 | 0.77 C | 0 | 0.99 | 0 | 0 | 3321 | 2031 CR | 0.77 | 0.00196 |
| CPCG0344 | 499 G | G | 0.21 | 0 | 0.78 | 0 G | 0 | 0 | 1 | 0 | 5510 | 767 CR | 0.22 | 0.129 |
| CPCG0046 | 564 G | G | 0.27 | 0.02 | 0.71 | 0 G | 0 | 0 | 1 | 0 | 5136 | 1358 CR | 0.29 | 0 |
| CPCG0342 | 564 G | A | 0.88 | 0 | 0.12 | 0 G | 0 | 0 | 1 | 0 | 7015 | 1140 CR | 0.88 | 0 |
| ICGC_PCA125 | 574 A | A | 0.83 | 0.17 | 0 | 0 A | 0.62 | 0.38 | 0 | 0 | 2350 | 2351 CR | 0.22 | 0.0064 |
| CPCG0067 | 617 G | G | 0.49 | 0 | 0.51 | 0 G | 0 | 0 | 1 | 0 | 4991 | 1353 TF | 0.49 | 0 |
| CPCG0189 | 650 T | T | 0 | 0.5 | 0 | 0.5 T | 0 | 0 | 0 | 1 | 7069 | 1697 RNR1 | 0.5 | 0.00327 |
| CPCG0189 | 690 T | T | 0 | 0.27 | 0 | 0.73 T | 0 | 0 | 0 | 1 | 7749 | 1636 RNR1 | 0.27 | 0 |
| CPCG0083 | 709 G | A | 0.56 | 0 | 0.44 | 0 G | 0 | 0 | 1 | 0 | 7699 | 2079 RNR1 | 0.32 | 0.481 |
| ICGC_PCA16 | 709 G | A | 0.61 | 0 | 0.39 | 0 G | 0.29 | 0 | 0.71 | 0 | 4203 | 2359 RNR1 | 0.32 | 0.481 |
| CPCG0073 | 719 G | G | 0.38 | 0 | 0.62 | 0 G | 0 | 0 | 1 | 0 | 7538 | 1856 RNR1 | 0.38 | 0.0371 |
| CPCG0019 | 933 G | A | 0.52 | 0 | 0.48 | 0 G | 0 | 0 | 1 | 0 | 6070 | 1334 RNR1 | 0.52 | 0 |
| CPCG0248 | 988 G | G | 0.42 | 0 | 0.58 | 0 G | 0 | 0 | 1 | 0 | 7286 | 1825 RNR1 | 0.42 | 0.00217 |
| CPCG0346 | 988 G | G | 0.38 | 0 | 0.62 | 0 G | 0 | 0 | 1 | 0 | 7487 | 2850 RNR1 | 0.38 | 0.00217 |
| EOPC-07 | 988 G | G | 0.36 | 0 | 0.64 | 0 G | 0 | 0 | 1 | 0 | 2637 | 1193 RNR1 | 0.36 | 0.00217 |
| CPCG0204 | 991 G | A | 0.66 | 0 | 0.34 | 0 G | 0 | 0 | 1 | 0 | 6944 | 3211 RNR1 | 0.66 | 0 |
| CPCG0211 | 1079 G | G | 0.26 | 0 | 0.74 | 0 G | 0 | 0 | 0.99 | 0 | 7251 | 955 RNR1 | 0.26 | 0 |
| ICGC_PCA057 | 1157 T | C | 0 | 0.53 | 0 | 0.47 T | 0 | 0 | 0 | 1 | 5267 | 3788 RNR1 | 0.53 | 0 |

TABLE 5-continued

Table of 293 somatic mtSNVs

| | | | | | | | | | | | | | | | | | |
|---|---|---|---|---|---|---|---|---|---|---|---|---|---|---|---|---|---|
| EOPC-04 | 1193 | T | T | 0 | 0.1 | 0 | 0.9 | T | 0 | 0.32 | 0 | 0.68 | 4416 | 5078 | RNR1 | 0.22 | 0.0184 |
| CPCG0090 | 1199 | G | A | 0.7 | 0 | 0.3 | 0 | G | 0 | 0 | 1 | 0 | 7220 | 1809 | RNR1 | 0.7 | 0 |
| ICGC_PCA192 | 1447 | G | G | 0.32 | 0 | 0.68 | 0 | G | 0 | 0 | 1 | 0 | 3833 | 3210 | RNR1 | 0.32 | 0 |
| ICGC_PCA032 | 1452 | T | T | 0 | 0 | 0 | 1 | C | 0 | 1 | 0 | 0 | 3591 | 2798 | RNR1 | 1 | 0.00255 |
| CPCG0185 | 1456 | T | T | 0 | 0.46 | 0 | 0.54 | T | 0 | 0 | 0 | 1 | 6988 | 1393 | RNR1 | 0.45 | 0 |
| CPCG0412 | 1469 | G | A | 0.51 | 0 | 0.49 | 0 | G | 0 | 0 | 1 | 0 | 7430 | 2608 | RNR1 | 0.51 | 0 |
| CPCG0268 | 1552 | G | G | 0.22 | 0 | 0.78 | 0 | G | 0 | 0 | 1 | 0 | 7268 | 1827 | RNR1 | 0.22 | 0 |
| CPCG0097 | 1644 | G | G | 0.25 | 0 | 0.74 | 0 | G | 0 | 0 | 1 | 0 | 7544 | 1857 | TV | 0.25 | 0 |
| ICGC_PCA103 | 1659 | T | T | 0 | 0.46 | 0 | 0.54 | T | 0 | 0 | 0 | 1 | 5490 | 3077 | TV | 0.46 | 0 |
| ICGC_PCA032 | 1716 | T | T | 0 | 0 | 0 | 1 | C | 0 | 1 | 0 | 0 | 3512 | 2843 | RNR2 | 1 | 0.00071 |
| ICGC_PCA161 | 1730 | T | C | 0 | 0.73 | 0 | 0.27 | T | 0 | 0 | 0 | 1 | 4449 | 1742 | RNR2 | 0.73 | 0 |
| ICGC_PCA075 | 1770 | G | G | 0.44 | 0 | 0.56 | 0 | G | 0 | 0 | 1 | 0 | 5071 | 4007 | RNR2 | 0.44 | 0.00024 |
| CPCG0339 | 1906 | G | A | 0.59 | 0 | 0.41 | 0 | G | 0 | 0 | 1 | 0 | 4152 | 2079 | RNR2 | 0.59 | 0 |
| CPCG0098 | 1975 | T | C | 0 | 0.77 | 0 | 0.23 | T | 0 | 0 | 0 | 1 | 7264 | 3250 | RNR2 | 0.77 | 0 |
| CPCG0100 | 2074 | A | G | 0.35 | 0 | 0.65 | 0 | A | 0.99 | 0 | 0 | 0 | 6650 | 1492 | RNR2 | 0.64 | 0 |
| CPCG0027 | 2115 | T | T | 0 | 0 | 0 | 1 | T | 0 | 0.25 | 0 | 0.75 | 7869 | 2386 | RNR2 | 0.25 | 0 |
| ICGC_PCA083 | 2269 | G | A | 0.6 | 0 | 0.4 | 0 | G | 0 | 0 | 1 | 0 | 3888 | 7545 | RNR2 | 0.6 | 0 |
| Baca05-3852 | 2333 | G | A | 0.91 | 0 | 0.09 | 0 | G | 0.03 | 0 | 0.97 | 0 | 5544 | 535 | RNR2 | 0.88 | 0 |
| CPCG0388 | 2478 | G | G | 0.36 | 0 | 0.64 | 0 | G | 0 | 0 | 1 | 0 | 6248 | 1625 | RNR2 | 0.35 | 0 |
| CPCG0183 | 2487 | A | A | 0.99 | 0 | 0 | 0 | A | 0.77 | 0.2 | 0.01 | 0.01 | 6505 | 980 | RNR2 | 0.22 | 0 |
| C2CG0081 | 2519 | G | A | 0.64 | 0 | 0.36 | 0 | G | 0 | 0 | 1 | 0 | 7720 | 2093 | RNR2 | 0.63 | 0 |
| ICGC_PCA029 | 2571 | G | G | 0.26 | 0 | 0.74 | 0 | G | 0 | 0 | 1 | 0 | 4628 | 3828 | RNR2 | 0.26 | 0 |
| CPCG0040 | 2607 | T | T | 0 | 0.26 | 0 | 0.74 | T | 0 | 0 | 0 | 1 | 7075 | 2426 | RNR2 | 0.26 | 0.00021 |
| CPCG0358 | 2634 | T | T | 0 | 0.41 | 0 | 0.59 | T | 0 | 0 | 0 | 1 | 7226 | 6151 | RNR2 | 0.41 | 0 |
| CPCG0005 | 2697 | G | G | 0.48 | 0 | 0.52 | 0 | G | 0 | 0 | 1 | 0 | 7295 | 1990 | RNR2 | 0.48 | 0 |
| ICGC_PCA182 | 2737 | T | C | 0 | 0.72 | 0 | 0.28 | T | 0 | 0 | 0 | 1 | 7240 | 3411 | RNR2 | 0.72 | 0 |
| TCGA-CH-5750 | 2817 | G | G | 0.47 | 0 | 0.53 | 0 | G | 0 | 0 | 1 | 0 | 7221 | 4353 | RNR2 | 0.47 | 0 |
| ICGC_PCA068 | 2844 | G | G | 0.5 | 0 | 0.5 | 0 | G | 0 | 0 | 1 | 0 | 5749 | 5208 | RNR2 | 0.5 | 0.00027 |
| CPCG0217 | 2894 | T | T | 0 | 0 | 0 | 1 | T | 0 | 0.24 | 0 | 0.76 | 7556 | 2046 | RNR2 | 0.24 | 0 |
| ICGC_PCA070 | 2914 | A | A | 0.69 | 0 | 0.31 | 0 | G | 0.22 | 0 | 0.78 | 0 | 5262 | 3922 | RNR2 | 0.48 | 0 |
| ICGC_PCA051 | 2916 | G | G | 0.32 | 0 | 0.68 | 0 | G | 0 | 0 | 1 | 0 | 5144 | 2334 | RNR2 | 0.32 | 0 |
| ICGC_PCA163 | 2916 | G | G | 0.44 | 0 | 0.56 | 0 | G | 0 | 0 | 1 | 0 | 6634 | 2865 | RNR2 | 0.44 | 0 |
| CPCG0331 | 2941 | G | A | 0.61 | 0 | 0.39 | 0 | G | 0 | 0 | 1 | 0 | 7516 | 2137 | RNR2 | 0.61 | 0 |
| CPCG0410 | 3022 | G | G | 0.25 | 0 | 0.75 | 0 | G | 0 | 0 | 1 | 0 | 6485 | 4343 | RNR2 | 0.25 | 0 |
| ICGC_PCA125 | 3063 | G | A | 0.69 | 0 | 0.31 | 0 | G | 0 | 0 | 1 | 0 | 7482 | 5738 | RNR2 | 0.69 | 0 |
| CPCG0324 | 3079 | G | A | 0.61 | 0 | 0.39 | 0 | G | 0 | 0 | 1 | 0 | 7139 | 1352 | RNR2 | 0.61 | 0 |
| CPCG0166 | 3174 | T | T | 0 | 0.28 | 0 | 0.72 | T | 0 | 0 | 0 | 1 | 367 | 1680 | RNR2 | 0.28 | 0 |
| CPCG0212 | 3297 | T | T | 0 | 0.23 | 0 | 0.77 | T | 0 | 0 | 0 | 1 | 5513 | 1785 | TL1 | 0.23 | 0 |
| CPCG0071 | 3492 | A | A | 0.75 | 0.24 | 0 | 0.01 | A | 0.97 | 0.03 | 0 | 0 | 4204 | 1332 | ND1 | 0.23 | 0.00194 |
| CPCG0265 | 3496 | G | G | 0.4 | 0 | 0.59 | 0 | G | 0 | 0 | 1 | 0 | 5814 | 1482 | ND1 | 0.41 | 0.00248 |
| TCGA-CH-5750 | 3526 | G | G | 0.23 | 0 | 0.77 | 0 | G | 0 | 0 | 1 | 0 | 6324 | 3582 | ND1 | 0.23 | 0 |
| CPCG0120 | 3697 | G | G | 0.35 | 0 | 0.65 | 0 | G | 0 | 0 | 1 | 0 | 3441 | 2086 | ND1 | 0.35 | 0 |
| CPCG0063 | 3842 | G | G | 0.22 | 0 | 0.77 | 0 | G | 0 | 0 | 1 | 0 | 6812 | 2780 | ND1 | 0.23 | 0 |
| ICGC_PCA122 | 3842 | G | G | 0.45 | 0 | 0.55 | 0 | G | 0 | 0 | 1 | 0 | 6541 | 3027 | ND1 | 0.45 | 0 |
| ICGC_PCA187 | 3842 | G | G | 0.21 | 0 | 0.79 | 0 | G | 0 | 0 | 1 | 0 | 5568 | 7177 | ND1 | 0.21 | 0 |
| CPCG0127 | 3946 | G | G | 0.22 | 0 | 0.78 | 0 | G | 0 | 0 | 1 | 0 | 6769 | 1093 | ND1 | 0.22 | 0.00011 |
| CPCG0233 | 3946 | G | G | 0.4 | 0 | 0.6 | 0 | G | 0 | 0 | 1 | 0 | 5649 | 2007 | ND1 | 0.4 | 0.00011 |
| ICGC_PCA125 | 3959 | G | G | 0.36 | 0 | 0.63 | 0 | G | 0 | 0 | 1 | 0 | 6863 | 4509 | ND1 | 0.36 | 0 |
| CPCG0213 | 3982 | G | G | 0.22 | 0 | 0.78 | 0 | G | 0 | 0 | 1 | 0 | 7271 | 1878 | ND1 | 0.22 | 0 |
| Baca05-3852 | 4053 | A | G | 0.34 | 0 | 0.65 | 0 | A | 0.96 | 0 | 0.03 | 0 | 3456 | 1689 | ND1 | 0.62 | 0.00103 |
| CPCG0027 | 4142 | G | A | 0.59 | 0 | 0.41 | 0 | G | 0 | 0 | 1 | 0 | 6519 | 580 | ND1 | 0.59 | 0 |

TABLE 5-continued

Table of 293 somatic mtSNVs

| | | | | | | | | | | | | | | | | | |
|---|---|---|---|---|---|---|---|---|---|---|---|---|---|---|---|---|---|
| TCGA-EJ-5506 | 4142 | G | G | 0.21 | 0 | 0.79 | 0 | G | 0 | 0 | 0.99 | 0 | 4987 | 2746 | ND1 | 0.21 | 0 |
| CPCG0003 | 4201 | G | G | 0.24 | 0 | 0.76 | 0 | G | 0 | 0 | 1 | 0 | 6785 | 632 | ND1 | 0.24 | 0 |
| CPCG0067 | 4231 | A | G | 0.58 | 0 | 0.42 | 0 | A | 1 | 0 | 0 | 0 | 2905 | 1230 | ND1 | 0.42 | 0.00257 |
| ICGC_PCA098 | 4233 | T | C | 0 | 0.53 | 0 | 0.47 | T | 0 | 0 | 0 | 1 | 3721 | 2957 | ND1 | 0.53 | 0.00147 |
| CPCG0067 | 4407 | G | A | 0.63 | 0 | 0.36 | 0 | G | 0 | 0 | 1 | 0 | 6634 | 1169 | TM | 0.64 | 0 |
| CPCG0387 | 4436 | C | C | 0 | 0.56 | 0 | 0.44 | C | 0 | 1 | 0 | 0 | 7674 | 4629 | TM | 0.44 | 0 |
| CPCG0262 | 4482 | G | G | 0.27 | 0 | 0.73 | 0 | G | 0 | 0 | 1 | 0 | 7254 | 1360 | ND2 | 0.27 | 0 |
| ICGC_PCA171 | 4491 | G | G | 0.46 | 0 | 0.54 | 0 | G | 0 | 0 | 1 | 0 | 7144 | 4922 | ND2 | 0.46 | 0.0858 |
| CPCG0204 | 4596 | G | A | 0.68 | 0 | 0.32 | 0 | G | 0 | 0 | 1 | 0 | 4280 | 1516 | ND2 | 0.68 | 0.00408 |
| CPCG0117 | 4648 | T | T | 0 | 0.36 | 0 | 0.63 | T | 0 | 0 | 0 | 1 | 7586 | 1489 | ND2 | 0.36 | 0 |
| CPCG0407 | 4770 | G | A | 0.75 | 0 | 0.25 | 0 | G | 0 | 0 | 1 | 0 | 7113 | 2902 | ND2 | 0.75 | 0 |
| EOPC-03 | 4831 | G | A | 0.61 | 0 | 0.39 | 0 | G | 0 | 0 | 1 | 0 | 7611 | 2736 | ND2 | 0.61 | 0 |
| CPCG0409 | 4858 | T | C | 0 | 0.6 | 0 | 0.4 | T | 0 | 0 | 0 | 1 | 7397 | 2673 | ND2 | 0.6 | 0 |
| CPCG0071 | 4887 | T | T | 0 | 0.49 | 0 | 0.5 | T | 0 | 0 | 0 | 1 | 6739 | 2006 | ND2 | 0.5 | 0 |
| CPCG0339 | 4905 | T | C | 0 | 0.67 | 0 | 0.33 | T | 0 | 0 | 0 | 1 | 7113 | 1937 | ND2 | 0.67 | 0 |
| CPCG0046 | 4920 | G | G | 0.25 | 0 | 0.72 | 0.03 | G | 0 | 0 | 1 | 0 | 288 | 1559 | ND2 | 0.28 | 0 |
| ICGC_PCA142 | 4958 | A | A | 0.96 | 0 | 0.04 | 0 | A | 0.74 | 0 | 0.26 | 0 | 7261 | 4736 | ND2 | 0.22 | 0.0118 |
| CPCG0201 | 5115 | T | C | 0 | 0.9 | 0 | 0.1 | T | 0 | 0 | 0 | 1 | 7055 | 3046 | ND2 | 0.9 | 0 |
| CPCG0020 | 5195 | C | C | 0.05 | 0.95 | 0 | 0 | C | 0.44 | 0.56 | 0 | 0 | 7404 | 1841 | ND2 | 0.39 | 0.00086 |
| CPCG0267 | 5227 | G | G | 0.28 | 0 | 0.72 | 0 | G | 0 | 0 | 1 | 0 | 6248 | 1665 | ND2 | 0.28 | 0 |
| ICGC_PCA185 | 5301 | A | A | 0.66 | 0 | 0.34 | 0 | G | 0.41 | 0 | 0.59 | 0 | 7102 | 4152 | ND2 | 0.24 | 0.0256 |
| CPCG0242 | 5511 | T | C | 0 | 0.82 | 0 | 0.17 | T | 0 | 0 | 0 | 1 | 7001 | 2241 | ND2 | 0.83 | 0 |
| ICGC_PCA013 | 5521 | G | A | 0.53 | 0 | 0.47 | 0 | G | 0 | 0 | 1 | 0 | 7020 | 3818 | TW | 0.53 | 0 |
| ICGC_PCA140 | 5774 | T | C | 0 | 0.61 | 0 | 0.39 | T | 0 | 0 | 0 | 1 | 6911 | 4936 | OLR/TC | 0.61 | 0.0118 |
| EOPC-07 | 5814 | T | C | 0 | 0.86 | 0 | 0.14 | T | 0 | 0 | 0 | 1 | 4007 | 1500 | TC | 0.86 | 0.0097 |
| CPCG0350 | 5910 | G | A | 0.67 | 0 | 0.33 | 0 | G | 0 | 0 | 1 | 0 | 6052 | 1047 | CO1 | 0.67 | 0.0058 |
| TCGA-G9-6336 | 5979 | G | G | 0.48 | 0 | 0.52 | 0 | G | 0 | 0 | 1 | 0 | 6381 | 1569 | CO1 | 0.48 | 0.00634 |
| CPCG0356 | 6020 | C | C | 0 | 0.91 | 0 | 0.09 | T | 0 | 0.42 | 0 | 0.57 | 7024 | 4267 | CO1 | 0.48 | 0.00462 |
| ICGC_PCA048 | 6046 | T | T | 0 | 0.28 | 0 | 0.72 | T | 0 | 0 | 0 | 1 | 5163 | 4643 | CO1 | 0.28 | 0 |
| CPCG0050 | 6054 | G | G | 0.21 | 0 | 0.79 | 0 | A | 0.87 | 0 | 0.13 | 0 | 5512 | 1528 | CO1 | 0.66 | 0.00066 |
| CPCG0189 | 6270 | G | G | 0.24 | 0 | 0.76 | 0 | G | 0 | 0 | 1 | 0 | 7176 | 1576 | CO1 | 0.24 | 0 |
| CPCG0251 | 6276 | G | A | 0.87 | 0 | 0.13 | 0 | G | 0.45 | 0 | 0.55 | 0 | 7014 | 1437 | CO1 | 0.42 | 0 |
| TCGA-G9-6336 | 6321 | G | A | 0.5 | 0 | 0.5 | 0 | G | 0 | 0 | 1 | 0 | 7462 | 1839 | CO1 | 0.5 | 0 |
| CPCG0123 | 6419 | A | A | 1 | 0 | 0 | 0 | A | 0.8 | 0.18 | 0.01 | 0.01 | 6441 | 1175 | CO1 | 0.2 | 0 |
| CPCG0211 | 6419 | A | A | 1 | 0 | 0 | 0 | A | 0.77 | 0.21 | 0.01 | 0 | 6273 | 552 | CO1 | 0.23 | 0 |
| CPCG0102 | 6496 | C | T | 0 | 0.42 | 0 | 0.58 | C | 0 | 1 | 0 | 0 | 6397 | 3188 | CO1 | 0.58 | 0 |
| CPCG0124 | 6664 | T | C | 0 | 0.8 | 0 | 0.2 | T | 0 | 0.44 | 0 | 0.56 | 7058 | 1440 | CO1 | 0.36 | 0 |
| ICGC_PCA060 | 6718 | G | A | 0.53 | 0 | 0.47 | 0 | G | 0 | 0 | 1 | 0 | 7205 | 7567 | CO1 | 0.53 | 0 |
| CPCG0096 | 6742 | T | C | 0 | 0.66 | 0 | 0.34 | T | 0 | 0 | 0 | 1 | 6034 | 2223 | CO1 | 0.66 | 0 |
| CPCG0331 | 6856 | T | C | 0 | 0.6 | 0 | 0.4 | T | 0 | 0 | 0 | 1 | 7235 | 1771 | CO1 | 0.6 | 0 |
| CPCG0090 | 6892 | G | A | 0.51 | 0 | 0.49 | 0 | G | 0 | 0 | 1 | 0 | 6649 | 1932 | CO1 | 0.51 | 0 |
| CPCG0189 | 6944 | T | T | 0 | 0.26 | 0 | 0.74 | T | 0 | 0 | 0 | 1 | 7555 | 1925 | CO1 | 0.25 | 0.00103 |
| ICGC_PCA155 | 7026 | G | G | 0.4 | 0 | 0.6 | 0 | G | 0 | 0 | 1 | 0 | 6855 | 819 | CO1 | 0.4 | 0 |
| EOPC-010 | 7293 | G | G | 0.25 | 0 | 0.75 | 0 | G | 0 | 0 | 1 | 0 | 7413 | 2975 | CO1 | 0.25 | 0 |
| ICGC_PCA029 | 7393 | G | G | 0.24 | 0 | 0.76 | 0 | G | 0 | 0 | 1 | 0 | 3325 | 2640 | CO1 | 0.24 | 0 |
| EOPC-010 | 7554 | G | G | 0.25 | 0 | 0.75 | 0 | G | 0 | 0 | 1 | 0 | 4490 | 1572 | TD | 0.25 | 0 |
| CPCG0124 | 7772 | A | G | 0.19 | 0 | 0.81 | 0 | A | 0.55 | 0 | 0.45 | 0 | 6491 | 1205 | CO2 | 0.36 | 0.0011 |
| ICCC_PCA156 | 7803 | T | T | 0 | 0.37 | 0 | 0.63 | T | 0 | 0 | 0 | 1 | 7302 | 3926 | CO2 | 0.37 | 0 |
| CPCG0378 | 7919 | G | G | 0.26 | 0 | 0.74 | 0 | G | 0 | 0 | 1 | 0 | 6772 | 5709 | CO2 | 0.26 | 0 |
| CPCG0266 | 7929 | G | G | 0 | 0 | 0.98 | 0.02 | G | 0 | 0 | 0.75 | 0.25 | 7012 | 1479 | CO2 | 0.23 | 0 |

TABLE 5-continued

Table of 293 somatic mtSNVs

| | | | | | | | | | | | | | | | | | |
|---|---|---|---|---|---|---|---|---|---|---|---|---|---|---|---|---|---|
| ICGC_PCA123 | 7997 | G | A | 0.59 | 0 | 0.41 | 0 | G | 0 | 0 | 1 | 0 | 7456 | 5877 | CO2 | 0.58 | 0 |
| ICGC_PCA023 | 8078 | G | G | 0.24 | 0 | 0.76 | 0 | G | 0 | 0 | 1 | 0 | 6794 | 6873 | CO2 | 0.24 | 0.00189 |
| ICGC_PCA174 | 8348 | A | G | 0.14 | 0 | 0.86 | 0 | G | 0.35 | 0 | 0.65 | 0 | 6855 | 3534 | TK | 0.21 | 0.00857 |
| CPCG0345 | 8391 | G | G | 0.32 | 0 | 0.68 | 0 | G | 0 | 0 | 1 | 0 | 7322 | 1822 | ATP8 | 0.32 | 0 |
| CPCG0103 | 8393 | C | T | 0 | 0.2 | 0 | 0.8 | C | 0 | 0.99 | 0 | 0 | 6860 | 2618 | ATP8 | 0.79 | 0.0246 |
| CPCG0196 | 8433 | T | T | 0 | 0.37 | 0 | 0.63 | T | 0 | 0 | 0 | 1 | 6447 | 2231 | ATP8 | 0.37 | 0.00559 |
| ICGC_PCA193 | 8547 | T | C | 0 | 0.54 | 0 | 0.46 | T | 0 | 0 | 0 | 1 | 5751 | 3664 | ATP8/ ATP6 | 0.54 | 0.00156 |
| CPCG0063 | 8643 | C | T | 0 | 0.1 | 0 | 0.9 | C | 0 | 0.63 | 0 | 0.37 | 6261 | 2790 | ATP6 | 0.53 | 0 |
| ICGC_PCA029 | 8697 | G | G | 0.32 | 0 | 0.68 | 0 | G | 0 | 0 | 1 | 0 | 5997 | 5168 | ATP6 | 0.32 | 0.201 |
| CPCG0082 | 8705 | T | C | 0 | 0.97 | 0 | 0.03 | T | 0 | 0.49 | 0 | 0.51 | 7435 | 1975 | ATP6 | 0.47 | 0.0283 |
| CPCG0217 | 8843 | T | T | 0 | 0 | 0 | 1 | T | 0 | 0.25 | 0 | 0.75 | 7444 | 2102 | ATP6 | 0.25 | 0.0274 |
| Berger3043 | 8999 | T | C | 0 | 0.9 | 0 | 0.1 | T | 0 | 0 | 0 | 1 | 5909 | 1314 | ATP6 | 0.9 | 0.00083 |
| CPCG0380 | 9182 | G | A | 0.62 | 0 | 0.38 | 0 | G | 0 | 0 | 1 | 0 | 7258 | 3467 | ATP6 | 0.62 | 0.00511 |
| ICGC_PCA026 | 9185 | T | T | 0 | 0.21 | 0 | 0.79 | T | 0 | 0 | 0 | 1 | 5862 | 2491 | ATP6 | 0.21 | 0.00053 |
| ICGC_PCA166 | 9378 | T | T | 0 | 0.41 | 0 | 0.59 | T | 0 | 0 | 0 | 1 | 6300 | 2166 | CO3 | 0.41 | 0 |
| CPCG0349 | 9380 | G | A | 0.8 | 0 | 0.2 | 0 | G | 0.19 | 0 | 0.81 | 0 | 7132 | 3251 | CO3 | 0.61 | 0.0812 |
| CPCG0262 | 9504 | G | A | 0.84 | 0 | 0.16 | 0 | G | 0 | 0 | 1 | 0 | 7125 | 1416 | CO3 | 0.84 | 0 |
| CPCG0234 | 9516 | T | T | 0 | 0.34 | 0 | 0.66 | T | 0 | 0 | 0 | 1 | 4614 | 1440 | CO3 | 0.34 | 0 |
| CPCG0070 | 9628 | G | A | 0.59 | 0 | 0.41 | 0 | G | 0 | 0 | 1 | 0 | 7552 | 3285 | CO3 | 0.59 | 0 |
| CPCG0089 | 9673 | G | G | 0.12 | 0.09 | 0.79 | 0 | G | 0 | 0 | 1 | 0 | 1850 | 3343 | CO3 | 0.21 | 0 |
| CPCG0269 | 9786 | G | G | 0.28 | 0 | 0.72 | 0 | G | 0 | 0 | 1 | 0 | 4745 | 1771 | CO3 | 0.28 | 0 |
| CPCG0356 | 9797 | T | T | 0 | 0.22 | 0 | 0.78 | C | 0 | 0.59 | 0 | 0.41 | 7503 | 4975 | CO3 | 0.37 | 0.00103 |
| CPCG0072 | 9804 | G | G | 0.27 | 0 | 0.73 | 0 | A | 0.8 | 0 | 0.2 | 0 | 7079 | 2208 | CO3 | 0.53 | 0.0198 |
| CPCG0249 | 9840 | T | C | 0 | 0.78 | 0 | 0.22 | T | 0 | 0 | 0 | 1 | 7215 | 1259 | CO3 | 0.78 | 0.00141 |
| ICGC_PCA086 | 9891 | T | T | 0 | 0.38 | 0 | 0.62 | T | 0 | 0 | 0 | 1 | 7088 | 2008 | CO3 | 0.38 | 0.00197 |
| ICGC_PCA095 | 9977 | T | T | 0 | 0.4 | 0 | 0.6 | T | 0 | 0 | 0 | 1 | 5302 | 2570 | CO3 | 0.4 | 0.00221 |
| ICGC_PCA193 | 10014 | G | A | 0.53 | 0 | 0.47 | 0 | G | 0 | 0 | 1 | 0 | 6772 | 4094 | TG | 0.53 | 0 |
| CPCG0128 | 10029 | A | A | 0.94 | 0 | 0.06 | 0 | A | 0.66 | 0 | 0.34 | 0 | 7724 | 1809 | TG | 0.27 | 0.002 |
| ICGC_PCA036 | 10182 | G | A | 0.76 | 0 | 0.24 | 0 | G | 0 | 0 | 1 | 0 | 6512 | 3122 | ND3 | 0.76 | 0 |
| CPCG0114 | 10277 | A | A | 0.97 | 0.03 | 0 | 0 | A | 0.69 | 0.3 | 0 | 0 | 2378 | 238 | ND3 | 0.28 | 0 |
| CPCG0166 | 10277 | A | A | 0.76 | 0.24 | 0 | 0 | A | 0.99 | 0.01 | 0 | 0 | 153 | 980 | ND3 | 0.22 | 0 |
| CPCG0211 | 10277 | A | A | 0.99 | 0.01 | 0 | 0 | A | 0.78 | 0.2 | 0 | 0.01 | 6462 | 499 | ND3 | 0.22 | 0 |
| EOPC-07 | 10558 | T | T | 0 | 0.4 | 0 | 0.6 | T | 0 | 0 | 0 | 1 | 5874 | 1890 | ND4L | 0.4 | 0 |
| CPCG0407 | 10586 | G | A | 0.77 | 0 | 0.23 | 0 | G | 0 | 0 | 1 | 0 | 6878 | 3234 | ND4L | 0.77 | 0.0365 |
| CPCG0256 | 10790 | T | T | 0 | 0.4 | 0 | 0.6 | T | 0 | 0 | 0 | 1 | 7519 | 2396 | ND4 | 0.4 | 0.00812 |
| CPCG0331 | 10800 | T | T | 0 | 0 | 0.26 | 0.74 | T | 0 | 0 | 0 | 1 | 7132 | 2482 | ND4 | 0.26 | 0 |
| CPCG0340 | 10866 | T | T | 0 | 0 | 0 | 1 | C | 0 | 0.5 | 0 | 0.5 | 7598 | 3995 | ND4 | 0.5 | 0 |
| CPCG0324 | 11150 | G | A | 0.24 | 0 | 0.76 | 0 | G | 0 | 0 | 1 | 0 | 7196 | 1616 | ND4 | 0.24 | 0.0111 |
| CPCG0040 | 11343 | T | C | 0 | 0.77 | 0 | 0.23 | T | 0 | 0 | 0 | 1 | 7313 | 2729 | ND4 | 0.77 | 0 |
| Berger0508 | 11493 | G | G | 0.33 | 0 | 0.67 | 0 | G | 0 | 0 | 1 | 0 | 4134 | 2002 | ND4 | 0.33 | 0 |
| Berger0508 | 11592 | G | A | 0.9 | 0 | 0.1 | 0 | G | 0 | 0 | 1 | 0 | 6491 | 2191 | ND4 | 0.89 | 0.00028 |
| CPCG0046 | 11651 | G | A | 0.85 | 0 | 0.15 | 0 | G | 0.16 | 0 | 0.84 | 0 | 6313 | 1618 | ND4 | 0.69 | 0 |
| CPCG0377 | 11711 | G | C | 0 | 0.72 | 0.28 | 0 | G | 0 | 0 | 1 | 0 | 6420 | 4942 | ND4 | 0.72 | 0.00031 |
| ICGC_PCA041 | 11711 | G | G | 0.48 | 0 | 0.52 | 0 | G | 0 | 0 | 1 | 0 | 2870 | 4121 | ND4 | 0.48 | 0.00031 |
| ICGC_PCA032 | 11788 | C | T | 0 | 0 | 1 | 1 | C | 0 | 1 | 0 | 0 | 3705 | 3293 | ND4 | 1 | 0.00765 |
| CPCG0410 | 11814 | T | C | 0 | 0.54 | 0 | 0.46 | T | 0 | 0 | 0 | 1 | 7377 | 4888 | ND4 | 0.54 | 0 |
| CPCG0103 | 11852 | G | G | 0.22 | 0 | 0.78 | 0 | G | 0 | 0 | 1 | 0 | 4684 | 2047 | ND4 | 0.21 | 0.00133 |
| CPCG0374 | 11878 | T | C | 0 | 0.57 | 0 | 0.43 | T | 0 | 0 | 0 | 1 | 7671 | 5544 | ND4 | 0.57 | 0.00517 |
| ICGC_PCA081 | 11940 | T | C | 0 | 0.54 | 0 | 0.46 | T | 0 | 0 | 0 | 1 | 4677 | 2560 | ND4 | 0.54 | 0.00031 |
| CPCG0095 | 11949 | G | G | 0.27 | 0 | 0.73 | 0 | G | 0 | 0 | 1 | 0 | 7450 | 2951 | ND4 | 0.27 | 0 |

TABLE 5-continued

Table of 293 somatic mtSNVs

| | | | | | | | | | | | | | | | | | |
|---|---|---|---|---|---|---|---|---|---|---|---|---|---|---|---|---|---|
| CPCG0076 | 12028 | T | T | 0 | 0.29 | 0 | 0.71 | C | 0 | 0.7 | 0 | 0.3 | 4736 | 1587 | ND4 | 0.4 | 0.00362 |
| Berger0508 | 12173 | T | C | 0 | 0.86 | 0 | 0.14 | T | 0 | 0 | 0 | 1 | 6497 | 2589 | TH | 0.86 | 0.00019 |
| CPCG0114 | 12276 | G | G | 0 | 0 | 1 | 0 | A | 0.57 | 0 | 0.43 | 0 | 3186 | 5946 | TL2 | 0.57 | 0 |
| ICGC_PCA161 | 12291 | T | T | 0 | 0.45 | 0 | 0.55 | T | 0 | 0.03 | 0 | 0.97 | 4292 | 1590 | TL2 | 0.43 | 0 |
| CPCG0201 | 12312 | T | C | 0 | 0.68 | 0 | 0.32 | T | 0 | 0 | 0 | 1 | 7591 | 2761 | TL2 | 0.68 | 0.00029 |
| CPCG0361 | 12501 | G | G | 0.26 | 0 | 0.74 | 0 | G | 0 | 0 | 1 | 0 | 7551 | 4234 | ND5 | 0.26 | 0.1 |
| BacaSTID 0000002872 | 12634 | A | A | 0.84 | 0 | 0.16 | 0 | G | 0.01 | 0 | 0.99 | 0 | 183 | 1474 | ND5 | 0.83 | 0.015 |
| ICGC_PCA065 | 12648 | A | C | 0.3 | 0.7 | 0 | 0 | A | 0.65 | 0.35 | 0 | 0 | 7408 | 1300 | ND5 | 0.35 | 0.00279 |
| CPCG0242 | 12651 | G | G | 0.21 | 0 | 0.79 | 0 | G | 0 | 0 | 1 | 0 | 7601 | 2456 | ND5 | 0.21 | 0.0141 |
| CPCG0030 | 12698 | T | T | 0 | 0.24 | 0 | 0.76 | T | 0 | 0 | 0 | 1 | 7622 | 1873 | ND5 | 0.24 | 0 |
| CPCG0352 | 12700 | C | A | 0.55 | 0.45 | 0 | 0 | C | 0 | 1 | 0 | 0 | 7357 | 4405 | ND5 | 0.55 | 0 |
| CPCG0336 | 12758 | T | C | 0 | 0.54 | 0 | 0.46 | T | 0 | 0 | 0 | 1 | 7419 | 2631 | ND5 | 0.54 | 0 |
| CPCG0030 | 12758 | T | T | 0 | 0.24 | 0 | 0.76 | T | 0 | 0 | 0 | 1 | 7629 | 1932 | ND5 | 0.24 | 0 |
| CPCG0236 | 12763 | G | A | 0.75 | 0 | 0.25 | 0 | G | 0 | 0 | 1 | 0 | 6877 | 2433 | ND5 | 0.75 | 0 |
| Baca09-37 | 12769 | G | A | 0.76 | 0 | 0.24 | 0 | G | 0.01 | 0 | 0.99 | 0 | 6642 | 6007 | ND5 | 0.75 | 0 |
| IGGC_PCA168 | 12818 | G | G | 0.28 | 0 | 0.72 | 0 | G | 0 | 0 | 1 | 0 | 6759 | 4656 | ND5 | 0.28 | 0 |
| Berger3043 | 12980 | G | G | 0.46 | 0 | 0.54 | 0 | G | 0 | 0 | 1 | 0 | 5006 | 990 | ND5 | 0.46 | 0 |
| CPCG0232 | 13121 | G | A | 0.58 | 0 | 0.42 | 0 | G | 0 | 0 | 1 | 0 | 6628 | 1541 | ND5 | 0.58 | 0 |
| CPCG0234 | 13143 | T | C | 0 | 0.61 | 0 | 0.39 | T | 0 | 0 | 0 | 1 | 295 | 1454 | ND5 | 0.61 | 0.00461 |
| Baca06-1749 | 13227 | C | C | 0 | 0.59 | 0 | 0.41 | C | 0 | 1 | 0 | 0 | 7251 | 3030 | ND5 | 0.41 | 0.00031 |
| ICGC_PCA036 | 13289 | G | A | 0.76 | 0 | 0.24 | 0 | G | 0 | 0 | 1 | 0 | 6801 | 4156 | ND5 | 0.76 | 0 |
| CPCG0379 | 13368 | G | A | 0.86 | 0 | 0.14 | 0 | A | 0.5 | 0 | 0.5 | 0 | 7201 | 3751 | ND5 | 0.35 | 0.211 |
| ICGC_PCA180 | 13463 | G | A | 0.77 | 0 | 0.23 | 0 | G | 0 | 0 | 1 | 0 | 6979 | 2001 | ND5 | 0.77 | 0 |
| Baca05-3595 | 13466 | G | A | 0.55 | 0 | 0.44 | 0 | G | 0 | 0 | 1 | 0 | 6961 | 2522 | ND5 | 0.56 | 0.00236 |
| CPCG0213 | 13484 | T | C | 0 | 0.54 | 0 | 0.46 | T | 0 | 0 | 0 | 1 | 7171 | 2098 | ND5 | 0.54 | 0 |
| CPCG0166 | 13507 | T | T | 0 | 0.22 | 0 | 0.78 | T | 0 | 0 | 0 | 1 | 7083 | 1554 | ND5 | 0.22 | 0 |
| CPCG0166 | 13543 | T | T | 0 | 0.2 | 0 | 0.79 | T | 0 | 0 | 0 | 1 | 398 | 1424 | ND5 | 0.21 | 0.0003 |
| CPCG0046 | 13568 | T | T | 0 | 0 | 0 | 1 | T | 0 | 0.35 | 0 | 0.65 | 6727 | 1402 | ND5 | 0.35 | 0 |
| ICGC_PCA075 | 13759 | G | A | 0.75 | 0 | 0.25 | 0 | G | 0.5 | 0 | 0.5 | 0 | 3756 | 3035 | ND5 | 0.25 | 0.114 |
| ICGC_PCA170 | 13888 | T | T | 0 | 0.23 | 0 | 0.77 | T | 0 | 0 | 0 | 1 | 7154 | 2599 | ND5 | 0.23 | 0 |
| CPCG0190 | 13895 | T | T | 0 | 0.46 | 0 | 0.54 | T | 0 | 0 | 0 | 1 | 7560 | 2513 | ND5 | 0.46 | 0.00027 |
| CPCG0217 | 13913 | T | T | 0 | 0.3 | 0 | 0.7 | T | 0 | 0 | 0 | 1 | 7275 | 1953 | ND5 | 0.3 | 0 |
| CPCG0410 | 13918 | T | C | 0 | 0.79 | 0 | 0.21 | T | 0 | 0.03 | 0 | 0.97 | 7279 | 4769 | ND5 | 0.76 | 0 |
| Baca05-1657 | 13928 | G | A | 0.62 | 0 | 0.38 | 0 | G | 0 | 0 | 1 | 0 | 6778 | 3786 | ND5 | 0.62 | 0.186 |
| CPCG0237 | 14002 | A | A | 1 | 0 | 0 | 0 | A | 0.78 | 0 | 0.22 | 0 | 7437 | 1036 | ND5 | 0.22 | 0.0164 |
| Berger3043 | 14151 | T | C | 0 | 0.88 | 0 | 0.12 | T | 0 | 0 | 0 | 1 | 6560 | 1893 | ND6 | 0.41 | 0 |
| CPCG0372 | 14172 | T | T | 0 | 0.41 | 0 | 0.59 | T | 0 | 0 | 0 | 1 | 7566 | 3645 | ND6 | 0.41 | 0 |
| EOPC-07 | 14560 | G | G | 0.1 | 0 | 0.9 | 0 | A | 0.7 | 0 | 0.3 | 0 | 4980 | 1721 | ND6 | 0.6 | 0.0729 |
| CPCG0249 | 14638 | T | C | 0 | 0.76 | 0 | 0.24 | T | 0 | 0 | 0 | 1 | 7357 | 1129 | ND6 | 0.76 | 0 |
| Baca07-4941 | 14831 | G | G | 0.29 | 0 | 0.71 | 0 | G | 0 | 0 | 1 | 0 | 3170 | 1959 | CYB | 0.29 | 0.0136 |
| CPCG0340 | 14846 | G | A | 0.88 | 0 | 0.12 | 0 | G | 0 | 0 | 1 | 0 | 7024 | 3083 | CYB | 0.88 | 0 |
| CPCG0387 | 14889 | G | G | 0.32 | 0 | 0.68 | 0 | G | 0 | 0 | 1 | 0 | 7477 | 5472 | CYB | 0.32 | 0 |
| CPCG0346 | 14985 | G | G | 0.25 | 0 | 0.75 | 0 | G | 0 | 0 | 1 | 0 | 4764 | 2409 | CYB | 0.25 | 0 |
| CPCG0078 | 15039 | T | C | 0 | 0.61 | 0 | 0.39 | T | 0 | 0 | 0 | 1 | 7038 | 1289 | CYB | 0.61 | 0.00033 |
| CPCG0355 | 15045 | G | G | 0.25 | 0 | 0.75 | 0 | G | 0 | 0 | 1 | 0 | 6335 | 1368 | CYB | 0.24 | 0.00031 |
| CPCG0412 | 15045 | G | G | 0.31 | 0 | 0.69 | 0 | G | 0 | 0 | 1 | 0 | 4519 | 2562 | CYB | 0.31 | 0.00031 |
| Baca08-4154 | 15229 | T | T | 0 | 0.07 | 0 | 0.93 | C | 0 | 0.71 | 0 | 0.28 | 221 | 5590 | CYB | 0.64 | 0.0067 |
| ICGC_PCA198 | 15323 | G | A | 0.66 | 0 | 0.34 | 0 | G | 0.01 | 0 | 0.99 | 0 | 7015 | 2528 | CYB | 0.65 | 0.0185 |
| CPCG0067 | 15375 | G | G | 0.24 | 0 | 0.76 | 0 | G | 0 | 0 | 1 | 0 | 4219 | 1679 | CYB | 0.24 | 0 |
| Berger3027 | 15446 | C | T | 0 | 0.13 | 0 | 0.87 | C | 0 | 0.52 | 0 | 0.48 | 4499 | 1352 | CYB | 0.39 | 0 |

TABLE 5-continued

Table of 293 somatic mtSNVs

| | | | | | | | | | | | | | | | | | |
|---|---|---|---|---|---|---|---|---|---|---|---|---|---|---|---|---|---|
| Baca03-1426 | 15498 | G | G | 0.25 | 0 | 0.75 | 0 | G | 0 | 0 | 1 | 0 | 6803 | 4209 | CYB | 0.25 | 0.00271 |
| CPCG0057 | 15661 | C | T | 0 | 0.27 | 0 | 0.73 | C | 0 | 1 | 0 | 0 | 7107 | 2735 | CYB | 0.73 | 0.003 |
| CPCG0412 | 15708 | G | G | 0.37 | 0 | 0.63 | 0 | G | 0 | 0 | 1 | 0 | 7517 | 2739 | CYB | 0.37 | 0 |
| CPCG0269 | 15731 | G | A | 0.62 | 0 | 0.38 | 0 | G | 0 | 0 | 1 | 0 | 7524 | 1818 | CYB | 0.62 | 0.00907 |
| CPCG0213 | 15762 | G | G | 0.28 | 0 | 0.72 | 0 | G | 0 | 0 | 1 | 0 | 7336 | 2332 | CYB | 0.28 | 0 |
| CPCG0269 | 15817 | A | G | 0.27 | 0 | 0.73 | 0 | A | 0.83 | 0 | 0.17 | 0 | 7399 | 1904 | CYB | 0.56 | 0.0137 |
| CPCG0356 | 15884 | G | A | 0.7 | 0 | 0.3 | 0 | G | 0.16 | 0 | 0.84 | 0 | 7391 | 5417 | CYB | 0.54 | 0.126 |
| CPCG0098 | 15924 | A | A | 0.97 | 0 | 0.03 | 0 | A | 0.76 | 0 | 0.24 | 0 | 7718 | 3054 | TT | 0.22 | 0.137 |
| CPCG0233 | 15986 | G | A | 0.81 | 0 | 0.19 | 0 | G | 0 | 0 | 1 | 0 | 7280 | 2657 | TP | 0.81 | 0 |
| ICGC_PCA180 | 16000 | G | G | 0.07 | 0 | 0.93 | 0 | G | 0.34 | 0 | 0.66 | 0 | 7261 | 2185 | TP | 0.28 | 0.00565 |
| ICGC_PCA091 | 16008 | T | T | 0 | 0.28 | 0 | 0.72 | T | 0 | 0 | 0 | 1 | 5566 | 6514 | TP | 0.28 | 0 |
| ICGC_PCA193 | 16012 | A | G | 0.39 | 0 | 0.61 | 0 | A | 1 | 0 | 0 | 0 | 5964 | 4106 | TP | 0.61 | 0 |
| CPCG0404 | 16027 | T | C | 0 | 0.84 | 0 | 0.15 | T | 0 | 0 | 0 | 1 | 6955 | 5096 | CR | 0.85 | 0 |
| CPCG0001 | 16035 | G | G | 0.23 | 0 | 0.77 | 0 | G | 0 | 0 | 1 | 0 | 5872 | 1725 | CR | 0.23 | 0 |
| ICGC_PCA098 | 16035 | G | G | 0.22 | 0 | 0.78 | 0 | G | 0 | 0 | 1 | 0 | 5399 | 4407 | CR | 0.22 | 0 |
| CPCG0269 | 16048 | G | G | 0.16 | 0 | 0.84 | 0 | G | 0.41 | 0 | 0.58 | 0 | 7225 | 1653 | CR | 0.25 | 0.0148 |
| CPCG0250 | 16051 | A | G | 0.44 | 0 | 0.56 | 0 | A | 0.77 | 0 | 0.23 | 0 | 6934 | 2719 | CR | 0.33 | 0.112 |
| CPCG0040 | 16086 | T | C | 0 | 0.69 | 0 | 0.3 | C | 0 | 1 | 0 | 0 | 7485 | 1734 | CR | 0.3 | 0.0679 |
| CPCG0128 | 16092 | T | T | 0 | 0.17 | 0 | 0.83 | C | 0 | 0.96 | 0 | 0.04 | 7595 | 1451 | CR | 0.79 | 0.0481 |
| CPCG0189 | 16093 | T | C | 0 | 0.72 | 0 | 0.28 | C | 0 | 0.96 | 0 | 0.04 | 7272 | 1972 | CR | 0.24 | 0.275 |
| CPCG0368 | 16093 | T | C | 0 | 0.72 | 0 | 0.28 | C | 0 | 0.99 | 0 | 0.01 | 7180 | 3200 | CR | 0.26 | 0.275 |
| CPCG0097 | 16093 | T | T | 0 | 0.03 | 0 | 0.97 | T | 0 | 0.45 | 0 | 0.55 | 6981 | 2403 | CR | 0.42 | 0.275 |
| TCGA-CH-5788 | 16093 | T | T | 0 | 0.16 | 0 | 0.84 | C | 0 | 0.93 | 0 | 0.07 | 7767 | 4952 | CR | 0.77 | 0.275 |
| TCGA-EJ-5506 | 16093 | T | C | 0 | 0.69 | 0 | 0.31 | C | 0 | 0.96 | 0 | 0.04 | 7178 | 4245 | CR | 0.27 | 0.275 |
| TCGA-HC-7075 | 16093 | T | T | 0 | 0.03 | 0 | 0.97 | C | 0 | 0.94 | 0 | 0.06 | 7451 | 2210 | CR | 0.91 | 0.275 |
| ICGC_PCA097 | 16093 | T | C | 0 | 0.56 | 0 | 0.44 | C | 0 | 0.94 | 0 | 0.06 | 7434 | 3754 | CR | 0.38 | 0.275 |
| ICGC_PCA170 | 16093 | T | T | 0 | 0.12 | 0 | 0.88 | C | 0 | 0.9 | 0 | 0.1 | 7134 | 2704 | CR | 0.79 | 0.275 |
| ICGC_PCA184 | 16093 | T | T | 0 | 0.2 | 0 | 0.8 | C | 0 | 0.98 | 0 | 0.02 | 7025 | 4272 | CR | 0.79 | 0.275 |
| CPCG0183 | 16147 | C | C | 0 | 0.77 | 0 | 0.23 | C | 0 | 0.99 | 0 | 0 | 6878 | 1782 | CR | 0.22 | 0.0331 |
| EOPC-04 | 16148 | C | T | 0 | 0.29 | 0 | 0.71 | C | 0 | 1 | 0 | 0 | 6318 | 6134 | CR | 0.71 | 0.0575 |
| CPCG0046 | 16153 | G | A | 0.84 | 0 | 0.16 | 0 | G | 0 | 0 | 1 | 0 | 5392 | 1447 | CR | 0.83 | 0.0425 |
| CPCG0355 | 16162 | A | G | 0.02 | 0 | 0.98 | 0 | G | 0.28 | 0 | 0.72 | 0 | 7034 | 2115 | CR | 0.26 | 0.0712 |
| ICGC_PCA032 | 16169 | C | C | 0 | 1 | 0 | 0 | G | 0 | 0 | 0.99 | 0 | 4047 | 3363 | CR | 0.99 | 0.0386 |
| Baca05-3595 | 16182 | A | C | 0.08 | 0.82 | 0.1 | 0 | C | 0.24 | 0.44 | 0.32 | 0 | 1937 | 421 | CR | 0.37 | 0.444 |
| CPCG0256 | 16183 | A | A | 0.59 | 0.41 | 0 | 0 | A | 0.95 | 0.05 | 0 | 0 | 4286 | 982 | CR | 0.36 | 0.831 |
| CPCG0352 | 16184 | C | T | 0 | 0.34 | 0 | 0.66 | C | 0 | 1 | 0 | 0 | 6912 | 3003 | CR | 0.66 | 0.0332 |
| CPCG0084 | 16188 | C | C | 0 | 0.77 | 0 | 0.23 | C | 0 | 1 | 0 | 0 | 6562 | 1739 | CR | 0.23 | 0.0562 |
| CPCG0114 | 16189 | C | T | 0 | 0.03 | 0 | 0.97 | C | 0 | 0.75 | 0 | 0.25 | 2572 | 6657 | CR | 0.72 | 0.756 |
| CPCG0259 | 16192 | C | C | 0 | 0.78 | 0 | 0.22 | C | 0 | 1 | 0 | 0 | 7485 | 2143 | CR | 0.22 | 0.185 |
| CPCG0198 | 16192 | C | T | 0 | 0.34 | 0 | 0.66 | T | 0 | 0.11 | 0 | 0.89 | 7328 | 3030 | CR | 0.23 | 0.185 |
| ICGC_PCA197 | 16192 | C | T | 0 | 0.42 | 0 | 0.58 | T | 0 | 0.1 | 0 | 0.9 | 6039 | 2439 | CR | 0.32 | 0.185 |
| ICGC_PCA065 | 16213 | G | G | 0.27 | 0 | 0.73 | 0 | A | 0.6 | 0 | 0.4 | 0 | 7620 | 1314 | CR | 0.33 | 0.0359 |
| EOPC-05 | 16278 | T | T | 0 | 0.5 | 0 | 0.5 | C | 0 | 1 | 0 | 0 | 4040 | 1831 | CR | 0.5 | 0.34 |
| ICGC_PCA169 | 16304 | T | T | 0 | 0.34 | 0 | 0.66 | C | 0 | 1 | 0 | 0 | 7178 | 3126 | CR | 0.66 | 0.264 |
| ICGC_PCA098 | 16342 | T | C | 0 | 0.85 | 0 | 0.15 | C | 0 | 0.57 | 0 | 0.43 | 4197 | 3207 | CR | 0.28 | 0.0315 |
| ICGC_PCA183 | 16390 | G | A | 0.86 | 0 | 0.14 | 0 | G | 0.23 | 0 | 0.76 | 0 | 3737 | 1891 | CR | 0.62 | 0.211 |
| ICGC_PCA184 | 16465 | C | C | 0 | 0.89 | 0 | 0.11 | C | 0 | 0.55 | 0 | 0.45 | 4483 | 2172 | CR | 0.34 | 0.0153 |

TABLE 5-continued

Table of 293 somatic mtSNVs

| chan-ge.in.AA | MutPred.path-ogenicity.sco | PolyPhen.2.HumDiv.Pro PolyPhen.2.HumDiv.Pred | Tumour A HF adju | Tumour C HF adju | Tumour G HF adjusted | Tumour T HF adju | | Tumour (Difference in HF adjusted by cellularity |
|---|---|---|---|---|---|---|---|---|
| | NA | | 0 | 0.247191011 | 0 | 0.752808989 | T | 0.247191011 |
| | NA | | 0 | 1 | 0 | 0 | C | 1 |
| | NA | | 0 | 0 | 0 | 1 | T | 1 |
| | NA | | 0 | 1 | 0 | 0 | C | 1 |
| | NA | NA | 0 | 0.89 | 0 | 0.11 | C | 0.89 |
| | NA | | 0 | 0 | 1 | 0 | G | 0.99 |
| | NA | | 0 | 0.897435897 | 0 | 0.102564103 | C | 0.897435897 |
| | NA | | 0 | 0.612941176 | 0 | 0.387058824 | C | 0.602941176 |
| | NA | NA | 0 | 0.69 | 0 | 0.31 | C | 0.49 |
| | NA | NA | 0 | 0.18 | 0 | 0.82 | T | 0.65 |
| | NA | | 0 | 1 | 0 | 0 | C | 0.82 |
| | NA | | 0 | 0.27 | 0 | 0.73 | T | 0.27 |
| | NA | NA | 0 | 0.99 | 0 | 0.01 | C | 0.99 |
| | NA | | 0.420454545 | 0 | 0.579545455 | 0 | G | 0.579545455 |
| | NA | | 0 | 0.346666667 | 0 | 0.653333333 | T | 0.346666667 |
| | NA | | 0 | 0.415730337 | 0 | 0.584269663 | T | 0.415730337 |
| | NA | NA | 0 | 0.56 | 0 | 0.43 | C | 0.46 |
| | NA | NA | 0 | 0.86 | 0 | 0.14 | G | 0.71 |
| | NA | NA | 0.2 | 0 | 0.8 | 0 | G | 0.51 |
| | NA | | 0.025641026 | 0 | 0.974358974 | 0 | G | 0.974358974 |
| | NA | | 1 | 0 | 0 | 0 | A | 0.84 |
| | NA | | 0 | 0 | 1 | 0 | G | 1 |
| | NA | NA | 0.16 | 0 | 0.84 | 0 | G | 0.77 |
| | NA | | 1 | 0 | 0 | 0 | A | 0.26 |
| | NA | | 1 | 0.05 | 0 | 0 | A | 1 |
| | NA | | 0 | 0.419354839 | 0 | 0.580645161 | T | 0.580645161 |
| | NA | | 0 | 0.073170732 | 0 | 0.926829268 | T | 0.926829268 |
| | NA | | 0 | 0.22 | 0 | 0.77 | T | 0.77 |
| | NA | | 0.75 | 0 | 0.214285714 | 0 | A | 0.785714286 |
| | NA | | 0.303370787 | 0.02247191 | 0.674157303 | 0 | G | 0.325842697 |
| | NA | | 1 | 0 | 0 | 0 | A | 1 |
| | NA | NA | 0.83 | 0.17 | 0 | 0 | A | 0.21 |
| | NA | | 0.49 | 0 | 0.51 | 0 | G | 0.49 |
| | NA | | 0 | 0.694444444 | 0 | 0.305555556 | C | 0.694444444 |
| | NA | | 0 | 0.375 | 0 | 0.625 | T | 0.375 |
| | NA | | 0.933333333 | 0 | 0.066666667 | 0 | A | 0.933333333 |
| | NA | NA | 0.61 | 0 | 0.39 | 0 | A | 0.32 |
| | NA | | 0.506666667 | 0 | 0.493333333 | 0 | A | 0.506666667 |
| | NA | | 1 | 0 | 0 | 0 | A | 1 |
| | NA | | 0.646153846 | 0 | 0.353846154 | 0 | A | 0.646153846 |
| | NA | | 1 | 0 | 0 | 0 | A | 1 |
| | NA | | 0.36 | 0 | 0.64 | 0 | G | 0.36 |
| | NA | | 0.75 | 0 | 0.25 | 0 | A | 0.75 |
| | NA | | 0.490566038 | 0 | 0.518301887 | 0 | G | 0.471698113 |
| | NA | NA | 0 | 0.53 | 0 | 0.47 | C | 0.53 |
| | NA | | 0 | 0.1 | 0 | 0.9 | T | 0.22 |

TABLE 5-continued

Table of 293 somatic mtSNVs

| | | | | | | | | | | |
|---|---|---|---|---|---|---|---|---|---|---|
| | | NA | | | 0.875 | 0 | 0.125 | 0 | A | 0.875 |
| | | NA | | NA | 0.32 | 0 | 0.68 | 0 | G | 0.32 |
| | | NA | | NA | 0 | 0 | 0 | 1 | T | 1 |
| | | NA | | | 0 | 0.779661017 | 0 | 0.220338983 | C | 0.779661017 |
| | | NA | | | 0.80952381 | 0 | 0.19047619 | 0 | A | 0.80952381 |
| | | NA | | | 1 | 0 | 0 | 0 | A | 1 |
| | | NA | | | 0.320512821 | 0 | 0.666666667 | 0 | G | 0.333333333 |
| | | NA | | NA | 0 | 0.46 | 0 | 0.54 | T | 0.46 |
| | | NA | | NA | 0 | 0 | 0 | 1 | T | 1 |
| | | NA | | NA | 0 | 0.73 | 0 | 0.27 | C | 0.73 |
| | | NA | | NA | 0.44 | 0 | 0.56 | 0 | G | 0.44 |
| | | NA | | | 1 | 0 | 0 | 0 | A | 1 |
| | | NA | | | 0 | 0.987179487 | 0 | 0.012820513 | C | 0.987179487 |
| | | NA | | | 0.048823529 | 0 | 0.955882353 | 0 | G | 0.941176471 |
| | | NA | | | 0 | 0 | 0 | 1 | T | 0.25 |
| | | NA | | NA | 0.6 | 0 | 0.4 | 0 | A | 0.6 |
| | | NA | | | 0.91 | 0 | 0.09 | 0 | A | 0.88 |
| | | NA | | | 0.486486486 | 0 | 0.513513514 | 0 | G | 0.486486486 |
| | | NA | | | 1 | 0 | 0 | 0 | A | 0.23 |
| | | NA | | | 1 | 0 | 0 | 0 | A | 1 |
| | | NA | | NA | 0.26 | 0 | 0.74 | 0 | G | 0.26 |
| | | NA | | | 0 | 0.313253012 | 0 | 0.686746988 | T | 0.313253012 |
| | | NA | | | 0 | 1 | 0 | 0 | C | 1 |
| | | NA | | | 0.615384615 | 0 | 0.384615385 | 0 | A | 0.615384615 |
| | | NA | | NA | 0 | 0.72 | 0 | 0.28 | C | 0.72 |
| | | NA | | | 0.47 | 0 | 0.53 | 0 | G | 0.47 |
| | | NA | | NA | 0.5 | 0 | 0.5 | 0 | G | 0.5 |
| | | NA | | | 0 | 0 | 0 | 1 | T | 0.24 |
| | | NA | | NA | 0.69 | 0 | 0.31 | 0 | A | 0.47 |
| | | NA | | NA | 0.32 | 0 | 0.68 | 0 | G | 0.32 |
| | | NA | | NA | 0.44 | 0 | 0.56 | 0 | G | 0.44 |
| | | NA | | | 1 | 0 | 0 | 0 | A | 1 |
| | | NA | | | 0.925925926 | 0 | 0.074074074 | 0 | A | 0.925925926 |
| | | NA | | NA | 0.69 | 0 | 0.31 | 0 | A | 0.69 |
| | | NA | | | 1 | 0 | 0 | 0 | A | 1 |
| | | NA | | | 0 | 1 | 0 | 0 | C | 1 |
| | | NA | | | 0 | 0.270588235 | 0 | 0.729411765 | T | 0.270588235 |
| K62N | | 0.563 | | 0.38 benign | 0.711176471 | 0.277058824 | 0 | 0.011764706 | A | 0.258823529 |
| A64T | | 0.354 | | 0 benign | 0.526315789 | 0 | 0.460526316 | 0 | A | 0.539473684 |
| A747 | | 0.618 | | 0.879 possiblydamaging | 0.23 | 0 | 0.77 | 0 | G | 0.23 |
| G131S | | 0.854 | | 1 probably damaging | 0.443037975 | 0 | 0.556962025 | 0 | G | 0.443037975 |
| Premature Stop Codon | NA | | | | 0.916666667 | 0 | 0.041666667 | 0 | A | 0.958333333 |
| Premature Stop Codon | NA | | NA | | 0.45 | 0 | 0.55 | 0 | G | 0.45 |
| Premature Stop Codon | NA | | NA | | 0.21 | 0 | 0.79 | 0 | G | 0.21 |
| E214K | | 0.778 | | 0.999probablydamaging | 0.239130435 | 0 | 0.760869565 | 0 | G | 0.239130435 |
| E214K | | 0.778 | | 0.999probablydamaging | 0.634920635 | 0 | 0.365079365 | 0 | A | 0.634920635 |
| G218D | | 0.775 | | 1 probably damaging | 0.36 | 0 | 0.63 | 0 | G | 0.37 |
| A226T | | 0.616 | | 0.995probablydamaging | 0.956521739 | 0 | 0.043478261 | 0 | A | 0.956521739 |

TABLE 5-continued

Table of 293 somatic mtSNVs

| | | | | | | | | | | |
|---|---|---|---|---|---|---|---|---|---|---|
| syn | NA | | | | 0.34 | 0 | 0.65 | 0 | G | 0.62 |
| R279Q | | 0.879 | | 0.974probablydamaging | 1 | 0 | 0 | 0 | A | 1 |
| R279Q | | 0.879 | | 0.974probablydamaging | 0.21 | 0 | 0.79 | 0 | G | 0.2 |
| A299T | | 0.632 | | 0.04 benign | 0.315789474 | 0 | 0.684210526 | 0 | G | 0.315789474 |
| I309V | | 0.427 | | 0 benign | 0.58 | 0 | 0.42 | 0 | A | 0.42 |
| syn | NA | | NA | | 0 | 0.53 | 0 | 0.47 | C | 0.53 |
| | NA | | | | 0.63 | 0 | 0.36 | 0 | A | 0.64 |
| | NA | | | | 0 | 0.102040816 | 0 | 0.897959184 | T | 0.897959184 |
| A5T | | 0.194 | | 1 probably damaging | 0.333333333 | 0 | 0.666666667 | 0 | G | 0.333333333 |
| V8I | | 0.439 | | 0 benign | 0.46 | 0 | 0.54 | 0 | G | 0.46 |
| V43I | | 0.366 | | 0.006 benign | 0.772727273 | 0 | 0.227272727 | 0 | A | 0.772727273 |
| F60S | | 0.796 | | 1 probably damaging | 0 | 0.580645161 | 0 | 0.403225806 | C | 0.596774194 |
| A101T | | 0.717 | | 1 probably damaging | 0.974025974 | 0 | 0.025974026 | 0 | A | 0.974025974 |
| G121D | | 0.809 | | 1 probably damaging | 0.61 | 0 | 0.39 | 0 | A | 0.61 |
| L130P | | 0.737 | | 0.999probablydamaging | 0 | 1 | 0 | 0 | C | 1 |
| S140P | | 0.875 | | 0.997probablydamaging | 0 | 0.576470588 | 0 | 0.411764706 | C | 0.588235294 |
| S146P | | 0.635 | | 0.925 possiblydamaging | 0 | 1 | 0 | 0 | C | 1 |
| V151M | | 0.499 | | 0.072 benign | 0.280898876 | 0 | 0.685393258 | 0.033707865 | G | 0.314606742 |
| syn | NA | | NA | | 0.96 | 0 | 0.04 | 0 | A | 0.22 |
| F216L | | 0.676 | | 0.221 benign | 0 | 1 | 0 | 0 | C | 1 |
| syn | NA | | | | 0.001797753 | 0.998202247 | 0 | 0 | C | 0.438202247 |
| G253D | | 0.851 | | 1 probably damaging | 0.933333333 | 0 | 0.066666667 | 0 | A | 0.933333333 |
| I278V | | 0.311 | | 0.005 benign | 0.66 | 0 | 0.34 | 0 | A | 0.25 |
| Stop | NA | | | | 0 | 1 | 0 | 0 | C | 1 |
| Codon->Q | NA | | NA | | 0.53 | 0 | 0.47 | 0 | A | 0.53 |
| | NA | | NA | | 0 | 0.61 | 0 | 0.39 | C | 0.61 |
| | NA | | | | 0 | 0.86 | 0 | 0.14 | C | 0.86 |
| A3T | | 0.239 | | 0.012 benign | 0.848101266 | 0 | 0.151898734 | 0 | A | 0.848101266 |
| A26T | | 0.769 | | 0.998probablydamaging | 0.48 | 0 | 0.52 | 0 | G | 0.48 |
| syn | NA | | | | 0 | 1 | 0 | 0 | C | 0.57 |
| L48P | | 0.785 | | 0.973probablydamaging | 0 | 0.28 | 0 | 0.72 | T | 0.28 |
| D51N | | 0.715 | | 0.998probablydamaging | 0.152608696 | 0 | 0.847391304 | 0 | G | 0.717391304 |
| Premature Stop Codon | NA | | | | 0.333333333 | 0 | 0.666666667 | 0 | G | 0.333333333 |
| G125S | | 0.926 | | 1 probably damaging | 1 | 0 | 0 | 0 | A | 0.55 |
| Premature Stop Codon | NA | | | | 0.5 | 0 | 0.5 | 0 | G | 0.5 |
| K172N | | 0.701 | | 1 probably damaging | 1 | 0 | 0 | 0 | A | 0.2 |
| K172N | | 0.701 | | 1 probably damaging | 1 | 0 | 0 | 0 | A | 0.23 |
| S198F | | 0.672 | | 1 probably damaging | 0 | 0.42 | 0 | 0.58 | T | 0.58 |
| I254T | | 0.708 | | 0.673 possiblydamaging | 0 | 0.89 | 0 | 0.11 | C | 0.45 |
| G272D | | 0.771 | | 1 probably damaging | 0.53 | 0 | 0.47 | 0 | A | 0.53 |
| I280T | | 0.69 | | 0.997probablydamaging | 0 | 0.76744186 | 0 | 0.23255814 | C | 0.76744186 |
| V318A | | 0.541 | | 0.998probablydamaging | 0 | 1 | 0 | 0 | C | 1 |
| S330N | | 0.519 | | 0.001 benign | 0.6375 | 0 | 0.3625 | 0 | A | 0.6375 |
| syn | NA | | | | 0 | 0.361111111 | 0 | 0.638888889 | T | 0.361111111 |
| A375T | | 0.675 | | 1 probably damaging | 0.4 | 0 | 0.6 | 0 | G | 0.4 |
| A464T | | 0.34 | | 0.999probablydamaging | 0.25 | 0 | 0.75 | 0 | G | 0.25 |
| G497E | | 0.356 | | 1 probably damaging | 0.24 | 0 | 0.76 | 0 | G | 0.24 |
| | NA | | | | 0.25 | 0 | 0.75 | 0 | G | 0.25 |
| T63A | | 0.523 | | 0.017 benign | 0.1 | 0 | 0.9 | 0 | G | 0.45 |

TABLE 5-continued

Table of 293 somatic mtSNVs

| | | | | | | | | | | |
|---|---|---|---|---|---|---|---|---|---|---|
| L73P | | 0.768 | | 1 probably damaging | 0 | 0.37 | 0 | 0.63 | T | 0.37 |
| D112N | | 0.634 | | 1 probably damaging | 0.412698413 | 0 | 0.587301587 | 0 | G | 0.412698413 |
| G115V | | 0.544 | | 0.989probablydamaging | 0 | 0 | 1 | 0 | C | 0.25 |
| V138I | | 0.609 | | 0.798 possiblydamaging | 0.59 | 0 | 0.41 | 0 | A | 0.59 |
| V165I | | 0.616 | | 0 benign | 0.24 | 0 | 0.76 | 0 | G | 0.24 |
| | NA | | NA | | 0.14 | 0 | 0.86 | 0 | G | 0.21 |
| Premature Stop Codon | NA | | | | 0.41025641 | 0 | 0.58974359 | 0 | G | 0.41025641 |
| P10S | | 0.569 | | 0.993probablydamaging | 0 | 0.2 | 0 | 0.8 | T | 0.79 |
| I23T | | 0.735 | | 0.005 benign | 0 | 0.415730337 | 0 | 0.584269663 | T | 0.415730337 |
| L61P | | 0.304 | | 0.988probablydamaging | 0 | 0.54 | 0 | 0.46 | C | 0.54 |
| syn | NA | | | | 0 | 0 | 0 | 1 | T | 0.63 |
| syn | NA | | NA | | 0.32 | 0 | 0.68 | 0 | G | 0.32 |
| M60T | | 0.202 | | 0 benign | 0 | 1 | 0 | 0 | C | 0.51 |
| I106T | | 0.642 | | 0.617 possiblydamaging | 0 | 0 | 0 | 1 | T | 0.25 |
| V158A | | 0.704 | | 0 benign | 0 | 0.9 | 0 | 0.1 | C | 0.9 |
| S219N | | 0.6 | | 0.995probablydamaging | 1 | 0 | 0 | 0 | A | 1 |
| L220P | | 0.751 | | 0.999probablydamaging | 0 | 0.21 | 0 | 0.79 | T | 0.21 |
| W58R | | 0.85 | | 0.998probablydamaging | 0 | 0.41 | 0 | 0.59 | T | 0.41 |
| syn | NA | | | | 1 | 0 | 0 | 0 | A | 0.81 |
| A100T | | 0.674 | | 0.999probablydamaging | 1 | 0 | 0 | 0 | A | 1 |
| S104P | | 0.732 | | 0.997probablydamaging | 0 | 0.365591398 | 0 | 0.634408602 | T | 0.365591398 |
| G141E | | 0.872 | | 1 probably damaging | 0.694117647 | 0 | 0.305882353 | 0 | A | 0.694117647 |
| R156Q/ R156P | 0.69/ 0.731 | | 0.999/1.0 | probably damaging/ probably damaging | 0.144578313 | 0.108433735 | 0.746987952 | 0 | G | 0.253012048 |
| G194S | | 0.893 | | 1 probably damaging | 0.373333333 | 0 | 0.626666667 | 0 | G | 0.373333333 |
| syn | NA | | | | 0 | 0 | 0 | 1 | T | 0.59 |
| A200T | | 0.708 | | 0.006 benign | 0.120512821 | 0 | 0.879487179 | 0 | G | 0.679487179 |
| S212P | | 0.636 | | 0.997probablydamaging | 0 | 1 | 0 | 0 | C | 1 |
| S229P | | 0.606 | | 0.003 benign | 0 | 0.38 | 0 | 0.62 | T | 0.38 |
| syn | NA | | NA | | 0 | 0.4 | 0 | 0.6 | T | 0.4 |
| | NA | | NA | | 0.53 | 0 | 0.47 | 0 | A | 0.53 |
| | NA | | | | 0.964347826 | 0 | 0.035652174 | 0 | A | 0.304347826 |
| D42N | | 0.742 | | 0.999probablydamaging | 0.76 | 0 | 0.24 | 0 | A | 0.76 |
| L73F | | 0.543 | | 1 probably damaging | 1 | 0 | 0 | 0 | A | 0.31 |
| L73F | | 0.543 | | 1 probably damaging | 0 | 1 | 0 | 0 | C | 0.99 |
| L73F | | 0.543 | | 1 probably damaging | 1 | 0 | 0 | 0 | A | 0.22 |
| L30P | | 0.874 | | 1 probably damaging | 0 | 0.4 | 0 | 0.6 | T | 0.4 |
| syn | NA | | NA | NA | 1 | 0 | 3.60462E−17 | 0 | A | 1 |
| syn | NA | | | | 1 | 1 | 0 | 0 | C | 1 |
| L14R | | 0.752 | | 0.999probablydamaging | 0 | 0 | 1 | 0 | G | 1 |
| I361 | | 0.558 | | 0.015 benign | 0 | 0 | 0 | 1 | T | 0.5 |
| A131T | | 0.65 | | 0.035 benign | 0.774193548 | 0 | 0.225806452 | 0 | A | 0.774193548 |
| M195T | | 0.684 | | 0.949 possiblydamaging | 0 | 0.927710843 | 0 | 0.072289157 | C | 0.927710843 |
| R245H | | 0.822 | | 0.999probablydamaging | 0.33 | 0 | 0.67 | 0 | G | 0.33 |
| R278Q | | 0.885 | | 0.995probablydamaging | 0.9 | 0 | 0.1 | 0 | A | 0.9 |
| V298M | | 0.605 | | 0.85 possiblydamaging | 0.935280899 | 0 | 0.064719101 | 0 | A | 0.775280899 |
| A318P | | 0.765 | | 1 probably damaging | 0 | 1 | 0 | 0 | C | 1 |
| A318T | | 0.602 | | 0.999probablydamaging | 0.48 | 0 | 0.52 | 0 | C | 0.48 |
| syn | NA | | NA | | 0 | 0 | 0 | 1 | T | 1 |
| L352P | | 0.783 | | 0.987probablydamaging | 0 | 1 | 0 | 0 | C | 1 |

TABLE 5-continued

Table of 293 somatic mtSNVs

| | | | | | | | | | | | |
|---|---|---|---|---|---|---|---|---|---|---|---|
| A365T | | 0.57 | | 0.004 | benign | 0.22 | 0 | 0.78 | 0 | G | 0.22 |
| syn | NA | | | | | 0 | 1 | 0 | 0 | C | 1 |
| L394P | | 0.669 | | 0.403 | benign | 0 | 0.54 | 0 | 0.46 | C | 0.54 |
| G397E | | 0.87 | | 1 | probably damaging | 0.3 | 0 | 0.7 | 0 | G | 0.3 |
| syn | NA | | | | | 0 | 0.217647059 | 0 | 0.782352941 | T | 0.482352941 |
| | NA | | | | | 0 | 0.86 | 0 | 0.14 | C | 0.86 |
| NA | NA | | NA | | NA | 0 | 0 | 1 | 0 | G | 0.57 |
| | NA | | NA | | | 0 | 0.45 | 0 | 0.55 | T | 0.42 |
| | NA | | | | | 0 | 0.829268293 | 0 | 0.170731707 | C | 0.829268293 |
| syn | NA | | | | | 0.838709677 | 0 | 0.161290323 | 0 | A | 0.838709677 |
| I100V | | 0.381 | | 0.925 | possiblydamaging | 0.84 | 0 | 0.16 | 0 | A | 0.83 |
| syn | NA | | NA | | | 0.3 | 0.7 | 0 | 0 | C | 0.35 |
| syn | NA | | | | | 0.304347826 | 0 | 0.695652174 | 0 | G | 0.304347826 |
| L121P | | 0.719 | | 1 | probably damaging | 0 | 0.272727273 | 0 | 0.727272727 | T | 0.272727273 |
| L122I | | 0.6 | | 0.996 | probablydamaging | 0.873015873 | 0.126984127 | 0 | 0 | A | 0.873015873 |
| F141S | | 0.671 | | 0.997 | probablydamaging | 0 | 1 | 0 | 0 | C | 1 |
| F141S | | 0.671 | | 0.997 | probablydamaging | 0 | 0.272727273 | 0 | 0.727272727 | T | 0.272727273 |
| G143S | | 0.637 | | 1 | probably damaging | 1 | 0 | 0 | 0 | A | 1 |
| E145K | | 0.813 | | 0.996 | probablydamaging | 0.76 | 0 | 0.24 | 0 | A | 0.75 |
| R161Q | | 0.801 | | 0.997 | probablydamaging | 0.28 | 0 | 0.72 | 0 | G | 0.28 |
| G215D | | 0.769 | | 1 | probably damaging | 0.46 | 0 | 0.54 | 0 | G | 0.46 |
| R262H | | 0.77 | | 0.999 | probablydamaging | 0.734177215 | 0 | 0.265822785 | 0 | A | 0.734177215 |
| syn | NA | | | | | 0 | 0.655913978 | 0 | 0.344086022 | C | 0.655913978 |
| syn | NA | | | | | 0 | 0.59 | 0 | 0.41 | C | 0.41 |
| G318D | | 0.781 | | 1 | probably damaging | 0.76 | 0 | 0.24 | 0 | A | 0.76 |
| syn | NA | | | | | 0.967532468 | 0 | 0.032467532 | 0 | A | 0.467532468 |
| G376D | | 0.82 | | 0.994 | probablydamaging | 0.77 | 0 | 0.23 | 0 | A | 0.77 |
| S377N | | 0.707 | | 0.003 | benign | 0.55 | 0 | 0.44 | 0 | A | 0.56 |
| M383T | | 0.631 | | 0.452 | benign | 0 | 1 | 0 | 0 | C | 1 |
| S391P | | 0.793 | | 0.997 | probablydamaging | 0 | 0.956521739 | 0 | 0.043478261 | C | 0.956521739 |
| Y403H | | 0.651 | | 0.008 | benign | 0 | 0.869565217 | 0 | 0.086956522 | C | 0.913043478 |
| I411T | | 0.702 | | 0.001 | benign | 0 | 0 | 0 | 1 | T | 0.35 |
| A475P | | 0.472 | | 0.101 | benign | 0.75 | 0 | 0.25 | 0 | A | 0.25 |
| C518R | | 0.501 | | 0.003 | benign | 0 | 0.23 | 0 | 0.77 | T | 0.23 |
| F520S | | 0.673 | | 0.997 | probablydamaging | 0 | 1 | 0 | 0 | C | 1 |
| L526P | | 0.836 | | 1 | probably damaging | 0 | 1 | 0 | 0 | C | 1 |
| F528L | | 0.72 | | 0.996 | probablydamaging | 0 | 1 | 0 | 0 | C | 0.97 |
| S531N | | 0.298 | | 0.002 | benign | 0.62 | 0 | 0.38 | 0 | A | 0.62 |
| T556P | | 0.556 | | 0.901 | possiblydamaging | 1 | 0 | 0 | 0 | A | 0.22 |
| Stop Codon->G | NA | | | | | 0 | 0.88 | 0 | 0.12 | C | 0.88 |
| I168V | | 0.534 | | 0.997 | probablydamaging | 0 | 1 | 0 | 0 | C | 1 |
| syn | NA | | | | | 0.1 | 0 | 0.9 | 0 | G | 0.6 |
| syn | NA | | | | | 0 | 1 | 0 | 0 | C | 1 |
| A29T | | 0.391 | | 0 | benign | 0.29 | 0 | 0.71 | 0 | G | 0.29 |
| G34S | | 0.846 | | 1 | probably damaging | 1 | 0 | 0 | 0 | A | 1 |
| G48E | | 0.825 | | 1 | probably damaging | 0.653061224 | 0 | 0.346938776 | 0 | A | 0.653061224 |
| R80H | | 0.833 | | 1 | probably damaging | 0.961538462 | 0 | 0.038461538 | 0 | A | 0.961538462 |
| I98T | | 0.669 | | 0.997 | probablydamaging | 0 | 1 | 0 | 0 | C | 1 |
| R100Q | | 0.824 | | 1 | probably damaging | 1 | 0 | 0 | 0 | A | 1 |
| R100Q | | 0.824 | | 1 | probably damaging | 0.492063492 | 0 | 0.507936508 | 0 | G | 0.492063492 |

TABLE 5-continued

Table of 293 somatic mtSNVs

| | | | | | | | | | | | |
|---|---|---|---|---|---|---|---|---|---|---|---|
| syn | NA | | | | | 0 | 0.07 | 0 | 0.93 | T | 0.64 |
| A193T | | 0.517 | | 0.001 | benign | 0.66 | 0 | 0.34 | 0 | A | 0.65 |
| G210E | | 0.68 | | 1 | probably damaging | 0.24 | 0 | 0.76 | 0 | G | 0.24 |
| L234F | | 0.217 | | 1 | probably damaging | 0 | 0.13 | 0 | 0.87 | T | 0.39 |
| G251D | | 0.502 | | 0.972 | probablydamaging | 0.25 | 0 | 0.75 | 0 | G | 0.25 |
| syn | NA | | | | | 1 | 1 | 0 | 1 | T | 1 |
| S321N | | 0.709 | | 0.996 | probablydamaging | 0.587301587 | 0 | 0.412698413 | 0 | A | 0.587301587 |
| A329T | | 0.323 | | 0 | benign | 0.826666667 | 0 | 0.173333333 | 0 | A | 0.826666667 |
| G339E | | 0.87 | | 1 | probably damaging | 1 | 0 | 0 | 0 | A | 1 |
| syn | NA | | | | | 0.083333333 | 0 | 0.916666667 | 0 | G | 0.746666667 |
| A380T | | 0.204 | | 0 | benign | 1 | 0 | 0 | 0 | A | 0.84 |
| | NA | | | | | 1 | 0 | 0 | 0 | A | 0.24 |
| | NA | | | | | 1 | 0 | 0 | 0 | A | 1 |
| | NA | | NA | | | 0.07 | 0 | 0.93 | 0 | G | 0.27 |
| | NA | | NA | | | 0 | 0.28 | 0 | 0.72 | T | 0.28 |
| | NA | | NA | | | 0.39 | 0 | 0.61 | 0 | G | 0.61 |
| | NA | | | | | 0 | 1 | 0 | 0 | C | 1 |
| | NA | | | | | 0.270588235 | 0 | 0.729411765 | 0 | G | 0.270588235 |
| | NA | | NA | | | 0.22 | 0 | 0.78 | 0 | G | 0.22 |
| | NA | | | | | 0.076666667 | 0 | 0.926666667 | 0 | G | 0.346666667 |
| | NA | | | | | 0 | 0 | 1 | 0 | G | 0.77 |
| | NA | | | | | 0 | 0.626506024 | 0 | 0.361445783 | C | 0.373493976 |
| | NA | | | | | 0 | 0.101304348 | 0 | 0.898695652 | T | 0.858695652 |
| | NA | | | | | 0 | 0.626666667 | 0 | 0.373333333 | C | 0.333333333 |
| | NA | | | | | 0 | 0 | 0 | 1 | T | 0.99 |
| | NA | | | | | 0 | 0 | 0 | 1 | T | 0.45 |
| | NA | | | | | 0 | 0.16 | 0 | 0.84 | T | 0.77 |
| | NA | | | | | 0 | 0.69 | 0 | 0.31 | C | 0.27 |
| | NA | | | | | 0 | 0.03 | 0 | 0.97 | T | 0.91 |
| | NA | | NA | | | 0 | 0.56 | 0 | 0.44 | C | 0.38 |
| | NA | | NA | | | 0 | 0.12 | 0 | 0.88 | T | 0.78 |
| | NA | | NA | | | 0 | 0.2 | 0 | 0.8 | T | 0.78 |
| | NA | | | | | 0 | 0.675714286 | 0 | 0.328571429 | C | 0.314285714 |
| | NA | | | | | 0 | 0.29 | 0 | 0.71 | T | 0.71 |
| | NA | | | | | 0.943820225 | 0 | 0.056179775 | 0 | A | 0.943820225 |
| | NA | | | | | 0 | 0 | 1 | 0 | G | 0.28 |
| | NA | | NA | | | 0 | 1 | 0 | 0 | C | 0.99 |
| | NA | | | | | 0.08 | 0.82 | 0.1 | 0 | C | 0.38 |
| | NA | | | | | 0 | 1 | 0 | 0 | C | 0.95 |
| | NA | | | | | 0 | 0 | 0 | 1 | T | 1 |
| | NA | | | | | 0 | 0.735632184 | 0 | 0.264367816 | C | 0.264367816 |
| | NA | | | | | 0 | 0 | 0 | 1 | T | 0.75 |
| | NA | | | | | 0 | 0 | 0 | 1 | T | 1 |
| | NA | | | | | 0 | 0.371363636 | 0 | 0.628636364 | T | 0.261363636 |
| | NA | | NA | | | 0 | 0.42 | 0 | 0.58 | T | 0.32 |
| | NA | | NA | | | 0.27 | 0 | 0.73 | 0 | G | 0.33 |
| | NA | | | | | 0 | 0.5 | 0 | 0.5 | T | 0.5 |
| | NA | | NA | | | 0 | 0.34 | 0 | 0.66 | T | 0.66 |
| | NA | | NA | | | 0 | 0.85 | 0 | 0.15 | C | 0.28 |

TABLE 5-continued

Table of 293 somatic mtSNVs

| | | | | | | | |
|---|---|---|---|---|---|---|---|
| NA | NA | 0.86 | 0 | 0.14 | 0 | A | 0.62 |
| NA | NA | 0 | 0.89 | 0 | 0.11 | C | 0.34 |

TABLE 6

| Mitochondrial mutation recurrence for 41 nuclear genomic features | | | | | | | | | | | | | | | | | | | |
|---|---|---|---|---|---|---|---|---|---|---|---|---|---|---|---|---|---|---|---|
| patient_id | Control region | tRNA | CYB | RNR1 | RNR2 | ND1 | ND2 | ND3 | ND4 | ND4L | ND5 | ND6 | CO1 | CO2 | CO3 | ATP6 | ATP8 | OHR | CSB1 |
| CPCG0001 | 1 | 0 | 0 | 0 | 0 | 0 | 0 | 0 | 0 | 0 | 0 | 0 | 0 | 0 | 0 | 0 | 0 | 0 | 0 |
| CPCG0003 | 0 | 0 | 0 | 0 | 0 | 1 | 0 | 0 | 0 | 0 | 0 | 0 | 0 | 0 | 0 | 0 | 0 | 0 | 0 |
| CPCG0006 | 0 | 0 | 0 | 0 | 0 | 0 | 0 | 0 | 0 | 0 | 0 | 0 | 0 | 0 | 0 | 0 | 0 | 0 | 0 |
| CPCG0020 | 0 | 0 | 0 | 0 | 0 | 0 | 1 | 0 | 0 | 0 | 0 | 0 | 0 | 0 | 0 | 0 | 0 | 0 | 0 |
| CPCG0040 | 1 | 0 | 0 | 0 | 1 | 0 | 0 | 0 | 1 | 0 | 0 | 0 | 0 | 0 | 0 | 0 | 0 | 0 | 0 |
| CPCG0046 | 1 | 0 | 0 | 0 | 0 | 0 | 1 | 0 | 1 | 0 | 1 | 0 | 0 | 0 | 0 | 0 | 0 | 0 | 0 |
| CPCG0047 | 0 | 0 | 0 | 0 | 0 | 0 | 0 | 0 | 0 | 0 | 0 | 0 | 0 | 0 | 0 | 0 | 0 | 0 | 0 |
| CPCG0048 | 0 | 0 | 0 | 0 | 0 | 0 | 0 | 0 | 0 | 0 | 0 | 0 | 0 | 0 | 0 | 0 | 0 | 0 | 0 |
| CPCG0057 | 0 | 0 | 1 | 0 | 0 | 0 | 0 | 0 | 0 | 0 | 0 | 0 | 0 | 0 | 0 | 0 | 0 | 0 | 0 |
| CPCG0063 | 0 | 0 | 0 | 0 | 0 | 1 | 0 | 0 | 0 | 0 | 0 | 0 | 0 | 0 | 0 | 1 | 0 | 0 | 0 |
| CPCG0073 | 1 | 0 | 0 | 0 | 0 | 0 | 0 | 0 | 0 | 0 | 0 | 0 | 0 | 0 | 0 | 0 | 0 | 1 | 0 |
| CPCG0078 | 1 | 0 | 1 | 0 | 0 | 0 | 0 | 0 | 0 | 0 | 0 | 0 | 0 | 0 | 0 | 0 | 0 | 0 | 0 |
| CPCG0081 | 1 | 0 | 0 | 0 | 1 | 0 | 0 | 0 | 0 | 0 | 0 | 0 | 0 | 0 | 0 | 0 | 0 | 1 | 0 |
| CPCG0083 | 0 | 0 | 0 | 1 | 0 | 0 | 0 | 0 | 0 | 0 | 0 | 0 | 0 | 0 | 0 | 0 | 0 | 0 | 0 |
| CPCG0087 | 0 | 0 | 0 | 0 | 0 | 0 | 0 | 0 | 0 | 0 | 0 | 0 | 0 | 0 | 0 | 0 | 0 | 0 | 0 |
| CPCG0094 | 0 | 0 | 0 | 0 | 0 | 0 | 0 | 0 | 0 | 0 | 0 | 0 | 0 | 0 | 0 | 0 | 0 | 0 | 0 |
| CPCG0095 | 0 | 0 | 0 | 0 | 0 | 0 | 0 | 0 | 1 | 0 | 0 | 0 | 0 | 0 | 0 | 0 | 0 | 0 | 0 |
| CPCG0098 | 1 | 1 | 0 | 0 | 1 | 0 | 0 | 0 | 0 | 0 | 0 | 0 | 0 | 0 | 0 | 0 | 0 | 1 | 1 |
| CPCG0099 | 0 | 0 | 0 | 0 | 0 | 0 | 0 | 0 | 0 | 0 | 0 | 0 | 0 | 0 | 0 | 0 | 0 | 0 | 0 |
| CPCG0102 | 0 | 0 | 0 | 0 | 0 | 0 | 0 | 0 | 0 | 0 | 0 | 0 | 1 | 0 | 0 | 0 | 0 | 0 | 0 |
| CPCG0114 | 1 | 1 | 0 | 0 | 0 | 0 | 0 | 1 | 0 | 0 | 0 | 0 | 0 | 0 | 0 | 0 | 0 | 0 | 0 |
| CPCG0117 | 0 | 0 | 0 | 0 | 0 | 0 | 1 | 0 | 0 | 0 | 0 | 0 | 0 | 0 | 0 | 0 | 0 | 0 | 0 |
| CPCG0121 | 0 | 0 | 0 | 0 | 0 | 0 | 0 | 0 | 0 | 0 | 0 | 0 | 0 | 0 | 0 | 0 | 0 | 0 | 0 |
| CPCG0123 | 0 | 0 | 0 | 0 | 0 | 0 | 0 | 0 | 0 | 0 | 0 | 0 | 1 | 0 | 0 | 0 | 0 | 0 | 0 |
| CPCG0124 | 0 | 0 | 0 | 0 | 0 | 0 | 0 | 0 | 0 | 0 | 0 | 0 | 1 | 1 | 0 | 0 | 0 | 0 | 0 |
| CPCG0127 | 0 | 0 | 0 | 0 | 0 | 1 | 0 | 0 | 0 | 0 | 0 | 0 | 0 | 0 | 0 | 0 | 0 | 0 | 0 |
| CPCG0128 | 1 | 1 | 0 | 0 | 0 | 0 | 0 | 0 | 0 | 0 | 0 | 0 | 0 | 0 | 0 | 0 | 0 | 0 | 0 |
| CPCG0154 | 0 | 0 | 0 | 0 | 0 | 0 | 0 | 0 | 0 | 0 | 0 | 0 | 0 | 0 | 0 | 0 | 0 | 0 | 0 |
| CPCG0158 | 1 | 0 | 0 | 0 | 0 | 0 | 0 | 0 | 0 | 0 | 0 | 0 | 0 | 0 | 0 | 0 | 0 | 1 | 0 |
| CPCG0166 | 1 | 0 | 0 | 0 | 1 | 0 | 0 | 1 | 0 | 0 | 1 | 0 | 0 | 0 | 0 | 0 | 0 | 0 | 0 |
| CPCG0182 | 0 | 0 | 0 | 0 | 0 | 0 | 0 | 0 | 0 | 0 | 0 | 0 | 0 | 0 | 0 | 0 | 0 | 0 | 0 |
| CPCG0183 | 1 | 0 | 0 | 0 | 1 | 0 | 0 | 0 | 0 | 0 | 0 | 0 | 0 | 0 | 0 | 0 | 0 | 0 | 0 |
| CPCG0184 | 0 | 0 | 0 | 0 | 0 | 0 | 0 | 0 | 0 | 0 | 0 | 0 | 0 | 0 | 0 | 0 | 0 | 0 | 0 |
| CPCG0185 | 0 | 0 | 0 | 1 | 0 | 0 | 0 | 0 | 0 | 0 | 0 | 0 | 0 | 0 | 0 | 0 | 0 | 0 | 0 |
| CPCG0189 | 1 | 0 | 0 | 1 | 0 | 0 | 0 | 0 | 0 | 0 | 0 | 0 | 1 | 0 | 0 | 0 | 0 | 0 | 0 |
| CPCG0190 | 0 | 0 | 0 | 0 | 0 | 0 | 0 | 0 | 0 | 0 | 1 | 0 | 0 | 0 | 0 | 0 | 0 | 0 | 0 |
| CPCG0191 | 0 | 0 | 0 | 0 | 0 | 0 | 0 | 0 | 0 | 0 | 0 | 0 | 0 | 0 | 0 | 0 | 0 | 0 | 0 |
| CPCG0196 | 1 | 0 | 0 | 0 | 0 | 0 | 0 | 0 | 0 | 0 | 0 | 0 | 0 | 0 | 0 | 0 | 1 | 1 | 0 |
| CPCG0199 | 0 | 0 | 0 | 0 | 0 | 0 | 0 | 0 | 0 | 0 | 0 | 0 | 0 | 0 | 0 | 0 | 0 | 0 | 0 |
| CPCG0201 | 0 | 1 | 0 | 0 | 0 | 0 | 1 | 0 | 0 | 0 | 0 | 0 | 0 | 0 | 0 | 0 | 0 | 0 | 0 |
| CPCG0205 | 1 | 0 | 0 | 0 | 0 | 0 | 0 | 0 | 0 | 0 | 0 | 0 | 0 | 0 | 0 | 0 | 0 | 1 | 1 |
| CPCG0206 | 1 | 0 | 0 | 0 | 0 | 0 | 0 | 0 | 0 | 0 | 0 | 0 | 0 | 0 | 0 | 0 | 0 | 1 | 0 |
| CPCG0208 | 0 | 0 | 0 | 0 | 0 | 0 | 0 | 0 | 0 | 0 | 0 | 0 | 0 | 0 | 0 | 0 | 0 | 0 | 0 |
| CPCG0210 | 0 | 0 | 0 | 0 | 0 | 0 | 0 | 0 | 0 | 0 | 0 | 0 | 0 | 0 | 0 | 0 | 0 | 0 | 0 |
| CPCG0211 | 0 | 0 | 0 | 1 | 0 | 0 | 0 | 1 | 0 | 0 | 0 | 0 | 1 | 0 | 0 | 0 | 0 | 0 | 0 |
| CPCG0212 | 0 | 1 | 0 | 0 | 0 | 0 | 0 | 0 | 0 | 0 | 0 | 0 | 0 | 0 | 0 | 0 | 0 | 0 | 0 |

TABLE 6-continued

Mitochondrial mutation recurrence for 41 nuclear genomic features

| | | | | | | | | | | | | | | | | | | | |
|---|---|---|---|---|---|---|---|---|---|---|---|---|---|---|---|---|---|---|---|
| CPCG0213 | 0 | 0 | 1 | 0 | 0 | 1 | 0 | 0 | 0 | 0 | 1 | 0 | 0 | 0 | 0 | 0 | 0 | 0 | 0 |
| CPCG0217 | 0 | 0 | 0 | 0 | 1 | 0 | 0 | 0 | 0 | 0 | 1 | 0 | 0 | 0 | 0 | 1 | 0 | 0 | 0 |
| CPCG0232 | 0 | 0 | 0 | 0 | 0 | 0 | 0 | 0 | 0 | 0 | 1 | 0 | 0 | 0 | 0 | 0 | 0 | 0 | 0 |
| CPCG0233 | 0 | 1 | 0 | 0 | 0 | 1 | 0 | 0 | 0 | 0 | 0 | 0 | 0 | 0 | 0 | 0 | 0 | 0 | 0 |
| CPCG0234 | 0 | 0 | 0 | 0 | 0 | 0 | 0 | 0 | 0 | 0 | 1 | 0 | 0 | 0 | 1 | 0 | 0 | 0 | 0 |
| CPCG0236 | 0 | 0 | 0 | 0 | 0 | 0 | 0 | 0 | 0 | 0 | 1 | 0 | 0 | 0 | 0 | 0 | 0 | 0 | 0 |
| CPCG0238 | 0 | 0 | 0 | 0 | 0 | 0 | 0 | 0 | 0 | 0 | 0 | 0 | 0 | 0 | 0 | 0 | 0 | 0 | 0 |
| CPCG0241 | 0 | 0 | 0 | 0 | 0 | 0 | 0 | 0 | 0 | 0 | 0 | 0 | 0 | 0 | 0 | 0 | 0 | 0 | 0 |
| CPCG0242 | 1 | 0 | 0 | 0 | 0 | 0 | 1 | 0 | 0 | 0 | 1 | 0 | 0 | 0 | 0 | 0 | 0 | 1 | 1 |
| CPCG0246 | 0 | 0 | 0 | 0 | 0 | 0 | 0 | 0 | 0 | 0 | 0 | 0 | 0 | 0 | 0 | 0 | 0 | 0 | 0 |
| CPCG0248 | 0 | 0 | 0 | 1 | 0 | 0 | 0 | 0 | 0 | 0 | 0 | 0 | 0 | 0 | 0 | 0 | 0 | 0 | 0 |
| CPCG0249 | 0 | 0 | 0 | 0 | 0 | 0 | 0 | 0 | 0 | 0 | 0 | 1 | 0 | 0 | 1 | 0 | 0 | 0 | 0 |
| CPCG0250 | 1 | 0 | 0 | 0 | 0 | 0 | 0 | 0 | 0 | 0 | 0 | 0 | 0 | 0 | 0 | 0 | 0 | 0 | 0 |
| CPCG0251 | 0 | 0 | 0 | 0 | 0 | 0 | 0 | 0 | 0 | 0 | 0 | 0 | 1 | 0 | 0 | 0 | 0 | 0 | 0 |
| CPCG0255 | 0 | 0 | 0 | 0 | 0 | 0 | 0 | 0 | 0 | 0 | 0 | 0 | 0 | 0 | 0 | 0 | 0 | 0 | 0 |
| CPCG0256 | 1 | 0 | 0 | 0 | 0 | 0 | 0 | 0 | 1 | 0 | 0 | 0 | 0 | 0 | 0 | 0 | 0 | 1 | 0 |
| CPCG0258 | 0 | 0 | 0 | 0 | 0 | 0 | 0 | 0 | 0 | 0 | 0 | 0 | 0 | 0 | 0 | 0 | 0 | 0 | 0 |
| CPCG0259 | 1 | 0 | 0 | 0 | 0 | 0 | 0 | 0 | 0 | 0 | 0 | 0 | 0 | 0 | 0 | 0 | 0 | 0 | 0 |
| CPCG0260 | 0 | 0 | 0 | 0 | 0 | 0 | 0 | 0 | 0 | 0 | 0 | 0 | 0 | 0 | 0 | 0 | 0 | 0 | 0 |
| CPCG0262 | 0 | 0 | 0 | 0 | 0 | 0 | 1 | 0 | 0 | 0 | 0 | 0 | 0 | 0 | 1 | 0 | 0 | 0 | 0 |
| CPCG0263 | 1 | 0 | 0 | 0 | 0 | 0 | 0 | 0 | 0 | 0 | 0 | 0 | 0 | 0 | 0 | 0 | 0 | 0 | 0 |
| CPCG0265 | 0 | 0 | 0 | 0 | 0 | 1 | 0 | 0 | 0 | 0 | 0 | 0 | 0 | 0 | 0 | 0 | 0 | 0 | 0 |
| CPCG0266 | 0 | 0 | 0 | 0 | 0 | 0 | 0 | 0 | 0 | 0 | 0 | 0 | 0 | 1 | 0 | 0 | 0 | 0 | 0 |
| CPCG0267 | 0 | 0 | 0 | 0 | 0 | 0 | 1 | 0 | 0 | 0 | 0 | 0 | 0 | 0 | 0 | 0 | 0 | 0 | 0 |
| CPCG0268 | 0 | 0 | 0 | 1 | 0 | 0 | 0 | 0 | 0 | 0 | 0 | 0 | 0 | 0 | 0 | 0 | 0 | 0 | 0 |
| CPCG0269 | 1 | 0 | 1 | 0 | 0 | 0 | 0 | 0 | 0 | 0 | 0 | 0 | 0 | 0 | 1 | 0 | 0 | 0 | 0 |
| CPCG0324 | 0 | 0 | 0 | 0 | 1 | 0 | 0 | 0 | 1 | 0 | 0 | 0 | 0 | 0 | 0 | 0 | 0 | 0 | 0 |
| CPCG0331 | 0 | 0 | 0 | 0 | 1 | 0 | 0 | 0 | 1 | 0 | 0 | 0 | 1 | 0 | 0 | 0 | 0 | 0 | 0 |
| CPCG0334 | 0 | 0 | 0 | 0 | 0 | 0 | 0 | 0 | 0 | 0 | 0 | 0 | 0 | 0 | 0 | 0 | 0 | 0 | 0 |
| CPCG0336 | 0 | 0 | 0 | 0 | 0 | 0 | 0 | 0 | 0 | 0 | 1 | 0 | 0 | 0 | 0 | 0 | 0 | 0 | 0 |
| CPCG0339 | 0 | 0 | 0 | 0 | 1 | 0 | 1 | 0 | 0 | 0 | 0 | 0 | 0 | 0 | 0 | 0 | 0 | 0 | 0 |
| CPCG0340 | 0 | 0 | 1 | 0 | 0 | 0 | 0 | 0 | 1 | 0 | 0 | 0 | 0 | 0 | 0 | 0 | 0 | 0 | 0 |
| CPCG0341 | 0 | 0 | 0 | 0 | 0 | 0 | 0 | 0 | 0 | 0 | 0 | 0 | 0 | 0 | 0 | 0 | 0 | 0 | 0 |
| CPCG0342 | 1 | 0 | 0 | 0 | 0 | 0 | 0 | 0 | 0 | 0 | 0 | 0 | 0 | 0 | 0 | 0 | 0 | 0 | 0 |
| CPCG0344 | 1 | 0 | 0 | 0 | 0 | 0 | 0 | 0 | 0 | 0 | 0 | 0 | 0 | 0 | 0 | 0 | 0 | 0 | 0 |
| CPCG0345 | 0 | 0 | 0 | 0 | 0 | 0 | 0 | 0 | 0 | 0 | 0 | 0 | 0 | 0 | 0 | 0 | 1 | 0 | 0 |
| CPCG0346 | 0 | 0 | 1 | 1 | 0 | 0 | 0 | 0 | 0 | 0 | 0 | 0 | 0 | 0 | 0 | 0 | 0 | 0 | 0 |
| CPCG0348 | 0 | 0 | 0 | 0 | 0 | 0 | 0 | 0 | 0 | 0 | 0 | 0 | 0 | 0 | 0 | 0 | 0 | 0 | 0 |
| CPCG0350 | 0 | 0 | 0 | 0 | 0 | 0 | 0 | 0 | 0 | 0 | 0 | 0 | 1 | 0 | 0 | 0 | 0 | 0 | 0 |
| CPCG0352 | 1 | 0 | 0 | 0 | 0 | 0 | 0 | 0 | 0 | 0 | 1 | 0 | 0 | 0 | 0 | 0 | 0 | 0 | 0 |
| CPCG0353 | 0 | 0 | 0 | 0 | 0 | 0 | 0 | 0 | 0 | 0 | 0 | 0 | 0 | 0 | 0 | 0 | 0 | 0 | 0 |
| CPCG0354 | 0 | 0 | 0 | 0 | 0 | 0 | 0 | 0 | 0 | 0 | 0 | 0 | 0 | 0 | 0 | 0 | 0 | 0 | 0 |
| CPCG0355 | 1 | 0 | 1 | 0 | 0 | 0 | 0 | 0 | 0 | 0 | 0 | 0 | 0 | 0 | 0 | 0 | 0 | 0 | 0 |
| CPCG0356 | 0 | 0 | 1 | 0 | 0 | 0 | 0 | 0 | 0 | 0 | 0 | 0 | 1 | 0 | 1 | 0 | 0 | 0 | 0 |
| CPCG0357 | 0 | 0 | 0 | 0 | 0 | 0 | 0 | 0 | 0 | 0 | 0 | 0 | 0 | 0 | 0 | 0 | 0 | 0 | 0 |
| CPCG0358 | 0 | 0 | 0 | 0 | 1 | 0 | 0 | 0 | 0 | 0 | 0 | 0 | 0 | 0 | 0 | 0 | 0 | 0 | 0 |
| CPCG0360 | 0 | 0 | 0 | 0 | 0 | 0 | 0 | 0 | 0 | 0 | 0 | 0 | 0 | 0 | 0 | 0 | 0 | 0 | 0 |
| CPCG0361 | 0 | 0 | 0 | 0 | 0 | 0 | 0 | 0 | 0 | 0 | 1 | 0 | 0 | 0 | 0 | 0 | 0 | 0 | 0 |
| CPCG0362 | 0 | 0 | 0 | 0 | 0 | 0 | 0 | 0 | 0 | 0 | 0 | 0 | 0 | 0 | 0 | 0 | 0 | 0 | 0 |
| CPCG0363 | 0 | 0 | 0 | 0 | 0 | 0 | 0 | 0 | 0 | 0 | 0 | 0 | 0 | 0 | 0 | 0 | 0 | 0 | 0 |
| CPCG0364 | 0 | 0 | 0 | 0 | 0 | 0 | 0 | 0 | 0 | 0 | 0 | 0 | 0 | 0 | 0 | 0 | 0 | 0 | 0 |

TABLE 6-continued

| Mitochondrial mutation recurrence for 41 nuclear genomic features | | | | | | | | | | | | | | | | | | | |
|---|---|---|---|---|---|---|---|---|---|---|---|---|---|---|---|---|---|---|---|
| CPCG0365 | 0 | 0 | 0 | 0 | 0 | 0 | 0 | 0 | 0 | 0 | 0 | 0 | 0 | 0 | 0 | 0 | 0 | 0 | 0 |
| CPCG0366 | 0 | 0 | 0 | 0 | 0 | 0 | 0 | 0 | 0 | 0 | 0 | 0 | 0 | 0 | 0 | 0 | 0 | 0 | 0 |
| CPCG0368 | 1 | 0 | 0 | 0 | 0 | 0 | 0 | 0 | 0 | 0 | 0 | 0 | 0 | 0 | 0 | 0 | 0 | 0 | 0 |
| CPCG0369 | 0 | 0 | 0 | 0 | 0 | 0 | 0 | 0 | 0 | 0 | 0 | 0 | 0 | 0 | 0 | 0 | 0 | 0 | 0 |
| CPCG0371 | 0 | 0 | 0 | 0 | 0 | 0 | 0 | 0 | 0 | 0 | 0 | 0 | 0 | 0 | 0 | 0 | 0 | 0 | 0 |
| CPCG0372 | 0 | 0 | 0 | 0 | 0 | 0 | 0 | 0 | 0 | 0 | 0 | 1 | 0 | 0 | 0 | 0 | 0 | 0 | 0 |
| CPCG0373 | 0 | 0 | 0 | 0 | 0 | 0 | 0 | 0 | 0 | 0 | 0 | 0 | 0 | 0 | 0 | 0 | 0 | 0 | 0 |
| CPCG0374 | 0 | 0 | 0 | 0 | 0 | 0 | 0 | 0 | 1 | 0 | 0 | 0 | 0 | 0 | 0 | 0 | 0 | 0 | 0 |
| CPCG0375 | 0 | 0 | 0 | 0 | 0 | 0 | 0 | 0 | 0 | 0 | 0 | 0 | 0 | 0 | 0 | 0 | 0 | 0 | 0 |
| CPCG0378 | 0 | 0 | 0 | 0 | 0 | 0 | 0 | 0 | 0 | 0 | 0 | 0 | 0 | 1 | 0 | 0 | 0 | 0 | 0 |
| CPCG0379 | 0 | 0 | 0 | 0 | 0 | 0 | 0 | 0 | 0 | 0 | 1 | 0 | 0 | 0 | 0 | 0 | 0 | 0 | 0 |
| CPCG0380 | 0 | 0 | 0 | 0 | 0 | 0 | 0 | 0 | 0 | 0 | 0 | 0 | 0 | 0 | 0 | 1 | 0 | 0 | 0 |
| CPCG0381 | 0 | 0 | 0 | 0 | 0 | 0 | 0 | 0 | 0 | 0 | 0 | 0 | 0 | 0 | 0 | 0 | 0 | 0 | 0 |
| CPCG0387 | 0 | 1 | 1 | 0 | 0 | 0 | 0 | 0 | 0 | 0 | 0 | 0 | 0 | 0 | 0 | 0 | 0 | 0 | 0 |
| CPCG0388 | 0 | 0 | 0 | 0 | 1 | 0 | 0 | 0 | 0 | 0 | 0 | 0 | 0 | 0 | 0 | 0 | 0 | 0 | 0 |
| CPCG0391 | 0 | 0 | 0 | 0 | 0 | 0 | 0 | 0 | 0 | 0 | 0 | 0 | 0 | 0 | 0 | 0 | 0 | 0 | 0 |
| CPCG0392 | 0 | 0 | 0 | 0 | 0 | 0 | 0 | 0 | 0 | 0 | 0 | 0 | 0 | 0 | 0 | 0 | 0 | 0 | 0 |
| CPCG0401 | 0 | 0 | 0 | 0 | 0 | 0 | 0 | 0 | 0 | 0 | 0 | 0 | 0 | 0 | 0 | 0 | 0 | 0 | 0 |
| CPCG0404 | 1 | 0 | 0 | 0 | 0 | 0 | 0 | 0 | 0 | 0 | 0 | 0 | 0 | 0 | 0 | 0 | 0 | 0 | 0 |
| CPCG0407 | 0 | 0 | 0 | 0 | 0 | 0 | 1 | 0 | 1 | 1 | 0 | 0 | 0 | 0 | 0 | 0 | 0 | 0 | 0 |
| CPCG0409 | 0 | 0 | 0 | 0 | 0 | 0 | 1 | 0 | 0 | 0 | 0 | 0 | 0 | 0 | 0 | 0 | 0 | 0 | 0 |
| CPCG0410 | 0 | 0 | 0 | 0 | 1 | 0 | 0 | 0 | 1 | 0 | 1 | 0 | 0 | 0 | 0 | 0 | 0 | 0 | 0 |
| CPCG0411 | 0 | 0 | 0 | 0 | 0 | 0 | 0 | 0 | 0 | 0 | 0 | 0 | 0 | 0 | 0 | 0 | 0 | 0 | 0 |
| CPCG0412 | 0 | 0 | 1 | 1 | 0 | 0 | 0 | 0 | 0 | 0 | 0 | 0 | 0 | 0 | 0 | 0 | 0 | 0 | 0 |
| CPCG0413 | 0 | 0 | 0 | 0 | 0 | 0 | 0 | 0 | 0 | 0 | 0 | 0 | 0 | 0 | 0 | 0 | 0 | 0 | 0 |
| CPCG0414 | 0 | 0 | 0 | 0 | 0 | 0 | 0 | 0 | 0 | 0 | 0 | 0 | 0 | 0 | 0 | 0 | 0 | 0 | 0 |
| CPCG0004 | 0 | 0 | 0 | 0 | 0 | 0 | 0 | 0 | 0 | 0 | 0 | 0 | 0 | 0 | 0 | 0 | 0 | 0 | 0 |
| CPCG0005 | 0 | 0 | 0 | 0 | 1 | 0 | 0 | 0 | 0 | 0 | 0 | 0 | 0 | 0 | 0 | 0 | 0 | 0 | 0 |
| CPCG0007 | 0 | 0 | 0 | 0 | 0 | 0 | 0 | 0 | 0 | 0 | 0 | 0 | 0 | 0 | 0 | 0 | 0 | 0 | 0 |
| CPCG0008 | 0 | 0 | 0 | 0 | 0 | 0 | 0 | 0 | 0 | 0 | 0 | 0 | 0 | 0 | 0 | 0 | 0 | 0 | 0 |
| CPCG0015 | 0 | 0 | 0 | 0 | 0 | 0 | 0 | 0 | 0 | 0 | 0 | 0 | 0 | 0 | 0 | 0 | 0 | 0 | 0 |
| CPCG0019 | 0 | 0 | 0 | 1 | 0 | 0 | 0 | 0 | 0 | 0 | 0 | 0 | 0 | 0 | 0 | 0 | 0 | 0 | 0 |
| CPCG0022 | 0 | 0 | 0 | 0 | 0 | 0 | 0 | 0 | 0 | 0 | 0 | 0 | 0 | 0 | 0 | 0 | 0 | 0 | 0 |
| CPCG0027 | 0 | 0 | 0 | 0 | 1 | 1 | 0 | 0 | 0 | 0 | 0 | 0 | 0 | 0 | 0 | 0 | 0 | 0 | 0 |
| CPCG0030 | 0 | 0 | 0 | 0 | 0 | 0 | 0 | 0 | 0 | 0 | 1 | 0 | 0 | 0 | 0 | 0 | 0 | 0 | 0 |
| CPCG0036 | 0 | 0 | 0 | 0 | 0 | 0 | 0 | 0 | 0 | 0 | 0 | 0 | 0 | 0 | 0 | 0 | 0 | 0 | 0 |
| CPCG0042 | 0 | 0 | 0 | 0 | 0 | 0 | 0 | 0 | 0 | 0 | 0 | 0 | 0 | 0 | 0 | 0 | 0 | 0 | 0 |
| CPCG0050 | 0 | 0 | 0 | 0 | 0 | 0 | 0 | 0 | 0 | 0 | 0 | 0 | 1 | 0 | 0 | 0 | 0 | 0 | 0 |
| CPCG0070 | 1 | 0 | 0 | 0 | 0 | 0 | 0 | 0 | 0 | 0 | 0 | 0 | 0 | 0 | 1 | 0 | 0 | 1 | 0 |
| CPCG0071 | 0 | 0 | 0 | 0 | 0 | 1 | 1 | 0 | 0 | 0 | 0 | 0 | 0 | 0 | 0 | 0 | 0 | 0 | 0 |
| CPCG0075 | 0 | 0 | 0 | 0 | 0 | 0 | 0 | 0 | 0 | 0 | 0 | 0 | 0 | 0 | 0 | 0 | 0 | 0 | 0 |
| CPCG0076 | 0 | 0 | 0 | 0 | 0 | 0 | 0 | 0 | 1 | 0 | 0 | 0 | 0 | 0 | 0 | 0 | 0 | 0 | 0 |
| CPCG0082 | 0 | 0 | 0 | 0 | 0 | 0 | 0 | 0 | 0 | 0 | 0 | 0 | 0 | 0 | 0 | 1 | 0 | 0 | 0 |
| CPCG0084 | 1 | 0 | 0 | 0 | 0 | 0 | 0 | 0 | 0 | 0 | 0 | 0 | 0 | 0 | 0 | 0 | 0 | 0 | 0 |
| CPCG0089 | 0 | 0 | 0 | 0 | 0 | 0 | 0 | 0 | 0 | 0 | 0 | 0 | 0 | 0 | 1 | 0 | 0 | 0 | 0 |
| CPCG0090 | 0 | 0 | 0 | 1 | 0 | 0 | 0 | 0 | 0 | 0 | 0 | 0 | 1 | 0 | 0 | 0 | 0 | 0 | 0 |
| CPCG0096 | 0 | 0 | 0 | 0 | 0 | 0 | 0 | 0 | 0 | 0 | 0 | 0 | 1 | 0 | 0 | 0 | 0 | 0 | 0 |
| CPCG0097 | 1 | 1 | 0 | 0 | 0 | 0 | 0 | 0 | 0 | 0 | 0 | 0 | 0 | 0 | 0 | 0 | 0 | 0 | 0 |
| CPCG0120 | 0 | 0 | 0 | 0 | 0 | 1 | 0 | 0 | 0 | 0 | 0 | 0 | 0 | 0 | 0 | 0 | 0 | 0 | 0 |
| CPCG0122 | 0 | 0 | 0 | 0 | 0 | 0 | 0 | 0 | 0 | 0 | 0 | 0 | 0 | 0 | 0 | 0 | 0 | 0 | 0 |
| CPCG0126 | 0 | 0 | 0 | 0 | 0 | 0 | 0 | 0 | 0 | 0 | 0 | 0 | 0 | 0 | 0 | 0 | 0 | 0 | 0 |

TABLE 6-continued

| Mitochondrial mutation recurrence for 41 nuclear genomic features | | | | | | | | | | | | | | | | | | | |
|---|---|---|---|---|---|---|---|---|---|---|---|---|---|---|---|---|---|---|---|
| CPCG0194 | 0 | 0 | 0 | 0 | 0 | 0 | 0 | 0 | 0 | 0 | 0 | 0 | 0 | 0 | 0 | 0 | 0 | 0 | 0 |
| CPCG0198 | 1 | 0 | 0 | 0 | 0 | 0 | 0 | 0 | 0 | 0 | 0 | 0 | 0 | 0 | 0 | 0 | 0 | 0 | 0 |
| CPCG0204 | 1 | 0 | 0 | 1 | 0 | 0 | 1 | 0 | 0 | 0 | 0 | 0 | 0 | 0 | 0 | 0 | 0 | 1 | 0 |
| CPCG0237 | 0 | 0 | 0 | 0 | 0 | 0 | 0 | 0 | 0 | 0 | 1 | 0 | 0 | 0 | 0 | 0 | 0 | 0 | 0 |
| CPCG0243 | 0 | 0 | 0 | 0 | 0 | 0 | 0 | 0 | 0 | 0 | 0 | 0 | 0 | 0 | 0 | 0 | 0 | 0 | 0 |
| CPCG0257 | 0 | 0 | 0 | 0 | 0 | 0 | 0 | 0 | 0 | 0 | 0 | 0 | 0 | 0 | 0 | 0 | 0 | 0 | 0 |
| CPCG0067 | 0 | 1 | 1 | 0 | 0 | 1 | 0 | 0 | 0 | 0 | 0 | 0 | 0 | 0 | 0 | 0 | 0 | 0 | 0 |
| CPCG0103 | 0 | 0 | 0 | 0 | 0 | 0 | 0 | 0 | 1 | 0 | 0 | 0 | 0 | 0 | 0 | 0 | 1 | 0 | 0 |
| CPCG0072 | 0 | 0 | 0 | 0 | 0 | 0 | 0 | 0 | 0 | 0 | 0 | 0 | 0 | 0 | 1 | 0 | 0 | 0 | 0 |
| CPCG0100 | 1 | 0 | 0 | 0 | 1 | 0 | 0 | 0 | 0 | 0 | 0 | 0 | 0 | 0 | 0 | 0 | 0 | 1 | 0 |
| CPCG0187 | 1 | 0 | 0 | 0 | 0 | 0 | 0 | 0 | 0 | 0 | 0 | 0 | 0 | 0 | 0 | 0 | 0 | 0 | 0 |
| CPCG0188 | 0 | 0 | 0 | 0 | 0 | 0 | 0 | 0 | 0 | 0 | 0 | 0 | 0 | 0 | 0 | 0 | 0 | 0 | 0 |
| CPCG0235 | 0 | 0 | 0 | 0 | 0 | 0 | 0 | 0 | 0 | 0 | 0 | 0 | 0 | 0 | 0 | 0 | 0 | 0 | 0 |
| CPCG0349 | 0 | 0 | 0 | 0 | 0 | 0 | 0 | 0 | 0 | 0 | 0 | 0 | 0 | 0 | 1 | 0 | 0 | 0 | 0 |
| CPCG0377 | 0 | 0 | 0 | 0 | 0 | 0 | 0 | 0 | 1 | 0 | 0 | 0 | 0 | 0 | 0 | 0 | 0 | 0 | 0 |
| CPCG0382 | 0 | 0 | 0 | 0 | 0 | 0 | 0 | 0 | 0 | 0 | 0 | 0 | 0 | 0 | 0 | 0 | 0 | 0 | 0 |
| CPCG0408 | 0 | 0 | 0 | 0 | 0 | 0 | 0 | 0 | 0 | 0 | 0 | 0 | 0 | 0 | 0 | 0 | 0 | 0 | 0 |
| Berger0508 | 0 | 1 | 0 | 0 | 0 | 0 | 0 | 0 | 1 | 0 | 0 | 0 | 0 | 0 | 0 | 0 | 0 | 0 | 0 |
| Berger0581 | 0 | 0 | 0 | 0 | 0 | 0 | 0 | 0 | 0 | 0 | 0 | 0 | 0 | 0 | 0 | 0 | 0 | 0 | 0 |
| Berger1701 | 0 | 0 | 0 | 0 | 0 | 0 | 0 | 0 | 0 | 0 | 0 | 0 | 0 | 0 | 0 | 0 | 0 | 0 | 0 |
| Berger1783 | 0 | 0 | 0 | 0 | 0 | 0 | 0 | 0 | 0 | 0 | 0 | 0 | 0 | 0 | 0 | 0 | 0 | 0 | 0 |
| Berger2832 | 0 | 0 | 0 | 0 | 0 | 0 | 0 | 0 | 0 | 0 | 0 | 0 | 0 | 0 | 0 | 0 | 0 | 0 | 0 |
| Berger3027 | 0 | 0 | 1 | 0 | 0 | 0 | 0 | 0 | 0 | 0 | 0 | 0 | 0 | 0 | 0 | 0 | 0 | 0 | 0 |
| Berger3043 | 0 | 0 | 0 | 0 | 0 | 0 | 0 | 0 | 0 | 0 | 1 | 1 | 0 | 0 | 0 | 1 | 0 | 0 | 0 |
| EOPC-02 | 0 | 0 | 0 | 0 | 0 | 0 | 0 | 0 | 0 | 0 | 0 | 0 | 0 | 0 | 0 | 0 | 0 | 0 | 0 |
| EOPC-03 | 0 | 0 | 0 | 0 | 0 | 0 | 1 | 0 | 0 | 0 | 0 | 0 | 0 | 0 | 0 | 0 | 0 | 0 | 0 |
| EOPC-04 | 1 | 0 | 0 | 1 | 0 | 0 | 0 | 0 | 0 | 0 | 0 | 0 | 0 | 0 | 0 | 0 | 0 | 0 | 0 |
| EOPC-05 | 1 | 0 | 0 | 0 | 0 | 0 | 0 | 0 | 0 | 0 | 0 | 0 | 0 | 0 | 0 | 0 | 0 | 0 | 0 |
| EOPC-06 | 0 | 1 | 0 | 0 | 0 | 0 | 0 | 0 | 0 | 0 | 0 | 0 | 0 | 0 | 0 | 0 | 0 | 0 | 0 |
| EOPC-07 | 0 | 0 | 0 | 1 | 0 | 0 | 0 | 0 | 1 | 1 | 0 | 1 | 0 | 0 | 0 | 0 | 0 | 0 | 0 |
| EOPC-08 | 0 | 0 | 0 | 0 | 0 | 0 | 0 | 0 | 0 | 0 | 0 | 0 | 0 | 0 | 0 | 0 | 0 | 0 | 0 |
| EOPC-09 | 0 | 0 | 0 | 0 | 0 | 0 | 0 | 0 | 0 | 0 | 0 | 0 | 0 | 0 | 0 | 0 | 0 | 0 | 0 |
| EOPC-010 | 0 | 1 | 0 | 0 | 0 | 0 | 0 | 0 | 0 | 0 | 0 | 0 | 1 | 0 | 0 | 0 | 0 | 0 | 0 |
| EOPC-011 | 0 | 0 | 0 | 0 | 0 | 0 | 0 | 0 | 0 | 0 | 0 | 0 | 0 | 0 | 0 | 0 | 0 | 0 | 0 |
| Baca03-1426 | 0 | 0 | 1 | 0 | 0 | 0 | 0 | 0 | 0 | 0 | 0 | 0 | 0 | 0 | 0 | 0 | 0 | 0 | 0 |
| Baca05-1657 | 0 | 0 | 0 | 0 | 0 | 0 | 0 | 0 | 0 | 0 | 1 | 0 | 0 | 0 | 0 | 0 | 0 | 0 | 0 |
| Baca05-3595 | 1 | 0 | 0 | 0 | 0 | 0 | 0 | 0 | 0 | 0 | 1 | 0 | 0 | 0 | 0 | 0 | 0 | 0 | 0 |
| Baca05-3852 | 0 | 0 | 0 | 0 | 1 | 1 | 0 | 0 | 0 | 0 | 0 | 0 | 0 | 0 | 0 | 0 | 0 | 0 | 0 |
| Baca06-1749 | 0 | 0 | 0 | 0 | 0 | 0 | 0 | 0 | 0 | 0 | 1 | 0 | 0 | 0 | 0 | 0 | 0 | 0 | 0 |
| Baca06-3199 | 1 | 0 | 0 | 0 | 0 | 0 | 0 | 0 | 0 | 0 | 0 | 0 | 0 | 0 | 0 | 0 | 0 | 1 | 0 |
| Baca07-4610 | 1 | 0 | 0 | 0 | 0 | 0 | 0 | 0 | 0 | 0 | 0 | 0 | 0 | 0 | 0 | 0 | 0 | 1 | 0 |
| Baca07-4941 | 0 | 0 | 1 | 0 | 0 | 0 | 0 | 0 | 0 | 0 | 0 | 0 | 0 | 0 | 0 | 0 | 0 | 0 | 0 |
| Baca07-5037 | 0 | 0 | 0 | 0 | 0 | 0 | 0 | 0 | 0 | 0 | 0 | 0 | 0 | 0 | 0 | 0 | 0 | 0 | 0 |
| Baca08-4154 | 0 | 0 | 1 | 0 | 0 | 0 | 0 | 0 | 0 | 0 | 0 | 0 | 0 | 0 | 0 | 0 | 0 | 0 | 0 |
| Baca08-716 | 0 | 0 | 0 | 0 | 0 | 0 | 0 | 0 | 0 | 0 | 0 | 0 | 0 | 0 | 0 | 0 | 0 | 0 | 0 |
| Baca09-37 | 0 | 0 | 0 | 0 | 0 | 0 | 0 | 0 | 0 | 0 | 1 | 0 | 0 | 0 | 0 | 0 | 0 | 0 | 0 |
| BacaSTID 0000000410 | 0 | 0 | 0 | 0 | 0 | 0 | 0 | 0 | 0 | 0 | 0 | 0 | 0 | 0 | 0 | 0 | 0 | 0 | 0 |
| BacaSTID 0000002872 | 0 | 0 | 0 | 0 | 0 | 0 | 0 | 0 | 0 | 0 | 1 | 0 | 0 | 0 | 0 | 0 | 0 | 0 | 0 |
| TCGA-CH- | 0 | 0 | 0 | 0 | 1 | 1 | 0 | 0 | 0 | 0 | 0 | 0 | 0 | 0 | 0 | 0 | 0 | 0 | 0 |

TABLE 6-continued

Mitochondrial mutation recurrence for 41 nuclear genomic features

| | | | | | | | | | | | | | | | | | | | |
|---|---|---|---|---|---|---|---|---|---|---|---|---|---|---|---|---|---|---|---|
| 5750 | | | | | | | | | | | | | | | | | | | |
| TCGA-CH-5763 | 0 | 0 | 0 | 0 | 0 | 0 | 0 | 0 | 0 | 0 | 0 | 0 | 0 | 0 | 0 | 0 | 0 | 0 | 0 |
| TCGA-CH-5771 | 0 | 0 | 0 | 0 | 0 | 0 | 0 | 0 | 0 | 0 | 0 | 0 | 0 | 0 | 0 | 0 | 0 | 0 | 0 |
| TCGA-CH-5788 | 1 | 0 | 0 | 0 | 0 | 0 | 0 | 0 | 0 | 0 | 0 | 0 | 0 | 0 | 0 | 0 | 0 | 0 | 0 |
| TCGA-CH-5789 | 0 | 0 | 0 | 0 | 0 | 0 | 0 | 0 | 0 | 0 | 0 | 0 | 0 | 0 | 0 | 0 | 0 | 0 | 0 |
| TCGA-EJ-5503 | 0 | 0 | 0 | 0 | 0 | 0 | 0 | 0 | 0 | 0 | 0 | 0 | 0 | 0 | 0 | 0 | 0 | 0 | 0 |
| TCGA-EJ-5506 | 1 | 0 | 0 | 0 | 0 | 1 | 0 | 0 | 0 | 0 | 0 | 0 | 0 | 0 | 0 | 0 | 0 | 0 | 0 |
| TCGA-EJ-7791 | 0 | 0 | 0 | 0 | 0 | 0 | 0 | 0 | 0 | 0 | 0 | 0 | 0 | 0 | 0 | 0 | 0 | 0 | 0 |
| TCGA-G9-6336 | 0 | 0 | 0 | 0 | 0 | 0 | 0 | 0 | 0 | 0 | 0 | 0 | 1 | 0 | 0 | 0 | 0 | 0 | 0 |
| TCGA-G9-6365 | 0 | 0 | 0 | 0 | 0 | 0 | 0 | 0 | 0 | 0 | 0 | 0 | 0 | 0 | 0 | 0 | 0 | 0 | 0 |
| TCGA-G9-6370 | 0 | 0 | 0 | 0 | 0 | 0 | 0 | 0 | 0 | 0 | 0 | 0 | 0 | 0 | 0 | 0 | 0 | 0 | 0 |
| TCGA-G9-7522 | 0 | 0 | 0 | 0 | 0 | 0 | 0 | 0 | 0 | 0 | 0 | 0 | 0 | 0 | 0 | 0 | 0 | 0 | 0 |
| TCGA-HC-7075 | 1 | 0 | 0 | 0 | 0 | 0 | 0 | 0 | 0 | 0 | 0 | 0 | 0 | 0 | 0 | 0 | 0 | 0 | 0 |
| TCGA-HC-7079 | 0 | 0 | 0 | 0 | 0 | 0 | 0 | 0 | 0 | 0 | 0 | 0 | 0 | 0 | 0 | 0 | 0 | 0 | 0 |
| TCGA-HC-7233 | 0 | 0 | 0 | 0 | 0 | 0 | 0 | 0 | 0 | 0 | 0 | 0 | 0 | 0 | 0 | 0 | 0 | 0 | 0 |
| TCGA-HC-7737 | 0 | 0 | 0 | 0 | 0 | 0 | 0 | 0 | 0 | 0 | 0 | 0 | 0 | 0 | 0 | 0 | 0 | 0 | 0 |
| TCGA-HC-7740 | 0 | 0 | 0 | 0 | 0 | 0 | 0 | 0 | 0 | 0 | 0 | 0 | 0 | 0 | 0 | 0 | 0 | 0 | 0 |
| TCGA-HC-7744 | 0 | 0 | 0 | 0 | 0 | 0 | 0 | 0 | 0 | 0 | 0 | 0 | 0 | 0 | 0 | 0 | 0 | 0 | 0 |
| TCGA-HC-8258 | 0 | 0 | 0 | 0 | 0 | 0 | 0 | 0 | 0 | 0 | 0 | 0 | 0 | 0 | 0 | 0 | 0 | 0 | 0 |
| TCGA-HI-7169 | 0 | 0 | 0 | 0 | 0 | 0 | 0 | 0 | 0 | 0 | 0 | 0 | 0 | 0 | 0 | 0 | 0 | 0 | 0 |

| patient_id | HV1 | HV2 | mitro_SNV Count | ETS | PGA (median dichot-omized) | kataegis_ind | chromo-thripsis_ind | nuclear SNV count (median dichotomized) |
|---|---|---|---|---|---|---|---|---|
| CPCG0001 | 1 | 0 | 1 | 1 | 1 | 0 | 0 | 1 |
| CPCG0003 | 0 | 0 | 1 | 0 | 1 | 0 | 0 | 1 |
| CPCG0006 | 0 | 0 | 0 | 0 | 1 | 1 | 0 | 1 |
| CPCG0020 | 0 | 0 | 1 | 0 | 0 | 0 | 0 | 1 |
| CPCG0040 | 1 | 0 | 3 | 0 | 1 | 1 | 0 | 1 |
| CPCG0046 | 1 | 0 | 5 | 0 | 0 | 0 | 0 | 0 |

TABLE 6-continued

Mitochondrial mutation recurrence for 41 nuclear genomic features

| | | | | | | | | |
|---|---|---|---|---|---|---|---|---|
| CPCG0047 | 0 | 0 | 0 | 1 | 1 | 0 | 0 | 1 |
| CPCG0048 | 0 | 0 | 0 | 1 | 0 | 0 | 0 | 0 |
| CPCG0057 | 0 | 0 | 1 | 1 | 1 | 0 | 0 | 1 |
| CPCG0063 | 0 | 0 | 2 | 0 | 1 | 0 | 0 | 1 |
| CPCG0073 | 0 | 1 | 2 | 1 | 1 | 0 | 0 | 1 |
| CPCG0078 | 0 | 1 | 2 | 0 | 1 | 0 | 0 | 1 |
| CPCG0081 | 0 | 1 | 2 | 1 | 1 | 1 | 0 | 1 |
| CPCG0083 | 0 | 0 | 1 | 1 | 1 | 0 | 0 | 1 |
| CPCG0087 | 0 | 0 | 0 | 1 | 1 | 1 | 0 | 1 |
| CPCG0094 | 0 | 0 | 0 | 1 | 1 | 1 | 0 | 1 |
| CPCG0095 | 0 | 0 | 1 | 1 | 1 | 0 | 0 | 0 |
| CPCG0098 | 0 | 1 | 4 | 0 | 1 | 1 | 1 | 1 |
| CPCG0099 | 0 | 0 | 0 | 0 | 1 | 0 | 0 | 1 |
| CPCG0102 | 0 | 0 | 1 | 0 | 0 | 0 | 0 | 0 |
| CPCG0114 | 1 | 1 | 4 | 1 | 0 | 0 | 0 | 0 |
| CPCG0117 | 0 | 0 | 1 | 0 | 1 | 0 | 1 | 0 |
| CPCG0121 | 0 | 0 | 0 | 1 | 1 | 0 | 0 | 0 |
| CPCG0123 | 0 | 0 | 1 | 1 | 0 | 0 | 0 | 1 |
| CPCG0124 | 0 | 0 | 2 | 1 | 0 | 0 | 0 | 1 |
| CPCG0127 | 0 | 0 | 1 | 0 | 0 | 0 | 0 | 0 |
| CPCG0128 | 1 | 0 | 2 | 0 | 0 | 0 | 1 | 1 |
| CPCG0154 | 0 | 0 | 0 | 1 | 0 | 0 | 0 | 0 |
| CPCG0158 | 0 | 1 | 1 | 1 | 1 | 0 | 0 | 1 |
| CPCG0166 | 0 | 1 | 5 | 0 | 0 | 0 | 0 | 0 |
| CPCG0182 | 0 | 0 | 0 | 1 | 0 | 0 | 0 | 0 |
| CPCG0183 | 1 | 0 | 2 | 0 | 1 | 0 | 0 | 1 |
| CPCG0184 | 0 | 0 | 0 | 0 | 1 | 0 | 0 | 0 |
| CPCG0185 | 0 | 0 | 1 | 1 | 1 | 0 | 0 | 1 |
| CPCG0189 | 1 | 0 | 5 | 1 | 1 | 0 | 1 | 1 |
| CPCG0190 | 0 | 0 | 1 | 0 | 1 | 0 | 0 | 0 |
| CPCG0191 | 0 | 0 | 0 | 1 | 1 | 0 | 1 | 0 |
| CPCG0196 | 0 | 1 | 2 | 1 | 1 | 0 | 0 | 0 |
| CPCG0199 | 0 | 0 | 0 | 0 | 0 | 0 | 0 | 0 |
| CPCG0201 | 0 | 0 | 2 | 1 | 1 | 1 | 1 | 1 |
| CPCG0205 | 0 | 1 | 1 | 0 | 0 | 0 | 0 | 0 |
| CPCG0206 | 0 | 1 | 1 | 0 | 1 | 0 | 0 | 0 |
| CPCG0208 | 0 | 0 | 0 | 0 | 0 | 0 | 1 | 1 |
| CPCG0210 | 0 | 0 | 0 | 0 | 1 | 0 | 0 | 0 |
| CPCG0211 | 0 | 0 | 3 | 1 | 1 | 0 | 0 | 1 |
| CPCG0212 | 0 | 0 | 1 | 0 | 1 | 0 | 0 | 1 |
| CPCG0213 | 0 | 0 | 3 | 1 | 1 | 0 | 0 | 0 |
| CPCG0217 | 0 | 0 | 3 | 0 | 0 | 0 | 1 | 0 |
| CPCG0232 | 0 | 0 | 1 | 1 | 1 | 0 | 1 | 1 |
| CPCG0233 | 0 | 0 | 2 | 0 | 1 | 1 | 1 | 1 |
| CPCG0234 | 0 | 0 | 2 | 0 | 0 | 0 | 0 | 0 |
| CPCG0236 | 0 | 0 | 1 | 0 | 1 | 1 | 1 | 1 |
| CPCG0238 | 0 | 0 | 0 | 1 | 1 | 0 | 1 | 0 |
| CPCG0241 | 0 | 0 | 0 | 1 | 1 | 0 | 0 | 1 |
| CPCG0242 | 0 | 1 | 3 | 1 | 1 | 0 | 0 | 1 |
| CPCG0246 | 0 | 0 | 0 | 0 | 0 | 0 | 0 | 0 |
| CPCG0248 | 0 | 0 | 1 | 1 | 1 | 1 | 0 | 1 |

TABLE 6-continued

Mitochondrial mutation recurrence for 41 nuclear genomic features

| | | | | | | | | |
|---|---|---|---|---|---|---|---|---|
| CPCG0249 | 0 | 0 | 2 | 0 | 1 | 1 | 1 | 1 |
| CPCG0250 | 1 | 0 | 1 | 1 | 0 | 0 | 0 | 0 |
| CPCG0251 | 0 | 0 | 1 | 0 | 0 | 1 | 0 | 0 |
| CPCG0255 | 0 | 0 | 0 | 0 | 1 | 1 | 1 | 1 |
| CPCG0256 | 1 | 1 | 3 | 1 | 0 | 1 | 0 | 0 |
| CPCG0258 | 0 | 0 | 0 | 1 | 0 | 0 | 0 | 0 |
| CPCG0259 | 1 | 0 | 1 | 0 | 0 | 0 | 0 | 1 |
| CPCG0260 | 0 | 0 | 0 | 1 | 1 | 0 | 1 | 1 |
| CPCG0262 | 0 | 0 | 2 | 1 | 1 | 1 | 0 | 1 |
| CPCG0263 | 0 | 1 | 1 | 0 | 1 | 0 | 1 | 0 |
| CPCG0265 | 0 | 0 | 1 | 1 | 0 | 1 | 0 | 1 |
| CPCG0266 | 0 | 0 | 1 | 1 | 1 | 0 | 0 | 1 |
| CPCG0267 | 0 | 0 | 1 | 0 | 0 | 0 | 0 | 0 |
| CPCG0268 | 0 | 0 | 1 | 0 | 1 | 1 | 1 | 0 |
| CPCG0269 | 1 | 0 | 4 | 0 | 0 | 0 | 0 | 1 |
| CPCG0324 | 0 | 0 | 2 | 1 | 1 | 1 | 1 | 1 |
| CPCG0331 | 0 | 0 | 3 | 1 | 1 | 0 | 0 | 1 |
| CPCG0334 | 0 | 0 | 0 | 0 | 1 | 0 | 0 | 1 |
| CPCG0336 | 0 | 0 | 1 | 1 | 0 | 1 | 0 | 0 |
| CPCG0339 | 0 | 0 | 2 | 0 | 0 | 0 | 0 | 0 |
| CPCG0340 | 0 | 0 | 2 | 1 | 1 | 1 | 1 | 1 |
| CPCG0341 | 0 | 0 | 0 | 1 | 1 | 0 | 0 | 1 |
| CPCG0342 | 0 | 0 | 1 | 1 | 0 | 0 | 0 | 1 |
| CPCG0344 | 0 | 0 | 1 | 0 | 1 | 0 | 0 | 0 |
| CPCG0345 | 0 | 0 | 1 | 0 | 1 | 0 | 0 | 1 |
| CPCG0346 | 0 | 0 | 2 | 1 | 1 | 0 | 0 | 0 |
| CPCG0348 | 0 | 0 | 0 | 0 | 0 | 0 | 0 | 0 |
| CPCG0350 | 0 | 0 | 1 | 1 | 1 | 1 | 1 | 1 |
| CPCG0352 | 1 | 0 | 2 | 1 | 1 | 0 | 0 | 0 |
| CPCG0353 | 0 | 0 | 0 | 0 | 0 | 0 | 0 | 0 |
| CPCG0354 | 0 | 0 | 0 | 1 | 0 | 1 | 0 | 1 |
| CPCG0355 | 1 | 0 | 2 | 0 | 0 | 0 | 0 | 0 |
| CPCG0356 | 0 | 0 | 3 | 1 | 1 | 1 | 0 | 0 |
| CPCG0357 | 0 | 0 | 0 | 1 | 1 | 0 | 0 | 1 |
| CPCG0358 | 0 | 0 | 1 | 1 | 1 | 0 | 0 | 0 |
| CPCG0360 | 0 | 0 | 0 | 0 | 1 | 0 | 0 | 0 |
| CPCG0361 | 0 | 0 | 1 | 1 | 0 | 0 | 0 | 0 |
| CPCG0362 | 0 | 0 | 0 | 1 | 0 | 0 | 0 | 0 |
| CPCG0363 | 0 | 0 | 0 | 0 | 0 | 0 | 0 | 0 |
| CPCG0364 | 0 | 0 | 0 | 1 | 0 | 0 | 1 | 1 |
| CPCG0365 | 0 | 0 | 0 | 0 | 0 | 0 | 0 | 0 |
| CPCG0366 | 0 | 0 | 0 | 1 | 1 | 0 | 0 | 0 |
| CPCG0368 | 1 | 0 | 1 | 0 | 0 | 0 | 0 | 0 |
| CPCG0369 | 0 | 0 | 0 | 1 | 1 | 0 | 0 | 1 |
| CPCG0371 | 0 | 0 | 0 | 1 | 1 | 1 | 0 | 1 |
| CPCG0372 | 0 | 0 | 1 | 1 | 1 | 1 | 0 | 1 |
| CPCG0373 | 0 | 0 | 0 | 0 | 0 | 0 | 0 | 0 |
| CPCG0374 | 0 | 0 | 1 | 0 | 1 | 1 | 0 | 0 |
| CPCG0375 | 0 | 0 | 0 | 0 | 1 | 0 | 0 | 1 |
| CPCG0378 | 0 | 0 | 1 | 0 | 1 | 0 | 0 | 1 |
| CPCG0379 | 0 | 0 | 1 | 1 | 1 | 0 | 1 | 1 |

TABLE 6-continued

Mitochondrial mutation recurrence for 41 nuclear genomic features

| | | | | | | | | | | | | | |
|---|---|---|---|---|---|---|---|---|---|---|---|---|---|
| CPCG0380 | 0 | 0 | 1 | | 1 | | 1 | | 0 | | 0 | | 1 |
| CPCG0381 | 0 | 0 | 0 | | 0 | | 0 | | 0 | | 0 | | 0 |
| CPCG0387 | 0 | 0 | 2 | | 0 | | 0 | | 0 | | 0 | | 1 |
| CPCG0388 | 0 | 0 | 1 | | 0 | | 1 | | 0 | | 0 | | 1 |
| CPCG0391 | 0 | 0 | 0 | | 0 | | 0 | | 0 | | 0 | | 0 |
| CPCG0392 | 0 | 0 | 0 | | 1 | | 1 | | 0 | | 1 | | 1 |
| CPCG0401 | 0 | 0 | 0 | | 0 | | 0 | | 0 | | 0 | | 0 |
| CPCG0404 | 1 | 0 | 1 | | 0 | | 1 | | 1 | | 0 | | 1 |
| CPCG0407 | 0 | 0 | 2 | | 1 | | 1 | | 0 | | 0 | | 1 |
| CPCG0409 | 0 | 0 | 1 | | 1 | | 0 | | 0 | | 0 | | 1 |
| CPCG0410 | 0 | 0 | 3 | | 1 | | 1 | | 0 | | 1 | | 0 |
| CPCG0411 | 0 | 0 | 0 | | 0 | | 0 | | 0 | | 0 | | 0 |
| CPCG0412 | 0 | 0 | 3 | | 1 | | 1 | | 1 | | 0 | | 1 |
| CPCG0413 | 0 | 0 | 0 | | 0 | | 0 | | 0 | | 0 | | 0 |
| CPCG0414 | 0 | 0 | 0 | | 0 | | 0 | | 1 | | 0 | | 0 |
| CPCG0004 | 0 | 0 | 0 | NA | | NA | | NA | | NA | | NA | |
| CPCG0005 | 0 | 0 | 1 | NA | | NA | | NA | | NA | | NA | |
| CPCG0007 | 0 | 0 | 0 | NA | | NA | | NA | | NA | | NA | |
| CPCG0008 | 0 | 0 | 0 | NA | | NA | | NA | | NA | | NA | |
| CPCG0015 | 0 | 0 | 0 | NA | | NA | | NA | | NA | | NA | |
| CPCG0019 | 0 | 0 | 1 | NA | | NA | | NA | | NA | | NA | |
| CPCG0022 | 0 | 0 | 0 | | 0 | | 0 | | 0 | | 0 | | 0 |
| CPCG0027 | 0 | 0 | 2 | | 0 | | 0 | | 0 | | 0 | | 0 |
| CPCG0030 | 0 | 0 | 2 | NA | | NA | | NA | | NA | | NA | |
| CPCG0036 | 0 | 0 | 0 | NA | | NA | | NA | | NA | | NA | |
| CPCG0042 | 0 | 0 | 0 | NA | | NA | | NA | | NA | | NA | |
| CPCG0050 | 0 | 0 | 1 | | 0 | | 0 | | 0 | | 0 | | 1 |
| CPCG0070 | 0 | 1 | 2 | NA | | NA | | NA | | NA | | NA | |
| CPCG0071 | 0 | 0 | 2 | NA | | NA | | NA | | NA | | NA | |
| CPCG0075 | 0 | 0 | 0 | NA | | NA | | NA | | NA | | NA | |
| CPCG0076 | 0 | 0 | 1 | NA | | NA | | NA | | NA | | NA | |
| CPCG0082 | 0 | 0 | 1 | NA | | NA | | NA | | NA | | NA | |
| CPCG0084 | 1 | 0 | 1 | NA | | NA | | NA | | NA | | NA | |
| CPCG0089 | 0 | 0 | 1 | NA | | NA | | NA | | NA | | NA | |
| CPCG0090 | 0 | 0 | 2 | | 0 | | 0 | | 0 | | 0 | | 1 |
| CPCG0096 | 0 | 0 | 1 | NA | | NA | | NA | | NA | | NA | |
| CPCG0097 | 1 | 0 | 2 | NA | | NA | | NA | | NA | | NA | |
| CPCG0120 | 0 | 0 | 1 | NA | | NA | | NA | | NA | | NA | |
| CPCG0122 | 0 | 0 | 0 | | 1 | | 0 | | 1 | | 0 | | 0 |
| CPCG0126 | 0 | 0 | 0 | NA | | NA | | NA | | NA | | NA | |
| CPCG0194 | 0 | 0 | 0 | NA | | NA | | NA | | NA | | NA | |
| CPCG0198 | 1 | 0 | 1 | NA | | NA | | NA | | NA | | NA | |
| CPCG0204 | 0 | 1 | 3 | NA | 0 | NA | | NA | | NA | | NA | |
| CPCG0237 | 0 | 0 | 1 | | 0 | | 0 | | 0 | | 0 | | 0 |
| CPCG0243 | 0 | 0 | 0 | | | | 0 | | 0 | | 0 | | 0 |
| CPCG0257 | 0 | 0 | 0 | NA | | NA | | NA | | NA | | NA | |
| CPCG0067 | 0 | 0 | 4 | NA | | NA | | NA | | NA | | NA | |
| CPCG0103 | 0 | 0 | 2 | NA | | NA | | NA | | NA | | NA | |
| CPCG0072 | 0 | 0 | 1 | NA | | NA | | NA | | NA | | NA | |
| CPCG0100 | 0 | 1 | 2 | NA | | NA | | NA | | NA | | NA | |
| CPCG0187 | 0 | 1 | 1 | NA | | NA | | NA | | NA | | NA | |

TABLE 6-continued

Mitochondrial mutation recurrence for 41 nuclear genomic features

| | | | | | | | | |
|---|---|---|---|---|---|---|---|---|
| CPCG0188 | 0 | 0 | 0 | NA | NA | NA | NA | NA |
| CPCG0235 | 0 | 0 | 0 | NA | NA | NA | NA | NA |
| CPCG0349 | 0 | 0 | 1 | NA | NA | NA | NA | NA |
| CPCG0377 | 0 | 0 | 1 | NA | NA | NA | NA | NA |
| CPCG0382 | 0 | 0 | 0 | NA | NA | NA | NA | NA |
| CPCG0408 | 0 | 0 | 0 | NA | NA | NA | NA | NA |
| Berger0508 | 0 | 0 | 3 | 0 | NA | 1 | NA | 0 |
| Berger0581 | 0 | 0 | 0 | NA | NA | NA | NA | NA |
| Berger1701 | 0 | 0 | 0 | 1 | NA | 0 | NA | 0 |
| Berger1783 | 0 | 0 | 0 | NA | NA | NA | NA | NA |
| Berger2832 | 0 | 0 | 0 | 1 | NA | 0 | NA | 0 |
| Berger3027 | 0 | 0 | 1 | NA | NA | NA | NA | NA |
| Berger3043 | 0 | 0 | 3 | 0 | NA | 0 | NA | 1 |
| EOPC-02 | 0 | 0 | 0 | 0 | NA | 0 | NA | 0 |
| EOPC-03 | 0 | 0 | 1 | NA | NA | NA | NA | NA |
| EOPC-04 | 1 | 0 | 2 | 0 | NA | 1 | NA | 1 |
| EOPC-05 | 1 | 0 | 1 | 0 | NA | 0 | NA | 0 |
| EOPC-06 | 0 | 0 | 0 | 0 | NA | 0 | NA | 0 |
| EOPC-07 | 0 | 0 | 4 | 0 | NA | 0 | NA | 0 |
| EOPC-08 | 0 | 0 | 0 | 0 | NA | 0 | NA | 0 |
| EOPC-09 | 0 | 0 | 0 | 0 | NA | 0 | NA | 0 |
| EOPC-010 | 0 | 0 | 2 | 0 | NA | 0 | NA | 0 |
| EOPC-011 | 0 | 0 | 0 | 0 | NA | 0 | NA | 0 |
| Baca03-1426 | 0 | 0 | 1 | 1 | 0 | 0 | 0 | 1 |
| Baca05-1657 | 0 | 0 | 1 | 1 | 0 | 0 | 0 | 0 |
| Baca05-3595 | 1 | 0 | 2 | 0 | 0 | 0 | 0 | 1 |
| Baca05-3852 | 0 | 0 | 2 | 1 | 0 | 0 | 0 | 0 |
| Baca06-1749 | 0 | 0 | 1 | 0 | 1 | 1 | 1 | 0 |
| Baca06-3199 | 0 | 1 | 1 | 1 | 1 | 1 | 0 | 1 |
| Baca07-4610 | 0 | 1 | 1 | 1 | 1 | 0 | 0 | 1 |
| Baca07-4941 | 0 | 0 | 1 | 1 | 0 | 0 | 0 | 1 |
| Baca07-5037 | 0 | 0 | 0 | 1 | 0 | 0 | 0 | 1 |
| Baca08-4154 | 0 | 0 | 1 | 0 | 1 | 1 | 0 | 1 |
| Baca08-716 | 0 | 0 | 0 | 0 | 0 | 1 | 0 | 1 |
| Baca09-37 | 0 | 0 | 1 | 1 | 0 | 0 | 0 | 1 |
| BacaSTID 0000000410 | 0 | 0 | 0 | 0 | 0 | 0 | 0 | 0 |
| BacaSTID 0000002872 | 0 | 0 | 1 | 1 | 0 | 1 | 0 | 0 |
| TCGA-CH-5750 | 0 | 0 | 2 | 0 | 0 | 1 | 0 | 1 |
| TCGA-CH-5763 | 0 | 0 | 0 | NA | NA | NA | NA | NA |
| TCGA-CH-5771 | 0 | 0 | 0 | NA | NA | NA | NA | NA |
| TCGA-CH-5788 | 1 | 0 | 1 | 0 | 1 | 1 | 1 | 1 |
| TCGA-CH-5789 | 0 | 0 | 0 | 0 | 0 | 0 | 0 | 0 |
| TCGA-EJ-5503 | 0 | 0 | 0 | NA | NA | NA | NA | NA |

TABLE 6-continued

Mitochondrial mutation recurrence for 41 nuclear genomic features

| | | | | | | | | |
|---|---|---|---|---|---|---|---|---|
| TCGA-EJ-5506 | 1 | 0 | 2 | NA | NA | NA | NA | NA |
| TCGA-EJ-7791 | 0 | 0 | 0 | 0 | 0 | 0 | 0 | 0 |
| TCGA-G9-6336 | 0 | 0 | 2 | 1 | 0 | 0 | 0 | 0 |
| TCGA-G9-6365 | 0 | 0 | 0 | 1 | 0 | 0 | 0 | 1 |
| TCGA-G9-6370 | 0 | 0 | 0 | 0 | 0 | 0 | 0 | 0 |
| TCGA-G9-7522 | 0 | 0 | 0 | 0 | 0 | 0 | 0 | 0 |
| TCGA-HC-7075 | 1 | 0 | 1 | 0 | 0 | 1 | 1 | 1 |
| TCGA-HC-7079 | 0 | 0 | 0 | 0 | 0 | 0 | 0 | 0 |
| TCGA-HC-7233 | 0 | 0 | 0 | 0 | 0 | 0 | 0 | 1 |
| TCGA-HC-7737 | 0 | 0 | 0 | NA | NA | NA | NA | NA |
| TCGA-HC-7740 | 0 | 0 | 0 | 0 | 0 | 0 | 0 | 0 |
| TCGA-HC-7744 | 0 | 0 | 0 | 1 | 0 | 1 | 1 | 1 |
| TCGA-HC-8258 | 0 | 0 | 0 | 0 | 0 | 0 | 0 | 0 |
| TCGA-HI-7169 | 0 | 0 | 0 | 0 | 0 | 0 | 0 | 1 |

| GR (median dichotomized) | CDH1_ CNA | CDK N1B_ CNA | CHD1_ CNA | MYC_ CNA | NKX3-1_ CNA | PTEN_ CNA | RB1_ CNA | TP53_ CNA | chr7: 14501 9604 | chr16: 6491 0033 | chr13: 5805 5742 | chr2: 13139 0479 |
|---|---|---|---|---|---|---|---|---|---|---|---|---|
| 0 | 0 | 0 | 0 | 0 | −1 | 0 | 0 | 0 | 0 | 0 | 0 | 0 |
| 0 | 0 | 0 | 0 | 1 | −1 | 0 | −1 | 0 | 0 | 0 | 0 | 0 |
| 0 | −1 | 0 | 0 | 1 | −1 | 0 | 0 | 0 | 0 | 0 | 0 | 0 |
| 0 | 0 | 0 | −1 | 0 | 0 | 0 | 0 | 0 | 0 | 0 | 0 | 0 |
| 0 | 0 | 0 | −1 | 1 | 0 | −1 | −1 | 1 | 0 | 0 | 0 | 0 |
| 0 | 0 | 0 | 0 | 0 | 0 | 0 | 0 | 0 | 0 | 0 | 0 | 0 |
| 0 | 0 | 0 | 0 | 0 | 0 | −1 | 0 | 0 | 0 | 0 | 0 | 0 |
| 1 | −1 | 0 | 0 | 0 | 0 | 0 | −1 | 0 | 0 | 0 | 0 | 0 |
| 0 | 0 | 0 | 0 | 0 | −1 | 0 | −1 | −1 | 0 | 0 | 1 | 0 |
| 0 | 0 | 0 | 0 | 1 | −1 | 0 | −1 | 0 | 0 | 0 | 0 | 0 |
| 0 | 0 | 0 | 0 | 1 | −1 | 0 | 0 | 0 | 1 | 1 | 0 | 0 |
| 0 | 0 | −1 | 0 | 1 | −1 | 0 | −1 | 0 | 0 | 0 | 0 | 0 |
| 1 | −1 | 0 | 0 | 1 | −1 | 0 | 0 | −1 | 0 | 0 | 0 | 0 |
| 0 | −1 | 0 | 0 | 1 | −1 | 0 | 0 | −1 | 0 | 0 | 0 | 0 |
| 1 | 0 | 0 | −1 | 0 | −1 | −1 | 0 | 0 | 0 | 0 | 0 | 0 |
| 0 | 0 | 0 | 0 | 0 | 0 | −1 | −1 | −1 | 0 | 0 | 0 | 0 |
| 0 | 0 | 0 | 0 | 0 | 0 | −1 | 0 | 0 | 0 | 0 | 0 | 0 |
| 1 | 0 | −1 | 0 | 1 | −1 | 0 | −1 | 0 | 1 | 0 | 0 | 0 |

TABLE 6-continued

Mitochondrial mutation recurrence for 41 nuclear genomic features

| | | | | | | | | | | | | |
|---|---|---|---|---|---|---|---|---|---|---|---|---|
| 1 | 0 | 0 | −1 | 0 | −1 | −1 | −1 | 0 | 0 | 0 | 0 | 0 |
| 0 | 0 | 0 | 0 | 0 | 0 | 0 | 0 | −1 | 0 | 0 | 0 | 0 |
| 0 | 0 | 0 | −1 | 0 | 0 | −1 | −1 | 0 | 0 | 0 | 0 | 0 |
| 1 | 0 | −1 | −1 | 0 | 0 | 0 | −1 | 0 | 0 | 0 | 0 | 0 |
| 0 | −1 | 0 | 0 | 0 | −1 | 0 | 0 | −1 | 0 | 0 | 0 | 0 |
| 0 | 0 | 0 | 0 | 0 | 0 | 0 | 0 | 1 | 0 | 0 | 0 | 0 |
| 1 | 0 | 0 | 0 | 0 | 0 | −1 | −1 | 0 | 0 | 0 | 0 | 0 |
| 0 | 0 | 0 | 0 | 0 | 0 | 0 | 0 | 0 | 0 | 0 | 0 | 0 |
| 1 | 0 | −1 | 0 | 0 | −1 | 0 | −1 | 0 | 0 | 0 | 0 | 0 |
| 0 | 0 | 0 | 0 | 0 | 0 | 0 | 0 | 0 | 1 | 0 | 0 | 1 |
| 1 | −1 | 0 | −1 | 0 | 0 | −1 | 0 | −1 | 0 | 0 | 0 | 0 |
| 0 | 0 | 0 | 0 | 0 | 0 | 0 | 0 | 0 | 0 | 0 | 0 | 0 |
| 0 | 0 | 0 | −1 | 0 | 0 | −1 | 0 | 0 | 0 | 0 | 0 | 0 |
| 1 | −1 | 0 | −1 | 0 | −1 | 0 | 0 | 0 | 0 | 0 | 0 | 0 |
| 0 | 1 | 0 | −1 | 1 | −1 | −1 | −1 | −1 | 0 | 1 | 0 | 0 |
| 1 | 0 | 0 | 0 | 0 | −1 | −1 | 0 | 0 | 0 | 0 | 1 | 0 |
| 1 | 0 | 0 | 0 | 0 | −1 | 0 | −1 | −1 | 0 | 1 | 0 | 0 |
| 1 | 0 | 0 | −1 | 0 | 0 | −1 | 0 | 0 | 0 | 0 | 0 | 0 |
| 1 | 0 | 0 | 0 | 0 | −1 | −1 | 0 | 0 | 0 | 0 | 0 | 0 |
| 1 | 0 | 1 | 0 | 0 | 0 | 0 | −1 | 0 | 0 | 0 | 0 | 0 |
| 0 | 0 | 0 | 0 | 0 | 0 | 0 | 0 | 0 | 0 | 0 | 0 | 0 |
| 1 | 0 | 0 | −1 | 0 | −1 | 0 | −1 | 0 | 0 | 0 | 0 | 0 |
| 0 | 0 | 0 | 0 | 0 | −1 | −1 | 0 | 0 | 0 | 0 | 0 | 0 |
| 1 | 0 | 0 | 0 | 1 | −1 | 0 | 0 | 0 | 0 | 1 | 0 | 0 |
| 1 | 0 | 0 | 0 | 0 | −1 | 0 | 0 | 0 | 0 | 0 | 0 | 0 |
| 1 | 0 | 0 | 0 | 0 | −1 | 0 | 0 | −1 | 0 | 0 | 0 | 0 |
| 1 | 0 | −1 | 0 | 0 | −1 | −1 | −1 | 0 | 0 | 0 | 0 | 0 |
| 0 | 0 | −1 | 0 | 0 | −1 | 0 | 0 | −1 | 0 | 0 | 0 | 0 |
| 0 | 0 | 0 | 0 | 0 | −1 | −1 | 0 | −1 | 0 | 0 | 0 | 0 |
| 0 | −1 | −1 | 0 | 0 | 0 | 0 | 0 | 0 | 0 | 0 | 0 | 0 |
| 1 | −1 | −1 | 0 | 0 | −1 | −1 | 0 | −1 | 0 | 0 | 0 | 0 |
| 1 | 0 | −1 | −1 | 0 | −1 | 0 | −1 | 0 | 0 | 0 | 0 | 0 |
| 0 | 0 | 0 | 0 | 0 | 0 | 0 | 0 | 0 | 0 | 0 | 0 | 0 |
| 1 | 0 | 0 | −1 | 1 | −1 | 0 | 0 | 0 | 0 | 0 | 0 | 0 |
| 1 | 0 | 0 | 0 | 0 | 0 | −1 | −1 | 0 | 0 | 0 | 0 | 0 |
| 1 | 0 | 0 | 0 | 0 | −1 | −1 | 0 | 0 | 0 | 0 | 0 | 0 |
| 1 | 0 | 0 | 0 | 1 | −1 | −1 | 0 | 0 | 0 | 0 | 0 | 0 |
| 0 | 0 | −1 | 0 | 0 | 0 | 0 | 0 | 0 | 0 | 0 | 1 | 0 |
| 1 | 0 | −1 | 0 | 0 | −1 | −1 | 0 | −1 | 0 | 0 | 0 | 0 |
| 1 | 0 | −1 | −1 | 0 | −1 | 0 | −1 | 0 | 0 | 1 | 0 | 0 |
| 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 0 |
| 1 | 0 | 0 | 0 | 0 | 0 | 0 | −1 | 0 | 0 | 0 | 0 | 0 |
| 0 | 0 | 0 | 0 | 0 | −1 | −1 | 0 | 0 | 0 | 0 | 0 | 0 |
| 0 | 0 | 0 | 0 | 0 | −1 | 0 | 0 | 0 | 0 | 0 | 0 | 0 |
| 0 | 0 | 0 | 0 | 0 | 0 | 0 | 0 | 0 | 1 | 0 | 0 | 0 |
| 1 | −1 | 0 | 0 | 0 | 0 | −1 | 0 | −1 | 0 | 0 | 0 | 0 |
| 1 | −1 | 0 | 0 | 0 | −1 | 0 | 0 | 0 | 0 | 0 | 1 | 0 |
| 1 | −1 | 0 | 0 | 0 | −1 | −1 | 0 | 0 | 0 | 0 | 0 | 0 |
| 0 | 0 | −1 | 0 | 0 | −1 | 0 | 0 | 0 | 0 | 0 | 0 | 0 |
| 0 | 0 | −1 | 0 | 0 | −1 | −1 | 0 | 0 | 0 | 0 | 0 | 0 |

TABLE 6-continued

Mitochondrial mutation recurrence for 41 nuclear genomic features

| | | | | | | | | | | | | |
|---|---|---|---|---|---|---|---|---|---|---|---|---|
| 1 | 0 | −1 | 0 | 0 | 0 | 0 | 0 | 0 | 0 | 0 | 1 | 0 |
| 1 | 0 | 0 | −1 | 0 | 0 | 0 | 0 | 0 | 0 | 0 | 0 | 0 |
| 0 | 0 | −1 | 0 | 0 | −1 | 0 | 0 | 0 | 0 | 0 | 0 | 0 |
| 1 | −1 | 0 | 0 | 0 | −1 | −1 | 0 | −1 | 0 | 0 | 0 | 0 |
| 1 | 0 | −1 | 0 | 0 | −1 | −1 | 0 | 0 | 0 | 0 | 0 | 0 |
| 1 | 0 | −1 | 0 | 0 | −1 | 0 | −1 | 0 | 0 | 0 | 0 | 1 |
| 1 | 0 | 0 | 0 | 0 | 0 | 0 | 0 | −1 | 0 | 0 | 0 | 0 |
| 1 | 0 | 0 | 0 | 1 | 0 | 0 | 0 | 0 | 0 | 0 | 0 | 0 |
| 1 | 0 | −1 | −1 | 0 | −1 | −1 | −1 | 0 | 0 | 0 | 0 | 0 |
| 0 | −1 | 0 | 0 | 0 | −1 | 0 | −1 | 0 | 0 | 1 | 0 | 0 |
| 1 | 0 | 0 | 0 | 0 | 0 | −1 | −1 | −1 | 0 | 0 | 1 | 0 |
| 1 | 0 | 0 | 0 | 0 | 0 | 0 | −1 | 0 | 0 | 0 | 0 | 0 |
| 0 | 0 | 1 | 0 | 1 | 1 | 0 | −1 | 0 | 1 | 0 | 0 | 0 |
| 1 | 0 | −1 | 0 | 0 | 0 | −1 | −1 | 0 | 0 | 0 | 0 | 0 |
| 0 | −1 | 0 | 0 | 0 | −1 | 0 | −1 | −1 | 0 | 0 | 0 | 0 |
| 1 | 0 | −1 | 0 | 0 | −1 | −1 | 0 | 0 | 0 | 1 | 0 | 0 |
| 0 | 0 | 0 | 0 | 0 | −1 | −1 | −1 | 0 | 0 | 0 | 0 | 0 |
| 0 | 0 | 0 | 0 | 0 | 0 | −1 | −1 | 0 | 0 | 0 | 0 | 0 |
| 1 | 0 | −1 | 0 | 0 | −1 | −1 | 0 | −1 | 0 | 0 | 0 | 1 |
| 1 | 0 | 0 | 0 | 0 | 0 | 0 | 0 | −1 | 0 | 0 | 0 | 0 |
| 0 | −1 | 0 | 0 | 0 | −1 | 0 | 0 | 0 | 0 | 0 | 0 | 0 |
| 1 | 0 | 0 | 0 | 0 | 0 | −1 | −1 | −1 | 0 | 0 | 0 | 0 |
| 0 | −1 | 0 | 0 | 0 | 0 | 0 | −1 | −1 | 0 | 0 | 0 | 0 |
| 1 | 0 | −1 | −1 | 0 | −1 | 0 | 0 | 0 | 1 | 0 | 0 | 0 |
| 0 | 0 | 0 | 0 | 0 | −1 | −1 | 0 | −1 | 0 | 0 | 0 | 0 |
| 0 | 0 | 0 | 0 | 0 | 0 | −1 | 0 | −1 | 0 | 0 | 0 | 0 |
| 0 | 0 | 0 | 0 | 0 | 0 | 0 | 0 | 0 | 0 | 0 | 1 | 0 |
| 1 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 |
| 1 | 0 | 0 | 0 | 0 | −1 | 0 | 0 | 0 | 0 | 0 | 0 | 0 |
| 0 | 0 | 0 | 0 | 0 | 0 | 0 | 0 | 0 | 1 | 1 | 0 | 1 |
| 1 | −1 | −1 | 0 | 1 | −1 | 0 | 0 | −1 | 0 | 0 | 0 | 0 |
| 1 | −1 | −1 | 0 | 0 | −1 | 0 | 0 | 0 | 0 | 0 | 0 | 0 |
| 1 | 0 | −1 | 0 | 0 | 0 | −1 | −1 | 0 | 1 | 0 | 0 | 0 |
| 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 1 |
| 1 | 0 | 0 | −1 | 0 | 0 | 0 | 0 | 0 | 0 | 0 | 0 | 0 |
| 1 | −1 | −1 | 0 | 0 | −1 | −1 | 0 | 0 | 0 | 0 | 0 | 0 |
| 1 | −1 | 0 | 0 | 1 | −1 | 0 | −1 | −1 | 0 | 0 | 0 | 0 |
| 1 | 0 | 0 | 0 | 1 | −1 | −1 | 0 | 0 | 1 | 0 | 0 | 0 |
| 0 | 0 | 0 | 0 | 0 | 0 | 0 | 0 | 0 | 0 | 0 | 0 | 0 |
| 1 | 0 | 0 | 0 | 0 | 0 | −1 | 0 | 0 | 0 | 0 | 0 | 0 |
| 1 | 0 | −1 | −1 | 0 | −1 | 0 | 0 | 0 | 0 | 0 | 0 | 0 |
| 0 | 0 | 0 | 0 | 0 | 0 | 0 | 0 | 0 | 0 | 0 | 0 | 0 |
| 1 | 0 | −1 | −1 | 0 | 0 | −1 | −1 | −1 | 0 | 0 | 0 | 0 |
| 0 | 0 | −1 | 0 | 0 | 0 | −1 | 0 | 0 | 0 | 0 | 0 | 0 |
| 1 | 0 | 0 | −1 | 0 | 0 | 0 | 0 | 0 | 0 | 0 | 0 | 0 |
| 1 | 0 | 0 | −1 | 0 | −1 | 0 | −1 | −1 | 0 | 0 | 0 | 0 |
| 1 | 0 | 0 | 0 | 0 | −1 | −1 | 0 | 0 | 0 | 0 | 0 | 0 |
| 1 | 0 | −1 | 0 | 0 | −1 | −1 | 0 | −1 | 0 | 0 | 0 | 0 |
| 0 | 0 | 0 | 0 | 0 | 0 | −1 | 0 | 0 | 0 | 0 | 0 | 1 |

TABLE 6-continued

| Mitochondrial mutation recurrence for 41 nuclear genomic features | | | | | | | | | | | | |
|---|---|---|---|---|---|---|---|---|---|---|---|---|
| 1 | −1 | 0 | 0 | 0 | −1 | −1 | −1 | −1 | 0 | 0 | 0 | 1 |
| 0 | 0 | −1 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 |
| NA | 0 | 0 | 0 | 0 | −1 | 0 | 0 | −1 | NA | NA | NA | NA |
| NA | 0 | 0 | 0 | 0 | 0 | 0 | 0 | 0 | NA | NA | NA | NA |
| NA | 0 | −1 | 0 | 0 | −1 | 0 | −1 | 0 | NA | NA | NA | NA |
| NA | −1 | 0 | 0 | 1 | 0 | 0 | 0 | 0 | NA | NA | NA | NA |
| NA | 0 | 0 | 0 | 0 | −1 | −1 | 0 | 0 | NA | NA | NA | NA |
| NA | 0 | 0 | 0 | 0 | 0 | −1 | −1 | 0 | NA | NA | NA | NA |
| 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 |
| NA | 0 | 0 | 0 | 0 | 1 | 0 | 0 | 1 | NA | NA | NA | NA |
| NA | 0 | 0 | 0 | 0 | 0 | 0 | 0 | 0 | NA | NA | NA | NA |
| NA | −1 | 0 | −1 | 0 | −1 | −1 | 0 | 0 | NA | NA | NA | NA |
| 0 | 0 | 0 | 0 | 0 | 0 | 0 | 0 | 0 | 0 | 0 | 0 | 0 |
| NA | 0 | 0 | 0 | 0 | 0 | 0 | 0 | 0 | NA | NA | NA | NA |
| NA | 0 | 0 | 0 | 0 | 0 | 0 | 0 | 0 | NA | NA | NA | NA |
| NA | −1 | 0 | 0 | 0 | 0 | −1 | 0 | 0 | NA | NA | NA | NA |
| NA | 0 | 0 | 0 | 0 | 0 | −1 | 0 | 0 | NA | NA | NA | NA |
| NA | −1 | 0 | 0 | 1 | −1 | 0 | 0 | 0 | NA | NA | NA | NA |
| NA | 0 | 0 | 0 | 0 | 0 | 0 | 0 | 1 | NA | NA | NA | NA |
| NA | 0 | 0 | 0 | 0 | 0 | 0 | 0 | 0 | NA | NA | NA | NA |
| 1 | 0 | 0 | 0 | 0 | 0 | 0 | 0 | 0 | 0 | 0 | 0 | 0 |
| NA | 0 | 0 | 0 | 0 | 0 | −1 | −1 | 0 | NA | NA | NA | NA |
| NA | 0 | 0 | 0 | 0 | 0 | 0 | 0 | 0 | NA | NA | NA | NA |
| NA | −1 | 0 | 0 | 1 | 1 | 0 | −1 | 0 | NA | NA | NA | NA |
| 0 | 0 | 0 | 0 | 0 | 0 | 0 | 0 | 0 | 0 | 0 | 0 | 0 |
| NA | 0 | 1 | 0 | 0 | −1 | 0 | −1 | 0 | NA | NA | NA | NA |
| NA | −1 | 0 | 0 | 0 | −1 | 0 | 0 | 0 | NA | NA | NA | NA |
| NA | 0 | 0 | 0 | 0 | 0 | 0 | 0 | 0 | NA | NA | NA | NA |
| NA | 0 | 0 | 0 | 0 | −1 | 0 | 0 | −1 | NA | NA | NA | NA |
| 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 0 |
| NA | 0 | 0 | 0 | 0 | −1 | 0 | 0 | 0 | NA | NA | NA | NA |
| NA | 0 | 0 | 0 | 0 | 0 | 0 | 0 | 0 | NA | NA | NA | NA |
| NA | 0 | 0 | 0 | 0 | 0 | 0 | 0 | −1 | NA | NA | NA | NA |
| NA | 0 | 0 | 0 | 1 | −1 | 0 | 0 | 0 | NA | NA | NA | NA |
| NA | −1 | 0 | −1 | 1 | −1 | −1 | 0 | −1 | NA | NA | NA | NA |
| NA | 1 | 0 | 0 | 1 | −1 | 0 | 0 | −1 | NA | NA | NA | NA |
| NA | 0 | 0 | 0 | 0 | −1 | 0 | −1 | −1 | NA | NA | NA | NA |
| NA | −1 | 0 | −1 | 1 | −1 | 0 | −1 | 0 | NA | NA | NA | NA |
| NA | 0 | 0 | −1 | 0 | −1 | 0 | −1 | 0 | NA | NA | NA | NA |
| NA | 0 | 0 | 0 | 0 | −1 | 0 | 0 | 0 | NA | NA | NA | NA |
| NA | −1 | 0 | −1 | 1 | −1 | 0 | −1 | 0 | NA | NA | NA | NA |
| NA | 0 | −1 | 0 | 0 | −1 | −1 | 0 | 0 | NA | NA | NA | NA |
| 1 | NA | NA | NA | NA | NA | NA | NA | NA | 0 | 0 | 0 | 0 |
| NA | NA | NA | NA | NA | NA | NA | NA | NA | NA | NA | NA | NA |
| 1 | NA | NA | NA | NA | NA | NA | NA | NA | 0 | 0 | 0 | 0 |
| NA | NA | NA | NA | NA | NA | NA | NA | NA | NA | NA | NA | NA |
| 0 | NA | NA | NA | NA | NA | NA | NA | NA | 0 | 0 | 0 | 0 |
| NA | NA | NA | NA | NA | NA | NA | NA | NA | NA | NA | NA | NA |

TABLE 6-continued

| Mitochondrial mutation recurrence for 41 nuclear genomic features | | | | | | | | | | | | | | | | | | | | | | | | | |
|---|---|---|---|---|---|---|---|---|---|---|---|---|---|---|---|---|---|---|---|---|---|---|---|---|---|
| | 1 | NA | | NA | | NA | | NA | | NA | | NA | | NA | | NA | | | 0 | | 0 | | 0 | | 0 |
| | 0 | NA | | NA | | NA | | | 0 | | -1 | NA | | NA | | NA | | | 0 | | 0 | | 0 | | 0 |
| NA | | NA | | NA | | NA | | | 1 | | -1 | NA | | NA | | NA | | NA | | NA | | NA | | NA | |
| | 0 | NA | | NA | | NA | | | 0 | | 0 | NA | | NA | | NA | | | 0 | | 0 | | 0 | | 0 |
| | 0 | NA | | NA | | NA | | | 0 | | 0 | NA | | NA | | NA | | | 0 | | 0 | | 0 | | 0 |
| | 0 | NA | | NA | | NA | | | 0 | | 0 | NA | | NA | | NA | | | 0 | | 0 | | 0 | | 0 |
| | 0 | NA | | NA | | NA | | | 0 | | -1 | NA | | NA | | NA | | | 0 | | 0 | | 0 | | 0 |
| | 0 | NA | | NA | | NA | | | 0 | | 0 | NA | | NA | | NA | | | 0 | | 0 | | 0 | | 0 |
| | 0 | NA | | NA | | NA | | | 0 | | 0 | NA | | NA | | NA | | | 0 | | 0 | | 0 | | 0 |
| | 0 | NA | | NA | | NA | | NA | | NA | | NA | | NA | | NA | | | 0 | | 0 | | 0 | | 0 |
| | 0 | NA | | NA | | NA | | | 0 | | 0 | NA | | NA | | NA | | | 0 | | 0 | | 0 | | 0 |
| | 1 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 1 | | 0 | | 0 | | 0 | | 0 | | 0 | | 0 | | 0 | | 0 | | 0 | | 0 | | 0 | | 0 |
| | 1 | | 0 | | 0 | | 0 | | 0 | | -1 | | -1 | | 0 | | 0 | | 0 | | 0 | | 0 | | 0 |
| | 1 | | 0 | | 0 | | 0 | | 1 | | -1 | | 0 | | 0 | | -1 | | 0 | | 0 | | 0 | | 0 |
| | 1 | | 0 | | 0 | | 0 | | 0 | | 0 | | 0 | | 0 | | 0 | | 0 | | 0 | | 0 | | 0 |
| | 1 | | -1 | | 0 | | 0 | | 1 | | 0 | | -1 | | 0 | | 0 | | 0 | | 0 | | 0 | | 0 |
| | 1 | | 0 | | 0 | | 0 | | 0 | | 0 | | -1 | | 0 | | 0 | | 0 | | 0 | | 0 | | 0 |
| | 1 | | 0 | | 0 | | 0 | | 0 | | 0 | | 0 | | 0 | | 0 | | 0 | | 0 | | 0 | | 0 |
| | 1 | | 0 | | 0 | | 0 | | 1 | | -1 | | -1 | | 0 | | 0 | | 0 | | 0 | | 0 | | 0 |
| | 1 | | 0 | | 0 | | 0 | | 0 | | 0 | | 0 | | 0 | | 0 | | 0 | | 0 | | 0 | | 0 |
| | 1 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| NA | | NA | | NA | | NA | | NA | | NA | | NA | | NA | | NA | | NA | | NA | | NA | | NA | |
| NA | | NA | | NA | | NA | | NA | | NA | | NA | | NA | | NA | | NA | | NA | | NA | | NA | |
| | 1 | | -1 | | 0 | | -1 | | 0 | | -1 | | 1 | | -1 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| NA | | NA | | NA | | NA | | NA | | NA | | NA | | NA | | NA | | NA | | NA | | NA | | NA | |
| NA | | NA | | NA | | NA | | NA | | NA | | NA | | NA | | NA | | NA | | NA | | NA | | NA | |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 1 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| NA | | NA | | NA | | NA | | NA | | NA | | NA | | NA | | NA | | NA | | NA | | NA | | NA | |
| | 0 | | 0 | | 0 | | 0 | | 0 | | 0 | | 0 | | 0 | | 0 | | 0 | | 0 | | 0 | | 0 |
| | 1 | | 0 | | 0 | | 0 | | 0 | | 0 | | 0 | | -1 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 | | 0 | | 0 | | 0 | | 0 |
| | | | | | | | | | | | | | chr22: 3182 6396 | | chr4: 3968 4557 | | ATM_ SNV | | FOXA1_ SNV | | MED12_ SNV | | SPOP_ SNV | | TP53_ SNV |
| | | | | | | | | | | | | | 0 | | 0 | | 0 | | 0 | | 0 | | 0 | | 0 |
| | | | | | | | | | | | | | 0 | | 0 | | 0 | | 1 | | 0 | | 0 | | 0 |

TABLE 6-continued

| Mitochondrial mutation recurrence for 41 nuclear genomic features | | | | | | |
|---|---|---|---|---|---|---|
| 0 | 0 | 0 | 0 | 0 | 0 | 0 |
| 0 | 0 | 0 | 0 | 0 | 1 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 1 | 0 | 0 | 0 |
| 0 | 0 | 1 | 0 | 0 | 0 | 0 |
| 0 | 1 | 0 | 0 | 0 | 0 | 0 |
| 0 | 0 | 0 | 0 | 0 | 0 | 0 |
| 0 | 0 | 1 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 1 | 0 | 0 | 0 |
| 0 | 0 | 0 | 0 | 0 | 1 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 1 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 1 | 1 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 1 | 0 | 0 | 0 | 0 | 1 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 1 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 1 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 1 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 1 | 0 | 0 |
| 0 | 0 | 0 | 0 | 0 | 0 | 0 |
| 0 | 0 | 0 | 0 | 0 | 1 | 0 |
| 0 | 0 | 0 | 0 | 0 | 0 | 1 |
| 0 | 0 | 0 | 0 | 0 | 1 | 0 |
| 1 | 0 | 0 | 0 | 0 | 0 | 0 |

TABLE 6-continued

Mitochondrial mutation recurrence for 41 nuclear genomic features

| | | | | | | |
|---|---|---|---|---|---|---|
| 0 | 0 | 0 | 0 | 0 | 0 | 0 |
| 0 | 1 | 0 | 0 | 0 | 0 | 0 |
| 0 | 0 | 0 | 0 | 0 | 0 | 0 |
| 0 | 0 | 0 | 0 | 0 | 0 | 0 |
| 0 | 1 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 1 | 0 | 0 | 0 | 0 | 0 | 1 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 1 | 0 | 0 | 0 | 0 | 0 | 0 |
| 0 | 0 | 0 | 0 | 1 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 1 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 1 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 1 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 1 | 0 | 0 | 0 | 0 | 0 | 0 |
| 0 | 0 | 0 | 0 | 0 | 0 | 1 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |

TABLE 6-continued

Mitochondrial mutation recurrence for 41 nuclear genomic features

| | | | | | | | | | | | | | |
|---|---|---|---|---|---|---|---|---|---|---|---|---|---|
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 1 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 1 | | 0 | | 0 | | 0 | | 0 | | 0 |
| | 0 | | 0 | | 0 | | 0 | | 0 | | 1 | | 0 |
| | 1 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 1 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 1 | | 0 |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 0 | | 0 |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 0 | | 0 |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |

TABLE 6-continued

Mitochondrial mutation recurrence for 41 nuclear genomic features

| | | | | | | | | | | | | | |
|---|---|---|---|---|---|---|---|---|---|---|---|---|---|
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 1 | | 0 |
| NA | | NA | | NA | | NA | | NA | | NA | | NA | |
| | 0 | | 0 | | 0 | | 0 | | 0 | | 0 | | 0 |
| NA | | NA | | NA | | NA | | NA | | NA | | NA | |
| | 0 | | 0 | | 0 | | 0 | | 0 | | 0 | | 0 |
| NA | | NA | | NA | | NA | | NA | | NA | | NA | |
| | 0 | | 0 | | 0 | | 0 | | 0 | | 1 | | 0 |
| | 0 | | 0 | | 0 | | 0 | | 0 | | 0 | | 0 |
| NA | | NA | | NA | | NA | | NA | | NA | | NA | |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 1 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 1 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 1 |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 1 | | 0 |
| | 0 | | 0 | | 0 | | 0 | | 0 | | 0 | | 0 |
| NA | | NA | | NA | | NA | | NA | | NA | | NA | |
| NA | | NA | | NA | | NA | | NA | | NA | | NA | |
| | 0 | | 0 | | 0 | | 0 | | 0 | | 0 | | 0 |
| | 0 | | 0 | | 0 | | 0 | | 0 | | 0 | | 0 |
| | 0 | | 0 | | 0 | | 0 | | 0 | | 0 | | 0 |

TABLE 6-continued

Mitochondrial mutation recurrence for 41 nuclear genomic features

| | | | | | | |
|---|---|---|---|---|---|---|
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| NA | NA | NA | NA | NA | NA | NA |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |

| chr3: 125Mbp_ Inv | chr3: 129Mbp_ Inv | chr3: 195Mbp_ Inv | chr10: 89Mbp_ Inv | chr21: 42Mbp_ Inv | chr4: 148Mbp_ Ctx | chr6: 97Mbp_ Ctx | chr7: 61Mbp_ Ctx | chr17: 25Mbp_ Ctx |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 1 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 1 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 1 | 0 | 0 | 0 | 0 |
| 0 | 0 | 0 | 0 | 1 | 0 | 0 | 0 | 0 |
| 0 | 0 | 0 | 0 | 0 | 0 | 0 | 1 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 1 | 1 | 0 | 0 |
| 0 | 0 | 0 | 0 | 0 | 0 | 0 | 0 | 0 |
| 0 | 0 | 0 | 1 | 0 | 0 | 0 | 0 | 1 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 1 | 1 | 0 | 0 |
| 0 | 0 | 0 | 0 | 0 | 0 | 0 | 0 | 1 |
| 0 | 0 | 0 | 0 | 0 | 0 | 0 | 0 | 0 |
| 0 | 0 | 0 | 0 | 0 | 0 | 0 | 1 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |

TABLE 6-continued

Mitochondrial mutation recurrence for 41 nuclear genomic features

| | | | | | | | | |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 1 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 1 | 0 | 0 | 0 | 0 | 0 |
| 0 | 0 | 0 | 0 | 0 | 0 | 0 | 0 | 0 |
| 0 | 0 | 0 | 1 | 0 | 0 | 0 | 0 | 0 |
| 0 | 0 | 0 | 0 | 0 | 0 | 0 | 0 | 0 |
| 0 | 0 | 0 | 0 | 0 | 1 | 1 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 1 |
| 0 | 0 | 0 | 0 | 0 | 0 | 0 | 0 | 0 |
| 0 | 0 | 0 | 0 | 0 | 1 | 1 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 1 | 1 | 0 | 0 |
| 0 | 0 | 0 | 0 | 0 | 0 | 0 | 0 | 0 |
| 0 | 0 | 0 | 0 | 0 | 1 | 1 | 0 | 0 |
| 0 | 0 | 0 | 0 | 1 | 0 | 0 | 0 | 0 |
| 0 | 0 | 0 | 0 | 0 | 0 | 0 | 0 | 1 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 1 | 0 | 0 | 0 | 0 | 0 |
| 0 | 0 | 0 | 0 | 0 | 0 | 0 | 0 | 0 |
| 0 | 0 | 0 | 0 | 0 | 1 | 1 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 1 | 0 | 0 | 1 | 1 | 0 | 0 |
| 0 | 0 | 0 | 0 | 0 | 0 | 0 | 0 | 0 |
| 0 | 0 | 0 | 0 | 0 | 0 | 0 | 1 | 0 |
| 1 | 1 | 0 | 0 | 0 | 0 | 0 | 0 | 0 |
| 1 | 1 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 1 | 1 | 0 | 0 | 0 | 0 | 0 | 0 | 0 |
| 0 | 0 | 0 | 0 | 0 | 0 | 0 | 0 | 0 |
| 0 | 0 | 0 | 0 | 1 | 0 | 0 | 0 | 0 |
| 0 | 0 | 0 | 0 | 0 | 1 | 1 | 0 | 0 |
| 0 | 0 | 0 | 1 | 1 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 1 | 1 | 0 | 0 | 0 | 0 | 0 | 0 | 0 |

TABLE 6-continued

| Mitochondrial mutation recurrence for 41 nuclear genomic features | | | | | | | | | | | | | | | | | |
|---|---|---|---|---|---|---|---|---|---|---|---|---|---|---|---|---|---|
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 1 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 1 | | 1 | | 0 | | 0 | | 0 | | 0 | | 0 | | 0 | | 0 |
| | 0 | | 0 | | 0 | | 0 | | 0 | | 1 | | 1 | | 0 | | 0 |
| | 0 | | 0 | | 0 | | 0 | | 0 | | 1 | | 1 | | 0 | | 0 |
| | 1 | | 1 | | 0 | | 0 | | 1 | | 0 | | 0 | | 0 | | 0 |
| | 0 | | 0 | | 0 | | 0 | | 0 | | 0 | | 0 | | 0 | | 0 |
| | 1 | | 1 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 1 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 1 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 1 | | 0 |
| | 0 | | 0 | | 0 | | 0 | | 0 | | 0 | | 0 | | 0 | | 0 |
| | 1 | | 1 | | 0 | | 0 | | 0 | | 0 | | 0 | | 0 | | 0 |
| | 0 | | 0 | | 0 | | 0 | | 1 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| | 0 | | 0 | | 0 | | 0 | | 0 | | 0 | | 0 | | 1 | | 0 |
| | 0 | | 0 | | 0 | | 0 | | 0 | | 0 | | 0 | | 0 | | 0 |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| | 0 | | 0 | | 0 | | 0 | | 0 | | 0 | | 0 | | 0 | | 0 |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |

TABLE 6-continued

| Mitochondrial mutation recurrence for 41 nuclear genomic features | | | | | | | | | | | | | | | | | |
|---|---|---|---|---|---|---|---|---|---|---|---|---|---|---|---|---|---|
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| | 0 | | 0 | | 0 | | 0 | | 0 | | 0 | | 0 | | 0 | | 1 |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| | 1 | | 1 | | 0 | | 0 | | 0 | | 0 | | 0 | | 0 | | 0 |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| | 1 | | 1 | | 0 | | 0 | | 1 | | 0 | | 0 | | 0 | | 0 |
| | 0 | | 0 | | 0 | | 0 | | 0 | | 0 | | 0 | | 0 | | 1 |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| NA | | NA | | NA | | NA | | NA | | NA | | NA | | NA | | NA | |
| | 0 | | 0 | | 0 | | 0 | | 0 | | 0 | | 0 | | 0 | | 0 |
| NA | | NA | | NA | | NA | | NA | | NA | | NA | | NA | | NA | |
| | 0 | | 0 | | 0 | | 1 | | 0 | | 0 | | 0 | | 0 | | 0 |
| NA | | NA | | NA | | NA | | NA | | NA | | NA | | NA | | NA | |
| | 0 | | 0 | | 0 | | 0 | | 0 | | 0 | | 0 | | 0 | | 0 |
| NA | | NA | | NA | | NA | | NA | | NA | | NA | | NA | | NA | |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| NA | | NA | | NA | | NA | | NA | | NA | | NA | | NA | | NA | |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 1 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 0 | | 0 | | 0 | | 0 | | 0 | | 0 | | 0 |
| | 0 | | 0 | | 1 | | 0 | | 0 | | 0 | | 0 | | 0 | | 0 |
| | 0 | | 0 | | 0 | | 0 | | 0 | | 0 | | 1 | | 0 | | 0 |
| | 0 | | 0 | | 0 | | 0 | | 1 | | 0 | | 0 | | 0 | | 1 |
| | 0 | | 0 | | 0 | | 0 | | 1 | | 0 | | 0 | | 0 | | 0 |

TABLE 6-continued

Mitochondrial mutation recurrence for 41 nuclear genomic features

| | | | | | | | | |
|---|---|---|---|---|---|---|---|---|
| 0 | 0 | 0 | 1 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 1 |
| 0 | 0 | 0 | 0 | 0 | 0 | 0 | 0 | 0 |
| 0 | 0 | 1 | 0 | 0 | 0 | 0 | 0 | 0 |
| 0 | 0 | 1 | 0 | 0 | 0 | 0 | 0 | 0 |
| NA | NA | NA | NA | NA | NA | NA | NA | NA |
| NA | NA | NA | NA | NA | NA | NA | NA | NA |
| 0 | 0 | 0 | 0 | 0 | 0 | 0 | 0 | 0 |
| 0 | 0 | 0 | 0 | 0 | 0 | 0 | 0 | 0 |
| NA | NA | NA | NA | NA | NA | NA | NA | NA |
| NA | NA | NA | NA | NA | NA | NA | NA | NA |
| 0 | 0 | 0 | 0 | 0 | 0 | 0 | 0 | 0 |
| 0 | 0 | 0 | 0 | 0 | 0 | 0 | 0 | 0 |
| 1 | 1 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 1 | 1 | 1 | 0 | 0 | 0 | 0 | 0 | 0 |
| NA | NA | NA | NA | NA | NA | NA | NA | NA |
| 0 | 0 | 1 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |

| chr21: 42Mbp_ Ctx | TCERG1L- 5'_Meth | TCERG1L- 3'_Meth | TUBA3C_ Meth | SOX14_ Meth | ACTL6B_ Meth | MIR129-2_ Meth |
|---|---|---|---|---|---|---|
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | 0 | 1 | 0 | 0 | 1 | 1 |
| 0 | NA | NA | NA | NA | NA | NA |
| 0 | 0 | 1 | 0 | 0 | 1 | 1 |
| 0 | 0 | 0 | 0 | 0 | 1 | 1 |
| 0 | 1 | 1 | 0 | 0 | 1 | 0 |
| 0 | NA | NA | NA | NA | NA | NA |
| 1 | 0 | 0 | 1 | 1 | 1 | 0 |
| 0 | 1 | 1 | 0 | 1 | 1 | 1 |
| 1 | NA | NA | NA | NA | NA | NA |
| 0 | 0 | 1 | 0 | 0 | 1 | 1 |
| 1 | 0 | 1 | 0 | 1 | 1 | 1 |
| 0 | 0 | 1 | 0 | 0 | 1 | 1 |
| 0 | NA | NA | NA | NA | NA | NA |
| 0 | NA | NA | NA | NA | NA | NA |
| 0 | 0 | 1 | 0 | 0 | 1 | 1 |
| 0 | 0 | 1 | 0 | 1 | 0 | 1 |

TABLE 6-continued

| Mitochondrial mutation recurrence for 41 nuclear genomic features | | | | | | | | | | | | |
|---|---|---|---|---|---|---|---|---|---|---|---|---|
| 0 | | 1 | | 0 | | 1 | | 0 | | 0 | | 1 |
| 0 | | 0 | | 1 | | 0 | | 0 | | 1 | | 0 |
| 1 | NA | | NA | | NA | | NA | | NA | | NA | |
| 0 | NA | | NA | | NA | | NA | | NA | | NA | |
| 0 | NA | | NA | | NA | | NA | | NA | | NA | |
| 0 | | 1 | | 0 | | 0 | | 0 | | 0 | | 0 |
| 0 | NA | | NA | | NA | | NA | | NA | | NA | |
| 0 | | 1 | | 0 | | 1 | | 1 | | 0 | | 1 |
| 0 | | 1 | | 0 | | 0 | | 0 | | 1 | | 1 |
| 0 | NA | | NA | | NA | | NA | | NA | | NA | |
| 0 | | 1 | | 0 | | 1 | | 1 | | 0 | | 0 |
| 0 | | 1 | | 0 | | 0 | | 0 | | 0 | | 1 |
| 0 | | 0 | | 1 | | 0 | | 0 | | 1 | | 1 |
| 0 | | 0 | | 1 | | 1 | | 1 | | 0 | | 1 |
| 0 | | 1 | | 0 | | 1 | | 1 | | 1 | | 0 |
| 0 | | 0 | | 1 | | 0 | | 0 | | 1 | | 1 |
| 0 | | 0 | | 1 | | 0 | | 0 | | 1 | | 1 |
| 0 | | 0 | | 1 | | 0 | | 1 | | 1 | | 1 |
| 0 | NA | | NA | | NA | | NA | | NA | | NA | |
| 0 | NA | | NA | | NA | | NA | | NA | | NA | |
| 0 | NA | | NA | | NA | | NA | | NA | | NA | |
| 0 | NA | | NA | | NA | | NA | | NA | | NA | |
| 0 | | 1 | | 0 | | 0 | | 1 | | 1 | | 1 |
| 0 | | 0 | | 1 | | 0 | | 0 | | 0 | | 1 |
| 0 | NA | | NA | | NA | | NA | | NA | | NA | |
| 0 | NA | | NA | | NA | | NA | | NA | | NA | |
| 0 | | 0 | | 0 | | 1 | | 1 | | 1 | | 0 |
| 0 | | 1 | | 0 | | 1 | | 1 | | 0 | | 0 |
| 0 | | 1 | | 1 | | 0 | | 1 | | 0 | | 0 |
| 0 | | 0 | | 1 | | 0 | | 0 | | 0 | | 0 |
| 0 | NA | | NA | | NA | | NA | | NA | | NA | |
| 0 | | 1 | | 1 | | 0 | | 0 | | 1 | | 1 |
| 0 | | 0 | | 1 | | 0 | | 0 | | 1 | | 1 |
| 0 | | 0 | | 1 | | 0 | | 0 | | 1 | | 1 |
| 0 | | 0 | | 0 | | 0 | | 0 | | 1 | | 1 |
| 0 | | 0 | | 1 | | 1 | | 0 | | 0 | | 1 |
| 1 | | 1 | | 0 | | 1 | | 1 | | 1 | | 1 |
| 0 | | 0 | | 1 | | 0 | | 0 | | 1 | | 0 |
| 0 | | 1 | | 0 | | 1 | | 1 | | 1 | | 0 |
| 1 | | 1 | | 0 | | 1 | | 0 | | 1 | | 0 |
| 0 | | 0 | | 1 | | 1 | | 1 | | 1 | | 1 |
| 1 | | 0 | | 1 | | 0 | | 1 | | 0 | | 1 |
| 0 | | 0 | | 0 | | 1 | | 1 | | 0 | | 0 |
| 0 | | 0 | | 0 | | 0 | | 0 | | 0 | | 0 |
| 0 | | 1 | | 0 | | 1 | | 1 | | 1 | | 0 |
| 1 | | 0 | | 1 | | 1 | | 0 | | 0 | | 0 |
| 1 | | 1 | | 0 | | 1 | | 1 | | 1 | | 1 |
| 1 | | 1 | | 0 | | 1 | | 1 | | 1 | | 1 |
| 0 | | 0 | | 0 | | 1 | | 1 | | 0 | | 0 |
| 0 | | 1 | | 1 | | 1 | | 1 | | 1 | | 0 |
| 0 | | 0 | | 1 | | 0 | | 0 | | 1 | | 1 |

TABLE 6-continued

Mitochondrial mutation recurrence for 41 nuclear genomic features

| | | | | | | |
|---|---|---|---|---|---|---|
| 0 | 1 | 0 | 0 | 1 | 0 | 1 |
| 0 | 0 | 0 | 0 | 1 | 1 | 1 |
| 0 | 1 | 0 | 1 | 0 | 0 | 1 |
| 0 | 0 | 1 | 1 | 1 | 1 | 0 |
| 0 | 1 | 0 | 0 | 1 | 0 | 0 |
| 0 | 1 | 0 | 1 | 1 | 1 | 0 |
| 0 | 0 | 1 | 0 | 1 | 0 | 0 |
| 0 | 0 | 0 | 0 | 1 | 0 | 0 |
| 0 | 1 | 1 | 0 | 1 | 0 | 0 |
| 0 | 0 | 0 | 1 | 0 | 1 | 0 |
| 0 | 0 | 1 | 0 | 1 | 1 | 1 |
| 1 | 0 | 1 | 1 | 0 | 0 | 0 |
| 1 | 1 | 0 | 1 | 0 | 1 | 1 |
| 0 | 0 | 1 | 0 | 1 | 0 | 0 |
| 0 | 1 | 0 | 0 | 0 | 0 | 1 |
| 0 | 0 | 1 | 0 | 0 | 1 | 0 |
| 0 | 0 | 1 | 1 | 0 | 0 | 1 |
| 0 | 1 | 0 | 0 | 1 | 0 | 0 |
| 0 | 0 | 1 | 0 | 1 | 0 | 0 |
| 0 | 1 | 0 | 1 | 0 | 1 | 0 |
| 0 | 0 | 0 | 1 | 0 | 0 | 0 |
| 0 | 0 | 1 | 0 | 1 | 1 | 1 |
| 0 | 0 | 0 | 1 | 0 | 1 | 0 |
| 0 | 1 | 0 | 0 | 1 | 1 | 1 |
| 0 | 1 | 0 | 1 | 0 | 0 | 0 |
| 1 | 0 | 0 | 0 | 0 | 0 | 0 |
| 0 | 1 | 0 | 1 | 1 | 1 | 1 |
| 0 | 0 | 0 | 1 | 1 | 0 | 0 |
| 0 | 1 | 0 | 1 | 0 | 0 | 0 |
| 0 | 1 | 1 | 0 | 1 | 0 | 0 |
| 1 | 1 | 1 | 1 | 0 | 1 | 1 |
| 0 | 1 | 0 | 0 | 1 | 0 | 1 |
| 0 | 1 | 0 | 0 | 1 | 0 | 0 |
| 0 | 1 | 1 | 1 | 1 | 0 | 0 |
| 0 | 0 | 1 | 0 | 0 | 0 | 1 |
| 0 | 0 | 1 | 0 | 1 | 1 | 1 |
| 0 | 0 | 1 | 0 | 0 | 1 | 1 |
| 0 | 0 | 1 | 0 | 1 | 0 | 1 |
| 0 | 1 | 0 | 0 | 0 | 0 | 0 |
| 0 | 0 | 1 | 0 | 0 | 0 | 0 |
| 0 | 0 | 1 | 0 | 1 | 1 | 1 |
| 0 | 1 | 0 | 1 | 0 | 0 | 0 |
| 0 | 0 | 0 | 1 | 1 | 1 | 1 |
| 0 | 0 | 1 | 0 | 1 | 1 | 0 |
| 0 | 0 | 1 | 1 | 1 | 0 | 1 |
| 0 | 0 | 1 | 1 | 1 | 0 | 0 |
| 0 | 0 | 0 | 0 | 0 | 0 | 1 |
| 1 | 1 | 1 | 1 | 0 | 0 | 0 |
| 0 | 0 | 0 | 0 | 0 | 1 | 0 |
| 0 | 0 | 0 | 1 | 1 | 0 | 0 |
| 0 | 0 | 1 | 0 | 1 | 0 | 1 |

TABLE 6-continued

Mitochondrial mutation recurrence for 41 nuclear genomic features

| | | | | | | | | | | | | | |
|---|---|---|---|---|---|---|---|---|---|---|---|---|---|
|  | 0 |  | 1 |  | 0 |  | 1 |  | 1 |  | 1 |  | 0 |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
|  | 0 |  | 0 |  | 1 |  | 0 |  | 0 |  | 1 |  | 1 |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
|  | 0 |  | 1 |  | 1 |  | 1 |  | 1 |  | 1 |  | 1 |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
| NA |  | NA |  | NA |  | NA |  | NA |  | NA |  | NA |  |
|  | 0 | NA |  | NA |  | NA |  | NA |  | NA |  | NA |  |
|  | 0 | NA |  | NA |  | NA |  | NA |  | NA |  | NA |  |

TABLE 6-continued

| Mitochondrial mutation recurrence for 41 nuclear genomic features | | | | | | |
|---|---|---|---|---|---|---|
| NA | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 1 | NA | NA | NA | NA | NA | NA |
| 1 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| NA | NA | NA | NA | NA | NA | NA |
| NA | NA | NA | NA | NA | NA | NA |
| 0 | NA | NA | NA | NA | NA | NA |
| 0 | NA | NA | NA | NA | NA | NA |
| NA | NA | NA | NA | NA | NA | NA |
| NA | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| NA | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |
| 0 | NA | NA | NA | NA | NA | NA |

TABLE 7

Table of mtSNVs with AHF values between 0.1 and 0.2

| Patient | Position | Reference | Tumour | Tumour HF-A | Tumour HF-C | Tumour HF-G | Tumour HF-T | Normal | Normal HF-A | Normal HF-C | Normal HF-G | Normal HF-T | Tumour Coverage | Normal Coverage | mtDNA Locus | Difference in HF |
|---|---|---|---|---|---|---|---|---|---|---|---|---|---|---|---|---|
| CPCG0120 | 61 | C | C | 0 | 0.88 | 0.04 | 0.08 | C | 0 | 1 | 0 | 0 | 2414 | 1066 | CR | 0.12 |
| ICGC_PCA087 | 72 | T | T | 0 | 0.13 | 0 | 0.87 | T | 0 | 0 | 0 | 1 | 1733 | 1357 | CR | 0.13 |
| ICCC_PCA161 | 146 | C | T | 0 | 0.01 | 0 | 0.99 | T | 0 | 0.17 | 0 | 0.83 | 2239 | 839 | CR | 0.16 |
| ICGC_PCA053 | 152 | C | T | 0 | 0.13 | 0 | 0.87 | T | 0 | 0 | 0 | 1 | 3817 | 3423 | CR | 0.13 |
| ICCC_PCA130 | 203 | G | G | 0.14 | 0 | 0.86 | 0 | G | 0 | 0 | 1 | 0 | 5419 | 597 | CR | 0.14 |
| CPCG0211 | 204 | T | C | 0 | 0.99 | 0 | 0.01 | C | 0 | 0.65 | 0 | 0.15 | 6273 | 732 | CR | 0.14 |
| CPCG0128 | 249 | A | A | 1 | 0 | 0 | 0 | A | 0.89 | 0 | 0.11 | 0 | 6347 | 859 | CR | 0.11 |
| CPCG0126 | 291 | A | A | 0.88 | 0 | 0 | 0.12 | A | 1 | 0 | 0 | 0 | 6805 | 1010 | CR | 0.12 |
| CPCG0126 | 294 | T | T | 0 | 0.13 | 0 | 0.87 | T | 0 | 0 | 0 | 1 | 6536 | 916 | CR | 0.13 |
| CPCG0126 | 296 | C | C | 0 | 0.88 | 0.12 | 0 | C | 0 | 1 | 0 | 0 | 6269 | 678 | CR | 0.12 |
| CPCG0126 | 297 | A | G | 0 | 0.15 | 0.85 | 0 | G | 0 | 0 | 1 | 0 | 5914 | 543 | CR | 0.15 |
| CPCG0126 | 299 | C | C | 0.11 | 0.89 | 0 | 0 | C | 0 | 1 | 0 | 0 | 7035 | 1001 | CR | 0.11 |
| CPCG0267 | 302 | A | A | 0.99 | 0.01 | 0 | 0 | A | 0.86 | 0.14 | 0 | 0 | 2788 | 429 | CR | 0.13 |
| CPCG0371 | 302 | A | A | 0.99 | 0.01 | 0 | 0 | A | 0.89 | 0.11 | 0 | 0 | 3650 | 1316 | CR | 0.1 |
| CPCG0071 | 302 | A | A | 0.87 | 0.12 | 0.01 | 0 | A | 0.98 | 0.02 | 0 | 0 | 2725 | 1059 | CR | 0.1 |
| CPCG0126 | 302 | A | A | 0.84 | 0.16 | 0 | 0 | A | 0.98 | 0.01 | 0 | 0 | 5384 | 584 | CR | 0.15 |
| Baca05-3595 | 303 | C | C | 0.02 | 0.97 | 0 | 0 | C | 0.2 | 0.8 | 0 | 0 | 4713 | 210 | CR | 0.17 |
| Baca05-3595 | 309 | C | T | 0 | 0.24 | 0 | 0.76 | T | 0 | 0.12 | 0 | 0.88 | 3340 | 1188 | CR | 0.13 |
| Baca05-3595 | 460 | T | T | 0.11 | 0 | 0 | 0.88 | T | 0.27 | 0 | 0 | 0.73 | 6244 | 2829 | CR | 0.15 |
| CPCG0204 | 529 | G | G | 0 | 0 | 1 | 0 | G | 0.11 | 0 | 0.89 | 0 | 6579 | 2313 | CR | 0.11 |
| CPCG0089 | 545 | G | G | 0.12 | 0.01 | 0.87 | 0 | G | 0 | 0 | 1 | 0 | 1106 | 2018 | CR | 0.13 |
| ICGC_PCA184 | 586 | G | G | 0.19 | 0 | 0.81 | 0 | G | 0 | 0 | 1 | 0 | 6197 | 3270 | TF | 0.19 |
| CPCG0096 | 653 | G | G | 0 | 0 | 1 | 0 | G | 0.11 | 0 | 0.89 | 0 | 7418 | 1911 | RNR1 | 0.1 |
| CPCG0036 | 709 | G | G | 0.19 | 0 | 0.81 | 0 | G | 0 | 0 | 1 | 0 | 7241 | 777 | RNR1 | 0.19 |
| ICGC_PCA053 | 827 | A | A | 0.88 | 0 | 0.12 | 0 | A | 1 | 0 | 0 | 0 | 5176 | 5170 | RNR1 | 0.12 |
| ICCC_PCA094 | 953 | T | T | 0 | 0.14 | 0 | 0.86 | T | 0 | 0 | 0 | 1 | 4544 | 1383 | RNR1 | 0.14 |
| CPCG0084 | 1072 | G | G | 0.19 | 0 | 0.81 | 0 | G | 0 | 0 | 1 | 0 | 5886 | 1888 | RNR1 | 0.19 |
| ICGC_PCA064 | 1252 | G | G | 0.19 | 0 | 0.81 | 0 | G | 0 | 0 | 1 | 0 | 7649 | 6466 | RNR1 | 0.19 |
| CPCG0070 | 1324 | T | T | 0 | 0 | 0 | 1 | T | 0 | 0.16 | 0 | 0.84 | 7774 | 3376 | RNR1 | 0.16 |
| ICCC_PCA124 | 1454 | G | G | 0.16 | 0 | 0.84 | 0 | G | 0 | 0 | 1 | 0 | 7325 | 2704 | RNR1 | 0.16 |
| ICGC_PCA132 | 1485 | G | G | 0.13 | 0 | 0.87 | 0 | G | 0 | 0 | 1 | 0 | 6697 | 2019 | RNR1 | 0.13 |
| CPCG0005 | 1826 | G | G | 0.15 | 0 | 0.85 | 0 | G | 0 | 0 | 1 | 0 | 7673 | 1994 | RNR2 | 0.15 |
| CPCG0089 | 1906 | G | G | 0.07 | 0.04 | 0.88 | 0 | G | 0 | 0 | 1 | 0 | 2144 | 3082 | RNR2 | 0.11 |
| CPCG0067 | 2203 | G | G | 0.04 | 0.01 | 0.9 | 0.06 | G | 0 | 0 | 1 | 0 | 213 | 1286 | RNR2 | 0.1 |
| CPCG0368 | 2233 | T | T | 0 | 0 | 0 | 1 | T | 0 | 0.16 | 0 | 0.84 | 7765 | 3094 | RNR2 | 0.15 |
| ICGC_PCA197 | 2296 | T | T | 0 | 0.19 | 0 | 0.81 | T | 0 | 0 | 0 | 1 | 7371 | 2948 | RNR2 | 0.19 |
| CPCG0413 | 2321 | A | G | 0.04 | 0 | 0.96 | 0 | G | 0.2 | 0 | 0.8 | 0 | 7059 | 3641 | RNR2 | 0.15 |
| CPCG0408 | 2345 | G | G | 0.14 | 0 | 0.86 | 0 | G | 0 | 0 | 1 | 0 | 7306 | 6130 | RNR2 | 0.14 |
| CPCG0114 | 2487 | A | A | 0.99 | 0.01 | 0 | 0 | A | 0.84 | 0.15 | 0 | 0.01 | 1953 | 252 | RNR2 | 0.15 |
| CPCG0123 | 2487 | A | A | 0.99 | 0.01 | 0 | 0 | A | 0.85 | 0.12 | 0.01 | 0 | 6361 | 1104 | RNR2 | 0.14 |
| CPCG0166 | 2487 | A | A | 1 | 0 | 0 | 0 | A | 1 | 0 | 0 | 0.01 | 126 | 1065 | RNR2 | 0.13 |
| CPCG0211 | 2487 | A | A | 0.86 | 0.13 | 0.01 | 0 | A | 0.81 | 0.17 | 0.01 | 0 | 6421 | 605 | RNR2 | 0.19 |
| Berger3027 | 2487 | A | A | 0.95 | 0.05 | 0 | 0 | A | 0.8 | 0.2 | 0 | 0 | 2734 | 7990 | RNR2 | 0.15 |
| CPCG0067 | 2536 | G | G | 0.11 | 0 | 0.89 | 0 | A | 0 | 0 | 1 | 0 | 5891 | 2001 | RNR2 | 0.11 |
| Baca06-3199 | 2553 | G | G | 0.12 | 0 | 0.88 | 0 | G | 0 | 0 | 1 | 0 | 6914 | 6249 | RNR2 | 0.12 |
| CPCG0361 | 2587 | G | G | 0.15 | 0 | 0.85 | 0 | G | 0 | 0 | 1 | 1 | 7215 | 3708 | RNR2 | 0.15 |

TABLE 7-continued

Table of mtSNVs with AHF values between 0.1 and 0.2

| Patient | Position | Reference | Tumour | Tumour HF-A | Tumour HF-C | Tumour HF-G | Tumour HF-T | Normal | Normal HF-A | Normal HF-C | Normal HF-G | Normal HF-T | Tumour Coverage | Normal Coverage | mtDNA Locus | Difference in HF |
|---|---|---|---|---|---|---|---|---|---|---|---|---|---|---|---|---|
| ICGC_PCA172 | 2609 | T | T | 0 | 0.18 | 0 | 0.82 | G | 0 | 0 | 0 | 0 | 5372 | 5848 | RNR2 | 0.18 |
| Baca06-1749 | 2698 | G | G | 0.15 | 0 | 0.85 | 0 | T | 0 | 0 | 1 | 0 | 6547 | 2793 | RNR2 | 0.15 |
| ICGC_PCA165 | 2698 | G | G | 0 | 0 | 0.88 | 0 | G | 0 | 0 | 1 | 0 | 7239 | 1912 | RNR2 | 0.12 |
| CPCG0046 | 2700 | G | G | 0.01 | 0 | 0.88 | 0.11 | G | 0 | 0 | 1 | 0 | 379 | 1626 | RNR2 | 0.12 |
| CPCG0201 | 2702 | G | G | 0.13 | 0 | 0.87 | 0 | G | 0 | 0 | 1 | 0 | 7436 | 2468 | RNR2 | 0.13 |
| ICGC_PCA059 | 2916 | G | G | 0.16 | 0 | 0.84 | 0 | G | 0 | 0 | 1 | 0 | 4442 | 2547 | RNR2 | 0.16 |
| TCGA-CH-5789 | 3243 | A | A | 0.89 | 0 | 0.11 | 0 | G | 1 | 0 | 0 | 0 | 7105 | 6797 | TL1 | 0.1 |
| ICGC_PCA034 | 3358 | G | G | 0.13 | 0 | 0.87 | 0 | A | 0 | 0 | 1 | 0 | 5359 | 2244 | ND1 | 0.13 |
| CPCG0094 | 3447 | A | A | 0.88 | 0.1 | 0.01 | 0.01 | A | 1 | 0 | 0 | 0 | 4366 | 939 | ND1 | 0.12 |
| CPCG0123 | 3447 | A | A | 1 | 0 | 0 | 0 | A | 0.84 | 0.12 | 0.02 | 0.02 | 5662 | 1018 | ND1 | 0.16 |
| CPCG0183 | 3447 | A | A | 1 | 0 | 0 | 0 | A | 0.85 | 0.11 | 0.02 | 0.02 | 6238 | 951 | ND1 | 0.15 |
| CPCG0211 | 3447 | A | A | 1 | 0 | 0 | 0 | A | 0.88 | 0.1 | 0.02 | 0 | 6535 | 637 | ND1 | 0.12 |
| CPCG0071 | 3447 | A | A | 0.85 | 0.14 | 0.01 | 0.01 | A | 0.95 | 0.05 | 0 | 0 | 4372 | 1535 | ND1 | 0.11 |
| BacaSTID0000002872 | 3447 | A | A | 1 | 0 | 0 | 0 | A | 0.88 | 0.1 | 0.01 | 0.01 | 4415 | 1634 | ND1 | 0.12 |
| Berger3043 | 3452 | T | T | 0 | 0.19 | 0 | 0.81 | T | 0 | 0 | 0 | 1 | 4071 | 795 | ND1 | 0.19 |
| ICGC_PCA023 | 3457 | G | G | 0.13 | 0 | 0.87 | 0 | G | 0 | 0 | 1 | 0 | 5304 | 5385 | ND1 | 0.13 |
| CPCG0089 | 3464 | T | T | 0.07 | 0.06 | 0 | 0.87 | T | 0 | 0 | 0 | 1 | 4676 | 3687 | ND1 | 0.13 |
| CPCG0123 | 3468 | A | A | 1 | 0 | 0 | 0 | A | 0.85 | 0.12 | 0.01 | 0.02 | 5725 | 954 | ND1 | 0.14 |
| CPCG0183 | 3468 | A | A | 0.99 | 0.01 | 0 | 0 | A | 0.87 | 0.09 | 0.01 | 0.02 | 6470 | 924 | ND1 | 0.12 |
| CPCG0071 | 3468 | A | A | 0.86 | 0.12 | 0 | 0.01 | A | 0.96 | 0.04 | 0 | 0 | 4425 | 1497 | ND1 | 0.1 |
| CPCG0123 | 3475 | A | A | 1 | 0 | 0 | 0 | A | 0.88 | 0.11 | 0 | 0.01 | 5599 | 907 | ND1 | 0.12 |
| ICGC_PCA173 | 3483 | G | G | 0 | 0 | 1 | 0 | G | 0.12 | 0 | 0.88 | 0 | 7586 | 4617 | ND1 | 0.12 |
| CPCG0089 | 3488 | T | T | 0.06 | 0.07 | 0.01 | 0.87 | T | 0 | 0 | 0 | 1 | 3368 | 3131 | ND1 | 0.13 |
| CPCG0123 | 3492 | A | A | 0.97 | 0.02 | 0 | 0 | A | 0.82 | 0.16 | 0.01 | 0 | 5220 | 813 | ND1 | 0.15 |
| CPCG0183 | 3492 | A | A | 1 | 0 | 0 | 0 | A | 0.81 | 0.18 | 0.01 | 0 | 5640 | 720 | ND1 | 0.19 |
| CPCG0211 | 3492 | A | A | 0.99 | 0.01 | 0 | 0 | A | 0.81 | 0.18 | 0 | 0 | 6252 | 475 | ND1 | 0.18 |
| CPCG0067 | 3531 | G | G | 0.08 | 0.02 | 0.89 | 0 | G | 0 | 0 | 1 | 0 | 2461 | 766 | ND1 | 0.1 |
| Baca09-37 | 3567 | C | C | 0 | 0.82 | 0 | 0.17 | C | 0 | 1 | 0 | 0 | 6043 | 4943 | ND1 | 0.17 |
| CPCG0127 | 3592 | G | G | 0.1 | 0 | 0.9 | 0 | G | 0 | 0 | 1 | 0 | 6787 | 1064 | ND1 | 0.1 |
| CPCG0210 | 3614 | T | T | 0 | 0.11 | 0 | 0.89 | T | 0 | 0 | 0 | 1 | 7477 | 1319 | ND1 | 0.11 |
| ICGC_PCA184 | 3715 | G | G | 0.12 | 0 | 0.88 | 0 | G | 0 | 0 | 1 | 0 | 6406 | 3722 | ND1 | 0.12 |
| CPCG0189 | 3834 | G | G | 0.2 | 0 | 0.8 | 0 | G | 0 | 0 | 1 | 0 | 7677 | 1734 | ND1 | 0.2 |
| ICGC_PCA048 | 4142 | G | G | 0.2 | 0 | 0.8 | 0 | G | 0 | 0 | 1 | 0 | 3163 | 2816 | ND1 | 0.2 |
| CPCG0346 | 4153 | G | G | 0.16 | 0 | 0.84 | 0 | G | 0 | 0 | 1 | 0 | 5516 | 1739 | ND1 | 0.16 |
| CPCG0267 | 4226 | T | T | 0 | 0.04 | 0 | 0.96 | T | 0 | 0.17 | 0 | 0.83 | 6856 | 1733 | ND1 | 0.13 |
| ICGC_PCA192 | 4408 | G | G | 0.1 | 0 | 0.9 | 0 | G | 0 | 0 | 1 | 0 | 3913 | 2915 | TM | 0.1 |
| ICGC_PCA132 | 4412 | G | G | 0.11 | 0 | 0.89 | 0 | G | 0 | 0 | 1 | 0 | 6704 | 2125 | TM | 0.11 |
| CPCG0378 | 4428 | G | G | 0.18 | 0 | 0.82 | 0 | G | 0 | 0 | 1 | 0 | 7468 | 4250 | TM | 0.18 |
| Baca07-5037 | 4762 | T | T | 0 | 0.17 | 0 | 0.83 | T | 0 | 0 | 0 | 1 | 7290 | 7502 | ND2 | 0.17 |
| CPCG0022 | 4848 | G | G | 0 | 0 | 0.87 | 0.13 | G | 0 | 0 | 0.98 | 0.02 | 1236 | 3356 | ND2 | 0.11 |
| CPCG0126 | 4969 | G | G | 0.19 | 0 | 0.81 | 0 | G | 0 | 0 | 1 | 0 | 7426 | 1891 | ND2 | 0.19 |
| CPCG0236 | 5177 | G | G | 0.14 | 0 | 0.86 | 0 | G | 0 | 0 | 1 | 0 | 7524 | 2322 | ND2 | 0.13 |
| CPCG0123 | 5208 | A | A | 1 | 0 | 0 | 0 | A | 0.88 | 0.09 | 0.01 | 0.02 | 5545 | 1037 | ND2 | 0.12 |
| CPCG0183 | 5208 | A | A | 1 | 0 | 0 | 0 | A | 0.88 | 0.09 | 0.01 | 0.02 | 6415 | 831 | ND2 | 0.12 |
| CPCG0211 | 5208 | A | A | 1 | 0 | 0 | 0 | A | 0.89 | 0.08 | 0.02 | 0 | 6277 | 413 | ND2 | 0.11 |
| CPCG0122 | 5208 | A | A | 1 | 0 | 0 | 0 | A | 0.89 | 0.09 | 0.01 | 0.01 | 6710 | 621 | ND2 | 0.11 |
| ICGC_PCA184 | 5476 | T | T | 0 | 0.19 | 0 | 0.81 | T | 0 | 0 | 0 | 1 | 7121 | 4051 | ND2 | 0.19 |
| CPCG0234 | 5511 | T | T | 0.02 | 0.08 | 0 | 0.9 | T | 0 | 0 | 0 | 1 | 106 | 1613 | ND2 | 0.1 |

TABLE 7-continued

| Table of mtSNVs with AHF values between 0.1 and 0.2 | | | | | | | | | | | | | | | | |
|---|---|---|---|---|---|---|---|---|---|---|---|---|---|---|---|---|
| Patient | Position | Reference | Tumour | Tumour HF-A | Tumour HF-C | Tumour HF-G | Tumour HF-T | Normal | Normal HF-A | Normal HF-C | Normal HF-G | Normal HF-T | Tumour Coverage | Normal Coverage | mtDNA Locus | Difference in HF |
| CPCG0344 | 5511 | T | T | 0 | 0.19 | 0 | 0.81 | T | 0 | 0 | 0 | 1 | 7434 | 2172 | ND2 | 0.19 |
| ICGC_PCA103 | 5521 | G | G | 0.14 | 0 | 0.86 | 0 | G | 0 | 0 | 1 | 0 | 6905 | 3724 | TW | 0.14 |
| CPCG0071 | 5734 | T | T | 0 | 0.11 | 0 | 0.88 | T | 0 | 0 | 0 | 1 | 4363 | 1110 | OLR | 0.12 |
| CPCG0346 | 5801 | T | T | 0 | 0.12 | 0 | 0.88 | T | 0 | 0 | 0 | 1 | 7580 | 3087 | TC | 0.12 |
| CPCG0089 | 6054 | G | G | 0.08 | 0.03 | 0.88 | 0 | G | 0 | 0 | 1 | 0 | 3712 | 3366 | CO1 | 0.12 |
| ICGC_PCA131 | 6128 | C | C | 0 | 0.6 | 0 | 0.4 | T | 0 | 0.4 | 0 | 0.6 | 7042 | 2821 | CO1 | 0.2 |
| ICGC_PCA069 | 6164 | C | C | 0.13 | 0.87 | 0 | 0 | C | 0 | 1 | 0 | 0 | 5295 | 2424 | CO1 | 0.13 |
| ICGC_PCA001 | 6221 | T | C | 0 | 1 | 0 | 0 | C | 0 | 0.89 | 0 | 0.11 | 4346 | 1283 | CO1 | 0.11 |
| ICGC_PCA017 | 6366 | G | G | 0.13 | 0 | 0.87 | 0 | G | 0 | 0 | 1 | 0 | 3616 | 4404 | CO1 | 0.13 |
| CPCG0048 | 6419 | A | A | 1 | 0 | 0 | 0 | A | 0.88 | 0.11 | 0 | 0 | 6135 | 1051 | CO1 | 0.11 |
| CPCG0005 | 6419 | A | A | 0.99 | 0.01 | 0 | 0 | A | 0.86 | 0.14 | 0 | 0 | 6158 | 1041 | CO1 | 0.13 |
| CPCG0084 | 6419 | A | A | 0.99 | 0.01 | 0 | 0 | A | 0.84 | 0.15 | 0 | 0 | 6190 | 1189 | CO1 | 0.15 |
| CPCG0100 | 6419 | A | A | 0.98 | 0.01 | 0 | 0 | A | 0.88 | 0.11 | 0 | 0 | 5818 | 896 | CO1 | 0.1 |
| CPCG0089 | 6430 | T | T | 0.06 | 0.04 | 0.01 | 0.9 | T | 0 | 0 | 0 | 1 | 3642 | 5059 | CO1 | 0.1 |
| CPCG0089 | 6438 | T | T | 0.05 | 0.05 | 0 | 0.9 | T | 0 | 0 | 0 | 1 | 3156 | 4906 | CO1 | 0.1 |
| CPCG0166 | 6480 | G | G | 0.24 | 0 | 0.76 | 0 | G | 0.43 | 0 | 0.57 | 0 | 6847 | 1518 | CO1 | 0.19 |
| CPCG0362 | 6532 | T | T | 0 | 0.11 | 0 | 0.89 | T | 0 | 0 | 0 | 1 | 7341 | 3512 | CO1 | 0.11 |
| CPCG0122 | 6555 | A | A | 1 | 0 | 0 | 0 | A | 0.9 | 0.07 | 0.03 | 0.01 | 7189 | 686 | CO1 | 0.1 |
| ICGC_PCA070 | 6627 | G | G | 0.17 | 0 | 0.83 | 0 | G | 0 | 0 | 1 | 0 | 5014 | 3745 | CO1 | 0.19 |
| CPCG0183 | 6819 | A | A | 1 | 0 | 0 | 0 | A | 0.89 | 0.08 | 0.01 | 0.01 | 6151 | 618 | CO1 | 0.11 |
| CPCG0122 | 6819 | A | A | 1 | 0 | 0 | 0 | A | 0.87 | 0.1 | 0.02 | 0 | 5544 | 369 | CO1 | 0.13 |
| Berger1701 | 6819 | A | A | 1 | 0 | 0 | 0 | A | 0.81 | 0.16 | 0.01 | 0.01 | 1949 | 371 | CO1 | 0.18 |
| Berger2832 | 6819 | A | A | 0.87 | 0.12 | 0.01 | 0 | A | 0.99 | 0.01 | 0 | 0 | 2556 | 356 | CO1 | 0.11 |
| TCGA-CH-5763 | 6819 | A | A | 1 | 0 | 0 | 0 | A | 0.88 | 0.1 | 0.01 | 0.01 | 2450 | 1031 | CO1 | 0.12 |
| ICGC_PCA189 | 6991 | T | T | 0 | 0.12 | 0 | 0.88 | T | 0 | 0 | 0 | 1 | 7055 | 7399 | CO1 | 0.12 |
| CPCG0020 | 7020 | G | G | 0.15 | 0 | 0.85 | 0 | G | 0 | 0 | 1 | 0 | 4448 | 711 | CO1 | 0.15 |
| CPCG0042 | 7102 | T | T | 0 | 0 | 0 | 1 | T | 0 | 0.1 | 0 | 0.9 | 6816 | 1647 | CO1 | 0.1 |
| CPCG0211 | 7236 | G | G | 0 | 0 | 1 | 0 | G | 0.12 | 0 | 0.88 | 0 | 6411 | 889 | CO1 | 0.12 |
| ICGC_PCA152 | 7391 | T | T | 0 | 0.11 | 0 | 0.89 | T | 0 | 0 | 0 | 1 | 6554 | 3031 | CO1 | 0.1 |
| TCGA-EJ-5506 | 7566 | G | G | 0.2 | 0 | 0.8 | 0 | G | 0 | 0 | 0.99 | 0 | 7401 | 4137 | TD | 0.19 |
| ICGC_PCA129 | 7859 | G | G | 0.04 | 0 | 0.96 | 0 | G | 0.22 | 0 | 0.78 | 0 | 7117 | 4475 | CO2 | 0.18 |
| ICGC_PCA132 | 7923 | A | A | 0.88 | 0 | 0.12 | 0 | A | 1 | 0 | 0 | 0 | 6656 | 2270 | CO2 | 0.12 |
| CPCG0166 | 8088 | T | T | 0 | 0.1 | 0 | 0.9 | T | 0 | 0 | 0 | 1 | 108 | 1604 | CO2 | 0.1 |
| CPCG0117 | 8403 | T | T | 0 | 0.18 | 0 | 0.82 | T | 0 | 0 | 0 | 1 | 7413 | 1495 | ATP8 | 0.18 |
| CPCG0183 | 8577 | A | A | 1 | 0 | 0 | 0 | A | 0.89 | 0.09 | 0.01 | 0.01 | 6412 | 1054 | ATP6 | 0.11 |
| ICGC_PCA145 | 8752 | A | A | 0.87 | 0 | 0.13 | 0 | A | 1 | 0 | 0 | 0 | 5177 | 1819 | ATP6 | 0.13 |
| CPCG0089 | 8959 | G | G | 0.07 | 0.03 | 0.89 | 0.01 | G | 0 | 0 | 1 | 0 | 3013 | 2740 | ATP6 | 0.1 |
| CPCG0243 | 8995 | G | G | 0 | 0 | 1 | 0 | G | 0.12 | 0 | 0.88 | 0 | 7381 | 1823 | ATP6 | 0.12 |
| CPCG0081 | 9035 | T | T | 0 | 0 | 0 | 1 | T | 0 | 0.16 | 0 | 0.84 | 7716 | 1845 | ATP6 | 0.16 |
| ICCC_PCA172 | 9165 | T | T | 0 | 0.14 | 0 | 0.86 | T | 0 | 0 | 0 | 1 | 5046 | 5174 | ATP6 | 0.14 |
| CPCG0050 | 9276 | G | G | 0.16 | 0 | 0.84 | 0 | G | 0 | 0 | 1 | 0 | 7018 | 1577 | CO3 | 0.16 |
| ICGC_PCA034 | 9552 | G | T | 0 | 0.12 | 0 | 0.88 | T | 0 | 0 | 0 | 1 | 5171 | 2128 | CO3 | 0.12 |
| CPCG0123 | 9726 | A | A | 1 | 0 | 0 | 0 | A | 0.88 | 0.08 | 0.01 | 0.02 | 6869 | 1607 | CO3 | 0.12 |
| CPCG0067 | 9744 | G | G | 0.11 | 0 | 0.89 | 0 | G | 0 | 0 | 1 | 0 | 6386 | 2243 | CO3 | 0.11 |
| TCCA-HC-7740 | 9746 | G | G | 0.46 | 0 | 0.54 | 0 | G | 0.27 | 0 | 0.73 | 0 | 6363 | 2884 | CO3 | 0.19 |
| ICGC_PCA174 | 9931 | G | G | 0.17 | 0 | 0.83 | 0 | G | 0 | 0 | 1 | 0 | 7355 | 4095 | CO3 | 0.17 |
| ICCC_PCA170 | 9942 | G | G | 0.1 | 0 | 0.9 | 0 | G | 0 | 0 | 1 | 0 | 7249 | 2955 | CO3 | 0.1 |
| CPCG0126 | 10197 | G | G | 0.15 | 0 | 0.85 | 0 | G | 0 | 0 | 1 | 0 | 5271 | 1260 | ND3 | 0.14 |

TABLE 7-continued

Table of mtSNVs with AHF values between 0.1 and 0.2

| Patient | Position | Reference | Tumour | Tumour HF-A | Tumour HF-C | Tumour HF-G | Tumour HF-T | Normal | Normal HF-A | Normal HF-C | Normal HF-G | Normal HF-T | Tumour Coverage | Normal Coverage | mtDNA Locus | Difference in HF |
|---|---|---|---|---|---|---|---|---|---|---|---|---|---|---|---|---|
| Baca05-3595 | 10203 | G | G | 0 | 0 | 1 | 0 | G | 0.2 | 0 | 0.8 | 0 | 2812 | 112 | ND3 | 0.19 |
| CPCG0324 | 10237 | T | T | 0 | 0 | 0 | 1 | T | 0 | 0.18 | 0 | 0.82 | 7346 | 1476 | ND3 | 0.18 |
| CPCG0123 | 10277 | A | A | 1 | 0 | 0 | 0 | A | 0.88 | 0.11 | 0 | 0 | 6675 | 1499 | ND3 | 0.12 |
| CPCG0183 | 10277 | A | A | 0.99 | 0 | 0 | 0 | A | 0.86 | 0.12 | 0.01 | 0.01 | 7016 | 1350 | ND3 | 0.13 |
| CPCG0184 | 10277 | A | A | 1 | 0 | 0 | 0 | A | 0.9 | 0.09 | 0 | 0 | 6598 | 1654 | ND3 | 0.1 |
| CPCG0234 | 10277 | A | A | 0.8 | 0.18 | 0.02 | 0 | A | 0.99 | 0.01 | 0 | 0 | 138 | 921 | ND3 | 0.19 |
| CPCG0097 | 10277 | A | A | 0.87 | 0.12 | 0 | 0 | A | 0.99 | 0.01 | 0 | 0 | 583 | 1107 | ND3 | 0.12 |
| CPCG0100 | 10277 | A | A | 0.99 | 0.01 | 0 | 0 | A | 0.89 | 0.1 | 0 | 0 | 6041 | 1016 | ND3 | 0.1 |
| CPCG0183 | 10283 | A | A | 1 | 0 | 0 | 0 | A | 0.88 | 0.1 | 0.01 | 0.01 | 6903 | 1395 | ND3 | 0.12 |
| CPCG0211 | 10283 | A | A | 1 | 0 | 0 | 0 | A | 0.89 | 0.1 | 0.01 | 0 | 6495 | 540 | ND3 | 0.11 |
| CPCG0048 | 10306 | A | A | 0.99 | 0.01 | 0 | 0 | A | 0.86 | 0.13 | 0 | 0 | 6152 | 1091 | ND3 | 0.13 |
| CPCG0081 | 10306 | A | A | 1 | 0 | 0 | 0 | A | 0.89 | 0.1 | 0 | 0 | 7641 | 1378 | ND3 | 0.11 |
| CPCG0123 | 10306 | A | A | 1 | 0 | 0 | 0 | A | 0.83 | 0.16 | 0 | 0.01 | 6752 | 1535 | ND3 | 0.17 |
| CPCG0183 | 10306 | A | A | 1 | 0 | 0 | 0 | A | 0.86 | 0.12 | 0.01 | 0 | 7275 | 1419 | ND3 | 0.14 |
| CPCG0211 | 10306 | A | A | 0.99 | 0.01 | 0 | 0 | A | 0.87 | 0.12 | 0 | 0 | 6406 | 556 | ND3 | 0.12 |
| CPCG0015 | 10306 | A | A | 0.99 | 0.01 | 0 | 0 | A | 0.88 | 0.12 | 0 | 0 | 5306 | 1884 | ND3 | 0.11 |
| Baca08-4154 | 10306 | A | A | 0.84 | 0.16 | 0 | 0 | A | 0.95 | 0.05 | 0 | 0 | 249 | 3705 | ND3 | 0.11 |
| BacaSTID0000002872 | 10306 | A | A | 1 | 0 | 0 | 0 | A | 0.86 | 0.13 | 0 | 0 | 4051 | 1542 | ND3 | 0.13 |
| CPCG0194 | 10326 | T | T | 0 | 0 | 0 | 1 | T | 0 | 0.2 | 0 | 0.8 | 5883 | 1053 | ND3 | 0.19 |
| ICGC_PCA138 | 10373 | G | A | 0.94 | 0 | 0.06 | 0 | A | 0.77 | 0 | 0.23 | 0 | 3764 | 1249 | ND3 | 0.17 |
| CPCG0212 | 10453 | A | A | 0.94 | 0 | 0.16 | 0 | A | 1 | 0 | 0 | 0 | 6070 | 1936 | TR | 0.16 |
| CPCG0234 | 10454 | T | T | 0 | 0.16 | 0 | 0.84 | T | 0 | 0 | 0 | 1 | 148 | 1705 | TR | 0.16 |
| CPCG0408 | 10591 | T | T | 0 | 0 | 0 | 1 | T | 0 | 0.14 | 0 | 0.86 | 7721 | 6744 | ND4L | 0.14 |
| EOPC-04 | 10603 | C | C | 0.15 | 0.85 | 0 | 0 | C | 0 | 0.99 | 0 | 0 | 3530 | 5885 | ND4L | 0.14 |
| CPCG0361 | 10677 | G | G | 0.1 | 0 | 0.89 | 0 | G | 0 | 0 | 1 | 0 | 5789 | 3685 | ND4L | 0.11 |
| CPCG0391 | 10686 | G | G | 0.12 | 0 | 0.88 | 0 | G | 0 | 0 | 1 | 0 | 7276 | 6103 | ND4L | 0.12 |
| ICGC_PCA053 | 10731 | G | G | 0.11 | 0 | 0.89 | 0 | G | 0 | 0 | 1 | 0 | 6919 | 6480 | ND4L | 0.11 |
| ICGC_PCA102 | 10768 | A | A | 0.74 | 0 | 0.26 | 0 | A | 0.61 | 0 | 0.39 | 0 | 4758 | 2928 | ND4 | 0.14 |
| CPCG0089 | 10934 | G | G | 0.07 | 0.03 | 0.89 | 0 | G | 0 | 0 | 1 | 0 | 2594 | 2217 | ND4 | 0.11 |
| CPCG0089 | 11031 | G | G | 0.08 | 0.03 | 0.89 | 0 | G | 0 | 0 | 1 | 0 | 2913 | 3705 | ND4 | 0.11 |
| CPCG0257 | 11124 | T | T | 0 | 0.18 | 0 | 0.82 | T | 0 | 0 | 0 | 1 | 7628 | 1926 | ND4 | 0.18 |
| ICGC-PCA192 | 11126 | G | G | 0.12 | 0 | 0.88 | 0 | G | 0 | 0 | 1 | 0 | 3845 | 2760 | ND4 | 0.12 |
| ICGC_PCA040 | 11166 | G | G | 0.03 | 0 | 0.97 | 0 | G | 0.14 | 0 | 0.86 | 0 | 5903 | 5831 | ND4 | 0.1 |
| CPCG0346 | 11223 | T | T | 0 | 0.13 | 0 | 0.87 | T | 0 | 0 | 0 | 1 | 7478 | 2780 | ND4 | 0.12 |
| CPCG0067 | 11225 | G | G | 0.11 | 0 | 0.89 | 0 | G | 0 | 0 | 1 | 0 | 6154 | 1591 | ND4 | 0.11 |
| CPCG0340 | 11250 | T | T | 0 | 0.19 | 0 | 0.81 | T | 0 | 0 | 0 | 1 | 7525 | 3514 | ND4 | 0.19 |
| CPCG0078 | 11557 | A | A | 0.94 | 0 | 0.06 | 0 | A | 0.82 | 0 | 0.18 | 0 | 7451 | 100 | ND4 | 0.12 |
| CPCG0072 | 11914 | A | G | 0.11 | 0 | 0.89 | 0 | G | 0 | 0 | 1 | 0 | 4976 | 1962 | ND4 | 0.11 |
| CPCG0046 | 12125 | G | G | 0 | 0 | 0.88 | 0.11 | G | 0 | 0 | 1 | 0 | 389 | 1921 | ND4 | 0.11 |
| CPCG0392 | 12134 | T | T | 0 | 0 | 0 | 1 | T | 0 | 0.14 | 0 | 0.86 | 7599 | 1948 | ND4 | 0.14 |
| CPCG0241 | 12235 | T | T | 0 | 0.15 | 0 | 0.85 | T | 0 | 0 | 0 | 1 | 7385 | 1447 | TS2 | 0.15 |
| CPCG0084 | 12457 | G | G | 0.13 | 0 | 0.87 | 0 | G | 0.01 | 0 | 0.99 | 0 | 3270 | 1337 | ND5 | 0.12 |
| CPCG0166 | 12471 | T | T | 0 | 0.2 | 0 | 0.8 | T | 0 | 0 | 0 | 1 | 193 | 1606 | ND5 | 0.2 |
| CPCG0388 | 12541 | G | G | 0.13 | 0 | 0.87 | 0 | G | 0 | 0 | 1 | 0 | 7537 | 2422 | ND5 | 0.13 |
| Baca05-3852 | 12631 | T | T | 0 | 0.15 | 0 | 0.85 | T | 0 | 0 | 0 | 1 | 6577 | 1992 | ND5 | 0.15 |
| CPCG0187 | 12772 | G | G | 0 | 0 | 1 | 0 | G | 0.17 | 0 | 0.83 | 0 | 7180 | 891 | ND5 | 0.17 |
| Berger1701 | 12775 | G | G | 0.16 | 0 | 0.84 | 0 | G | 0 | 0 | 0.99 | 0 | 2788 | 841 | ND5 | 0.15 |
| ICGC_PCA156 | 12977 | T | T | 0 | 0.18 | 0 | 0.82 | T | 0 | 0 | 0 | 1 | 6751 | 3729 | ND5 | 0.18 |

TABLE 7-continued

Table of mtSNVs with AHF values between 0.1 and 0.2

| Patient | Position | Reference | Tumour | Tumour HF-A | Tumour HF-C | Tumour HF-G | Tumour HF-T | Normal | Normal HF-A | Normal HF-C | Normal HF-G | Normal HF-T | Tumour Coverage | Normal Coverage | mtDNA Locus | Difference in HF |
|---|---|---|---|---|---|---|---|---|---|---|---|---|---|---|---|---|
| ICGC_PCA127 | 13042 | G | G | 0.17 | 0 | 0.83 | 0 | G | 0 | 0 | 1 | 0 | 6856 | 3318 | ND5 | 0.17 |
| CPCG-0122 | 13094 | T | T | 0 | 0.12 | 0 | 0.88 | T | 0 | 0 | 0 | 0.99 | 7441 | 983 | ND5 | 0.11 |
| ICGC_PCA172 | 13105 | G | G | 0.09 | 0 | 0.91 | 0 | G | 0.23 | 0 | 0.77 | 0 | 5389 | 5714 | ND5 | 0.14 |
| TCGA-EJ-7791 | 13376 | T | T | 0 | 0 | 0 | 0.99 | T | 0 | 0.14 | 0 | 0.86 | 6535 | 2460 | ND5 | 0.13 |
| Baca06-1749 | 13424 | T | T | 0 | 0.16 | 0 | 0.84 | T | 0 | 0 | 0 | 1 | 7371 | 3119 | ND5 | 0.15 |
| ICGC_PCA031 | 13466 | G | G | 0 | 0 | 1 | 01 | 3 | 0.17 | 0 | 0.83 | 0 | 5931 | 5521 | ND5 | 0.17 |
| CPCG0020 | 13590 | G | G | 0.16 | 0 | 0.84 | 0 | G | 0 | 0 | 1 | 0 | 7611 | 1841 | ND5 | 0.16 |
| CPCG0089 | 13674 | T | T | 0.05 | 0.07 | 0.01 | 0.87 | T | 0 | 0 | 0 | 1 | 3237 | 4163 | ND5 | 0.13 |
| CPCG0353 | 13708 | G | G | 0.1 | 0 | 0.9 | 0 | G | 0 | 0 | 1 | 0 | 6663 | 3432 | ND5 | 0.1 |
| CPCG0046 | 13940 | G | G | 0.06 | 0 | 0.89 | 0.05 | G | 0 | 0 | 1 | 0 | 318 | 1344 | ND5 | 0.11 |
| CPCG0123 | 14102 | T | T | 0 | 0.19 | 0 | 0.81 | T | 0 | 0 | 0 | 0.99 | 7411 | 2392 | ND5 | 0.18 |
| ICGC_PCA024 | 14311 | T | T | 0 | 0.14 | 0 | 0.86 | T | 0 | 0 | 0 | 1 | 4940 | 2480 | ND6 | 0.14 |
| CPCG0030 | 14423 | G | G | 0.15 | 0 | 0.84 | 0 | G | 0.02 | 0 | 0.98 | 0 | 7206 | 1664 | ND6 | 0.14 |
| CPCG0072 | 14470 | T | T | 0 | 0.12 | 0 | 0.88 | T | 0 | 0 | 0 | 1 | 6689 | 2084 | ND6 | 0.12 |
| CPCG0234 | 14560 | G | G | 0 | 0 | 0.89 | 0.1 | G | 0 | 0 | 1 | 0 | 997 | 1290 | ND6 | 0.11 |
| CPCG0234 | 14698 | G | G | 0 | 0 | 0.9 | 0.1 | G | 0 | 0 | 1 | 0 | 1360 | 1364 | TE | 0.1 |
| ICGC_PCA143 | 14798 | T | C | 0 | 0.85 | 0 | 0.15 | C | 0 | 0.7 | 0 | 0.3 | 7083 | 4223 | CYB | 0.15 |
| CPCG0236 | 14859 | G | G | 0.18 | 0 | 0.82 | 0 | G | 0 | 0 | 1 | 0 | 7208 | 2114 | CYB | 0.18 |
| ICGC_PCA055 | 14985 | G | G | 0.12 | 0 | 0.88 | 0 | G | 0 | 0 | 1 | 0 | 7069 | 4679 | CYB | 0.12 |
| CPCG0046 | 15200 | G | G | 0.01 | 0 | 0.9 | 0.09 | G | 0 | 0 | 1 | 0 | 424 | 1479 | CYB | 0.1 |
| EOPC-07 | 15211 | C | T | 0 | 0.01 | 0 | 0.99 | T | 0 | 0.11 | 0 | 0.89 | 5386 | 1718 | CYB | 0.11 |
| CPCG0363 | 15216 | G | G | 0.11 | 0 | 0.89 | 0.01 | G | 0 | 0 | 1 | 0 | 6276 | 3366 | CYB | 0.11 |
| ICGC_PCA022 | 15228 | T | T | 0 | 0.18 | 0 | 0.82 | T | 0 | 0 | 0 | 1 | 4273 | 6156 | CYB | 0.18 |
| ICGC_PCA137 | 15255 | T | T | 0 | 0.11 | 0 | 0.89 | T | 0 | 0 | 0 | 1 | 6969 | 2363 | CYB | 0.11 |
| ICGC_PCA035 | 15356 | G | G | 0.15 | 0 | 0.84 | 0 | G | 0 | 0 | 1 | 0 | 7076 | 4723 | CYB | 0.15 |
| EOPC-02 | 15458 | T | C | 0 | 0.71 | 0 | 0.28 | C | 0 | 0.91 | 0 | 0.09 | 4983 | 3285 | CYB | 0.19 |
| CPCG0183 | 15536 | A | A | 1 | 0 | 0 | 0 | A | 0.89 | 0.07 | 0.01 | 0.02 | 7009 | 1083 | CYB | 0.11 |
| CPCG0211 | 15536 | A | A | 1 | 0 | 0 | 0 | A | 0.89 | 0.08 | 0.02 | 0.01 | 6942 | 570 | CYB | 0.11 |
| ICGC_PCA118 | 15614 | G | G | 0.15 | 0 | 0.85 | 0 | G | 0 | 0 | 1 | 0 | 7135 | 3573 | CYB | 0.15 |
| ICGC_PCA172 | 15825 | C | T | 0 | 0.1 | 0 | 0.9 | T | 0 | 0.25 | 0 | 0.75 | 5181 | 5498 | CYB | 0.15 |
| ICGC_PCA078 | 15900 | T | T | 0 | 0.14 | 0 | 0.86 | T | 0 | 0 | 0 | 1 | 3010 | 3847 | TT | 0.14 |
| CPCG0046 | 15927 | G | G | 0.1 | 0 | 0.85 | 0.05 | G | 0 | 0 | 1 | 0 | 419 | 1717 | TT | 0.15 |
| CPCG0235 | 15976 | T | T | 0 | 0.2 | 0 | 0.8 | T | 0 | 0 | 0 | 1 | 7757 | 2096 | TP | 0.2 |
| CPCG0048 | 16092 | T | C | 0 | 0.85 | 0 | 0.15 | C | 0 | 0.96 | 0 | 0.04 | 7162 | 1622 | CR | 0.11 |
| CPCG0057 | 16093 | T | C | 0 | 0.87 | 0 | 0.13 | C | 0 | 0.97 | 0 | 0.03 | 7070 | 246 | CR | 0.11 |
| CPCG0199 | 16093 | T | C | 0 | 0.8 | 0 | 0.2 | C | 0 | 0.94 | 0 | 0.06 | 7365 | 2534 | CR | 0.13 |
| CPCG0250 | 16093 | T | C | 0 | 0.84 | 0 | 0.16 | C | 0 | 0.96 | 0 | 0.04 | 7176 | 2788 | CR | 0.13 |
| CPCG0259 | 16093 | T | C | 0 | 0.85 | 0 | 0.15 | C | 0 | 0.97 | 0 | 0.03 | 7063 | 2312 | CR | 0.12 |
| CPCG0354 | 16093 | T | C | 0 | 0.87 | 0 | 0.13 | C | 0 | 0.98 | 0 | 0.02 | 7123 | 4981 | CR | 0.11 |
| Baca08-4154 | 16093 | T | C | 0 | 0.92 | 0 | 0.08 | C | 0 | 0.73 | 0 | 0.27 | 104 | 6163 | CR | 0.19 |
| ICGC_PCA053 | 16093 | T | C | 0 | 0.79 | 0 | 0.21 | C | 0 | 0.98 | 0 | 0.02 | 6911 | 7080 | CR | 0.19 |
| ICGC_PCA095 | 16093 | T | C | 0 | 0.81 | 0 | 0.19 | C | 0 | 0.97 | 0 | 0.03 | 4785 | 2264 | CR | 0.16 |
| ICGC_PCA151 | 16093 | T | C | 0 | 0.88 | 0 | 0.12 | C | 0 | 0.98 | 0 | 0.01 | 5414 | 1639 | CR | 0.11 |
| CPCG0378 | 16117 | T | T | 0 | 0.16 | 0 | 0.84 | T | 0 | 0 | 0 | 1 | 7660 | 7058 | CR | 0.16 |
| CPCG0194 | 16129 | A | G | 0 | 0 | 1 | 0 | G | 0.14 | 0 | 0.85 | 0 | 3933 | 498 | CR | 0.14 |
| CPCG0346 | 16145 | G | G | 0.12 | 0 | 0.88 | 0 | G | 0 | 0 | 1 | 0 | 7495 | 3317 | CR | 0.12 |
| ICGC_PCA153 | 16147 | C | C | 0 | 0.87 | 0 | 0.13 | C | 0 | 1 | 0 | 0 | 6929 | 2343 | CR | 0.13 |
| CPCG0122 | 16175 | A | A | 1 | 0 | 0 | 0 | A | 0.9 | 0.1 | 0.01 | 0 | 5458 | 475 | CR | 0.1 |

TABLE 7-continued

Table of mtSNVs with AHF values between 0.1 and 0.2

| Patient | Position | Reference | Tumour | Tumour HF-A | Tumour HF-C | Tumour HF-G | Tumour HF-T | Normal | Normal HF-A | Normal HF-C | Normal HF-G | Normal HF-T | Tumour Coverage | Normal Coverage | mtDNA Locus | Difference in HF |
|---|---|---|---|---|---|---|---|---|---|---|---|---|---|---|---|---|
| CPCG0194 | 16183 | A | C | 0.17 | 0.83 | 0 | 0 | C | 0.27 | 0.73 | 0 | 0 | 1329 | 490 | CR | 0.1 |
| ICGC_PCA127 | 16184 | C | C | 0 | 0.89 | 0 | 0.11 | C | 0 | 1 | 0 | 0 | 6185 | 3060 | CR | 0.11 |
| CPCG0007 | 16187 | T | T | 0 | 0.02 | 0 | 0.98 | T | 0 | 0.14 | 0 | 0.86 | 6350 | 1529 | CR | 0.11 |
| Baca05-3852 | 16187 | T | C | 0 | 0.98 | 0 | 0.02 | C | 0 | 0.86 | 0 | 0.14 | 6536 | 1173 | CR | 0.12 |
| CPCG0070 | 16189 | C | T | 0 | 0.03 | 0 | 0.97 | T | 0.01 | 0.14 | 0 | 0.86 | 7212 | 2311 | CR | 0.11 |
| CPCG0194 | 16189 | C | C | 0 | 0.98 | 0 | 0.01 | C | 0 | 0.87 | 0 | 0.12 | 1847 | 550 | CR | 0.11 |
| EOPC-02 | 16189 | C | T | 0 | 0.16 | 0 | 0.84 | T | 0.01 | 0.03 | 0 | 0.96 | 2314 | 1217 | CR | 0.12 |
| BacaSTID0000000410 | 16189 | C | T | 0 | 0.28 | 0 | 0.72 | T | 0 | 0.12 | 0 | 0.87 | 6024 | 402 | CR | 0.16 |
| BacaSTID0000002872 | 16189 | C | C | 0 | 0.86 | 0 | 0.14 | C | 0 | 1 | 0 | 0 | 3393 | 2188 | CR | 0.13 |
| CPCG0194 | 16223 | T | T | 0 | 0.01 | 0 | 0.99 | T | 0 | 0.14 | 0 | 0.86 | 3820 | 597 | CR | 0.13 |
| ICGC_PCA001 | 16223 | T | T | 0 | 0 | 0 | 1 | T | 0 | 0.12 | 0 | 0.88 | 5297 | 1828 | CR | 0.12 |
| EOPC-02 | 16231 | T | C | 0 | 0.86 | 0 | 0.14 | C | 0 | 1 | 0 | 0 | 2802 | 1558 | CR | 0.14 |
| ICGC_PCA171 | 16247 | A | A | 0.96 | 0 | 0.04 | 0 | A | 0.86 | 0 | 0.14 | 0 | 4771 | 2537 | CR | 0.1 |
| ICGC_PCA026 | 16258 | A | A | 0.81 | 0 | 0.19 | 0 | A | 1 | 0 | 0 | 0 | 4236 | 1740 | CR | 0.19 |
| EOPC-02 | 16261 | C | T | 0 | 0.13 | 0 | 0.87 | T | 0 | 0.01 | 0 | 0.99 | 3465 | 2005 | CR | 0.12 |
| EOPC-02 | 16265 | A | C | 0.11 | 0.89 | 0 | 0 | C | 0 | 1 | 0 | 0 | 3807 | 2232 | CR | 0.1 |
| CPCG0363 | 16266 | C | C | 0 | 0.9 | 0 | 0.1 | C | 0 | 1 | 0 | 0 | 6878 | 2983 | CR | 0.1 |
| CPCG0194 | 16266 | C | T | 0 | 0.01 | 0 | 0.99 | T | 0 | 0.13 | 0 | 0.87 | 4844 | 875 | CR | 0.12 |
| CPCG0194 | 16274 | G | A | 1 | 0 | 0 | 0 | A | 0.89 | 0 | 0.11 | 0 | 5382 | 956 | CR | 0.1 |
| CPCG0260 | 16278 | T | C | 0 | 0.88 | 0 | 0.11 | C | 0 | 1 | 0 | 0 | 6258 | 1496 | CR | 0.11 |
| CPCG0349 | 16296 | C | T | 0 | 0.01 | 0 | 0.99 | T | 0 | 0.18 | 0 | 0.82 | 7025 | 3138 | CR | 0.16 |
| TCGA-HC-7233 | 16311 | C | T | 0 | 0.01 | 0 | 0.99 | T | 0 | 0.13 | 0 | 0.87 | 3246 | 1622 | CR | 0.12 |
| CPCG0183 | 16318 | A | A | 1 | 0 | 0 | 0 | A | 0.86 | 0 | 0.14 | 0 | 7392 | 1684 | CR | 0.14 |
| CPCG0194 | 16390 | G | A | 1 | 0 | 0 | 0 | A | 0.89 | 0 | 0.11 | 0 | 5047 | 1010 | CR | 0.1 |
| CPCG0382 | 16519 | C | C | 0 | 1 | 0 | 0 | C | 0 | 0.9 | 0 | 0.1 | 4052 | 1521 | CR | 0.1 |
| CPCG0089 | 16522 | T | T | 0.06 | 0.05 | 0 | 0.89 | T | 0 | 0 | 0 | 1 | 2521 | 2119 | CR | 0.11 |
| CPCG0256 | 16527 | C | T | 0 | 0.16 | 0 | 0.84 | T | 0 | 0.06 | 0 | 0.94 | 2232 | 692 | CR | 0.1 |

The invention claimed is:

1. A method of detecting one or more mitochondrial single nucleotide variations (mtSNVs) in a human subject with prostate cancer, the method comprising:

detecting a single nucleotide variation at position 8393 or 8433 of a mitochondrial genome with respect to the Reconstructed Sapiens Reference Sequence (RSRS) reference genome by sequencing mitochondrial genetic material from prostate cancer cells from the subject, wherein the single nucleotide variation is a C>T substitution at position 8393 or a T>C substitution at position 8433.

2. The method of claim 1, wherein the prostate cancer is localized prostate cancer.

3. The method of claim 1, further comprising treating the subject with hormone therapy, chemotherapy, or radiotherapy.

4. The method of claim 1, wherein the method further comprises detecting single nucleotide variations at one or more of positions 146, 152, 183, 195, 199, 207, 215, 227, 234, 248, 255, 307, and 309.

5. The method of claim 1, wherein the method further comprises detecting a single nucleotide variation at one or more of positions 146, 152, 183, 195, 199, 207, 215, 227, 234, 248, 255, 307, 7772, 7803, 7919, 7929, 7997, 8078, 8391, 8547, 9378, 9380, 9504, 9516, 9628, 9673, 9786, 9797, 9840, 9891, 9977, 10558, 10586, 16027, 16035, 16048, 16051, 16086, 16092, 16093, 16147, 16148, 16153, 16162, 16169, 16182, 16183, 16184, 16188, 16189, 16192, 16213, 16278, 16304, and 16342.

6. The method of claim 1, wherein the single nucleotide variation is a C>T substitution at position 8393.

7. The method of claim 1, wherein the single nucleotide variation is a T>C substitution at position 8433.

8. A method for treating a human subject for prostate cancer, the method comprising treating the subject with surgery, hormone therapy, chemotherapy, or radiotherapy, wherein the subject was determined to have a mitochondrial single nucleotide variation (mtSNV) at position 8393 or 8433 of a mitochondrial genome from prostate cancer cells from the subject with respect to the RSRS reference genome, wherein the single nucleotide variation is a C>T substitution at position 8393 or a T>C substitution at position 8433.

9. The method of claim 8, wherein the subject was further determined to have a mutation in a region of a MYC gene from the prostate cancer cells.

10. The method of claim 8, wherein the subject was further determined to have a mtSNV at one or more of positions 146, 152, 183, 195, 199, 207, 215, 227, 234, 248, 255, 307, and 309.

11. The method of claim 8, wherein the subject was further determined to have a mtSNV at one or more of positions 146, 152, 183, 195, 199, 207, 215, 227, 234, 248, 255, 307, 309, 8391, 8547, 10558, 10586, 16027, 16035, 16048, 16051, 16086, 16092, 16093, 16147, 16148, 16153, 16162, 16169, 16182, 16183, 16184, 16188, 16189, 16192, 16213, 16278, 16304, and 16342.

12. The method of claim 8, wherein the single nucleotide variation is a C>T substitution at position 8393.

13. The method of claim 8, wherein the single nucleotide variation is a T>C substitution at position 8433.

* * * * *